United States Patent
Handa et al.

(10) Patent No.: US 10,272,117 B2
(45) Date of Patent: Apr. 30, 2019

(54) METHODS OF USING AN ACTIVATOR OF CEREBLON FOR NEURAL CELL EXPANSION AND THE TREATMENT OF CENTRAL NERVOUS SYSTEM DISORDERS

(71) Applicant: Celgene Corporation, Summit, NJ (US)

(72) Inventors: Hiroshi Handa, Tokyo (JP); Hideki Ando, Tokyo (JP); Takumi Ito, Kanagawa (JP)

(73) Assignee: Celgene Corporation, Summit, NJ (US)

( * ) Notice: Subject to any disclaimer, the term of this patent is extended or adjusted under 35 U.S.C. 154(b) by 107 days.

(21) Appl. No.: 15/121,017

(22) PCT Filed: Feb. 23, 2015

(86) PCT No.: PCT/US2015/017066
§ 371 (c)(1),
(2) Date: Aug. 23, 2016

(87) PCT Pub. No.: WO2015/127351
PCT Pub. Date: Aug. 27, 2015

(65) Prior Publication Data
US 2017/0007645 A1     Jan. 12, 2017

Related U.S. Application Data

(60) Provisional application No. 62/109,542, filed on Jan. 29, 2015, provisional application No. 62/062,641, filed on Oct. 10, 2014, provisional application No. 62/049,260, filed on Sep. 11, 2014, provisional application No. 62/049,191, filed on Sep. 11, 2014, provisional application No. 62/035,936, filed on Aug. 11, 2014, provisional application No. 61/943,857, filed on Feb. 24, 2014.

(51) Int. Cl.
| | |
|---|---|
| *A61K 35/30* | (2015.01) |
| *G01N 33/48* | (2006.01) |
| *G01N 33/50* | (2006.01) |
| *C12N 5/0797* | (2010.01) |
| *C12N 15/113* | (2010.01) |
| *A61K 35/545* | (2015.01) |
| *A61K 38/17* | (2006.01) |
| *C12N 5/079* | (2010.01) |
| *C12Q 1/6883* | (2018.01) |
| *A61K 48/00* | (2006.01) |

(52) U.S. Cl.
CPC ............ *A61K 35/30* (2013.01); *A61K 35/545* (2013.01); *A61K 38/1709* (2013.01); *C12N 5/0618* (2013.01); *C12N 5/0623* (2013.01); *C12N 15/113* (2013.01); *C12Q 1/6883* (2013.01); *G01N 33/5088* (2013.01); *A61K 48/00* (2013.01); *C12N 2310/11* (2013.01); *C12N 2310/14* (2013.01); *C12N 2310/3233* (2013.01); *C12N 2320/30* (2013.01); *C12N 2501/60* (2013.01); *C12N 2501/70* (2013.01); *C12N 2501/998* (2013.01); *C12Q 2600/118* (2013.01); *C12Q 2600/158* (2013.01); *G01N 2800/28* (2013.01); *G01N 2800/2821* (2013.01); *G01N 2800/2828* (2013.01); *G01N 2800/2835* (2013.01); *G01N 2800/52* (2013.01)

(58) Field of Classification Search
None
See application file for complete search history.

(56) References Cited

U.S. PATENT DOCUMENTS

| | | |
|---|---|---|
| 2005/0182097 A1 | 8/2005 | Zeldis et al. |
| 2010/0021437 A1 | 1/2010 | Isacson et al. |
| 2011/0070218 A1 | 3/2011 | Teichberg et al. |
| 2012/0077741 A1 | 3/2012 | Delfani et al. |

(Continued)

FOREIGN PATENT DOCUMENTS

| | | |
|---|---|---|
| WO | WO 2014028445 A2 | 2/2014 |
| WO | WO 2014028445 A3 | 2/2014 |

OTHER PUBLICATIONS

Chen et al., "An Open-Label Phase 2 Study of Lenalidomide in Combination with Oral Dexamethasone in the Previously Untreated, Symptomatic Patients with Chronic Lymphocytic Leukemia (CLL)", Blood, 120(21), abstract 2895 (2012).

Gandhi et al., "Immunomodulatory agents lenalidomide and pomalidomide co-stimulate T cells by inducing degradation of T cell repressors Ikaros and Aiolos via modulation of the E3 ubiquitin ligase complex CRL4(CRBN)", Br J Haematol., 164(6):811-821 (2014).

Heintel et al., "High expression of the thalidomide-binding proteincereblon (CRBN) is associated with improved clinical response in patients with multiple myelomatreated with lenalidomide and dexamethasone", Blood, 118(21), abstract 2879 (2011).

(Continued)

*Primary Examiner* — Michelle F. Paguio Frising
(74) *Attorney, Agent, or Firm* — Jones Day

(57) ABSTRACT

Provided herein, for example, are methods generally relating to the expansion and/or regeneration of central nervous system (CNS) cells, such as nerve cells, astrocytes and oligodendrocytes, using an activator of cereblon (CRBN), such as an inhibitor of a CRBN substrate or downstream protein. Also provided herein, for example, are methods related to the expansion of neural stem cells, neural progenitor cells, or neural precursor cells and/or differentiation of these cells into CNS cells using a BRD7 antagonist, Ikaros antagonist, or CRBN activator. In certain embodiments, the methods further comprise differentiation of certain stem cells into the neural stem cells, neural progenitor cells, or neural precursor cells using a BRD7 antagonist, Ikaros antagonist, or CRBN activator. Also provided herein, for example, are methods of preventing or treating a CNS cell defective disease, disorder or condition, or a symptom thereof, using a BRD7 antagonist, Ikaros antagonist, or CRBN activator.

23 Claims, 32 Drawing Sheets

Specification includes a Sequence Listing.

(56) References Cited

U.S. PATENT DOCUMENTS

2012/0134969 A1    5/2012  Handa et al.
2016/0024504 A1*   1/2016  Albrecht ............ C07K 14/4702
                                                          514/44 A

OTHER PUBLICATIONS

International Search Report and Written Opinon of Corresponding International Patent Application No. PCT/US2015/017066 dated Jun. 3, 2015 (13 pages).
Lee et al., "Functional effects of a pathogenic mutation in Cereblon (CRBN) on the regulation of protein synthesis via the AMPK-mTOR cascade", J Biol Chem., 289(34):23343-23352 (2014).
Kiaei et al., "Thalidomide and lenalidomide extend survival in a transgenic mouse model of amyotrophic lateral sclerosis", J Neurosci., 26(9):2467-2473 (2006).
Mosley et al., "Control of neuroinflammation as a therapeutic strategy for amyotrophic lateral sclerosis and other neurodegenerative disorders", Exp Neurol., 222(1):1-5 (2010).
Neymotin et al., "Lenalidomide (Revlimid) administration at symptom onset is neuroprotective in a mouse model of amyotrophic lateral sclerosis", Exp Neurol., 220(1):191-197 (2009).
Traynor et al., "Neuroprotective agents for clinical trials in ALS: a systematic assessment", Neurology, 67(1):20-27 (2006).

\* cited by examiner p: Pineal organ
vpt: ventroposterior tuberculum
rn: raphe nuclei
RG: radial glia (green)

METHODS OF USING AN ACTIVATOR OF CEREBLON FOR NEURAL CELL EXPANSION AND THE TREATMENT OF CENTRAL NERVOUS SYSTEM DISORDERS

CROSS-REFERENCE TO RELATED APPLICATIONS

This application is a U.S. National Stage Application under 35 U.S.C. § 371 of the International Patent Application No. PCT/US2015/017066, filed Feb. 23, 2015, which claims the benefit of U.S. Ser. No. 61/943,857 filed Feb. 24, 2014, U.S. Ser. No. 62/049,191 filed Sep. 11, 2014, U.S. Ser. No. 62/035,936 filed Aug. 11, 2014, U.S. Ser. No. 62/049,260 filed Sep. 11, 2014, U.S. Ser. No. 62/062,641 filed Oct. 10, 2014, U.S. Ser. No. 62/109,542 filed Jan. 29, 2015, each of which is incorporated herein by reference in its entirety.

1. FIELD

Provided herein, for example, are methods generally relating to the expansion and/or regeneration of central nervous system (CNS) cells, such as nerve cells, astrocytes and oligodendrocytes, using (i) an antagonist of Bromodomain Containing 7 (BRD7), (ii) an antagonist of Ikaros (Ikaros family zinc finger protein1), or (iii) an upregulation of Yamanaka factors and induced neuronal (iN) cell-inducing factors, such as BAM factors, by cereblon (CRBN) or a CRBN activator. Also provided herein, for example, are methods related to the expansion of neural stem cells, neural progenitor cells, or neural precursor cells and/or differentiation of these cells into CNS cells using (i) an antagonist of BRD7, (ii) an antagonist of Ikaros, or (iii) an upregulation of Yamanaka factors and iN cell-inducing factors, such as BAM factors, by CRBN or a CRBN activator. In certain embodiments, the methods further comprise differentiation of certain stem cells into the neural stem cells, neural progenitor cells, or neural precursor cells using (i) an antagonist of BRD7, (ii) an antagonist of Ikaros, or (iii) an upregulation of Yamanaka factors and iN cell-inducing factors, such as BAM factors, by CRBN or a CRBN activator. Also provided herein, for example, are methods of preventing or treating a CNS cell defective disease, disorder or condition, or a symptom thereof, using (i) an antagonist of BRD7, (ii) an antagonist of Ikaros, or (iii) an upregulation of Yamanaka factors and iN cell-inducing factors, such as BAM factors, by CRBN or a CRBN activator.

2. BACKGROUND

The mammalian nervous system comprises a peripheral nervous system (PNS) and a central nervous system (CNS). CNS comprises brain and spinal cord, and is composed of two principal classes of cells: neurons and glial cells. The fundamental cell of the brain is the neuron. The glial cells fill the spaces between neurons, nourishing them and modulating their function. Certain glial cells, such as oligodendrocytes in the CNS, also provide a myelin sheath that surrounds neural processes. The myelin sheath enables rapid conduction along the neuron. Besides, radial glia contains a population of neural stem and precursor cells, so it can function as a supplier of newborn neurons and glia.

CNS disorders affect a wide range of the population with differing severity. These disorders can be caused by various factors such as trauma, infections, degeneration, structural defects, tumors, blood flow disruption, and autoimmune disorders. CNS disorders encompass numerous afflictions such as neurodegenerative diseases (e.g., Alzheimer's and Parkinson's), acute brain injury (e.g., stroke, head injury, cerebral palsy) and a large number of CNS dysfunctions (e.g., depression, epilepsy, and schizophrenia). The common signs and symptoms of these CNS disorders are physical and/or cognitive impairments and personality changes. Dementia, for example, is characterized by several cognitive impairments including significant memory deficit and can stand alone or be an underlying characteristic feature of a variety of diseases, including Alzheimer Disease, Parkinson Disease, Huntington's Disease, and Multiple Sclerosis. Some of these disorders and diseases relate to cerebral cortex or a surgical injury of cerebral cortex. Exemplary diseases of cerebral cortex include Alzheimer's disease, Parkinson's disease, Creutzfeldt-Jakob disease, Huntington's disease, progressive supranuclear palsy, and corticobasal degeneration.

2.1 Neurodegenerative Diseases of CNS

Among these CNS disorders, neurodegenerative diseases of the CNS, which cause progressive loss of neuronal structure and function, are particularly devastating diseases. They are characterized by the death of nerve cells in different regions of the nervous system and eventually functional impartment of the nervous system. These diseases often associate with abnormal aggregation of biological molecules. Among these neurodegenerative diseases are, for example, Multiple Sclerosis (MS), Parkinson's disease, Alzheimer's disease, amyotrophic lateral sclerosis (ALS) and stroke. Many of these diseases are only poorly understood to date due to the complexity of the CNS and no cure is available for most of these diseases. Many neurodegenerative diseases are late-onset, indicating aging is the greatest risk factor for such diseases (Rubinsztein, (2006) The roles of intracellular protein-degradation pathways in neurodegeneration, Nature 443 (7113):780-6).

2.2 Alzheimer Disease

Alzheimer disease (AD), also called Alzheimer's disease, is a prevalent form of neurodegenerative disease and currently affects an estimated 15 million people worldwide. Alzheimer disease is at present the most common cause of dementia, which associates with a serious loss of cognitive functioning such as thinking, remembering, and reasoning, and behavioral abilities, that it interferes with a person's daily life.

Alzheimer disease is an irreversible, progressive brain disease that slowly destroys memory and thinking skills, and may eventually destroys the ability to carry out the simplest tasks, due to death of pyramidal neurons and loss of neuronal synapses in brains regions associated with higher mental functions (Francis et al., (1999) J. Neurol. Neurosurg. Psychiatry 66:137-47) Alzheimer disease usually begins with mildly memory loss, moderate movement difficulties, and sometimes problems with the sense of smell. The very early symptom may also include a decline in other aspects of cognition, such as vision/spatial issues and impaired reasoning or judgment. As Alzheimer disease progresses, loss of memory and other cognitive abilities become evident. The patients, at this stage, often have problems such as getting lost, trouble handling tasks with their hands, repeating questions, taking longer to complete normal daily tasks, deterioration in operational judgment, loss of insight, and having personality changes. As the disease gets even worse, damage occurs in areas of the brain that control language, reasoning, sensory processing, and conscious thought. The patients, at this stage, may have more serious problems such as failing to recognize family and friends, to learn new things and cope with new situations, and to carry out tasks that involve multiple steps. Finally, due to wide spread of plaques and tangles in the brain and significant shrink of brain volume, Alzheimer disease ends in severe disorientation and confusion, apraxia of gait, generalized rigidity and incontinence (Gilroy and Meyer, (1979) Medical Neurology, pp. 175-179 MacMillan Publishing Co.).

The exact cause of Alzheimer disease is not yet fully understood, but it is believed that the disease is caused by a complex series of events over a long period of time. There is evidence that both genetic and environmental factors may contribute to the disease. For example, it is speculated that genetics contributes to the development of Alzheimer disease because early-onset Alzheimer disease can often be traced back to changes of several genes inherited from the family. Evidence also suggests that environmental and lifestyle factors beyond basic genetics may also contribute to the development of Alzheimer disease. For example, elevated concentrations of aluminum have been found in the brains of some patients dying with Alzheimer disease (Crapper et al., (1976) Brain, 99:67-80). For another example, associations between cognitive decline and vascular and metabolic conditions such as heart disease, diabetes, and obesity have been observed, indicating that Alzheimer disease may be one of lifestyle related diseases.

At present, most therapeutics and treatments focus on helping people maintain mental function, managing behavioral symptoms, and slowing or delaying the symptoms of Alzheimer disease. For example, U.S. Food and Drug Administration has approved Donepezil (Aricept®), rivastigmine (Exelon®), galantamine (Razadyne®), and Memantine (Namenda®) to treat certain Alzheimer diseases to maintain thinking, memory, and speaking skills, and help with certain behavioral problems. However, currently no effective drug or treatment can cure the disease or change the underlying disease process.

2.3 Parkinson Disease

Parkinson disease (PD) is another very common neurodegenerative disease of central nervous system. It is estimated that one million Americans suffer from Parkinson disease, and each year 50,000 individuals are diagnosed with the disorder (Olson, (2000) Science 290:721-724). Parkinson disease usually affects people over the age of 50 (Olson, (2000), Science 290:721-724).

Parkinson disease is a kind of motor system disorders, which are the result of loss of dopamine neurons in the nigrostriatal pathway of the brain. Four primary physical manifestations of Parkinson disease include resting tremors, muscular rigidity, postural instability, and slowness of movement (Jankovic, (2008) Parkinson's disease: clinical features and diagnosis, J. Neurol. Neurosurg. Psychiatr. 79 (4): 368-76). Other motor symptoms include gait and posture disturbances such as rapid shuffling steps and a forward-flexed posture when walking, speech and swallowing disturbances including voice disorders, mask-like face expression or small handwriting (Jankovic, (2008) Parkinson's disease: clinical features and diagnosis, J. Neurol. Neurosurg. Psychiatr. 79 (4): 368-76; Russell et al., (2010) Targeted exercise therapy for voice and swallow in persons with Parkinson's disease, Brain Res. 1341: 3-11).

The main pathologic characteristic of Parkinson disease is cell death in the substantia nigra region of the brain and presence of Lewy Bodies in remaining nerve cells in various areas of the brain (Nussbaum and Polymeropoulos, (1997), Hum. Molec. Genet. 6: 1687-1691). The primary symptoms of Parkinson's disease result from reduced activity of dopamine-secreting cells due to cell death in the substantia nigra (Obeso et al., (2008) Functional organization of the basal ganglia: therapeutic implications for Parkinson's disease, Mov. Disord. 23 (Suppl 3): S548-59). Several mechanisms have been proposed to explain cell death in brain, such as abnormal accumulation of the protein alpha-synuclein bound to ubiquitin, proteosomal and lysosomal system dysfunction, and reduced mitochondrial activity (Obeso et al., (2010) Missing pieces in the Parkinson's disease puzzle, Nat. Med. 16 (6): 653-61).

Currently, there is no cure available for Parkinson disease, and most therapeutics and treatments focus on providing relief from the symptoms. Over the past 30 years, the most commonly used drug is levodopa, which is dopamine precursor and is converted into dopamine in the dopaminergic neurons by dopa decarboxylase. Unfortunately, it has become clear that long-term levodopa administration can have side effects. A variety of other therapeutic strategies have been developed for the treatment of Parkinson disease. For example, several dopamine agonists that bind to dopaminergic post-synaptic receptors in the brain have similar effects to levodopa, and have been used as complementary therapies to levodopa and now mainly on their own. Similar to dopamine agonists, MAO-B inhibitors are also used to improve motor symptoms. However, they produce more adverse effects and are less effective than levodopa (Symptomatic pharmacological therapy in Parkinson's disease, (2006) Parkinson's Disease, Royal College of Physicians. pp. 59-100).

2.4 Creutzfeldt-Jakob Disease

Creutzfeldt-Jakob Disease (CJD) is a severe neurodegenerative disease that leads to a rapid decrease of mental function and movement, and is currently invariably fatal. It is a member of a family of human and animal diseases known as the transmissible spongiform encephalopathies (TSEs) (Dugdale et al., Creutzfeldt-Jakob disease: Transmissible spongiform encephalopathy; vCJD; CJD; Jacob-Creutzfeldt disease (2011 Sep. 26), VeriMed Healthcare Network).

The symptoms of Creutzfeldt-Jakob disease include rapidly progressive dementia, leading to memory loss, personality changes and hallucinations, anxiety, depression, paranoia, obsessive-compulsive symptoms, and psychosis. The symptoms of Creutzfeldt-Jakob disease may also include physical problems such as speech impairment, jerky movements (myoclonus), balance and coordination dysfunction (ataxia), changes in gait, rigid posture, and seizures. In most patients, these symptoms are followed by involuntary movements and the appearance of an atypical diagnostic electro-encephalogram tracing (Murray et al., (2012) Depression and Psychosis in Neurological Practice, Neurology in Clinical Practice, 6th Edition).

The symptoms of Creutzfeldt-Jakob disease are caused by the progressive death of the brain's nerve cells, which is associated with the build-up of abnormal prion proteins forming amyloids. When brain tissue from a Creutzfeldt-Jakob disease patient is examined under a microscope, many tiny holes can be seen where whole areas of nerve cells have died (Beck and Daniel, (1969) Degenerative diseases of the central nervous system transmissible to experimental animals, Postgrad Med J, 45(524), 361-70).

Currently, no generally accepted treatment for Creutzfeldt-Jakob disease exists. Till now, several methods have been proposed to treat Creutzfeldt-Jakob disease, such as pentosan polysulphate (PPS) used to treat interstitial cystitis (Rainov et al., (2007) "Experimental treatments for human transmissible spongiform encephalopathies: Is there a role for pentosan polysulfate?", Expert Opin Biol Ther 7 (5): 713-26), RNA interference to slow the progression of scrapie (Pfeifer et al., (2006) "Lentivector-mediated RNAi efficiently suppresses prion protein and prolongs survival of scrapie-infected mice," The Journal of Clinical Investigation 116 (12): 3204-10), treatment for sporadic CJD using quinacrine (Collinge et al., (2009) Safety and efficacy of quinacrine in human prion disease (PRION-1 study): a patient-preference trial, Lancet neurology 8 (4): 334-44), and so on. However, none of these has been proved effective to cure Creutzfeldt-Jakob disease.

2.4 Huntington's Disease

Huntington's Disease (HD) is a neurodegenerative genetic disorder with progressive disorder of motor, cognitive and psychiatric disturbances. The physical symptoms may include jerky, random, and uncontrollable movements, general restlessness, small unintentionally initiated or uncompleted motions, lack of coordination, slowed saccadic eye movements, abnormal facial expression, and difficulties chewing, swallowing, and speaking (Walker, (2007) Huntington's disease, Lancet 369 (9557): 218-28). Cognitive abilities are usually progressively impaired. The symptoms include reduced executive functions (including, e.g., planning, cognitive flexibility, abstract thinking, rule acquisition, initiating appropriate actions and inhibiting inappropriate actions). It is also associated with memory deficits. Cognitive problems tend to worsen over time, ultimately leading to dementia (Montoya et al., (2006) Brain imaging and cognitive dysfunctions in Huntington's disease, J Psychiatry Neurosci 31 (1): 21-9). Huntington's Disease patients also often suffer from anxiety, depression, a reduced display of emotions (blunted affect), egocentrism, aggression, compulsive behavior, addictions to alcoholism, gambling, and hypersexuality (van Duijn E et al., (2007) Psychopathology in verified Huntington's disease gene carriers, J Neuropsychiatry Clin Neurosci 19 (4): 441-8).

Huntington's Disease is caused by an autosomal dominant mutation in either of an individual's two copies of a gene called Huntingtin. Treatments for Huntington's disease are currently very limited. Numerous drugs and treatment methods have been proposed, such as overexpression of chaperonins or induction of the heat shock response with the compound geldanamycin, targeting members of the apoptotic pathway, and using coenzyme Q10. However, none has yet been proven effective (Walker, (2007) Huntington's disease, Lancet 369 (9557): 218-28).

2.5 Progressive Supranuclear Palsy

Progressive Supranuclear Palsy (PSP) is a degenerative disease involving the gradual deterioration and death of specific volumes of the brain.

Pathologically, there is severe neuronal loss in the substantia nigra, globus pallidus, subthalamic nucleus, midbrain, and pontine reticular formation with frequent neurofibrillary tangles composed of straight tau filaments (Burn and Lees, (2002) Progressive supranuclear palsy: where are we now? Lancet Neurol., 1(6):359-69). In addition to the extensive and multifocal neuropathological changes there are multiple neurotransmitter abnormalities, including dopamine, acetylcholine, gamma-aminobutyric acid and the noradrenaline systems (Rajput and Rajput, (2001) Progressive supranuclear palsy: clinical features, pathophysiology and management, Drugs Aging, 18 (12): 913-25).

The initial symptoms often include loss of balance, lunging forward when mobilizing, fast walking, bumping into objects or people, and falls, changes in personality, general slowing of movement, and visual symptoms (Goetz et al., (2003) Progression of gait, speech and swallowing deficits in progressive supranuclear palsy, Neurology, 60 (6): 917-22). At a later stage, these symptoms usually progress to the point where walking becomes very difficult, eye movement problems get to be more disabling, and cognitive impairment progresses to dementia.

Till now, effects of dopamine agonists, monoamine oxidase inhibitors, and catechol-O-methyl transferase inhibitors on treating Progressive Supranuclear Palsy have been studied, and yet have no proven benefit (Warren and Burn, (2007) Progressive supranuclear palsy, Pract Neurol., 7(1): 16-23).

2.6 Corticobasal Degeneration

Corticobasal degeneration (CBD) is a progressive neurological disorder characterized by nerve cell loss and atrophy (shrinkage) of multiple areas of the brain including the cerebral cortex and the basal ganglia. Symptoms include poor coordination, akinesia, rigidity, disequilibrium, limb dystonia, cognitive and visual-spatial impairments, apraxia, hesitant and halting speech, myoclonus, and dysphagia. These symptoms are very similar to those found in Parkinson disease. Currently, there is no treatment available for the disease, and the exact cause is still unclear (Lang, (2005) Treatment of progressive supranuclear palsy and corticobasal degeneration, Movement Disorders 20: S83-S91).

2.7 Regeneration of CNS

As discussed above, loss of nerve cells is a primary cause for symptoms of many CNS disorders and injuries, in particular, neurodegenerative diseases. On the other hand, the adult, mammalian CNS does not regenerate after injury despite the fact that there are many molecules present which promote nerve and axonal growth. The adult mammalian peripheral nervous system (PNS), in contrast, does regenerate to some extent. Without wishing to be bound by theory, it is believed that the lack of regeneration in the CNS is caused by the presence of molecules which actively prevent or inhibit regeneration. In the PNS, to the extent that neurons can regenerate, these inhibitors are thought to be removed or inactive and are thus not encountered by the re-growing axon. Hence, the well documented inability of the adult mammalian CNS to regenerate after injury is believed to result from a predominance of inhibitory molecules.

Consistent with this theory, it has been established that neural stem cells (NSCs) exist in the adult mammalian brain. This fact is of particular importance since the adult brain was thought to have very limited regenerative capacity. New neurons are continuously added to specific regions of the adult mammalian CNS. These neurons are derived from multipotent stem cells that originate from the ependymal layer in the lateral ventricular wall (Johansson et al., (1999), Cell 96:25-34). Ependymal cells give rise to proliferating cells in the subventricular zone of the ventricle wall, which in turn form neuroblasts. Following migration and differentiation the neuroblasts generate neurons. NSCs also exist in the hippocampal dentate gyrus (Gould et al., (2000), Biol. Psychiatry 48:715-720). Recently it was demonstrated that the human lateral ventricle and the hippocampus also harbor stem cells capable of generating neurons and glia (Johansson et al., (1999), Exp Cell Research 253:733-736).

Therefore, factors capable of inducing proliferation of CNS stem cells, neural progenitor cells or neural precursor cells, inducing differentiation into these cells and further into nerve cells, and removing CNS inhibitors may play important roles in regulating the capacity of a neuron to undergo regeneration, and thus become potential targets for CNS disorder therapies.

Repair of the damaged CNS relies on promoting the survival of damaged neurons and on overcoming the intrinsic barriers presented by the hostile nature of the injured CNS. Given the range of barriers the regenerating neuron can encounter, there is a wide range of strategies that have been employed. These include the inhibition of apoptosis, strategies designed to block the effects of growth inhibitory molecules, stem cell therapy (particularly the use of the embryonic stem cell), PNS grafting (including the use of purified Schwann cells), the transplantation of olfactory ensheathing cells (OECs), and neurotrophic factor delivery.

However, although the possibility of CNS regeneration has been demonstrated using certain of these methods, so far these approaches yield only a limited response, and thus there remains a great need for an effective method that allows CNS regeneration and treating various CNS cell diseases, disorders and conditions, and symptoms thereof. In this regard, the method for in vivo direct conversion, that is believed as a most suitable way for CNS regeneration therapy by artificial control of proliferation of endogenous neural stem cells, progenitor cells or precursor cells, and differentiation of them directly into functional neurons in the brain of patients, has been required.

In such CNS regeneration (for example, brain regeneration), factors capable of inducing proliferation of nerve cells and their progenitors or precursors, and inducing differentiation into nerve cells play important roles, and thus are potential targets for treating a CNS cell disease or injury such as Alzheimer's disease. Lhx2, a cerebral cortex selector factor, has been recently reported to induce neural stem cells or neural progenitor cells to become the cortex (Mangale et al., (2008) Science, Vol. 319, No. 5861, 304-309).

We have also recently discovered that a protein called cereblon (CRBN) functions as a downstream factor of Lhx2. In particular, CRBN induces differentiation of stem cells into neural stem cells or neural progenitor/precursor cells, and further into nerve cells, and it also induces proliferation of central nervous stem cells or neural progenitor/precursor cells, for example, by upregulation of genes required for the maintenance of pluripotency (Yamanaka factors), such as Pou5f1 (Oct3/4), Sox2, Myca (c-Myc), Klf4, Nanog (reviewed by Yamanaka. S. et al., Nature 465, 704-712, 2010) and genes required for efficient conversion of mouse fibroblasts into functional iN cells (iN cell-inducing factors), such as Brn2 (also known as Pou3f2), Ascl1a, and Mytl1 (BAM factors) (Adler. A F. et al., Mol. Ther. Nucleic Acids. 2012). This is the first protein to play integrative regulation of these genes followed by harmonious increase of neurons in the brain of living animal.

CRBN is a protein that forms a ubiquitin ligase complex and its amino acid sequence is also publicly known; however, it was the first time that CRBN was shown to function in inducing proliferation of central nervous stem cells or neural progenitor/precursor cells and differentiation of these cells into nerve cells (U.S. Ser. No. 13/322,195, filed May 24, 2010 (U.S. Publ. No. 2012/0134969), the entire contents of which are incorporated herein by reference).

CRBN's capability to induce proliferation of central nervous stem cells and neural progenitor/precursor cells and differentiation of these cells into nerve cells makes this protein, and agents based either on this protein or on its upstream or downstream factors, potential tools for CNS regeneration and treating CNS disorders.

The present invention is based, in part, on the finding that BRD7 is a downstream factor of CRBN and that it functions in inhibiting CNS nerve cell development. Previously, BRD7 was identified as a subunit of SWI/SNF chromatin-remodeling complex (Kaeser et al. (2008) J Biol Chem. 283: 32254-63). SWI/SNF complex uses energy released from ATP hydrolysis to change chromatin structure, in particular, the interactions between DNA and histones, and thus it has been shown to function in some DNA based cellular processes, such as transcription and DNA damage repairs. SWI/SNF has also been identified as a tumor suppressor consistent with the recently discovered role of BRD7 as a transcriptional cofactor for p53 (Drost et al. (2010) Nat Cell Biol. 12: 380-9). However, neither SWI/SNF complex nor BRD7 itself has been shown to function in inhibiting the regeneration of CNS nerve cells.

The present invention is also based, in part, on the finding that Ikaros is a downstream factor of CRBN and that it functions in inhibiting CNS nerve cell development. Previously, Ikaros was identified as a catalytic substrate of CRBN in the presence of lenalidomide (Krönke J, et al., (2014) Science 343, 301-305). Ikaros, a DNA binding zinc-finger type transcription factor, displays crucial functions in the hematopoietic system and its loss of function has been linked to the development of lymphoid leukemia. In particular, Ikaros has been found in recent years to be a major tumor suppressor involved in human B-cell acute lymphoblastic leukemia. However, specific function of Ikaros in CNS development has been obscure despite that it is highly expressed in CNS.

The present invention is also based, in part, on the finding that CRBN is an activator of Yamanaka factors and other genes required for pluripotency maintenance, as well as iN cell-inducing factors, such as BAM factors. We further show, for example, that CRBN's capability to induce proliferation of central nervous stem cells and neural progenitor/precursor cells and differentiation of these cells into nerve cells makes this CRBN protein, and agents either based on this protein or its upstream or downstream factors, potential tools for CNS regeneration and treating CNS disorders.

3. SUMMARY

The present invention is based, in part, on the finding that both BRD7 and Ikaros are downstream factors of CRBN, and that BRD7 antagonists or Ikaros antagonists are able to increase proliferation and differentiation of stem cells. The present invention is also based, in part, on the finding that CRBN plays a role in increasing expression of pluripotency genes and neural reprogramming genes, and that CRBN itself and CRBN activators are able to increase proliferation and differentiation of stem cells. In some embodiments, the stem cells are neural stem cells, neural progenitor cells or neural precursor cells, which can be differentiated into nerve cells. Accordingly, provided herein are methods generally relating to expansion of stem cells (e.g., neural stem cells), progenitor cells (e.g., neural progenitor cells), or precursor cells (e.g., neural precursor cells). Also provided are methods for improving proliferation of certain cells. In some embodiments, the cells are stem cells, progenitor cells, CNS cells, nerve cells, neural stem cells, neural progenitor cells, and neural precursor cells. Also provided herein are methods generally related to the differentiation of certain cells (e.g., stem cells, such as neural stem cells), progenitor cells (e.g., such as neural progenitor cells), or precursor cells (e.g., neural precursor cells) into other cell types (e.g., nerve cells). Further provided herein are methods generally related to the regeneration of certain cells (e.g., nerve cells). Also provided are in vitro and in vivo methods for generating and expanding certain cells, such as stem cells, CNS cells, neural progenitor cells, and neural precursor cells. Further provided here are methods for engraftment of certain cells (e.g., CNS cells or CNS progenitor/precursor cells). Further provided are methods for treating an injured CNS tissue (e.g., spinal cord, brain) in a patient. Also provided herein are methods of preventing or treating a CNS cell defective disease, disorder or condition, or a symptom thereof, using a BRD7 antagonist, Ikaros antagonist, or an activator of CRBN. Further provided here are methods for assessing the efficacy of the BRD7 antagonist, Ikaros antagonist, or CRBN activator in preventing or treating the CNS cell defective disease, disorder or condition, or a symptom thereof.

In one aspect, provided herein is a method of expanding a population of cells, the method comprising contacting a population of cells with an effective amount of a BRD7 antagonist, Ikaros antagonist, or CRBN activator, thereby expanding the population of cells. In certain embodiments, the cells are stem cells. In some embodiments, the cells are progenitor cells. In some embodiments, the cells are precursor cells. In other embodiments, the cells are neural stem cells. In some embodiments, the cells are neural progenitor cells. In other embodiments, the cells are neural precursor cells. In yet other embodiments, the cells are CNS cells. In some embodiments, the CNS cells are nerve cells, neurons, glial cells, astrocytes or oligodendrocytes. In certain embodiments, the CNS cells are CNS progenitor cells. In some embodiments, the cells are CNS precursor cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiments, the cells are neural crest stem cells. Other tissue stem cells and tissue progenitor cells are also contemplated herein. In some embodiments, the method is an in vitro method. In other embodiments, the method is an in vivo or ex vivo method. In some embodiments, the cells are contacted with a BRD7 antagonist. In another embodiment, the cells are contacted with an Ikaros antagonist. In other embodiments, the cells are contacted with a CRBN activator.

In certain embodiments of the methods provided herein, the population of cells is also contacted with an agent that preserves or enhances the cell proliferation, expansion, differentiation and/or function. In one embodiment, the agent is growth factor or cytokine. In other embodiments, the agent is selected from the group consisting of epidermal growth factor (EGF), erythropoietin, fibroblast growth factor (FGF), galectin-1, G-CSF, Six3, Lhx2, Foxg1, Sox2, Oct3/4, c-Myc, Klf4, Nanog, NeuroD, Ascl1, Pou3f2/3, Myt1l, Wnt, Frizzled, β-catenin, Tcf, Lef, NeuroD, Shh, Patched, GPCR, BMP, BMPR, Noggin, Chordin, Follistatin, Notch, Nrp2, Elavl3, Zic2/3, P53, P63, Nodal, ADAMTS1, BMI-1, CRABP1, and thyroid releasing hormone. In certain embodiments, the agent is a Yamanaka factor. In other embodiments, the agent is a BAM factor.

In another aspect, provided herein is a method of expanding a population of cells in a patient, comprising contacting the population of cells in the patient with an effective amount of a BRD7 antagonist, Ikaros antagonist, or CRBN activator, thereby expanding the population of cells in the patient. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In some embodiments, the cells are CNS progenitor cells. In some embodiments, the cells are precursor cells. In some embodiments, the cells are CNS precursor cells. In certain embodiments, the cells are stem cells. In other embodiments, the cells are neural stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells and tissue progenitor/precursor cells are also contemplated herein. In some embodiments, the cells are neural progenitor cells. In some embodiments, the cells are neural precursor cells. In yet other embodiments, the cells are CNS cells, such as nerve cells. In certain embodiments, the method comprises administering to the CNS an effective amount of a BRD7 antagonist, Ikaros antagonist, or CRBN activator. In some embodiments, the cells are contacted directly with the BRD7 antagonist, Ikaros antagonist, or CRBN activator. In other embodiments, the cells are contacted indirectly with the BRD7 antagonist, Ikaros antagonist, or CRBN activator.

In some embodiments, the cells are expanded by from about 10% to about 100%, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%, or any range of the recited percentages thereof. In certain embodiments, the cell mass or population is increased from about 10% to about 10-fold, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 2-fold, about 3-fold, about 4-fold, about 5-fold, about 6-fold, about 7-fold, about 8-fold, about 9-fold or about 10-fold, or any range or interval thereof. In some embodiments, the cells are expanded to an amount within about 20%, about 10%, or about 5% of the number of cells present in the general population (e.g., as determined by an average or median).

In other aspects, provided herein are methods for regenerating CNS cells in a subject, comprising administering to the subject an effective amount of a BRD7 antagonist, Ikaros antagonist, or CRBN activator, thereby regenerating the CNS cells in the subject. In some embodiments, the CNS cells are nerve cells. In some embodiments, the subject is administered a BRD7 antagonist. In another embodiment, the subject is administered an Ikaros antagonist. In other embodiments, the subject is administered a CRBN activator. In some embodiments, the methods provided herein induce proliferation of the CNS cells (e.g., nerve cells) and their progenitor/precursor cells (e.g., neural stem cells or neural progenitor/precursor cells). In some embodiments, the methods provide herein induce differentiation of neural stem cells or neural progenitor/precursor cells into nerve cells.

In some embodiments of the methods provided herein, the effective amount is from about 1 mg/kg to about 100 mg/kg.

In certain embodiments, the effective amount is administered in one or more doses, such as 1, 2, 3, 4, 5, 6, 7, 8, 9, 10 or more doses, or any interval thereof. In other embodiments, the effective amount is delivered weekly for four or more weeks, such as about 5 weeks, about 6 weeks, about 8 weeks, about 10 weeks, about 12 weeks, about 4 months, about 5 months, about 6 months, about 1 year, about 2 years or longer, or any interval thereof.

In certain embodiments, BRD7 antagonists include, but not limited to, inhibitors of BRD7 protein, a nucleic acid comprising at least part of nucleic acid sequence of BRD7 gene, or an antisense compound thereof, and a stem cell or a neural progenitor/precursor cell in which BRD7 is down-regulated.

In certain embodiments, Ikaros antagonists include, but not limited to, inhibitors of Ikaros protein, a nucleic acid comprising at least part of nucleic acid sequence of Ikaros gene, or an antisense compound thereof, and a stem cell or a neural progenitor/precursor cell in which Ikaros is down-regulated.

In certain embodiments, an activator of CRBN includes, but is not limited to, an active modulator of CRBN protein, a nucleic acid comprising at least part of nucleic acid sequence of CRBN gene, or an antisense compound for its inhibitory protein thereof, and a stem cell or a neural progenitor/precursor cell in which CRBN is up-regulated.

In another aspect provided herein is a method for treating an injured CNS tissue in a patient, comprising contacting a population of CNS cells, or progenitor/precursor cells thereof, with a BRD7 antagonist, Ikaros antagonist, or CRBN activator, such that the injured CNS tissue is treated. In certain embodiments, the population of CNS cells, or progenitor/precursor cells thereof, are within or derived from the injured CNS tissue. In some embodiments, the cells are contacted with a BRD7 antagonist. In another embodiment, the cells are contacted with an Ikaros antagonist. In other embodiments, the cells are contacted with a CRBN activator.

In yet another aspect, provided herein is a method for treating an injured CNS tissue in a patient, comprising contacting a population of CNS cells, or progenitor/precursor cells thereof, with an effective amount of a BRD7 antagonist, Ikaros antagonist, or CRBN activator, and contacting the injured CNS tissue of the patient with the CNS cells, or progenitor/precursor cells thereof, such that the injured CNS tissue is treated. In some embodiments, the cells are contacted with a BRD7 antagonist. In another embodiment, the cells are contacted with an Ikaros antagonist. In other embodiments, the cells are contacted with a CRBN activator.

In other aspects, provided herein is a method for treating an injured CNS tissue in a patient, comprising contacting a population of CNS cells, or progenitor/precursor cells thereof, with an effective amount of a BRD7 antagonist, Ikaros antagonist, or CRBN activator, contacting the injured CNS tissue of the patient with the CNS cells, or progenitor/precursor cells thereof, and further contacting the injured CNS tissue with a BRD7 antagonist, Ikaros antagonist, or CRBN activator, such that the injured CNS tissue is treated. In some embodiments, the cells are contacted with a BRD7 antagonist. In another embodiment, the cells are contacted with an Ikaros antagonist. In other embodiments, the cells are contacted with a CRBN activator.

In certain embodiments of the methods provided herein, the injured CNS tissue is the spinal cord. In other embodiments, the injured CNS tissue is brain tissue. In other embodiments, the injured CNS tissue is the cerebral cortex. In certain embodiments, the injured CNS tissue has decreased CNS cell (e.g., nerve cell; neuron) number, function or both.

In certain embodiments, the CNS cells, or progenitor/precursor cells thereof, are nerve cells. In certain embodiments, the CNS cells, or progenitor/precursor cells thereof, are neurons. In some embodiments, the CNS cells, or progenitor/precursor cells thereof, are astrocytes. In other embodiments, the CNS cells, or progenitor/precursor cells thereof, are oligodendrocytes. In yet other embodiments, the CNS cells, or progenitor/precursor cells thereof, are glial cells. In certain embodiments, the CNS cells, or progenitor/precursor cells thereof, are nerve cells. In some embodiments, the CNS cells, or progenitor/precursor cells thereof, are stem cells. In certain embodiments, the stem cells are neural stem cells. In other embodiments, the CNS cells, or progenitor/precursor cells thereof, are neural progenitor cells.

In another aspect, provided herein is a method of treating or preventing a CNS cell defective disease, disorder or condition, or a symptom thereof, in a patent, comprising: administering to CNS comprising a population of cells (e.g., CNS cells, or progenitor/precursor cells thereof) in the patient an effective amount of a BRD7 antagonist, Ikaros antagonist, or CRBN activator, wherein the amount is effective to expand the population of cells and/or increase the cell function in the patient, thereby treating or preventing the CNS cell defective disease, disorder or condition, or a symptom thereof. In some embodiments, a BRD7 antagonist is administered. In another embodiment, an Ikaros antagonist is administered. In other embodiments, a CRBN activator is administered.

A CNS cell defective disease, disorder or condition includes, but is not limited to, Alzheimer Disease, Parkinson Disease, Huntington's Disease, Creutzfeldt-Jakob Disease, Progressive Supranuclear Palsy, Corticobasal Degeneration, and other disorders such as Amyotrophic Lateral Sclerosis; Multiple Sclerosis; progressive motor weakness; neuroimmunological disorders, CNS trauma; Alzheimer disease with parkinsonism; bradykinesia; alkinesia; movement disorders that impair fine motor control and finger dexterity; hypophonia; monotonic speech; rigidity; dystonia; inflammation associated with Parkinson Disease; tremors of the face, jaw, tongue, posture; parkinsonian gait; shuffling; short steps; festinating gait; disorders of mood, cognition, sensation, sleep; dementia; depression; drug induced parkinsonism; vascular parkinsonism; multiple system atrophy; progressive supranuclear palsy; disorders with primary tau pathology; cortical basal ganglia degeneration; parkinsonism with dementia; hyperkinetic disorders; chorea; dystonia; Wilson disease; Tourette syndrome; essential tremor; myoclonus; and a tardive movement disorder.

In certain embodiments, the method further comprises assessing the efficacy of the BRD7 antagonist, Ikaros antagonist, or CRBN activator in preventing or treating the CNS cell defective disease, disorder or condition, or a symptom thereof, in the patient, comprising comparing CNS cell (e.g., nerve cell; neuron), or a progenitor/precursor cell thereof, number and/or function in the patient before and after administration of the BRD7 antagonist, Ikaros antagonist, or CRBN activator, wherein an increase in CNS cell (e.g., nerve cell; neuron) or a progenitor/precursor cell thereof, number and/or function after administration of the BRD7 antagonist, Ikaros antagonist, or CRBN activator as compared to before administration of the BRD7 antagonist, Ikaros antagonist, or CRBN activator is indicative of the efficacy of the BRD7 antagonist, Ikaros antagonist, or CRBN activator in preventing or treating the CNS cell defective disease, disorder or condition, or symptom thereof. In some embodiments, efficacy of the BRD7 antagonist is assessed. In another embodiment, efficacy of the Ikaros antagonist is assessed. In other embodiments, efficacy of the CRBN activator is assessed.

In some embodiments, the method further comprises assessing the efficacy of the BRD7 antagonist or Ikaros antagonist in preventing or treating the CNS cell defective disease, disorder or condition, or a symptom thereof, in the patient, comprising comparing expression levels of Oct 3/4, Nanog, NeuroD, Sox2, Zic3, Huc, Brn2, Ascl1, Pou3f2b, Myt1l, a BAM factor, or a Yamanaka factor in the patient before and after administration of the antagonist, wherein an increase in expression levels of Oct 3/4, Nanog, NeuroD, Sox2, Zic3, Huc, Brn2, Ascl1, Pou3f2b, Myt1l, a BAM factor, or a Yamanaka factor after administration of the BRD7 antagonist or Ikaros antagonist as compared to before administration of the BRD7 antagonist or Ikaros antagonist is indicative of the efficacy of the BRD7 antagonist or Ikaros antagonist in preventing or treating the CNS cell defective disease, disorder or condition, or symptom thereof. In some embodiments, the expression level of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) is compared. In some embodiments, the expression levels assessed are those of pluripotency genes. In some embodiments, efficacy of the BRD7 antagonist is assessed. In another embodiment, efficacy of the Ikaros antagonist is assessed.

In some embodiments, the method further comprises assessing the efficacy of the CRBN activator in preventing or treating the CNS cell defective disease, disorder or condition, or a symptom thereof, in the patient, comprising comparing expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) in the patient before and after administration of the CRBN activator, wherein an increase in expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) after administration of the CRBN activator as compared to before administration of the CRBN activator is indicative of the efficacy of the CRBN activator in preventing or treating the CNS cell defective disease, disorder or condition, or symptom thereof. In some embodiments, the method further comprises one or more subsequent administrations of the CRBN activator to the patient following the assessment of efficacy. In some embodiments, the expression levels of Oct 3/4, Nanog, NeuroD, Sox2, Zic3, Huc, Brn2, Ascl1, Pou3f2b, Myt1l, a BAM factor, or a Yamanaka factor are compared. In some embodiments, the expression levels assessed are those of pluripotency genes.

In other embodiments, the method further comprises selecting a group of patients having a CNS cell defective disease, disorder or condition, or a symptom thereof, based on CNS cell (e.g., nerve cell; neuron), or a progenitor/precursor cell thereof, number and/or function for the purposes of predicting clinical response, monitoring clinical response, or monitoring patient compliance to dosing with the BRD7 antagonist, Ikaros antagonist, or CRBN activator. In certain embodiments, the method further comprises selecting a group of patients having a CNS cell defective disease, disorder or condition, or a symptom thereof, based on expression levels of Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) for the purposes of predicting clinical response, monitoring clinical response, or monitoring patient compliance to dosing with the BRD7 antagonist, Ikaros antagonist, or CRBN activator. In other embodiments, the method further comprises selecting a group of patients having a CNS cell defective disease, disorder or condition, or a symptom thereof, based on expression levels of Oct 3/4, Nanog, NeuroD, Sox2, Zic3, Huc, Sox2, Brn2, Ascl1, Pou3f2b, Myt1l, a BAM factor, or a Yamanaka factor for the purposes of predicting clinical response, monitoring clinical response, or monitoring patient compliance to dosing with the BRD7 antagonist, Ikaros antagonist, or CRBN activator. In some embodiments, the method is for the purpose of predicting clinical response, monitoring clinical response, or monitoring patient compliance to dosing with the BRD7 antagonist. In some embodiments, the method is for the purpose of predicting clinical response, monitoring clinical response, or monitoring patient compliance to dosing with the Ikaros antagonist. In some embodiments, the method is for the purpose of predicting clinical response, monitoring clinical response, or monitoring patient compliance to dosing with the CRBN activator.

In another aspect, provided herein is a method for improving survival of a CNS cell (e.g., nerve cell; neuron), or a progenitor/precursor cell thereof, in a CNS tissue, comprising contacting the CNS cell, or a progenitor/precursor cell thereof, with an effective amount of a BRD7 antagonist, Ikaros antagonist, or CRBN activator, such that survival of the CNS cell, or a progenitor/precursor cell thereof, is improved relative to the survival of a CNS cell that has not been contacted with the BRD7 antagonist, Ikaros antagonist, or CRBN activator. In some embodiments, the cell is contacted with a BRD7 antagonist. In another embodiment, the cell is contacted with an Ikaros antagonist. In other embodiments, the cell is contacted with a CRBN activator.

In another aspect, provided herein is a method for improving survival of CNS cells, or a progenitor/precursor cell thereof, in a CNS tissue, comprising contacting a population of CNS cells, or progenitor/precursor cells thereof, with an effective amount of a BRD7 antagonist, Ikaros antagonist, or CRBN activator, such that survival of the CNS cells, or CNS progenitor/precursor cells thereof, is improved relative to the survival of CNS cells, or CNS progenitor/precursor cells thereof, that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In another aspect, provided herein is a method for generating CNS cells in a patient, comprising contacting a population of CNS cells, or CNS progenitor/precursor cells thereof, with an effective amount of a BRD7 antagonist, Ikaros antagonist, or CRBN activator, such that CNS cells are generated. In some embodiments, the cells are contacted with a BRD7 antagonist. In another embodiment, the cells are contacted with an Ikaros antagonist. In other embodiments, the cells are contacted with a CRBN activator.

In another aspect, provided herein is a method for engraftment of CNS cells, or CNS progenitor/precursor cells thereof, in a CNS tissue of a patient, comprising contacting a population of CNS cells, or CNS progenitor/precursor cells thereof, with an effective amount of a BRD7 antagonist, Ikaros antagonist, or CRBN activator, and contacting the CNS tissue with the CNS cells, or CNS progenitor/precursor cells thereof, such that engraftment of the cells occurs. In some embodiments, the cells are contacted with a BRD7 antagonist. In another embodiment, the cells are contacted with an Ikaros antagonist. In other embodiments, the cells are contacted with a CRBN activator. In an embodiment, the method further comprises contacting the CNS tissue with a BRD7 antagonist, Ikaros antagonist, or CRBN activator. In an embodiment, the method further comprises contacting the CNS tissue with a BRD7 antagonist. In an embodiment, the method further comprises contacting the CNS tissue with a Ikaros antagonist. In an embodiment, the method further comprises contacting the CNS tissue with a CRBN activator.

In another aspect, provided herein is a method for improving proliferation of CNS cells, or CNS progenitor/precursor cells thereof, in a CNS tissue of a patient, comprising contacting a population of CNS cells, or CNS progenitor/precursor cells thereof, with an effective amount of a BRD7 antagonist, Ikaros antagonist, or CRBN activator, and contacting the CNS tissue with the CNS cells, or CNS progenitor/precursor cells thereof, such that proliferation of the CNS cells, or CNS progenitor/precursor cells thereof, is improved relative to proliferation of CNS cells, or CNS progenitor/precursor cells thereof, that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In other aspects, provided herein is a method for increasing CNS cell number and/or function in a CNS tissue of a patient, comprising contacting a population of CNS cells, or CNS progenitor/precursor cells thereof, with an effective amount of a BRD7 antagonist, Ikaros antagonist, or CRBN activator, and contacting the CNS tissue with the CNS cells, or CNS progenitor/precursor cells thereof, such that CNS cell number and/or function is improved relative to CNS cell number and/or function prior to contact with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In other aspects, provided herein is a method for (a) inducing differentiation of CNS progenitor/precursor cells into CNS cells, (b) improving proliferation of CNS cells or CNS progenitor/precursor cells, or (c) improving survival of CNS cells or CNS progenitor/precursor cells, comprising contacting said cells with (i) a BRD7 antagonist, (ii) an Ikaros antagonist, or (iii) a CRBN activator.

In some embodiments, the CNS cells or CNS progenitor/precursor cells are selected from a group consisting of stem cells, neural stem cells, neural progenitor cells, neural precursor cells, nerve cells, astrocytes, glial cells, radial glia, and oligodendrocytes.

In other aspects, provided herein is a composition comprising (i) a BRD7 antagonist, (ii) an Ikaros antagonist, and/or (iii) a CRBN activator, for use in a method of (a) treating or preventing a central nervous system (CNS) cell disease, disorder or condition, or a symptom thereof, in a patient; (b) treating an injured CNS tissue in a patient; (c) engraftment of CNS cells, or CNS progenitor/precursor cells thereof, in a CNS tissue of a subject; (d) improving proliferation of CNS cells, or CNS progenitor/precursor cells thereof, in a CNS tissue of a subject; or (e) increasing CNS cell mass in a CNS tissue of a subject.

In some embodiments, the composition provided here is for use in a method, which comprises: (a) harvesting a population of CNS cells, or CNS progenitor/precursor cells thereof, from a donor, preferably wherein the donor is the patient; (b) culturing the population of CNS cells, or CNS progenitor/precursor cells thereof; (c) contacting the population of CNS cells, or CNS progenitor/precursor cells thereof, with said composition, thereby expanding the population of CNS cells, or CNS progenitor/precursor cells thereof; and (d) transplanting the CNS cells, or CNS progenitor/precursor cells thereof, of the expanded population into the patient, thereby treating the CNS cell defective disease, disorder or condition, or symptom thereof, in the patient.

In some embodiments, the composition provided herein is for use in a method, which further comprises administering the composition to the patient.

In some embodiments, the composition provided herein is for use in a method of assessing efficacy of said composition by (i) comparing a CNS cell mass in the patient before and after administration of the composition, wherein an increase in CNS cell mass after administration of the composition as compared to before administration of the composition is indicative of the efficacy of the composition in preventing or treating the CNS-cell defective disease, disorder or condition, or symptom thereof; or (ii) comparing expression level of a Yamanaka factor, Nanog, NeuroD, Zic3, Elavl3, and/or a BAM factor in the patient before and after administration of the composition, wherein an increase in the expression levels of the Yamanaka factor, Nanog, NeuroD, Zic3, Elavl3, and/or BAM factor after administration of the composition as compared to before administration of the composition is indicative of the efficacy of the composition in preventing or treating the CNS-cell defective disease, disorder or condition, or symptom thereof.

In some embodiments, the composition provided herein is for use in a method of selecting a group of patients having a CNS cell defective disease, disorder or condition, or a symptom thereof, based on (i) CNS cell mass, or (ii) expression level of a Yamanaka factor, Nanog, NeuroD, Zic3, Elavl3, and/or BAM factor in the patient, for the purposes of predicting clinical response, monitoring clinical response, or monitoring patient compliance to dosing with said composition.

In some embodiments, the Yamanaka factor is Oct 3/4, Sox2, c-Myc, or Klf4, and/or wherein the BAM factor is Brn2 (Pou3f2), Ascl1 or Myt1l. In some embodiments, the CNS cell defective disease, disorder or condition is a disease of cerebral cortex, a surgical injury of cerebral cortex, or a neurodegenerative disease.

In some embodiments, the CNS cell disease, disorder or condition is selected from a group consisting of Parkinson disease; Alzheimer disease; Creutzfeldt-Jakob disease; corticobasal degeneration; Amyotrophic Lateral Sclerosis; Multiple Sclerosis; progressive motor weakness; neuroimmunological disorders, CNS trauma; Alzheimer disease with parkinsonism; bradykinesia; alkinesia; movement disorders that impair fine motor control and finger dexterity; hypophonia; monotonic speech; rigidity; dystonia; inflammation associated with Parkinson Disease; tremors of the face, jaw, tongue, posture; parkinsonian gait; shuffling; short steps; festinating gait; disorders of mood, cognition, sensation, sleep; dementia; depression; drug induced parkinsonism;

vascular parkinsonism; multiple system atrophy; progressive supranuclear palsy; disorders with primary tau pathology; cortical basal ganglia degeneration; parkinsonism with dementia; hyperkinetic disorders; chorea; Huntington's disease; dystonia; Wilson disease; Tourette syndrome; essential tremor; myoclonus; and a tardive movement disorder.

In some embodiments of the various methods or various compositions provided herein, the BRD7 antagonist is selected from a group consisting of an inhibitor of BRD7 protein, a nucleic acid comprising at least part of nucleic acid sequence of BRD7 gene, and a stem cell, neural progenitor cell, or neural precursor cell in which BRD7 is down-regulated. In some embodiments, the inhibitor of BRD7 protein is selected from a group consisting of an inhibitor of BRD7 production, an inhibitor of BRD7 action, and a nucleic acid comprising a coding region of an inhibitor of BARD. In some embodiments, the nucleic acid is an antisense molecule specific to a BRD7 gene, an RNAi molecule or a Morpholino oligonucleotide specific to BRD7 gene.

In some embodiments of the various methods or various compositions provided herein, the antagonist of Ikaros is selected from a group consisting of an inhibitor of Ikaros protein, a nucleic acid comprising at least part of nucleic acid sequence of Ikaros gene, and a stem cell, neural progenitor cell, or neural precursor cell in which Ikaros is down-regulated. In some embodiments, the inhibitor of Ikaros protein is selected from a group consisting of an inhibitor of Ikaros production, an inhibitor of Ikaros action, and a nucleic acid comprising a coding region of an inhibitor of Ikaros. In some embodiments, the nucleic acid is an antisense molecule specific to an Ikaros gene, an RNAi molecule or a Morpholino oligonucleotide specific to Ikaros gene.

In some embodiments of the various methods or various compositions provided herein, the CRBN activator is selected from a group consisting of an inhibitor of CRBN substrate or downstream protein, a nucleic acid comprising at least part of nucleic acid sequence of a CRBN substrate or downstream protein gene, and a stem cell, neural progenitor cell or neural precursor cell in which a CRBN substrate or downstream protein is down-regulated. In some embodiments, the inhibitor of a CRBN substrate or downstream protein is selected from a group consisting of an inhibitor of a CRBN substrate or downstream protein production, an inhibitor of a CRBN substrate or downstream protein action, and a nucleic acid comprising a coding region of an inhibitor of a CRBN substrate or downstream protein. In some embodiments, the nucleic acid is an antisense molecule specific to a CRBN substrate or downstream protein gene, an RNAi molecule, or a Morpholino oligonucleotide specific to a CRBN substrate or downstream protein gene.

In certain embodiments of the various methods or various compositions provided herein, a population of CNS cells, or CNS progenitor/precursor cells thereof, are contacted with the BRD7 antagonist, Ikaros antagonist, or CRBN activator in vitro. In other embodiments, a population of CNS cells, or CNS progenitor/precursor cells thereof, are contacted with the BRD7 antagonist, Ikaros antagonist, or CRBN activator ex vivo. In some embodiments, the cells are contacted with a BRD7 antagonist. In another embodiment, the cells are contacted with an Ikaros antagonist. In other embodiments, the cells are contacted with a CRBN activator. In some embodiments, the CNS cells, or CNS progenitor/precursor cells thereof, are patient CNS cells, or CNS progenitor/precursor cells thereof. In other embodiments, the CNS cells, or CNS progenitor/precursor cells thereof, are donor CNS cells, or CNS progenitor/precursor cells thereof. In another embodiment, the patient has a CNS cell defective disease, disorder or condition, or a symptom thereof.

In some embodiments, of the various methods or various compositions provided herein, the patient is a patient in need thereof.

In other aspects, provided herein are pharmaceutical compositions, single unit dosage forms, and kits, which comprise a BRD7 antagonist, Ikaros antagonist, or CRBN activator and a carrier, for use in the prevention or treatment of a CNS cell defective disease, disorder or condition, or a symptom thereof.

4. BRIEF DESCRIPTION OF THE DRAWINGS

The present invention will now be described by way of example only, with reference to the accompanying figures, wherein:

FIG. 1 shows fluorescent microscopic pictures of primary neurons stained by anti-acetylated tubulin antibody in zebrafish embryos. In these pictures, the upper left panel shows a normal embryo, the upper right panel shows an embryo in which the CRBN gene is overexpressed, the lower left panel shows an embryo in which the lhx2 gene is knocked down, and the lower right panel shows an embryo in which the lhx2 gene is knocked down while the CRBN gene is overexpressed.

FIG. 2 shows microscopic pictures of zebrafish embryos. The picture on the right shows an embryo in which the CRBN gene is overexpressed, and the picture on the left shows an untreated embryo. Both pictures were taken at the same magnification.

FIG. 3 shows microscopic pictures of zebrafish, into which CRBN-overexpressing cells (fluorescently labeled with rhodamine) are transplanted. The top pictures and the bottom pictures were taken at 200-fold magnification and 100-fold magnification, respectively. Also, the pictures on the left column are bright-field images, and the pictures on the right column are fluorescent images.

FIG. 4 shows electrophoresis images for the detection of the ubiquitin ligase activity of a CRBN complex (FH-CRBN complex) using an in vitro reaction system. The images on the left, middle, and right show ubiquitin, Cul4A (a CRBN complex-forming factor), and ubiquitinated CRBN, respectively, each detected by immunoblotting. Mock indicates a control experimental sample.

FIG. 5 shows an electrophoresis image for the detection of the ubiquitin ligase activity of the CRBN complex in live cells.

FIG. 6 shows close-up pictures of zebrafish heads in which radial glia cells and astrocytes were fluorescently stained. The left part of the picture corresponds to the front end portion. The picture on the left shows a normal individual, and the picture on the right shows an individual with overexpressed CRBN.

FIG. 7 shows close-up pictures of zebrafish heads in which serotonin-producing cells were fluorescently stained. These pictures were taken from the dorsal side of the brain. The top part of the picture corresponds to the front end portion. The picture on the left shows a normal individual, and the picture on the right shows an individual with overexpressed CRBN. In the figure, numbers 1, 2, and 3 indicate the pineal gland, the ventral posterior tuberculum, and the raphe nucleus, respectively.

FIGS. 8A-8H show pictures of zebrafish, of which undifferentiated cells are transplanted into the cerebral ventricle.

Pictures 8A to 8D show the zebrafish in which cells that do not express CRBN are transplanted, and pictures 8E to 8H show the zebrafish in which cells that express CRBN are transplanted. Pictures 8A and 8E are bright-field images, pictures 8B and 8F are fluorescent images of Alexa Fluor® (indicating the distribution of acetylated tubulin), pictures 8C and 8G are fluorescent images of rhodamine (indicating the distribution of donor cells), and pictures 8D and 8H are fluorescent images of Alexa Fluor® and rhodamine.

FIGS. 9A-9F show that knockdown of BRD7 enlarges the brain in zebrafish embryos, and that overexpression of BRD7 reduces the brain in zebrafish embryos. FIGS. 9A, 9B, and 9C show microscopic pictures of untreated, BRD7-knockdown, and BRD7-overexpressing zebrafish embryos, respectively. These pictures were taken at the same magnification. FIGS. 9D, 9E, and 9F show fluorescent microscopic pictures of neurons labeled with anti-acetylated tubulin antibody in the brains of the untreated, the BRD7-knockdown, and the BRD7-overexpressing zebrafish embryos, respectively. These pictures were taken at the same magnification.

FIGS. 10G-10V show knockdown of BRD7 activates expression of Pou5f1 (Oct3/4), Klf4, c-Myc, and HuC (Elavl3) in zebrafish embryos. FIGS. 10G and 10I show Pou5f1 (Oct3/4) expression in untreated zebrafish embryos by in situ hybridization at 10 hours post fertilization (hpf) and 11 hpf, respectively. FIGS. 10H and 10J show Pou5f1 (Oct3/4) expression in BRD7-knockdown zebrafish embryos by in situ hybridization at 10 hpf and 11 hpf, respectively. FIGS. 10K and 10L show Klf4 expression in the untreated and the BRD7-knockdown zebrafish embryos by in situ hybridization at 18 hpf. FIGS. 10M and 10N show expression of C-Myc in the tectal proliferation zone in the medial and lateral areas, and in the most peripheral region of the ciliary marginal zone (CMZ) in the retina of the untreated zebrafish embryos by in situ hybridization at 30 hpf. FIGS. 10O and 10P show expression of C-Myc in the tectal proliferation zone in the medial and lateral areas, and in the most peripheral region of the ciliary marginal zone (CMZ) in the retina of the BRD7-knockdown zebrafish embryos by in situ hybridization at 30 hpf. FIGS. 10Q and 10T show HuC expression in the brain and spinal cord in the untreated zebrafish embryos by in situ hybridization at 11 hpf. FIGS. 10R and 10U show HuC expression in the brain and spinal cord in the CRBN-overexpressing zebrafish embryos by in situ hybridization at 11 hpf. FIGS. 10S and 10V show HuC expression in the brain and spinal cord in the BRD7-knockdown zebrafish embryos by in situ hybridization at 11 hpf.

FIGS. 11A-11C show that BRD7-knockdown zebrafish embryos have similar phenotype to CRBN-overexpressing zebrafish embryos, and that BRD7-knockdown zebrafish embryos have increased neural precursor cells. FIG. 11A is a histogram showing HuC expression level by quantitative PCR in untreated, CRBN-overexpressing, and BRD7-knockdown zebrafish embryos, respectively. FIG. 11B shows HuC-positive neural progenitor cells in the brain and spinal cord of the untreated and the BRD7-knockdown zebrafish embryos by in situ hybridization at 15 hpf. FIG. 11C shows closeup view of the telencephalic neurons and the spinal cord neurons in the untreated and the BRD7-knockdown embryos at 16 hpf.

FIG. 12 shows that BRD7-knockdown zebrafish are resistant to thalidomide treatment in brain development. FIGS. 12A and 12B show normal zebrafish treated with 400 μM thalidomide. FIGS. 12C and 12D show BRD7-knockdown zebrafish treated with 400 μM thalidomide. FIGS. 12A' and 12C' show the brain regions of the normal zebrafish treated with 400 μM thalidomide. FIGS. 12B' and 12D' show the brain regions of the BRD7-knockdown zebrafish treated with 400 μM thalidomide. FIG. 12E is a histogram showing percentages of brain thickness to body length of the normal and the BRD7-knockdown zebrafish, with or without thalidomide treatments.

FIG. 13 is a histogram showing expression levels of Pou5f1, Nanog, Zic3, and Sox2 by quantitative PCR in untreated, CRBN-overexpressing, CRBN-knockdown, BRD7-overexpressing, BRD7-knockdown, and thalidomide-treated zebrafish embryos at 11 hpf.

FIG. 14 shows that knockdown of BRD7 increases expression of Ascl1, Pou3f3a, Pou3f2b, and Myt1la. The left part of FIG. 14 is a histogram showing the expression levels of Ascl1, brn2 (Pou3f2b), and Myt1la by quantitative PCR in untreated and BRD7-knockdown zebrafish embryos at 11 hpf. The right part of FIG. 14 is a histogram showing the expression levels of Ascl1, Pou3f3a, and Myt1la by quantitative PCR in untreated and BRD7-knockdown zebrafish embryos at 28 hpf.

FIGS. 15A-15C show knockdown of Ikaros enlarges the brain in zebrafish embryos, and overexpression of Ikaros reduces the brain in zebrafish embryos. FIGS. 15A, 15B, and 15C show microscopic pictures of untreated, Ikaros-knockdown, and Ikaros-overexpressing zebrafish embryos at 55 hpf, respectively. These pictures were taken at the same magnification.

FIGS. 16A-16F show overexpression of Ikaros variants causes reduction of brain development in zebrafish embryos. FIGS. 16A, 16B, 16C, and 16E show microscopic pictures of the brains of untreated, Ikaros-knockdown, ikzf1-007 (an Ikaros variant)-overexpressing, and ikzf1-006 (an Ikaros variant)-overexpressing zebrafish embryos at 22 hpf, respectively. FIGS. 16D and 16F are EGFP fluorescent microscopic pictures of the brains of the ikzf1-007 (Ikzf1-007: EGFP)-overexpressing and the ikzf1-006 (Ikzf1-006: EGFP)-overexpressing zebrafish embryos at 22 hpf, respectively. These pictures were taken at the same magnification.

FIGS. 17A-17F show that knockdown of Ikaros promotes cell proliferation and neural differentiation. FIGS. 17A and 17D show the primary neurons in the CNS of untreated and Ikaros-knockdown zebrafish embryos, respectively, at 27 hpf by immunostaining with anti-acetylated tubulin antibody. FIGS. 17B and 17E show the proliferating cells in the CNS of the untreated and the Ikaros-knockdown zebrafish embryos, respectively, at 27 hpf by immunostaining with anti-phosphorylated histone antibody. FIG. 17C shows merged image of FIGS. 17A and 17B. FIG. 17F shows merged image of FIGS. 17D and 17E.

FIG. 18 is a histogram showing the number of H3-positive proliferating cells in the telecephalon, diencephalon, and midbrain regions of untreated and Ikaros-knockdown zebrafish embryos at 27 hpf (n=3). The numbers of the cells were counted in a stacked focal plane of laser confocal microscope.

FIGS. 19A-19H show increased number of radial glia cells and serotonin-positive cells in Ikaros-knockdown zebrafish embryos. FIGS. 19A and 19C-19E show fluorescent microscopic pictures of the brains of untreated zebrafish embryos at 54 hpf. FIGS. 19B and 19F-19H show fluorescent microscopic pictures of the brains of the Ikaros-knockdown zebrafish embryos at 54 hpf. Cells were immunostained with anti-radia glia marker (Zrf-2) antibodies (green) and anti-serotonin antibodies (red).

FIG. 20 is a histogram showing Pou5f1, c-Myc, Sox2 and Nanog expression levels by quantitative PCR in untreated and Ikaros-knockdown zebrafish embryos at 28 hpf.

FIG. 21 shows that knockdown of Ikaros increases expression of Ascl1, Pou3f3a, Pou3f2b, and Myt11a; and that overexpression of Ikaros decreases expression of Ascl1, Pou3f3a, Pou3f2b, and Myt11a. FIG. 21 is a histogram showing the expression levels of Ascl1, Pou3f3a, Pou3f2b, and Myt11a by quantitative PCR in untreated, Ikaros-knockdown, and Ikaros-overexpressing zebrafish embryos at 28 hpf.

Figure 22:
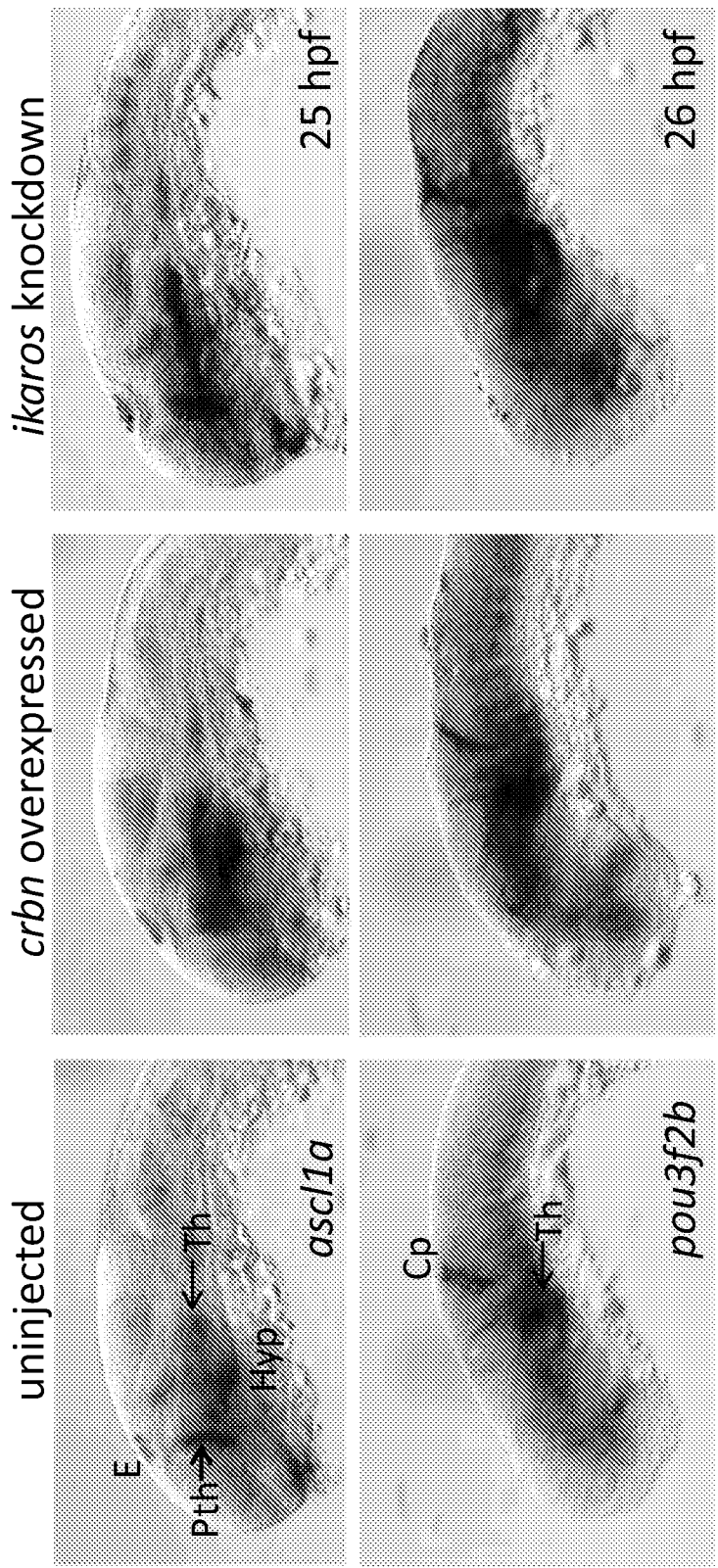

FIG. 22 shows increased Ascl1a and Pou3f2b expression in CRBN-overexpressing and Ikaros-knockdown zebrafish embryos by in situ hybridization. The upper panel of FIG. 22 shows Ascl1a expression in untreated, the CRBN-overexpressing, and the Ikaros-knockdown zebrafish embryos by in situ hybridization at 25 hpf. The lower panel of FIG. 22 shows Pou3f2b expression in the untreated, the CRBN-overexpressing, and the Ikaros-knockdown zebrafish embryos by in situ hybridization at 26 hpf.

Figure 23:
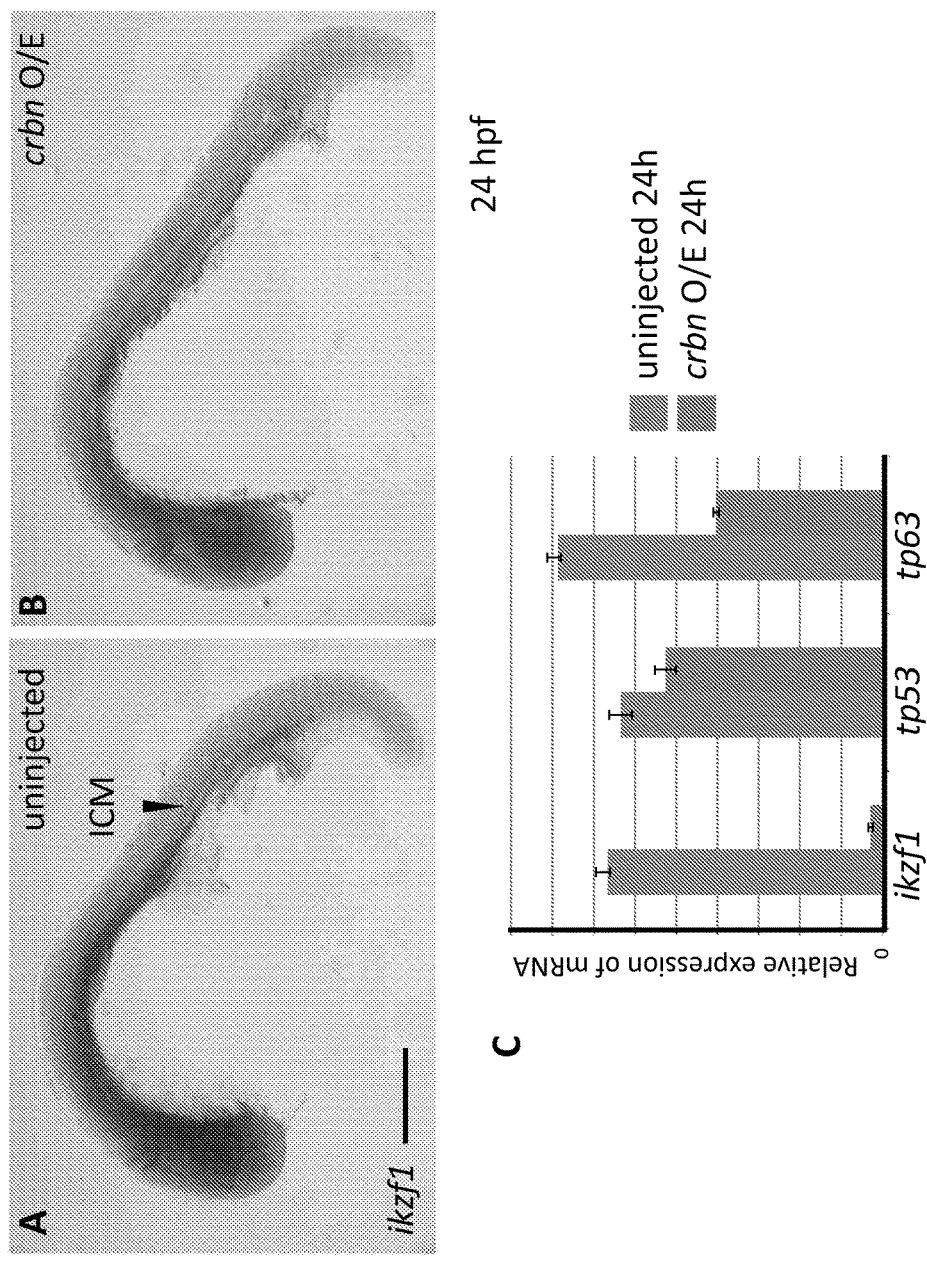

FIGS. 23A-23C show overexpression of CRBN decreases Ikaros expression. FIGS. 23A and 23B show the Ikaros mRNA expression by in situ hybridization in untreated and CRBN-overexpressing zebrafish embryos at 24 hpf. FIG. 23C shows Ikaros, Tp53, and Tp63 expression levels by quantitative PCR in the untreated and the CRBN-overexpressing zebrafish embryos at 24 hpf.

Figure 24:
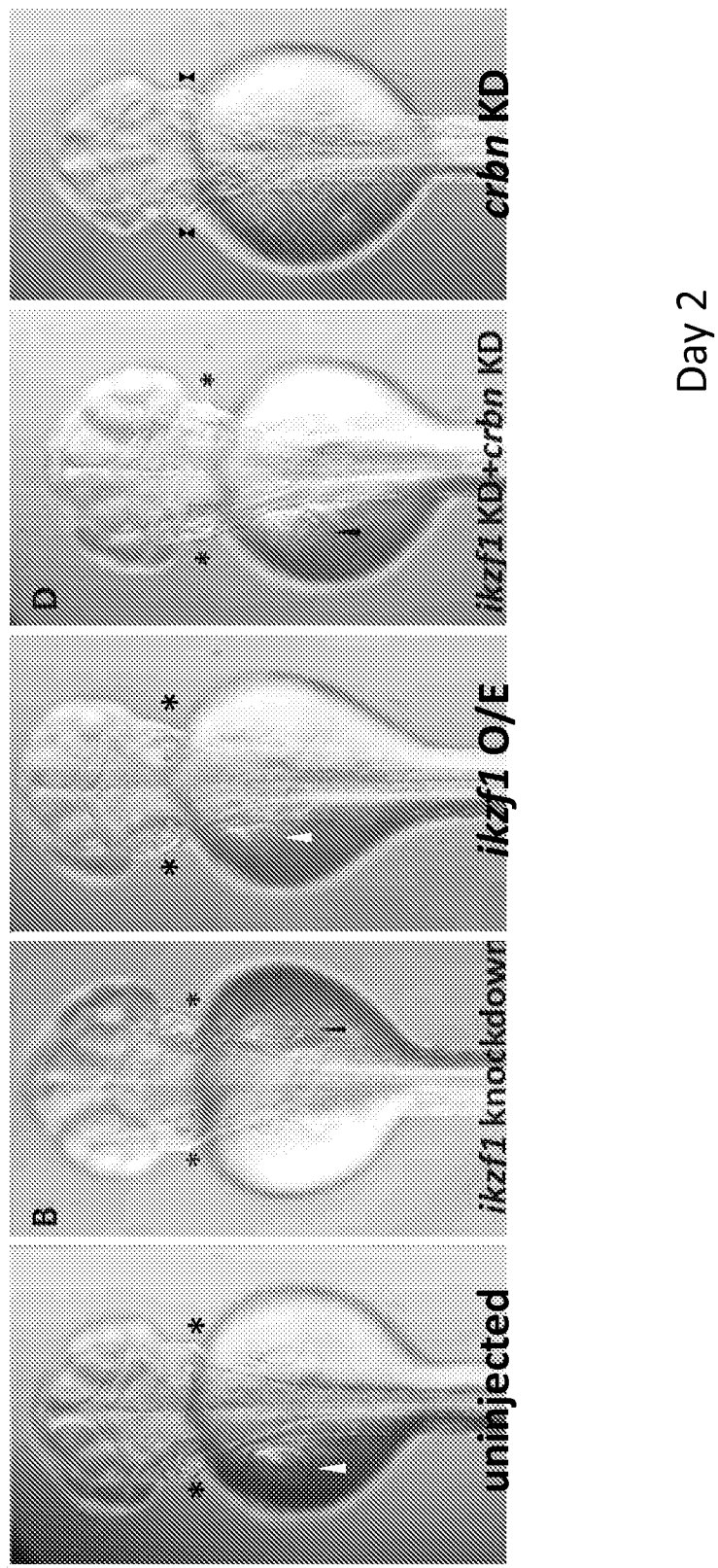

FIG. 24 shows that Ikaros-knockdown larvae have enlarged brains at day 2, that CRBN-knockdown and Ikaros-overexpressing larvae have smaller brains at day 2, and that CRBN- and Ikaros-double knockdown larvae have enlarged brains at day 2. FIG. 24 shows microscopic pictures of untreated, the Ikaros-knockdown, the Ikaros-overexpressing, the Ikaros- and CRBN-double knockdown, and the CRBN-knockdown zebrafish embryos at day 2 (from left to right). These pictures were taken at the same magnification.

Figure 25:
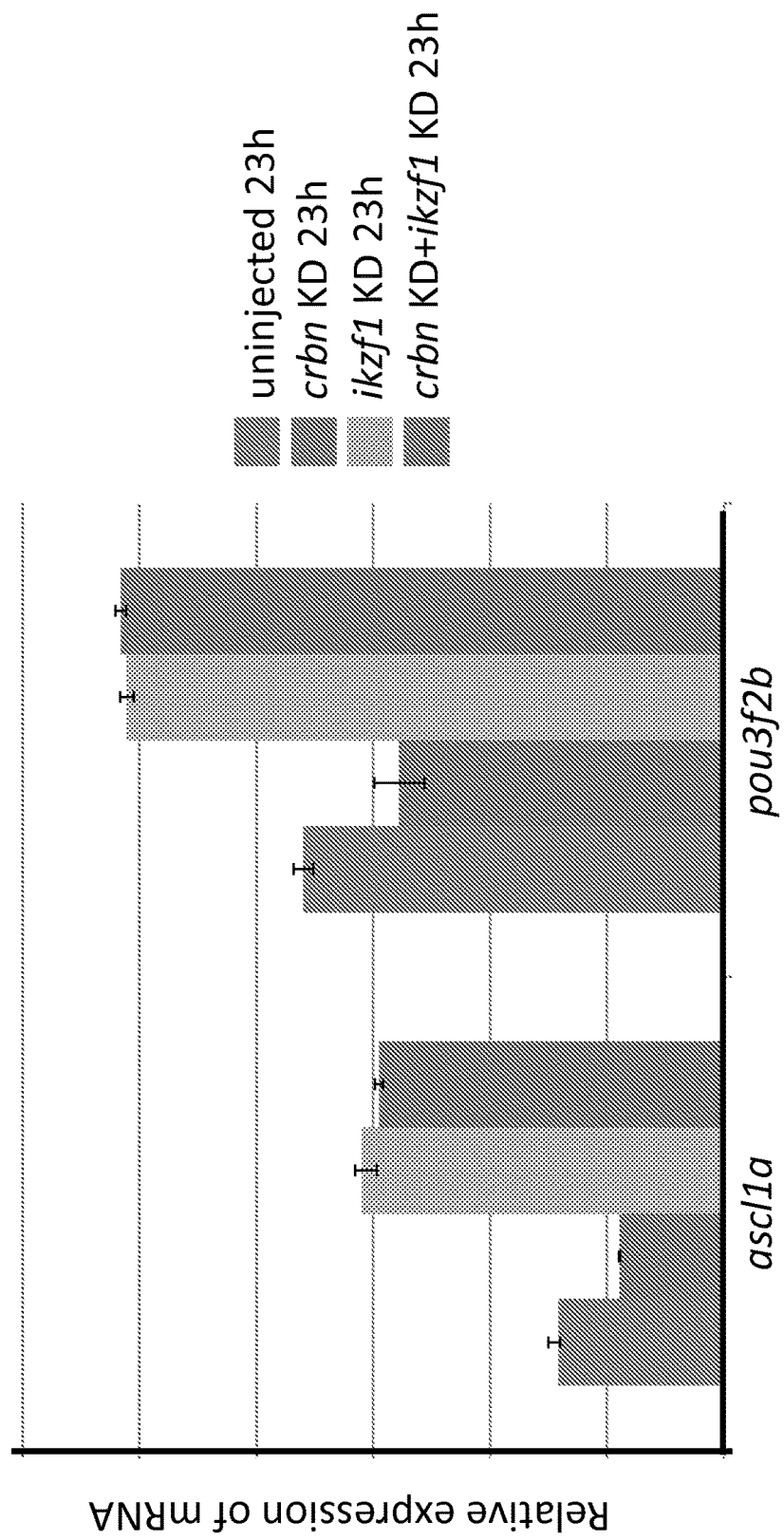
Figure 26:
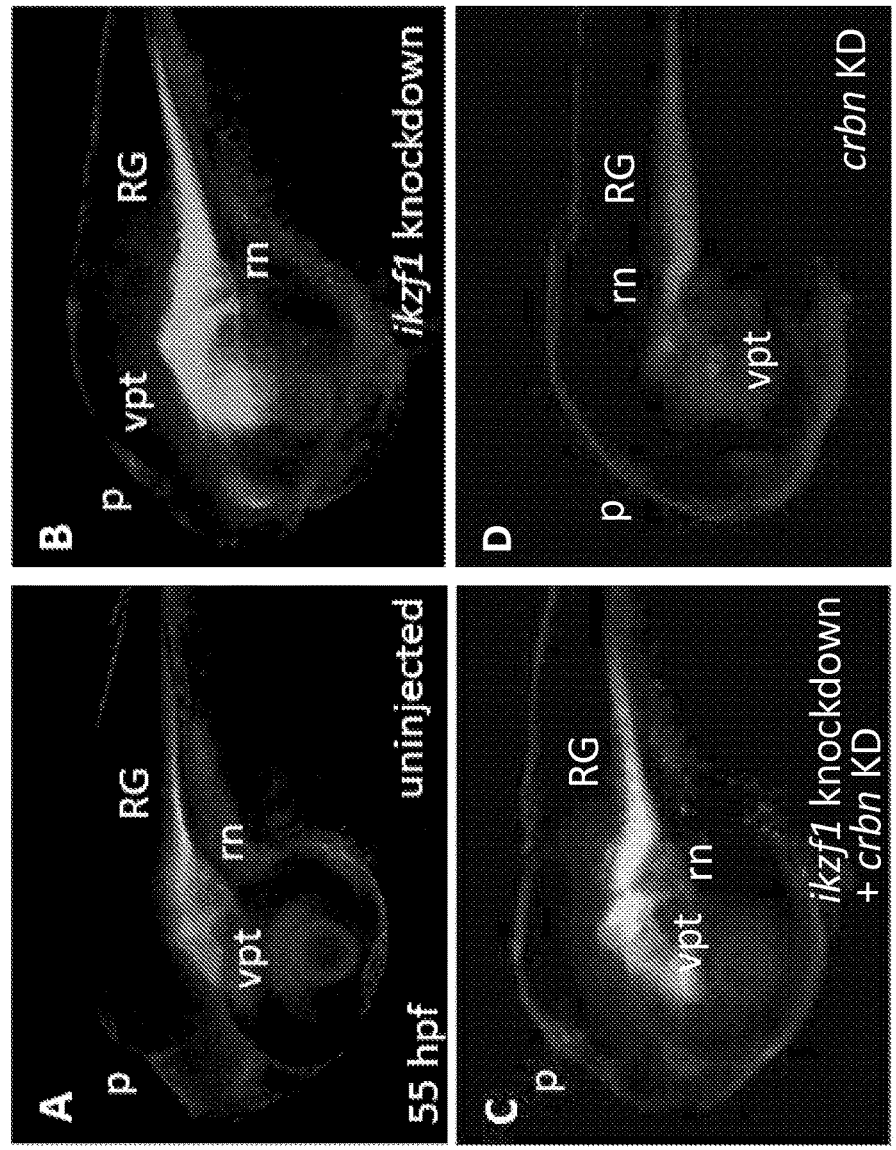

FIG. 25 shows increased Ascl1a and Pou3f2b expression in Ikaros-knockdown and Ikaros- and CRBN-double knockdown zebrafish embryos by quantitative PCR. FIG. 25 is a histogram showing the expression levels of Ascl1 and Pou3f2b by quantitative PCR in untreated, CRBN-knockdown, the Ikaros-knockdown, and the Ikaros- and CRBN-double knockdown zebrafish embryos at 23 hpf.

FIGS. 26A-26D show that knockdown of Ikaros and double knockdown of Ikaros and CRBN increase the numbers of radial glia and serotonin-positive cells in the CNS of zebrafish embryos. FIGS. 26A, 26B, 26C, and 26D show fluorescent microscopic pictures of the brains of untreated, Ikaros-knockdown, Ikaros- and CRBN-double knockdown, and CRBN-knockdown zebrafish embryos, respectively, at 55 hfp. The embryos were immunostained with anti-radial glia marker (Zrf-2) antibodies (green) and anti-serotonin antibodies (red).

Figure 27:
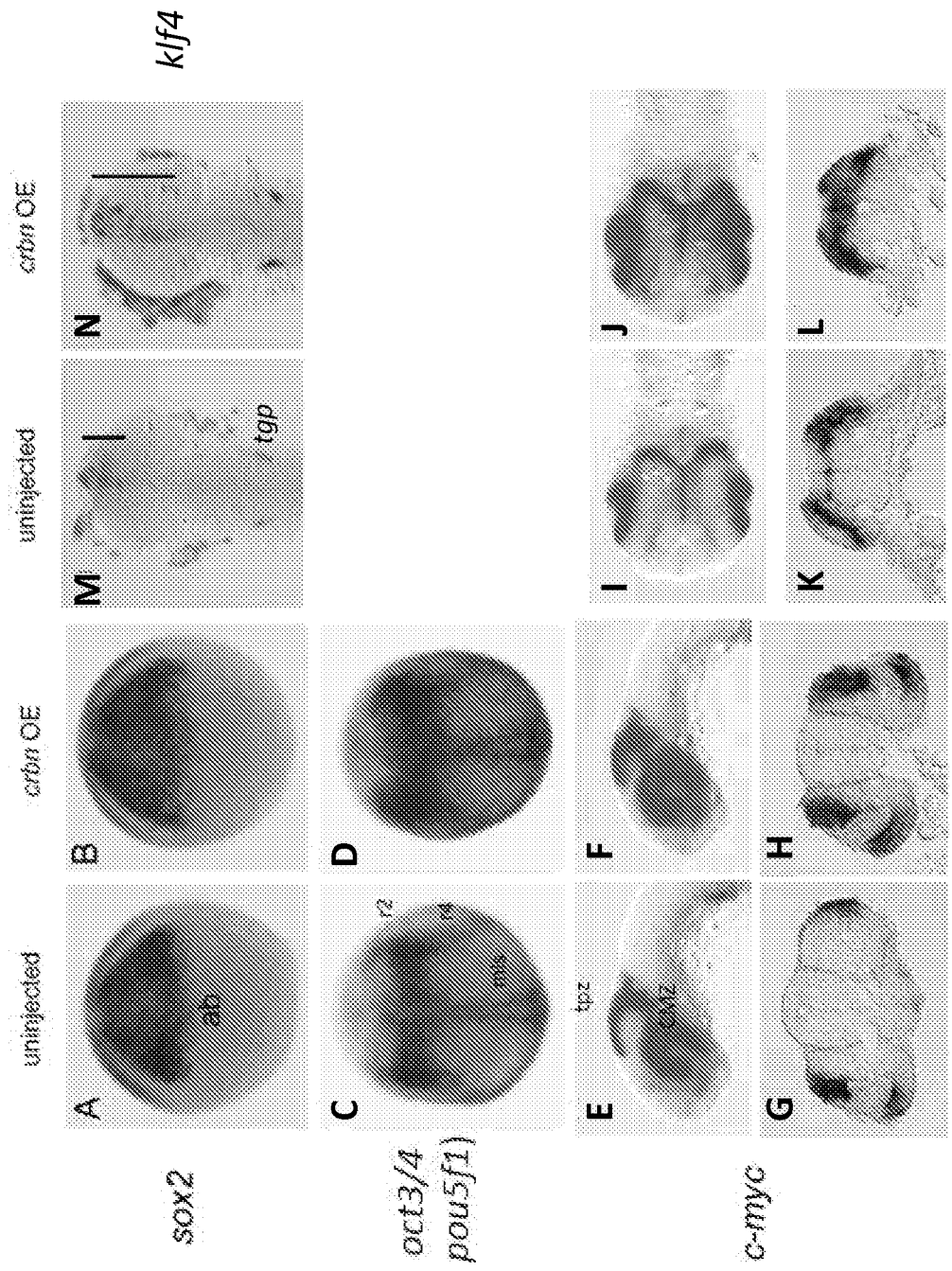

FIGS. 27A-27N show that overexpression of CRBN activates expression of Sox2, Pou5f1 (Oct3/4), c-Myc, and Klf4. FIGS. 27A and 27B show Sox2 expression in untreated and CRBN-overexpressing zebrafish embryos at 9 hpf, respectively, by in situ hybridization. FIGS. 27C and 27D show Pou5f1 expression in untreated and CRBN-overexpressing zebrafish embryos at 10 hpf, respectively, by in situ hybridization. FIGS. 27E, 27G, 27I, and 27K show c-Myc expression in untreated zebrafish embryos at 30 hpf by in situ hybridization. FIGS. 27F, 27H, 27J, and 27L show c-Myc expression in CRBN-overexpressing zebrafish embryos at 30 hpf by in situ hybridization. FIGS. 27M and 27N show Klf4 expression in untreated and CRBN-overexpressing zebrafish embryos at 18 hpf, respectively, by in situ hybridization.

Figure 28:
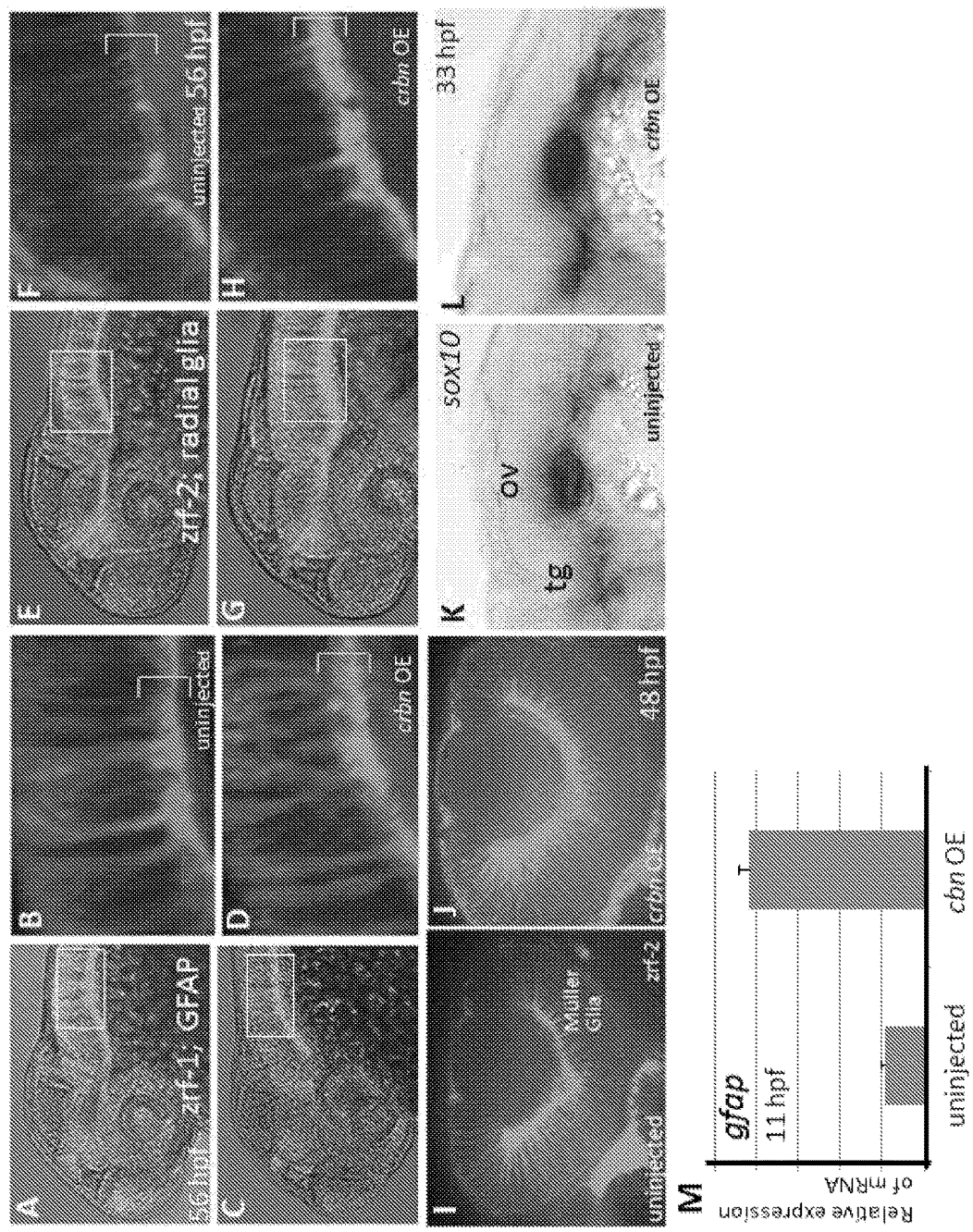

FIGS. 28A-28M show that overexpression of CRBN increases the numbers of radial glial cells and matured neurons. FIGS. 28A and 28B show the brain regions of untreated zebrafish embryos at 56 hpf immunostained with Zrf-1 antibodies, which label glial fibrillary acidic protein (GFAP) in astrocytes. FIGS. 28C and 28D show the brain regions of CRBN-overexpressing zebrafish embryos at 56 hpf immunostained with Zrf-1 antibodies, which label glial fibrillary acidic protein (GFAP) in astrocytes. FIGS. 28E and 28F show the brain regions of untreated zebrafish embryos at 56 hpf immunostained with Zrf-2 antibodies, which label radial glial cells. FIGS. 28G and 28H show the brain regions of CRBN-overexpressing zebrafish embryos at 56 hpf immunostained with Zrf-2 antibodies, which label radial glial cells. FIGS. 28I and 28J show the brain regions of untreated and CRBN-overexpressing zebrafish embryos at 48 hpf immunostained with Zrf-2 antibodies, which label Müller glia in the retina. FIGS. 28K and 28L show Sox10 in the otic vesicles and the neural crest cells (NCCs) in the spinal cord in untreated and CRBN-overexpressing zebrafish embryos at 33 hpf, respectively. FIG. 28M is a histogram showing Gfap mRNA level in untreated and CRBN-overexpressing zebrafish embryos at 11 hpf, respectively, by quantitative PCR.

Figure 29:
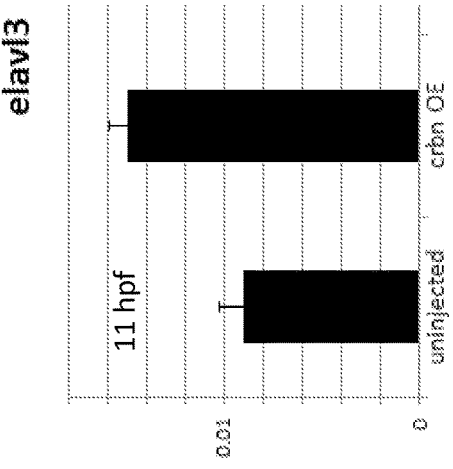
Figure 29:
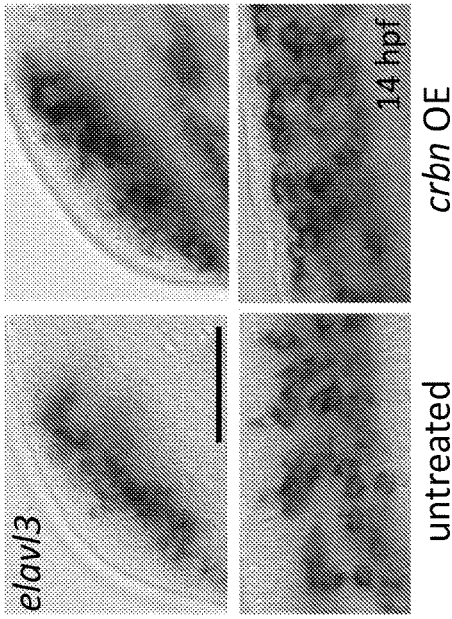
Figure 29:
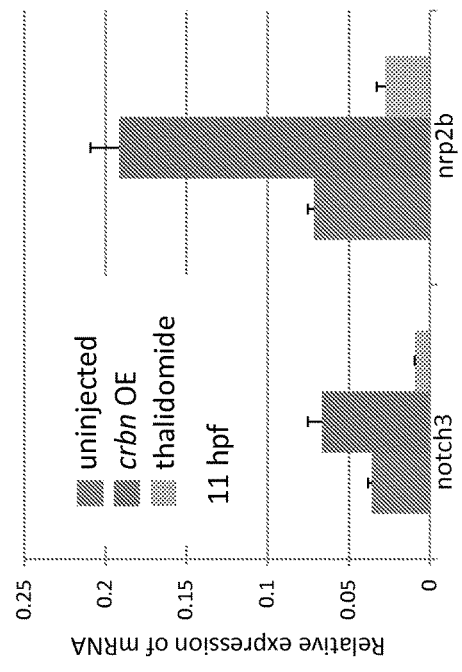
Figure 29:
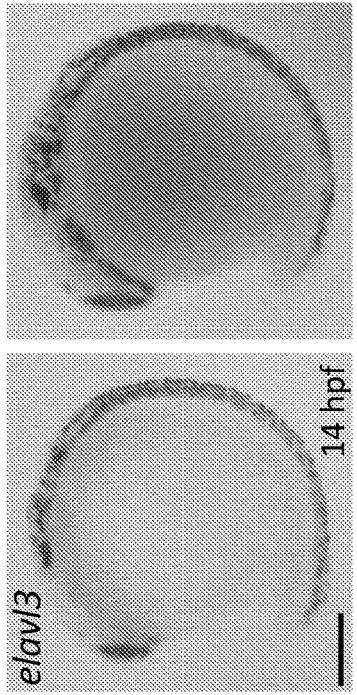

FIGS. 29A-29D show that overexpression of CRBN increases expression of Notch3, Neuropilin 2b (Nrp2b), and Elavl3 (Huc). FIG. 29A is a histogram showing the mRNA levels of Notch3 and Nrp2b in untreated, CRBN-overexpressing, and thalidomide-treated zebrafish embryos at 11 hpf by quantitative PCR. FIG. 29B is a histogram showing the Elavl3 mRNA level in untreated and CRBN-overexpressing zebrafish embryos at 11 hpf by quantitative PCR. FIGS. 29C and 29D show Elavl3-positive neural progenitor cells in untreated and CRBN-overexpressing zebrafish embryos at 14 hpf by in situ hybridization (scale bar: 100 μm in FIG. 29C and 50 μm in FIG. 29D).

Figure 30:
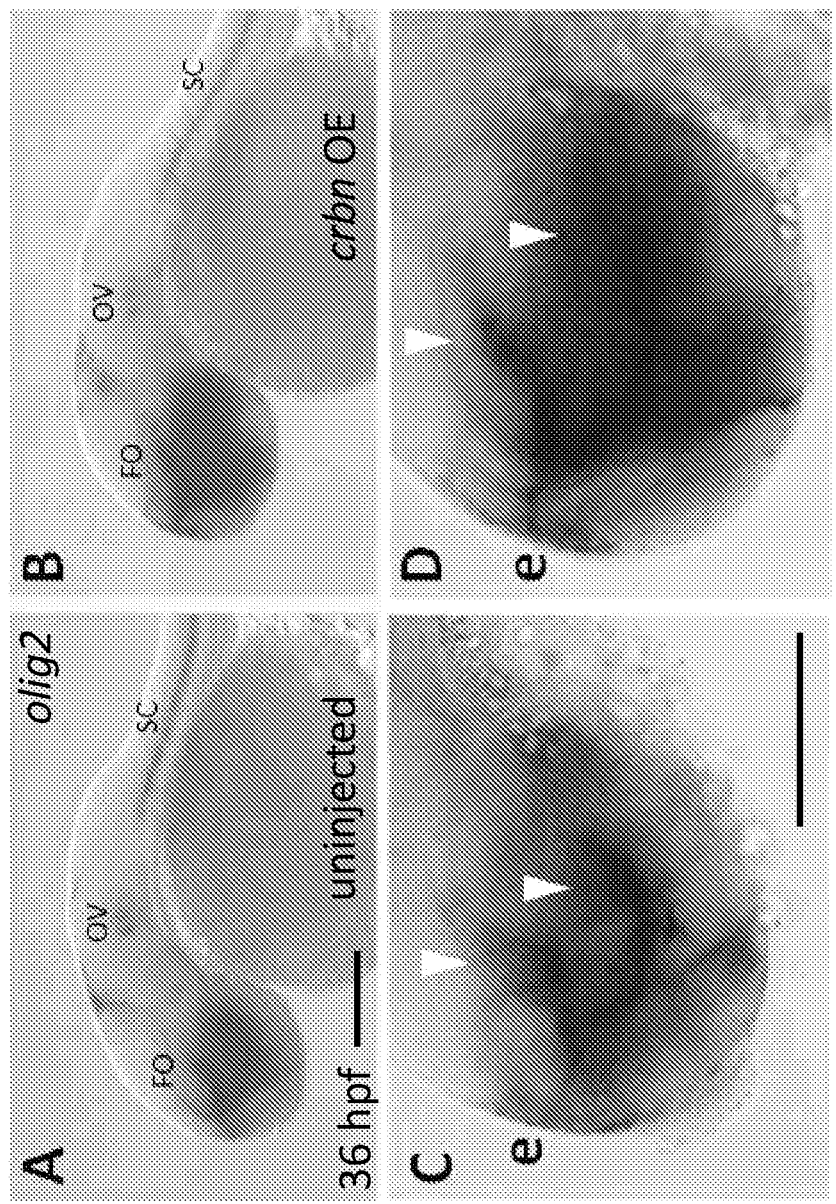

FIGS. 30A-30D show that overexpression of CRBN increases oligodendrocytes. FIGS. 30A and 30B show oligodendrocytes in the forebrain, the otic vesicle, and the spinal cord of untreated and CRBN-overexpressing zebrafish embryos at 36 hpf by in situ hybridization. FIGS. 30C and 30D show oligodendrocytes in epiphysis of the untreated and the CRBN-overexpressing zebrafish embryos at 36 hpf. In these figures, FO indicates the forebrain; OV indicates the otic vesicle; SC indicates the spinal cord; and e indicates the epiphysis. Arrowheads indicate the dorsal and ventral clusters of oligodendrocytes (scale bar: 100 μm).

Figure 31:
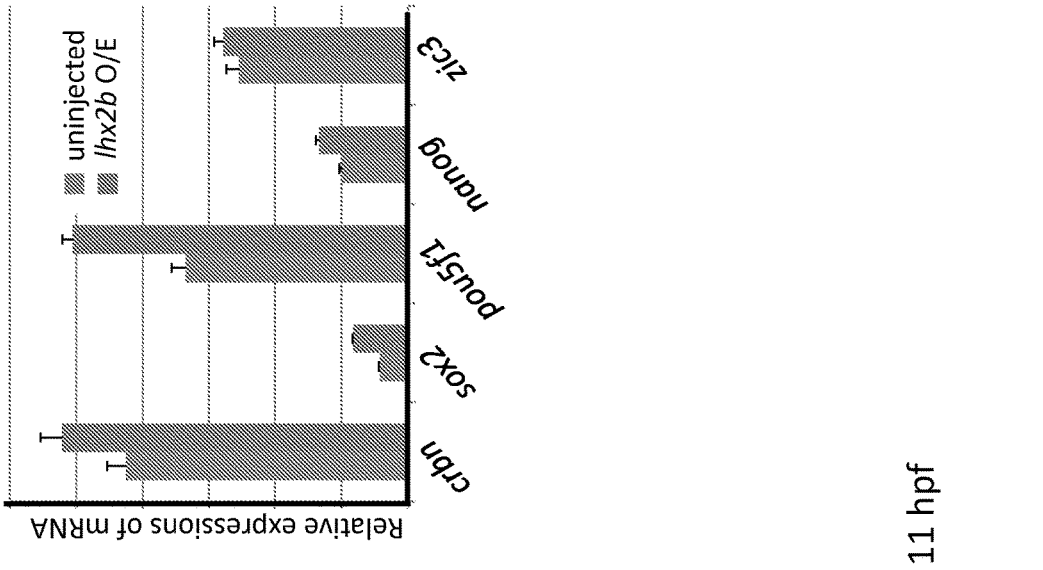

FIGS. 31A-31C show that overexpression of Six3b, Lhx2b, and CRBN increases expression of pluripotency genes. FIG. 31A is a histogram showing expression levels of Lhx2b, Wnt3a, CRBN, Sox2, Pou5f1, and Nanog in untreated and Six3b-overexpressing zebrafish embryos at 11 hpf by quantitative PCR. FIG. 31B is a histogram showing expression levels of CRBN, Sox2, Pou5f1, Nanog, and Zic3 in untreated and Lhx2b-overexpressing zebrafish embryos at 11 hpf by quantitative PCR. FIG. 31C is a histogram showing expression levels of Sox2, Pou5f1, Nanog, and Zic3 in untreated, CRBN-overexpressing, CRBN-knockdown, and 100 μM thalidomide-treated zebrafish embryos at 11 hpf by quantitative PCR.

Figure 32:
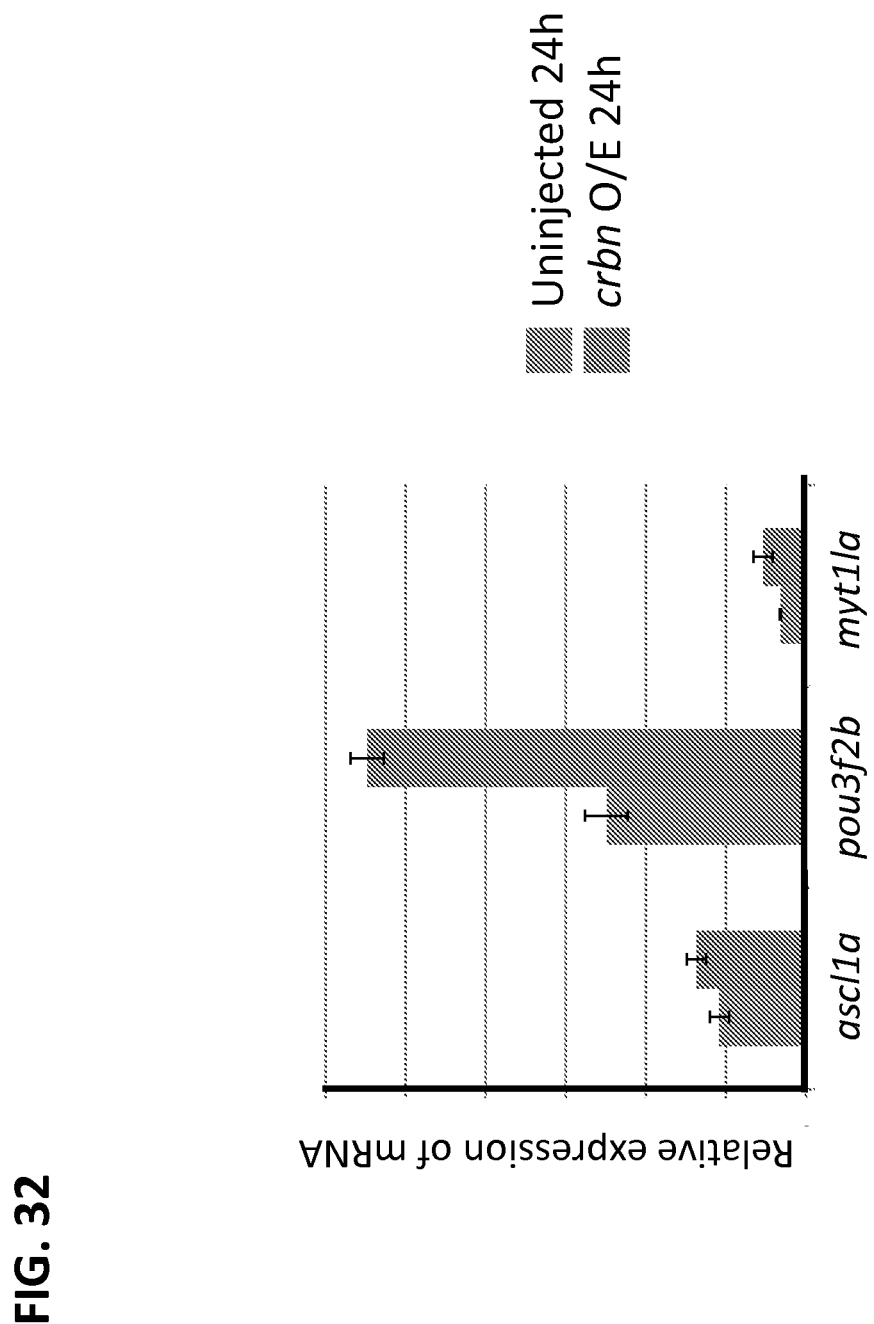

FIG. 32 is a histogram showing expression levels of Ascl1a, Pou3f2b, and Myt11a in untreated and CRBN-overexpressing zebrafish embryos at 24 hpf by quantitative PCR.

5. DETAILED DESCRIPTION

5.1 Definitions

All patents, applications, published applications and other publications are incorporated by reference in their entirety. In the event that there is a plurality of definitions for a term herein, those in this section prevail unless stated otherwise. Unless defined otherwise, all technical and scientific terms used herein have the same meaning as is commonly understood by one of ordinary skill in the art.

As used herein, the term "about" or "approximately" means within 20%, preferably within 10%, and more preferably within 5% (or 1% or less) of a given value or range.

As used herein, the term "active fractions" is intended to mean any fragments or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to CRBN's natural binding proteins in the cell.

As used herein, "administer" or "administration" refers to the act of injecting or otherwise physically delivering a substance as it exists outside the body (e.g., BRD7 antagonist, Ikaros antagonist, or CRBN activator provided herein) into a patient, such as by mucosal, intradermal, intravenous, intramuscular delivery and/or any other method of physical delivery described herein or known in the art. When a CNS cell defective disease, disorder or condition, or a symptom thereof, is being treated, administration of the substance typically occurs after the onset of the CNS cell defective disease, disorder or condition or symptoms thereof. When a CNS cell defective disease, disorder or condition, or symptoms thereof, are being prevented, administration of the substance typically occurs before the onset of the CNS cell defective disease, disorder or condition or symptoms thereof.

The terms "antagonist of Bromodomain Containing 7 (BRD7)" and "BRD7 antagonist" are used interchangeably herein and are intended to mean an agent that directly or indirectly inhibits, down-regulates (e.g., suppresses or inhibits), or negatively regulates the presence and/or at least one bioactivity of BRD7. In some embodiments, the antagonist of BRD7 suppresses BRD7's inhibitory functions in CNS cells proliferation and differentiation. In some embodiments, an antagonist of BRD7 is an inhibitor of BRD7 protein. As used herein, an "inhibitor of BRD7 protein" is intended to mean any molecule modulating BRD7 protein production and/or action in such a way that BRD7 production and/or action is attenuated, reduced, or partially, substantially or completely prevented or blocked. The term "inhibitor of BRD7 protein" is meant to encompass inhibitors of BRD7-production, as well as of inhibitors of BRD7 action.

The terms "antagonist of Ikaros" and "Ikaros antagonist" are used interchangeably herein and are intended to mean an agent that directly or indirectly inhibits, down-regulates (e.g., suppresses or inhibits), or negatively regulates the presence and/or at least one bioactivity of Ikaros. In some embodiments, the antagonist of Ikaros suppresses Ikaros' inhibitory functions in CNS cells proliferation and differentiation. In some embodiments, an antagonist of Ikaros is an inhibitor of Ikaros protein. As used herein, an "inhibitor of Ikaros protein" is intended to mean any molecule modulating Ikaros protein production and/or action in such a way that Ikaros production and/or action is attenuated, reduced, or partially, substantially or completely prevented or blocked. The term "inhibitor of Ikaros protein" is meant to encompass inhibitors of Ikaros production, as well as of inhibitors of Ikaros action.

The terms "CRBN activator" or "activator of CRBN" are used interchangeably herein and are intended to mean an agent that directly or indirectly up-regulates (e.g., stimulates), or positively regulates the presence and/or at least one bioactivity of CRBN. In some embodiments, a "CRBN activator" (or "activator of CRBN") is intended to mean any molecule that modulates CRBN protein production and/or action in such a way that CRBN production or action is not attenuated, reduced, or partially, substantially or completely prevented or blocked. In some embodiments, the activator of CRBN suppresses an inhibitory function in CNS cells proliferation and differentiation. In certain embodiments, an activator of CRBN includes, but is not limited to, an active modulator of CRBN protein, a nucleic acid comprising at least part of nucleic acid sequence of CRBN gene, or an antisense compound for its inhibitory protein thereof, and a stem cell or a neural progenitor/precursor cell in which CRBN is up-regulated. The term "CRBN activator" (or "activator of CRBN") is meant to encompass activators of CRBN production, as well as of up-regulators of CRBN action.

The term "autologous" as used herein refers to organs, tissues, cells, fluids or other bioactive molecules that are reimplanted in the same individual that they originated from.

As used herein, the term "CNS cell" and similar terms refer to those cells of the CNS, including, but not limited to, the spinal cord or brain. In one embodiment, the CNS cell is a nerve cell. In another embodiments, the CNS cell is a neuron. In other embodiments, the CNS cell is a glial cell. In another embodiment, the CNS cell is a radial glia. In another embodiment, the CNS cell is an oligodendrocyte. In yet another embodiment, the CNS cell is an astrocyte.

As used herein, the term "CNS progenitor cells," "progenitor of a CNS cell," "CNS progenitor/precursor cells" and similar terms refers to, for example, stem cells and other progenitor/precursor cells that can differentiate into a CNS cell. In one embodiment, the CNS progenitor/precursor cell is a neural stem cell. In other embodiments, the CNS progenitor/precursor cell is a neural progenitor/precursor cell. Other exemplary stem cell and progenitor/precursor cells are provided elsewhere herein.

A "CNS cell defective disease, disorder or condition" and "CNS cell-mediated disorder" are used interchangeably and refer to any disease that is completely or partially caused by or is the result of defect or other deficiency or lack of functionality of CNS cells. In certain embodiments, the CNS cell defective disease, disorder or condition is Alzheimer Disease, Parkinson Disease, Huntington's Disease, Creutzfeldt-Jakob Disease, Progressive Supranuclear Palsy, Corticobasal Degeneration, and other disorders such as Amyotrophic Lateral Sclerosis; Multiple Sclerosis; progressive motor weakness; neuroimmunological disorders, CNS trauma; Alzheimer disease with parkinsonism; bradykinesia; alkinesia; movement disorders that impair fine motor control and finger dexterity; hypophonia; monotonic speech; rigidity; dystonia; inflammation associated with Parkinson Disease; tremors of the face, jaw, tongue, posture; parkinsonian gait; shuffling; short steps; festinating gait; disorders of mood, cognition, sensation, sleep; dementia; depression; drug induced parkinsonism; vascular parkinsonism; multiple system atrophy; progressive supranuclear palsy; disorders with primary tau pathology; cortical basal ganglia degeneration; parkinsonism with dementia; hyperkinetic disorders; chorea; dystonia; Wilson disease; Tourette syndrome;

essential tremor; myoclonus; a tardive movement disorder, or any combination of two or more thereof. As used herein, a "CNS cell defective disease, disorder or condition" includes a disease, disorder or condition caused by, or secondary to, any of the foregoing. In certain embodiments, the CNS cell defective disease, disorder or condition is characterized by a relative number or percentage of CNS cells that is lower than that present in the general population (e.g., as determined by an average or median). In other embodiments, the CNS cell defective disease, disorder or condition is characterized by CNS cell function that is lower than that present in the general population (e.g., as determined by an average or median).

As used herein, the term "composition" is intended to encompass a product containing the specified ingredients (e.g., a BRD7 antagonist, Ikaros antagonist, or CRBN activator provided herein) and, optionally, in the specified amounts, as well as any product which results, directly or indirectly, from combination of the specified ingredients in, optionally, the specified amounts.

The term "culturing" as used herein refers to propagating or cultivation of a cell, a population of cells, a tissue, or an organ, by incubating in an environment under conditions and for a period of time sufficient to support cell propagation or viability. Culturing can include expanding or proliferating a cell or a population of cells, such as CNS cells.

In the context of a polypeptide, the term "derivative" as used herein refers to a polypeptide that comprises an amino acid sequence of a polypeptide or a fragment of a polypeptide, which has been altered by the introduction of amino acid residue substitutions, deletions or additions. The term "derivative" as used herein also refers to a polypeptide or a fragment of a polypeptide, which has been chemically modified, e.g., by the covalent attachment of any type of molecule to the polypeptide. For example, but not by way of limitation, a polypeptide or a fragment of a polypeptide can be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a polypeptide or a fragment of a polypeptide can be chemically modified by chemical modifications using techniques known to those of skill in the art, including, but not limited to specific chemical cleavage, acetylation, formulation, metabolic synthesis of tunicamycin, etc. Further, a derivative of a polypeptide or a fragment of a polypeptide can contain one or more non-classical amino acids. A polypeptide derivative may possess a similar or identical function as a polypeptide or a fragment of a polypeptide described herein.

The term "effective amount" as used herein refers to the amount of a therapy (e.g., a BRD7 antagonist, Ikaros antagonist, CRBN activator, or pharmaceutical composition provided herein) which is sufficient to reduce and/or ameliorate the severity and/or duration of a given CNS cell defective disease, disorder or condition and/or a symptom related thereto. This term also encompasses an amount necessary for the reduction or amelioration of the advancement or progression of a given CNS cell defective disease, disorder or condition, reduction or amelioration of the recurrence, development or onset of a given CNS cell defective disease, disorder or condition, and/or to improve or enhance the prophylactic or therapeutic effect(s) of another therapy (e.g., a therapy other than BRD7 antagonist, Ikaros antagonist, or CRBN activator provided herein). In some embodiments, the effective amount of a BRD7 antagonist, Ikaros antagonist, or CRBN activator provided herein is from about 0.1 mg/kg (mg of BRD7 antagonist, Ikaros antagonist, or CRBN activator per kg weight of the subject) to about 100 mg/kg. In certain embodiments, an effective amount of a BRD7 antagonist, Ikaros antagonist, or CRBN activator provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, or about 100 mg/kg (or a range therein). In some embodiments, "effective amount" as used herein also refers to the amount of a BRD7 antagonist, Ikaros antagonist, or CRBN activator provided herein to achieve a specified result (e.g., modulation of a CRBN biological activity in a cell; or expansion of a population of CNS cells).

The term "engraftment" as used herein refers to the process by which transplanted CNS cells (or CNS progenitor/precursor cells thereof) are accepted by a host tissue, survive and persist in that environment. In certain embodiments, the transplanted CNS cells further reproduce or proliferate.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.) (See, also, Remington's Pharmaceutical Sciences (1990) Mack Publishing Co., Easton, Pa., which is hereby incorporated by reference in its entirety).

As used herein, a population of cells is "expanded" when it is propagated in vitro or in vivo and gives rise by cell division to other cells. Expansion of cells can spontaneously occur as cells proliferate, e.g., in a culture, or may require certain growth conditions, such as confluence on the surface of a cell culture plate, a minimum cell density, or the addition of agents, such as growth, differentiation or signaling factors. In certain embodiments, the cells are CNS cells. In other embodiments, the cells are CNS progenitor cells. In other embodiments, the cell are CNS precursor cells. In other embodiments, the cells are stem cells. In yet other embodiments, the cells are neural stem cells. In some embodiments, the cells are neural progenitor cells. In some embodiments, the cells are neural precursor cells. In other embodiments, the cells are nerve cells or neurons.

As used herein, the term "functional derivatives" is intended to include derivatives of CRBN's natural binding proteins in the cell, and their muteins and fused proteins, which may be prepared from the functional groups which occur as side chains on the residues or the N- or C-terminal groups, by means known in the art, and they are contemplated herein as long as they remain pharmaceutically acceptable, for example, they do not confer toxic properties on compositions containing it.

The terms "generate," "generation" and "generating" as used herein refer to the production of new ells in a subject. In some embodiments, generation of cells comprises regeneration of the cells. In certain embodiments, generation of cells comprises improving survival, engraftment and/or proliferation of the cementss. In certain embodiments, the cells are CNS cells. In other embodiments, the cells are CNS progenitor cells. In other embodiments, the cells are CNS precursor cells.

As used herein, the term "host versus graft (HVG) rejection" or "host versus graft response" refers to a cell-mediated reaction in which host immune system cells attack the foreign grafted or transplanted material (e.g., CNS cells). As used herein, the terms "graft versus host (GVH) rejection" or "graft versus host response" refer to a cell-mediated reaction, in which T-cells of the transplanted material react with antigens of the host.

The term "host" as used herein refers to an animal, such as a mammal, such as a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that can occur in succeeding generations or integration of the nucleic acid molecule into the host cell genome.

The term "immunomodulatory agent" and variations thereof including, but not limited to, immunomodulatory agents, as used herein refer to an agent that modulates a host's immune system. In certain embodiments, an immunomodulatory agent used in the combination therapies provided herein does not include a BRD7 antagonist, Ikaros antagonist, or CRBN activator. Immunomodulatory agents include, but are not limited to, small molecules, peptides, polypeptides, proteins, fusion proteins, antibodies, inorganic molecules, mimetic agents, and organic molecules. The term "small molecule" and analogous terms include, but are not limited to, peptides, peptidomimetics, amino acids, amino acid analogues, polynucleotides, polynucleotide analogues, nucleotides, nucleotide analogues, organic or inorganic compounds (i.e., including heterorganic and/or ganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. In certain embodiments, an immunomodulatory agent is an immunostimulatory agent. In specific embodiments, an immunomodulatory agent is an immunosuppressant agent.

As used herein, the term "immunosuppressive agent" refers to any agent that prevents, delays the occurrence, or reduces the intensity of an immune reaction against a foreign cell in a host, such as a transplanted CNS cell, or a CNS progenitor/precursor cell thereof. In certain embodiments, an immunosuppressive agent provided herein suppresses a cell-mediated immune response against cells that are identified as non-self by a host immune system. Exemplary immunosuppressive agents include, but are not limited to, dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, a corticosteroid (e.g., acetonide, alclometasone dipropionate, amcinonide, betamethasone dipropionate, betamethasone sodium phosphate, betamethasone valerate, betamethasone, budesonide, clobetasol-17-propionate, cortisone acetate, desonide, dexamethasone sodium phosphate, dexamethasone, fluocinolone, acetonide, fluocinonide, fluocortolone caproate, fluocortolone pivalate, fluprednidene acetate, fluocortolone, halcinonide, halometasone, hydrocortisone acetate, hydrocortisone, hydrocortisone-17-aceponate, hydrocortisone-17-buteprate, hydrocortisone-17-butyrate, hydrocortisone-17-valerate, methylprednisolone, mometasone, prednicarbate, prednicarbate, clobetasone-17-butyrate, prednisolone, prednisone, tixocortol pivalate, or triamcinolone alcohol), an antibody against CD3, an antibody against CD20, antithymocyte globulin, cyclophosphamide, FK506, mycophenolic acid, 15-deoxyspergualin, mimoribine, misoprostol, an OKT3 antibody, anti-IL-2 receptor antibody, or any combination thereof. Other immunosuppressive agents include a broad array of receptor agonists, receptor antagonists and antibodies known to those skilled in the art.

The term "immune response" as used herein refers to an immune system response to a foreign substance. Such an immune response can include, but is not limited to, antibody production, transplant or graft rejection, inflammation, or the response of antigen specific lymphocytes to antigen. Immune response can be detected by any means known in the art, for example, by determining if transplanted cells have been successfully engrafted or rejected. Graft rejection can be analyzed, for example, by staining for viability or performing immunocytochemical staining at the site of the grafted material at a suitable time following transplantation. Transplanted cells or tissue is successfully engrafted (e.g., little to no rejection) if the transplanted cells or tissue is still detectable at the site or has further proliferated into a cell or tissue mass. Immune responses can be dampened or prevented, thereby increasing the chances for successful engraftment, for example, by using an immunomodulatory agent, such as an immunosuppressive agent, provided herein. In certain embodiments, an immune response occurs if production of a specific antibody (e.g., that binds specifically to an antigen on the transplanted material) is detected using immunological methods known in the art, such as Western blot analysis, enzyme-linked immunosorbant assays (ELISA), immunostaining, and immunoprecipitation.

The term "immunosuppression" as used herein refers to prevention of the immune response (e.g., by administration of an immunomodulatory agent, such as an immunosuppressive agent) in an effective amount to decrease the intensity or eliminate to a level below detection of an immune response of a subject. The term "immunosuppression as used herein also refers a decrease in the intensity of an immune response. In some embodiments, the intensity of an immune response is decreased from about 5% to about 100%, such as from about 50% to 100% or from about 75% to about 100%, of the intensity of the immune response of a transplant recipient that has not received an immunosuppressive agent. In certain embodiments, the intensity of an immune response is measured by determining the time point at which transplanted material is rejected, or by assessing the amount of an antibody that can bind to the transplanted material that directly correlates with immune response intensity. In other embodiments, immune response intensity is determined by assessing the time point that the antibody is detected. As used herein, the term "immunosuppression" also refers to a delay in the occurrence or onset of an immune response as compared to a transplant recipient that did not receive the immunosuppressive agent, Such a delay can be of any length, including a short delay (e.g., 1-24 hours, 1-7 days, or 1-4 weeks or any interval thereof), or a long delay (e.g., 1, 2, 3, 6 or 9 months, or 1, 2, 5 or 10 years or longer, or any interval thereof).

As used herein, the term "in combination" in the context of the administration of other therapies refers to the use of more than one therapy. The use of the term "in combination" does not restrict the order in which therapies are administered to a subject. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a CNS cell defective disease, disorder or condition. Any additional therapy can be administered in any order with other additional therapies. In certain embodiments, the BRD7 antagonist, Ikaros antagonist, or CRBN activator provided herein can be administered in combination with one or more therapies (e.g., therapies that are not the BRD7 antagonist, Ikaros antagonist, or CRBN activator provided herein and are currently administered to prevent, treat, manage, and/or ameliorate a CNS cell defective disease, disorder or condition). Non-limiting examples of therapies that can be administered in combination with a BRD7 antagonist, Ikaros antagonist, or CRBN activator provided herein include analgesic agents, anesthetic agents, antibiotics, immunomodulatory agents, or any other agent listed in the "U.S. Pharmacopoeia" and/or "Physician's Desk Reference."

An "isolated" or "purified" BRD7 antagonist, Ikaros antagonist, or CRBN activator is substantially free of cellular material or other contaminating proteins from the cell or tissue source from which the BRD7 antagonist, Ikaros antagonist, or CRBN activator is derived, or substantially free of chemical precursors or other chemicals when chemically synthesized. The language "substantially free of cellular material" includes preparations of a BRD7 antagonist, Ikaros antagonist, or CRBN activator, in which the BRD7 antagonist, Ikaros antagonist, or CRBN activator is separated from cellular components of the cells from which it is isolated or recombinantly produced. Thus, a BRD7 antagonist, Ikaros antagonist, or CRBN activator that is substantially free of cellular material includes preparations of BRD7 antagonist, Ikaros antagonist, or CRBN activator having less than about 30%, 20%, 10%, or 5% (by dry weight) of heterologous protein (also referred to herein as a "contaminating protein"). When a BRD7 antagonist, Ikaros antagonist, or CRBN activator is recombinantly produced, it can also be substantially free of culture medium, i.e., culture medium represents less than about 20%, 10%, or 5% of the volume of the protein preparation. When the BRD7 antagonist, Ikaros antagonist, or CRBN activator is produced by chemical synthesis, it can be substantially free of chemical precursors or other chemicals, i.e., it is separated from chemical precursors or other chemicals which are involved in the synthesis of the protein. Accordingly such preparations of the antagonist have less than about 30%, 20%, 10%, 5% (by dry weight) of chemical precursors or compounds other than the antagonist of interest. In a specific embodiment, BRD7 antagonist, Ikaros antagonist, or CRBN activator provided herein are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding a BRD7 antagonist, Ikaros antagonist, or CRBN activator provided herein is isolated or purified.

As used herein, "isolating" a cell (e.g., a CNS cell, or a CNS progenitor/precursor cell thereof) refers to a process of dissociating or otherwise removing a cell from a tissue sample (e.g., CNS tissue), and separating the cells from other cells or non-cells in the tissue. Isolated cells will generally free from contamination by other cell types and will generally be able to be propagated and expanded. In some embodiments, an isolated cell exists in the presence of a small fraction of other cell types that do not interfere with the utilization of the cell for analysis, production or expansion of the cells. A population of isolated cells can be at least 30%, 40%, 50%, 60%, 70%, 80%, 85%, 90%, 95%, 98%, or 99% pure, or any interval thereof. In a specific embodiment, a population of isolated cells are at least 98% or at least 99% pure. In some embodiments, the isolated cell is an isolated CNS cell.

As used herein, the terms "manage," "managing," and "management" refer to the beneficial effects that a subject derives from a therapy (e.g., a prophylactic or therapeutic agent), which does not result in a cure of the therapy. In certain embodiments, a subject is administered one or more therapies (e.g., prophylactic or therapeutic agents, such as a BRD7 antagonist, Ikaros antagonist, or CRBN activator provided herein) to "manage" a CNS cell-defective CNS cell defective disease, disorder or condition, one or more symptoms thereof, so as to prevent the progression or worsening of the CNS cell defective disease, disorder or condition.

As used herein, the term "neurodegenerative disease" is intended to mean a disease with a condition of progressive loss of structure or function of neurons, including death of neurons. Exemplary neurodegenerative diseases include, but not limited to, Parkinson's, Alzheimer's, and Huntington's disease, Prion disease, Motor neuron diseases (MND), Huntington's Disease (HD), Spinocerebellar ataxia (SCA), Spinal muscular atrophy (SMA), and related disorders.

The terms "optional" or "optionally" as used herein mean that the subsequently described event or circumstance may or may not occur, and that the description includes, without limitation, instances where said event or circumstance occurs and instances in which it does not.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans. As used herein, the term "pharmaceutically acceptable" is also meant to encompass any carrier, which does not interfere with effectiveness of the biological activity of the active ingredient and that is not toxic to the host to which it is administered. By way of example, for parenteral administration, the active protein(s) may be formulated in a unit dosage form for injection in vehicles such as saline, dextrose solution, serum albumin and Ringer's solution.

As used herein, the term "polynucleotide," "nucleotide," nucleic acid" "nucleic acid molecule" and other similar terms are used interchangeable and include DNA, RNA, mRNA and the like.

As used herein, the terms "preserve," "preservation of" and "preserving" in the context of injured tissue refer to protection and/or maintenance of the tissue, or the functions thereof, such that the tissue is not further injured or compromised, or that the rate of further injury or compromise is slowed relative to the rate in the absence of the methods provided herein. In certain embodiments, preserving injured tissue comprises prevention or reduction of the destruction of CNS cells and/or CNS cell function thereof.

As used herein, the terms "prevent," "preventing," and "prevention" refer to the total or partial inhibition of the development, recurrence, onset or spread of a CNS cell defective disease, disorder or condition and/or symptom related thereto, resulting from the administration of a therapy or combination of therapies provided herein (e.g., a combination of prophylactic or therapeutic agents, such as a BRD7 antagonist, Ikaros antagonist, or CRBN activator provided herein). Prevention can be, for example, in subjects predisposed to having a particular disorder(s).

As used herein, a "progenitor cell" is intended to mean a cell that has the capacity to create progeny that are more differentiated than itself. For example, the term may refer to an undifferentiated cell or a cell differentiated to an extent short of final differentiation that is capable of proliferation and giving rise to more progenitor cells having the ability to generate a large number of mother cells that can in turn give rise to differentiated or differentiable daughter cells. In certain embodiments, the term progenitor cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells. A "precursor cell" as use herein refers to a partially differentiated call. Exemplary precursor cells include osteoprogenitor cells such as for example, mesenchymal precursor cells, osteoblasts, and chondroblasts. To the extent the term "progenitor/precursor cell" is used herein, it is understood that a "progenitor cell" or a "precursor cell," or a combination thereof, can be used.

As used herein, the term "prophylactic agent" refers to any agent that can totally or partially inhibit the development, recurrence, onset or spread of a CNS cell defective disease, disorder or condition and/or symptom related thereto in a subject. In certain embodiments, the term "prophylactic agent" refers to a BRD7 antagonist, Ikaros antagonist, or CRBN activator provided herein. In certain other embodiments, the term "prophylactic agent" refers to an agent other than a BRD7 antagonist, Ikaros antagonist, or CRBN activator provided herein. In certain embodiments, a prophylactic agent is an agent which is known to be useful to or has been or is currently being used to prevent a CNS cell defective disease, disorder or condition and/or a symptom related thereto or impede the onset, development, progression and/or severity of a CNS cell defective disease, disorder or condition and/or a symptom related thereto.

The terms "regenerate," "regeneration" and "regenerating" as used herein in the context of injured tissue refer to the process of growing and/or developing new cells and/or new tissue in a CNS that has been injured, for example, injured due to disease. In certain embodiments, CNS tissue regeneration comprises activation and/or enhancement of CNS cell proliferation.

As used herein, the term "regenerating central nervous system" is intended to mean at least partial re-growth or at least partial repair of nervous tissues, cells or cell products in the central nervous system. "Regenerating central nervous system" includes, but is not limited to, at least partial generation of new neurons, glia, axons, myelin, or synapses. "Regenerating central nervous system" also includes, at least partial repair damaged neurons, glia, axons, myelin, or synapses.

The term "rejection" as used herein refers to rejection of a transplanted material, e.g., transplanted CNS cells, by the immune system of the host recipient. In certain embodiments, the term "rejection" refers to 75%, 80%, 85%, 90% or more necrosis of the transplanted cells or tissue caused all, or in part, by a host immune response. In other embodiments, the term "rejection" refers to a 75%, 80%, 85%, 90% or more decrease in viability of the transplanted material, e.g., transplanted CNS cells, as compared to the viability of the transplanted material prior to transplantation, caused all, or in part, by a host immune response. Decreases in viability can be assessed using methods known in the art, such as trypan blue stains. In other embodiments, the term "rejection" refers to the lack of proliferation of the transplanted cells. Exemplary methods of measuring proliferation, included hematoxylin and eosin (H&E) staining, but any methods know in the art can be used. The frequency and/or timing of onset of transplant rejection occurs following transplantation can be dependent on a variety of factors, including the cell type and number of the transplanted material, as well as the host (e.g., whether or not administered an immunosuppressive agent).

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspnea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the Physician's Desk Reference (60th ed., 2006).

As used herein, the term "stem cells" refers to cells that have the capacity to self-renew and to generate differentiated progeny. The term "pluripotent stem cells" refers to stem cells that has complete differentiation versatility, i.e., the capacity to grow into any of the fetal or adult mammalian body's approximately 260 cell types. For example, pluripotent stem cells have the potential to differentiate into three germ layers: endoderm (e.g., blood vessels), mesoderm (e.g., muscle, bone and blood) and ectoderm (e.g., epidermal tissues and nervous system), and therefore, can give rise to any fetal or adult cell type. The term "induced pluripotent stem cells" as used herein refers to differentiated mammalian somatic cells (e.g., adult somatic cells, such as skin) that have been reprogrammed to exhibit at least one characteristic of pluripotency. The term "multipotent stem cells" as used herein refers to a stem cell that has the capacity to grow into any subset of the fetal or adult mammalian body's approximately 260 cell types. For example, certain multipotent stem cells can differentiate into at least one cell type of ectoderm, mesoderm and endoderm germ layers. The term "embryonic stem cells" as used herein refers to stem cells derived from the inner cell mass of an early stage embryo, e.g., human, that can proliferate in vitro in an undifferentiated state and are pluripotent. The term "bone marrow stem cells" as used herein refers to stem cells obtained from or derived from bone marrow. The term "placenta-derived stem cells" or "placental stem cells" as used herein refers to stem cells obtained from or derived from a mammalian placenta, or a portion thereof (e.g., amnion or chorion). The term "amniotic stem cells" as used herein refers to stem cells collected from amniotic fluid or amniotic membrane. The term "embryonic germ cells" as used herein refers to cells derived from primordial germ cells, which exhibit an embryonic pluripotent cell phenotype.

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a CNS cell defective disease, disorder or condition. In another embodiment, the subject is a mammal (e.g., a human) at risk of developing a CNS cell defective disease, disorder or condition.

As used herein, the term "therapeutic agent" refers to any agent that can be used in the treatment, management or amelioration of a CNS cell defective disease, disorder or condition and/or a symptom related thereto. In certain embodiments, the term "therapeutic agent" refers to a BRD7 antagonist, Ikaros antagonist, or CRBN activator provided herein. In certain other embodiments, the term "therapeutic agent" refers to an agent other than a BRD7 antagonist, Ikaros antagonist, or CRBN activator provided herein. In certain embodiments, a therapeutic agent is an agent which is known to be useful for, or has been or is currently being used for the treatment, management or amelioration of a CNS cell defective disease, disorder or condition or one or more symptoms related thereto.

As used herein, the term "therapy" refers to any protocol, method and/or agent that can be used in the prevention, management, treatment and/or amelioration of a CNS cell defective disease, disorder or condition. In certain embodiments, the terms "therapies" and "therapy" refer to a biological therapy, supportive therapy, and/or other therapies useful in the prevention, management, treatment and/or amelioration of a CNS cell defective disease, disorder or condition known to one of skill in the art such as medical personnel.

As used herein, the terms "transplant," "transplantation" and related terms refer to the transfer of a tissue, cells, or an organ, or a portion thereof, from one subject to another subject, from one subject to another part of the same subject, or from one subject to the same part of the same subject. An "autologous transplant" refers to transplantation of a tissue, cells, or a portion thereof from one location to another in the same individual, or transplantation of a tissue or a portion thereof from one individual to another, wherein the two individuals are genetically identical. An "allogeneic transplant" refers to transplantation from one individual to another. An allogeneic transplant can occur between two individuals of the same species, who differ genetically, or between individuals of two different species. A cell provided herein can also be "transplanted" or "introduced" into a subject when it is transferred from a culture vessel into the subject. "Transplantation" of cells can also include the step of isolating a population of cells from a subject and subsequently transferring into a subject, and can optionally include culturing and/or expanding the population of cells. Transplantation can involve transferring a population of cells into a subject by injection of a cell suspension into the subject, surgical implantation of a cell mass into a tissue or organ of the subject, or perfusion of a tissue or organ with a cell suspension. Transplanted cells can, in certain embodiments, be comprised within a population of other cells. In certain embodiments, the cells are CNS cells. In other embodiments, the cells are CNS progenitor cells. In other embodiments, the cells are CNS precursor cells.

As used herein, the terms "treat," "treatment" and "treating" refer to the reduction or amelioration of the progression, severity, and/or duration of a CNS cell defective disease, disorder or condition resulting from the administration of one or more therapies (including, but not limited to, the administration of one or more prophylactic or therapeutic agents, such as a BRD7 antagonist, Ikaros antagonist, or CRBN activator provided herein). In specific embodiments, the agent is a BRD7 antagonist, Ikaros antagonist, or CRBN activator. Treatment as used herein includes, but is not limited to, preserving injured CNS tissue (such as CNS cells), regenerating new CNS tissue (such as CNS cells), increasing CNS cell function, increasing CNS cell mass, or any combination thereof.

5.2 Methods for CNS Cell Expansion

The present invention is based, in part, on the finding that BRD7 inhibits CNS nerve cell development (e.g., proliferation and differentiation), and that BRD7 antagonists are able to increase proliferation and differentiation of cells, such as stem cells or progenitor/precursor cells. The present invention is also based, in part, on the finding that Ikaros inhibits CNS nerve cell development (e.g., proliferation and differentiation), and that Ikaros antagonists are able to increase proliferation and differentiation of cells, such as stem cells or progenitor/precursor cells. The present invention is also based, in part, on the finding that CRBN plays a role in increasing expression of pluripotency genes and neural reprogramming genes, and that CRBN itself and its activators are able to increase proliferation and differentiation of cells, such as stem cells or progenitor/precursor cells. In some embodiments, the cells are neural stem cells or progenitor/precursor cells, which can be differentiated into nerve cells. Accordingly, provided herein are methods generally relating to expansion of stem cells (e.g., neural stem cells) or progenitor/precursor cells (e.g., neural progenitor/precursor cells). Also provided are methods for improving proliferation of certain cells (e.g., CNS cells (such as nerve cells) and CNS progenitor/precursor cells (such as neural stem cells and neural progenitor/precursor cells)). Also provided herein are methods generally related to inducing differentiation of certain cells (e.g., neural stem cells) or progenitor/precursor cells (e.g., neural progenitor/precursor cells) into other cell types (e.g., nerve cells). Further provided herein are methods generally related to the regeneration of certain cells (e.g., nerve cells). Also provided are in vitro and in vivo methods for generating and expanding certain cells, such as CNS cells, as well as stem cells (e.g., neural stem cell), neural progenitor/precursor cells, and other CNS progenitor/precursor cells. Further provided here are methods for engraftment of certain cells (e.g., CNS cells, or CNS progenitor/precursor cells thereof). Further provided are methods for treating an injured CNS tissue (e.g., spinal cord, brain) in a patient. Also provided herein are methods of preventing or treating a CNS cell defective disease, disorder or condition, or a symptom thereof, using an activator of CRBN. Further provided here are methods for assessing the efficacy of the CRBN activator in preventing or treating the CNS cell defective disease, disorder or condition, or a symptom thereof.

In one aspect, provided herein is a method of expanding a population of cells, the method comprising contacting a population of the cells with an effective amount of a BRD7 antagonist, Ikaros antagonist, or CRBN activator, thereby expanding the population of cells. In some embodiments, the cells are contacted with a BRD7 antagonist. In another embodiment, the cells are contacted with an Ikaros antagonist. In other embodiments, the cells are contacted with a CRBN activator. In certain embodiments, the cells are stem cells. In other embodiments, the cells are neural stem cells. In some embodiments, the cells are neural progenitor cells. In some embodiments, the cells are neural precursor cells. In yet other embodiments, the cells are CNS cells, such as nerve cells. In certain embodiments, the cells are CNS progenitor cells. In certain embodiments, the cells are CNS precursor cells. In some embodiments, the method is an in vitro method. In other embodiments, the method is an in vivo or ex vivo method.

In one embodiment, the method further comprises harvesting a population of CNS cells, or CNS progenitor/precursor cells thereof, from a donor. In another embodiment, the method further comprises harvesting a CNS tissue from a donor, wherein the tissue comprises a population of CNS cells, or CNS progenitor/precursor cells thereof. In certain embodiments of the methods provided herein, the method further comprises culturing a CNS tissue. In some embodiments, the method further comprises preparing a CNS tissue into a cell suspension. In some embodiments, the method further comprises transplanting CNS cells, or CNS progenitor/precursor cells thereof, of the expanded population to a patient. In certain embodiments, the CNS cells, or CNS progenitor/precursor cells thereof, are transplanted with one or more other cell types. In certain embodiments, the patient is the donor. In other embodiments, the patient is not the donor.

In another aspect, provided herein is a method of transplanting CNS cells in a patient, the method comprising: (a) harvesting a population of CNS cells, or CNS progenitor/precursor cells thereof, from a donor, (b) culturing the population of CNS cells, or CNS progenitor/precursor cells thereof; (c) contacting the population of CNS cells, or CNS progenitor/precursor cells thereof, with an effective amount of a BRD7 antagonist, Ikaros antagonist, or CRBN activator, thereby expanding the population of CNS cells, or CNS progenitor/precursor cells thereof; and (d) transplanting CNS cells, or CNS progenitor/precursor cells thereof, of the expanded population into the patient. In some embodiments, the cells are contacted with a BRD7 antagonist. In another embodiment, the cells are contacted with an Ikaros antagonist. In other embodiments, the cells are contacted with a CRBN activator. In one embodiment, the method further comprises harvesting a population of CNS cells, or CNS progenitor/precursor cells thereof, from a donor. In another embodiment, the method further comprises harvesting a CNS tissue from a donor, wherein the CNS tissue comprises a population of CNS cells, or CNS progenitor/precursor cells thereof. In some embodiments, the method further comprises dissociating the CNS tissue into a CNS cell suspension. In some embodiments, the method further comprises transplanting CNS cells, or CNS progenitor/precursor cells thereof, of the expanded population to a patient. In certain embodiments, the patient has a CNS cell defective disease, disorder or condition, or a symptom thereof. In certain embodiments, the patient is the donor. In other embodiments, the patient is not the donor.

In certain embodiments, the CNS cells comprise CNS progenitor cells. In some embodiments, the CNS cells consist essentially of CNS progenitor cells. In other embodiments, the CNS cells consist of CNS progenitor cells. In certain embodiments, the CNS cells comprise CNS precursor cells. In some embodiments, the CNS cells consist essentially of CNS precursor cells. In other embodiments, the CNS cells consist of CNS precursor cells.

In another aspect, provided herein is a method of preventing or treating a CNS cell defective disease, disorder or condition, or a symptom thereof, in a patent, comprising: (a) harvesting a population of CNS cells, or CNS progenitor/precursor cells thereof, from a donor, (b) culturing the population of CNS cells, or CNS progenitor/precursor cells thereof, (c) contacting the population of CNS cells, or CNS progenitor/precursor cells thereof, with an effective amount of a BRD7 antagonist, Ikaros antagonist, or CRBN activator, thereby expanding the population of CNS cells, or CNS progenitor/precursor cells thereof; and (d) transplanting CNS cells, or CNS progenitor/precursor cells thereof, of the expanded population into the patient, thereby treating the CNS cell defective disease, disorder or condition, or symptom thereof, in the patient. In some embodiments, the cells are contacted with a BRD7 antagonist. In another embodiment, the cells are contacted with an Ikaros antagonist. In other embodiments, the cells are contacted with a CRBN activator. In one embodiment, the method is a method for preventing a CNS cell defective disease, disorder or condition, or a symptom thereof. In another embodiment, the method is a method for treating a CNS cell defective disease, disorder or condition, or a symptom thereof. In other embodiments, the method comprises harvesting a CNS tissue from a patient, wherein the tissue comprises a population of CNS cells, or CNS progenitor/precursor cells thereof. In some embodiments, the method further comprises dissociating a CNS tissue into a CNS cell suspension. In certain embodiments, the donor is the patient. In other embodiments, the donor is not the patient. In some embodiments, CNS tissue comprising a population of CNS progenitor/precursor cells is cultured in vitro as neurospheres. In certain embodiments, the neurospheres comprise neural stem cells, neural progenitor cells, neural precursor cells, radial glia, or any combination thereof.

In some embodiments of the various methods or various compositions provided herein, the CNS cells are generated or derived from other cells. In certain embodiments, the cells are CNS progenitor cells. In certain embodiments, the cells are CNS precursor cells. In some embodiments, the cells are multipotent cells. In some embodiments, the cells are pluripotent cells. In certain embodiments, the pluripotent cells are stem cells. In some embodiments, the stem cells are embryonic stem cells (e.g., human embryonic stem cells). In other embodiments, the stem cells are induced pluripotent stem cells. In certain embodiments, the cells are bone marrow stem cells, placenta-derived stem cells, amniotic stem cells or embryonic germ cells. In certain embodiment, the CNS cells are neural stem cells. In other embodiments, the CNS cells are neural progenitor cells. In other embodiments, the CNS cells are neural precursor cells. In yet other embodiments, the CNS cells are nerve cells or neurons.

In certain embodiments of the methods provided herein, the population of CNS cells, or CNS progenitor/precursor cells thereof, is also contacted with an agent, for example, an agent that preserves or enhances CNS cells (or CNS progenitor/precursor cells thereof) proliferation, expansion, and/or function. In one embodiment, the agent is growth factor or cytokine. In other embodiments, the agent is selected from the group consisting of epidermal growth factor (EGF), erythropoietin, fibroblast growth factor (FGF), galectin-1, G-CSF, Six3, Lhx2, Foxg1, Sox2, Oct3/4, C-Myc, Klf4, Nanog, NeuroD, Ascl1, Pou3f2/3, Mytl1, Wnt3, Frizzled, β-catenin, Tcf, Lef, NeuroD, Shh, Patched, GPCR, BMP, BMPR, Noggin, Chordin, Follistatin, Notch, Nrp2, Elavl3, Zic2/3, P53, P63, Nodal, ADAMTS1, BMI-1, CRABP1, and thyroid releasing hormone. Any combination of two or more of the foregoing agents is also contemplated. In certain embodiments, one or more of these agents is or are contacted in combination with a BRD7 antagonist, Ikaros antagonist, or CRBN activator. In some embodiments, one or more of these agents is or are contacted in combination with a BRD7 antagonist. In another embodiment, one or more of these agents is or are contacted in combination with an Ikaros antagonist. In other embodiments, one or more of these agents is or are contacted in combination with a CRBN activator.

In some embodiments of the methods provided herein, the method further comprises administering an immunomodulatory agent to the patient. In certain embodiments, the immunomodulatory agent is an immunosuppressive agent. In one embodiment, the immunosuppressive agent prevents an immune response. In some embodiments, the immunosuppressive agent delays the occurrence of an immune response. In other embodiments, the immunosuppressive agent lessens the intensity or severity of an immune response. In some embodiments, the immune response is a transplant rejection. In some embodiments, the immunosuppressive agent is from the group consisting of dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, a corticosteroid (e.g., acetonide, alclometasone dipropionate, amcinonide, betamethasone dipropionate, betamethasone sodium phosphate, betamethasone valerate, betamethasone, budesonide, clobetasol-17-propionate, cortisone acetate, desonide, dexamethasone sodium phosphate, dexamethasone, fluocinolone, acetonide, fluocinonide, fluocortolone caproate, fluocortolone pivalate, fluprednidene acetate, fluocortolone, halcinonide, halometasone, hydrocortisone acetate, hydrocortisone, hydrocortisone-17-aceponate, hydrocortisone-17-buteprate, hydrocortisone-17-butyrate, hydrocortisone-17-valerate, methylprednisolone, mometasone, prednicarbate, prednicarbate, clobetasone-17-butyrate, prednisolone, prednisone, tixocortol pivalate, or triamcinolone alcohol), an antibody against CD3, an antibody against CD20, antithymocyte globulin, cyclophosphamide, FK506, mycophenolic acid, 15-deoxyspergualin, mimoribine, misoprostol, an OKT3 antibody, anti-IL-2 receptor antibody, or any combination thereof. The immunosuppressive agent(s) can be administered at the beginning, for example, 24 to 0 hours prior to administration of the CNS cells, or CNS progenitor/precursor cells thereof, to the patient and continuing up to two weeks thereafter. The immunosuppressive agent can be administered for any time period following administration the CNS cells, or CNS progenitor/precursor cells thereof, for example, at least 4, 5, 6, 7, 8, 9, 10, 11, 12, 13, 14 days or longer, or any interval time thereof.

In another aspect, provided herein is a method of expanding a population of cells in a patient, comprising contacting the population of cells in the patient with an effective amount of a BRD7 antagonist, Ikaros antagonist, or CRBN activator, thereby expanding the population of cells in the patient. In one embodiment, the cells are progenitor cells. In some embodiments, the cells are contacted with a BRD7 antagonist. In another embodiment, the cells are contacted with an Ikaros antagonist. In other embodiments, the cells are contacted with a CRBN activator. In some embodiments, the cells are CNS progenitor cells. In one embodiment, the cells are precursor cells. In some embodiments, the cells are CNS precursor cells. In certain embodiments, the cells are stem cells. In other embodiments, the cells are neural stem cells. In some embodiments, the cells are neural progenitor cells. In some embodiments, the cells are neural precursor cells. In yet other embodiments, the cells are CNS cells. In some embodiments, the cells are nerve cells. In certain embodiments, the method comprises administering to the CNS an effective amount of a BRD7 antagonist, Ikaros antagonist, or CRBN activator. In some embodiments, the cells are contacted directly with the BRD7 antagonist, Ikaros antagonist, or CRBN activator. In other embodiments, the cells are contacted indirectly with the BRD7 antagonist, Ikaros antagonist, or CRBN activator.

In some embodiments, the cells are expanded by from about 10% to about 100%, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%, or any range of the recited percentages thereof. In certain embodiments, the CNS cell mass or population is increased from about 10% to about 10-fold, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 2-fold, about 3-fold, about 4-fold, about 5-fold, about 6-fold, about 7-fold, about 8-fold, about 9-fold or about 10-fold, or any range or interval thereof. In some embodiments, the cells are expanded to an amount within about 20%, about 10%, or about 5% of the number of cells present in the general population (e.g., as determined by an average or median).

In other embodiments, the method further comprises harvesting the CNS tissue and/or population of CNS cells, or CNS progenitor/precursor cells thereof. In some embodiments, the method further comprises culturing the harvested CNS tissue and/or CNS cells, or CNS progenitor/precursor cells thereof. In certain embodiments, the method further comprises contacting the harvested CNS tissue and/or CNS cells, or CNS progenitor/precursor cells thereof, with an effective amount of a BRD7 antagonist, Ikaros antagonist, or CRBN activator, thereby further expanding the population of CNS cells, or CNS progenitor/precursor cells thereof. In an embodiment, the method further comprises transplanting the expanded population of CNS cells, or CNS progenitor/precursor cells thereof, into a transplant recipient. In some embodiments, the transplant recipient is the patient. In other embodiments, the transplant recipient is not the patient. In certain embodiments, the CNS tissue and/or CNS cells, or CNS progenitor/precursor cells thereof, are harvested from a donor. In certain embodiments, the donor is the patient. In other embodiments, the donor is not the patient. In some embodiments, the donor is a cadaver.

In some embodiments, the patient has a CNS cell defective disease, disorder or condition, or a symptom thereof. In other embodiments, the transplant recipient has a CNS cell defective disease, disorder or condition, or a symptom thereof. In certain embodiments, one or more symptoms is or are prevented or treated.

In some aspects, provided herein are methods for regenerating nerve cells in a subject, comprising administering to the subject an effective amount of a BRD7 antagonist, Ikaros antagonist, or CRBN activator. In some embodiments, a BRD7 antagonist is administered. In another embodiment, an Ikaros antagonist is administered. In other embodiments, a CRBN activator is administered. In some embodiments, the methods provided herein induce proliferation of nerve cells and their progenitor/precursor cells. In some embodiments, the methods provide herein induce differentiation into nerve cells.

In some aspects, provided herein are methods for regenerating CNS in a subject, comprising administering to the subject an effective amount of a BRD7 antagonist, Ikaros antagonist, or CRBN activator. In some embodiments, a BRD7 antagonist is administered. In another embodiment, an Ikaros antagonist is administered. In other embodiments, a CRBN activator is administered. In some embodiments, the methods provided herein induce the proliferation of central neural stem cells, neural progenitor cells, neural precursor cells, nerve cells and/or radial glia. In some embodiments, the methods provided herein induce differentiation into nerve cells. In some embodiments, the methods provided herein enlarge brain volume.

In some embodiments, the regeneration includes or results in at least partial re-growth or at least partial repair of nervous tissues, cells or cell products in the central nervous system. In certain embodiments, the regeneration includes or results in at least partial generation of new neurons, glia, axons, myelin, or synapses. In certain embodiments, the regeneration includes or results in at least partial generation or new radial glia. In other embodiments, regeneration includes or results in at least partial repair damaged neurons, glia, axons, myelin, or synapses. In certain embodiments, regeneration includes or results in at least partial repair damaged radial glia. In some embodiments, the regeneration includes or results in the stimulation of proliferation of nerve cells and/or their progenitors or precursors. In yet other embodiments, the regeneration includes or results in the inducement of differentiation into nerve cells.

In certain embodiments, an increase in, for example, CNS cell number and/or function is determined at a time point following contacting CNS cells, or CNS progenitor/precursor cells thereof, and/or CNS tissue with a BRD7 antagonist, Ikaros antagonist, or CRBN activator provided herein. In other embodiments, an increase in, for example, CNS cell number and/or function is determined at a time point following administration of a population of CNS cells, or CNS progenitor/precursor cells thereof, provided herein. In some embodiments, the time point is at 1 week, 2 weeks, 4 weeks, 6 weeks, 8 weeks, 10 weeks, 12 weeks, 4 months, 5 months, 6 months, 7 months, 8 months, 9 months, 10 months, 11 months, 12 months, 2 years, 5 years 10 years or later, of any interval thereof. An increase in CNS cell number can be assessed or quantity using any methods known in the art, for example, PET-scans, point counting, morphology, or mean-infrared imaging probes.

In some embodiments, CNS cell function is improved following contact of a CNS cell with an effective amount of a BRD7 antagonist, Ikaros antagonist, or CRBN activator provided herein, for example, as compared to CNS cells, or CNS progenitor/precursor cells thereof, that have not been contacted with the BRD7 antagonist, Ikaros antagonist, or CRBN activator. In some embodiments of the methods provided herein the CNS cell improvement can be assessed by an increase in expression levels of Oct 3/4, Nanog, NeuroD, Sox2, Zic3, Huc, Brn2, Ascl1, Pou3f2b, Myt1l, a BAM factor, or a Yamanaka factor.

In some embodiments of the methods provided herein, the effective amount is from about 1 mg/kg to about 100 mg/kg.

In certain embodiments, the effective amount is administered in one or more doses, such as 1, 2, 3, 4, 5, 6, 7, 8, 9, 10 or more doses, or any interval thereof. In other embodiments, the effective amount is delivered weekly for four or more weeks, such as about 5 weeks, about 6 weeks, about 8 weeks, about 10 weeks, about 12 weeks, about 4 months, about 5 months, about 6 months, about 1 year, about 2 years or longer, or any interval thereof.

In certain embodiments, antagonists of BRD7 include, but not limited to, inhibitors of BRD7 protein, a nucleic acid comprising at least part of nucleic acid sequence of BRD7 gene, and a stem cell or a neural progenitor or precursor cell in which BRD7 is down-regulated.

In certain embodiments, antagonists of Ikaros include, but not limited to, inhibitors of Ikaros protein, a nucleic acid comprising at least part of nucleic acid sequence of Ikaros gene, and a stem cell or a neural progenitor or precursor cell in which Ikaros is down-regulated.

In certain embodiments, an activator of CRBN includes, but is not limited to, an active modulator of CRBN protein, a nucleic acid comprising at least part of nucleic acid sequence of CRBN gene, or an antisense compound for its inhibitory protein thereof, and a stem cell or a neural progenitor or precursor cell in which CRBN is up-regulated.

In yet another aspect, provided herein is a method for treating an injured CNS tissue in a patient, comprising contacting a population of CNS cells, or CNS progenitor/precursor cells thereof, of the injured CNS tissue in the patient with an effective amount of a BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In another aspect, provided herein is a method for treating an injured CNS tissue in a patient, comprising contacting a population of CNS cells, or CNS progenitor/precursor cells thereof, with an effective amount of a BRD7 antagonist, Ikaros antagonist, or CRBN activator, and contacting the injured CNS tissue of the patient with the CNS cells, or CNS progenitor/precursor cells thereof, such that the injured CNS tissue is treated. In some embodiments, the cells are contacted with a BRD7 antagonist. In another embodiment, the cells are contacted with an Ikaros antagonist. In other embodiments, the cells are contacted with a CRBN activator.

In other aspects, provided herein is a method for treating an injured CNS tissue in a patient, comprising contacting a population of CNS cells, or CNS progenitor/precursor cells thereof, with an effective amount of a BRD7 antagonist, Ikaros antagonist, or CRBN activator, contacting the injured CNS tissue of the patient with the CNS cells, or CNS progenitor/precursor cells thereof, and further contacting the injured CNS tissue with a BRD7 antagonist, Ikaros antagonist, or CRBN activator, such that the injured CNS tissue is treated. In some embodiments, the cells are contacted with a BRD7 antagonist. In another embodiment, the cells are contacted with an Ikaros antagonist. In other embodiments, the cells are contacted with a CRBN activator.

The CNS injury or damage provided herein relates to any injury to the brain or spinal cord, regardless of the age at onset, or the underlying cause. The underlying cause may e.g., be mechanical, or an infection. CNS injury includes e.g., trauma, or any other damage of the brain or spinal cord, and it may also be called neurotrauma. Brain injury may for example include or result in any one, or more, of the following: attention impairment; cognition impairment; language impairment; memory impairment; conduct disorder; motor disorder; and any other neurological dysfunction. Spinal cord injury may for example result in paraplegia or tetraplegia.

Complications or late effects of CNS injury or damage may also be treated and/or prevented in accordance with the methods provided herein. Complications and late effects of brain injuries include, but are not limited to, for example, coma, meningitis, post-traumatic epilepsy, post-traumatic dementia, degeneration of nerve fibers, or post-traumatic syringomyelia, or hemorrhage.

In certain embodiments of the methods provided herein, the injured CNS tissue is the spinal cord. In other embodiments, the injured CNS tissue is brain tissue. In other embodiments, the injured CNS tissue is the cerebral cortex. In certain embodiments, the injured CNS tissue has decreased CNS cell (e.g., nerve cell; neuron) number, function or both.

In another aspect, provided herein is a method of treating or preventing a CNS cell defective disease, disorder or condition, or a symptom thereof, in a patent, comprising: administering to CNS comprising a population of cells in the patient an effective amount of a BRD7 antagonist, Ikaros antagonist, or CRBN activator, wherein the amount is effective to expand the population of cells and/or increase the cell function in the patient, thereby treating or preventing the CNS cell defective disease, disorder or condition, or a symptom thereof. In some embodiments, a BRD7 antagonist is administered. In another embodiment, an Ikaros antagonist is administered. In other embodiments, a CRBN activator is administered.

A CNS cell defective disease, disorder or condition includes, but is not limited to, Alzheimer Disease, Parkinson Disease, Huntington's Disease, Creutzfeldt-Jakob Disease, Progressive Supranuclear Palsy, Corticobasal Degeneration, and other disorders such as Amyotrophic Lateral Sclerosis; Multiple Sclerosis; progressive motor weakness; neuroimmunological disorders, CNS trauma; Alzheimer disease with parkinsonism; bradykinesia; alkinesia; movement disorders that impair fine motor control and finger dexterity; hypophonia; monotonic speech; rigidity; dystonia; inflammation associated with Parkinson Disease; tremors of the face, jaw, tongue, posture; parkinsonian gait; shuffling; short steps; festinating gait; disorders of mood, cognition, sensation, sleep; dementia; depression; drug induced parkinsonism; vascular parkinsonism; multiple system atrophy; progressive supranuclear palsy; disorders with primary tau pathology; cortical basal ganglia degeneration; parkinsonism with dementia; hyperkinetic disorders; chorea; dystonia; Wilson disease; Tourette syndrome; essential tremor; myoclonus; and a tardive movement disorder. In one embodiment, the CNS cell defective disease, disorder or condition is Alzheimer Disease. In another embodiment, the CNS cell defective disease, disorder or condition is Parkinson Disease. In some embodiments, the CNS cell defective disease, disorder or condition is Huntington's Disease. In other embodiments, the CNS cell defective disease, disorder or condition is Creutzfeldt-Jakob Disease. In one embodiment, the CNS cell defective disease, disorder or condition is Progressive Supranuclear Palsy. In another embodiment, the CNS cell defective disease, disorder or condition is Corticobasal Degeneration. In one embodiment, the CNS cell defective disease, disorder or condition is Amyotrophic Lateral Sclerosis. In another embodiment, the CNS cell defective disease, disorder or condition is Multiple Sclerosis. In some embodiments, the CNS cell defective disease, disorder or condition is progressive motor weakness. In other embodiments, the CNS cell defective disease, disorder or condition is a neuroimmunological disorder. In one embodiment, the CNS cell defective disease, disorder or condition is CNS trauma. In another embodiment, the CNS cell defective disease, disorder or condition is Alzheimer disease with parkinsonism. In one embodiment, the CNS cell defective disease, disorder or condition is bradykinesia. In another embodiment, the CNS cell defective disease, disorder or condition is alkinesia. In some embodiments, the CNS cell defective disease, disorder or condition is a movement disorder that impairs fine motor control and finger dexterity. In other embodiments, the CNS cell defective disease, disorder or condition is hypophonia. In one embodiment, the CNS cell defective disease, disorder or condition is monotonic speech. In another embodiment, the CNS cell defective disease, disorder or condition is rigidity. In one embodiment, the CNS cell defective disease, disorder or condition is dystonia. In another embodiment, the CNS cell defective disease, disorder or condition is inflammation associated with Parkinson Disease. In some embodiments, the CNS cell defective disease, disorder or condition is a tremor of the face, jaw, or tongue. In other embodiments, the CNS cell defective disease, disorder or condition is associated with posture. In one embodiment, the CNS cell defective disease, disorder or condition is parkinsonian gait. In another embodiment, the CNS cell defective disease, disorder or condition is shuffling. In one embodiment, the CNS cell defective disease, disorder or condition is short steps. In another embodiment, the CNS cell defective disease, disorder or condition is festinating gait. In some embodiments, the CNS cell defective disease, disorder or condition is a disorder of mood, cognition, sensation or sleep. In other embodiments, the CNS cell defective disease, disorder or condition is dementia. In one embodiment, the CNS cell defective disease, disorder or condition is depression. In another embodiment, the CNS cell defective disease, disorder or condition is drug induced parkinsonism. In one embodiment, the CNS cell defective disease, disorder or condition is vascular parkinsonism. In another embodiment, the CNS cell defective disease, disorder or condition is multiple system atrophy. In some embodiments, the CNS cell defective disease, disorder or condition is progressive supranuclear palsy. In other embodiments, the CNS cell defective disease, disorder or condition is a disorder with primary tau pathology. In one embodiment, the CNS cell defective disease, disorder or condition is cortical basal ganglia degeneration. In another embodiment, the CNS cell defective disease, disorder or condition is parkinsonism with dementia. In one embodiment, the CNS cell defective disease, disorder or condition is hyperkinetic disorders. In another embodiment, the CNS cell defective disease, disorder or condition is chorea. In some embodiments, the CNS cell defective disease, disorder or condition is dystonia. In other embodiments, the CNS cell defective disease, disorder or condition is Wilson disease. In one embodiment, the CNS cell defective disease, disorder or condition is Tourette syndrome. In another embodiment, the CNS cell defective disease, disorder or condition is essential tremor. In one embodiment, the CNS cell defective disease, disorder or condition is myoclonus. In another embodiment, the CNS cell defective disease, disorder or condition is and a tardive movement disorder.

In certain embodiments, the method further comprises assessing the efficacy of the BRD7 antagonist, Ikaros antagonist, or CRBN activator in preventing or treating the CNS cell defective disease, disorder or condition, or a symptom thereof, in the patient, comprising comparing the CNS cell (e.g., nerve cell) number and/or function in the patient before and after administration of the BRD7 antagonist, Ikaros antagonist, or CRBN activator, wherein an increase in CNS cell (e.g., nerve cell; neuron) number and/or function after administration of the BRD7 antagonist, Ikaros antagonist, or CRBN activator as compared to before administration of the BRD7 antagonist, Ikaros antagonist, or CRBN activator is indicative of the efficacy of the BRD7 antagonist, Ikaros antagonist, or CRBN activator in preventing or treating the CNS cell defective disease, disorder or condition, or symptom thereof. In some embodiments, efficacy of the BRD7 antagonist is assessed. In another embodiment, efficacy of the Ikaros antagonist is assessed. In other embodiments, efficacy of the CRBN activator is assessed.

In some embodiments, the method further comprises assessing the efficacy of the BRD7 antagonist, Ikaros antagonist, or CRBN activator in preventing or treating the CNS cell defective disease, disorder or condition, or a symptom thereof, in the patient, comprising comparing expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) in the patient before and after administration of the BRD7 antagonist, Ikaros antagonist, or CRBN activator, wherein an increase in expression levels of the Yamanaka factor (e.g., Oct 3/4, Sox2, c-Myc, Klf4), Nanog, NeuroD, Zic3, Elavl3, and/or the BAM factor (e.g., Brn2 (Pou3f2), Ascl1, Myt1l) after administration of the BRD7 antagonist, Ikaros antagonist, or CRBN activator as compared to before administration of the BRD7 antagonist, Ikaros antagonist, or CRBN activator is indicative of the efficacy of the BRD7 antagonist, Ikaros antagonist, or CRBN activator in preventing or treating the CNS cell defective disease, disorder or condition, or symptom thereof. In some embodiments, efficacy of the BRD7 antagonist is assessed. In another embodiment, efficacy of the Ikaros antagonist is assessed.

In some embodiments, the method further comprises assessing the efficacy of the CRBN activator in preventing or treating the CNS cell defective disease, disorder or condition, or a symptom thereof, in the patient, comprising comparing expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) in the patient before and after administration of the CRBN activator, wherein an increase in expression levels of the Yamanaka factor (e.g., Oct 3/4, Sox2, c-Myc, Klf4), Nanog, NeuroD, Zic3, Elavl3, and/or the BAM factor (e.g., Brn2 (Pou3f2), Ascl1, Myt1l) after administration of the CRBN activator as compared to before administration of the CRBN activator is indicative of the efficacy of the CRBN activator in preventing or treating the CNS cell defective disease, disorder or condition, or symptom thereof.

In some embodiments, the method further comprises assessing the efficacy of the BRD7 antagonist in preventing or treating the CNS cell defective disease, disorder or condition, or a symptom thereof, in the patient, comprising comparing expression levels of Oct 3/4, Nanog, NeuroD, Sox2, Zic3, Huc, Brn2, Ascl1, Myt1l, a BAM factor, or a Yamanaka factor in the patient before and after administration of the antagonist, wherein an increase in expression levels of Oct 3/4, Nanog, NeuroD, Sox2, Zic3, Huc, Brn2, Ascl1, Myt1l, a BAM factor, or a Yamanaka factor after administration of the BRD7 antagonist as compared to before administration of the BRD7 antagonist is indicative of the efficacy of the BRD7 antagonist in preventing or treating the CNS cell defective disease, disorder or condition, or symptom thereof. In some embodiments, the method further comprises one or more subsequent administrations of the BRD7 antagonist to the patient following the assessment of efficacy.

In some embodiments, the method further comprises assessing the efficacy of the Ikaros antagonist in preventing or treating the CNS cell defective disease, disorder or condition, or a symptom thereof, in the patient, comprising comparing expression levels of Oct 3/4, Nanog, NeuroD, Sox2, Zic3, Huc, Sox2, Brn2, Ascl1, Pou3f2b, Myt1l, a BAM factor, or a Yamanaka factor in the patient before and after administration of the antagonist, wherein an increase in expression levels of Oct 3/4, Nanog, NeuroD, Sox2, Zic3, Huc, Sox2, Brn2, Ascl1, Pou3f2b, Myt1l, a BAM factor, or a Yamanaka factor after administration of the Ikaros antagonist as compared to before administration of the Ikaros antagonist is indicative of the efficacy of the Ikaros antagonist in preventing or treating the CNS cell defective disease, disorder or condition, or symptom thereof. In some embodiments, the method further comprises one or more subsequent administrations of the Ikaros antagonist to the patient following the assessment of efficacy.

In some embodiments, the method further comprises one or more subsequent administrations of the BRD7 antagonist, Ikaros antagonist, or CRBN activator to the patient following the assessment of efficacy.

In other embodiments, the method further comprises selecting a group of patients having a CNS cell defective disease, disorder or condition, or a symptom thereof, based on CNS cell (e.g., nerve cell; neuron) number and/or function for the purposes of predicting clinical response, monitoring clinical response, or monitoring patient compliance to dosing with the BRD7 antagonist, Ikaros antagonist, or CRBN activator. In some embodiments, the method is for the purpose of predicting clinical response, monitoring clinical response, or monitoring patient compliance to dosing with the BRD7 antagonist. In some embodiments, the method is for the purpose of predicting clinical response, monitoring clinical response, or monitoring patient compliance to dosing with the Ikaros antagonist. In some embodiments, the method is for the purpose of predicting clinical response, monitoring clinical response, or monitoring patient compliance to dosing with the CRBN activator.

In certain embodiments, the method further comprises selecting a group of patients having a CNS cell defective disease, disorder or condition, or a symptom thereof, based on expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) for the purposes of predicting clinical response, monitoring clinical response, or monitoring patient compliance to dosing with the BRD7 antagonist, Ikaros antagonist, or CRBN activator. In certain embodiments, the levels are as compared to the normal population. In some embodiments, the expression level is of Oct 3/4, Sox 2, c-Myc, Klf4, Nanog, NeuroD, Zic3, Elavl3 (Huc), Brn2 (Pou3f2), Ascl1, Myt1l, or any combination thereof. In one embodiment, the patient is monitored for compliance to dosing with a BRD7 antagonist. In another embodiment, the patient is monitored for compliance to dosing with an Ikaros antagonist. In other embodiments, the patient is monitored for compliance to dosing with a CRBN activator. In certain embodiments, the levels are as compared to the normal population. In some embodiments, the expression level is of Oct 3/4, Sox 2, c-Myc, Klf4, Nanog, NeuroD, Zic3, Elavl3 (Huc), Brn2 (Pou3f2), Ascl1, Myt1l, or any combination thereof. In some embodiments, the expression level is of a Yamanaka factor. In other embodiments, the expression level is of a BAM factor. In one embodiment, the expression level is of Oct 3/4. In another embodiment, the expression level is of Sox 2. In one embodiment, the expression level is of c-Myc. In another embodiment, the expression level is of Klf4. In an embodiment, the expression level is of Nanog. In one embodiment, the expression level is of Zic3. In one embodiment, the expression level is of Elavl3 (Huc). In some embodiments, the expression level is of Brn2 (Pou3f2). In one embodiment, the expression level is of Ascl1. In another embodiment, the expression level is of Myt1l. In some embodiments, the method is for the purpose of predicting clinical response, monitoring clinical response, or monitoring patient compliance to dosing with the BRD7 antagonist. In some embodiments, the method is for the purpose of predicting clinical response, monitoring clinical response, or monitoring patient compliance to dosing with the Ikaros antagonist. In some embodiments, the method is for the purpose of predicting clinical response, monitoring clinical response, or monitoring patient compliance to dosing with the CRBN activator.

In certain embodiments, the method further comprises selecting a group of patients having a CNS cell defective disease, disorder or condition, or a symptom thereof, based on expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) for the purposes of predicting clinical response, monitoring clinical response, or monitoring patient compliance to dosing with the CRBN activator.

In certain embodiments, the method further comprises selecting a group of patients having a CNS cell defective disease, disorder or condition, or a symptom thereof, based on expression levels of Oct 3/4, Nanog, NeuroD, Sox2, Zic3, Huc, Brn2, Ascl1, Myt1l, a BAM factor, or a Yamanaka factor for the purposes of predicting clinical response, monitoring clinical response, or monitoring patient compliance to dosing with the BRD7 antagonist. In certain embodiments, the levels are as compared to the normal population. In some embodiments, the expression level is Oct 3/4, Nanog, NeuroD, Sox2, Zic3, Huc, or any combination thereof.

In certain embodiments, the method further comprises selecting a group of patients having a CNS cell defective disease, disorder or condition, or a symptom thereof, based on expression levels of Oct 3/4, Nanog, NeuroD, Sox2, Zic3, Huc, Sox2, Brn2, Ascl1, Pou3f2b, Myt1l, a BAM factor, or a Yamanaka factor for the purposes of predicting clinical response, monitoring clinical response, or monitoring patient compliance to dosing with the Ikaros antagonist. In certain embodiments, the levels are as compared to the normal population. In some embodiments, the expression level is Oct 3/4, Nanog, NeuroD, Sox2, Zic3, Sox2, Ascl1, Pou3f3a, Pou3f2b or Myt1la, or any combination thereof.

In certain embodiments, the method further comprises selecting a group of patients having a CNS cell defective disease, disorder or condition, or a symptom thereof, based on expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) for the purposes of predicting clinical response, monitoring clinical response, or monitoring patient compliance to dosing with the CRBN activator.

In another aspect, provided herein is a method for improving survival of a CNS cell (e.g., nerve cell; neuron) in a CNS tissue, comprising contacting the CNS cell with an effective amount of a BRD7 antagonist, Ikaros antagonist, or CRBN activator, such that survival of the CNS cell is improved relative to the survival of a CNS cell that have not been contacted with the BRD7 antagonist, Ikaros antagonist, or CRBN activator. In some embodiments, the cell is contacted with a BRD7 antagonist. In another embodiment, the cell is contacted with an Ikaros antagonist. In other embodiments, the cell is contacted with a CRBN activator.

In another aspect, provided herein is a method for improving survival of a CNS progenitor cell (e.g., a neural stem cell or a neural progenitor cells) in a CNS tissue, comprising contacting the CNS progenitor cell with an effective amount of a BRD7 antagonist, Ikaros antagonist, or CRBN activator, such that survival of the CNS progenitor cell is improved relative to the survival of a CNS progenitor cell that has not been contacted with the BRD7 antagonist, Ikaros antagonist, or CRBN activator. In some embodiments, the cell is contacted with a BRD7 antagonist. In another embodiment, the cell is contacted with an Ikaros antagonist. In other embodiments, the cell is contacted with a CRBN activator. In one embodiment, the CNS progenitor cells are further differentiated into CNS cells. Also provided herein is a method for improving survival of a CNS precursor cell (e.g., a neural precursor cell) in a CNS tissue, comprising contacting the CNS precursor cell with an effective amount of a BRD7 antagonist, Ikaros antagonist, or CRBN activator, such that survival of the CNS precursor cell is improved relative to the survival of a CNS precursor cell that has not been contacted with the BRD7 antagonist, Ikaros antagonist, or CRBN activator. In some embodiments, the cell is contacted with a BRD7 antagonist. In another embodiment, the cell is contacted with an Ikaros antagonist. In other embodiments, the cell is contacted with a CRBN activator. In one embodiment, the CNS precursor cells are further differentiated into CNS cells.

In another aspect, provided herein is a method for generating CNS cells in a patient, comprising contacting a population of CNS cells with an effective amount of a BRD7 antagonist, Ikaros antagonist, or CRBN activator, such that CNS cells are generated. In some embodiments, the cells are contacted with a BRD7 antagonist. In another embodiment, the cells are contacted with an Ikaros antagonist. In other embodiments, the cells are contacted with a CRBN activator.

In another aspect, provided herein is a method for generating CNS cells in a patient, comprising contacting a population of CNS progenitor cells with an effective amount of a BRD7 antagonist, Ikaros antagonist, or CRBN activator, such that CNS cells are generated. In some embodiments, the cells are contacted with a BRD7 antagonist. In another embodiment, the cells are contacted with an Ikaros antagonist. In other embodiments, the cells are contacted with a CRBN activator. In one embodiment, the CNS progenitor cells are further differentiated into CNS cells. Also provided herein is a method for generating CNS cells in a patient, comprising contacting a population of CNS precursor cells with an effective amount of a BRD7 antagonist, Ikaros antagonist, or CRBN activator, such that CNS cells are generated. In one embodiment, the CNS precursor cells are further differentiated into CNS cells.

In another aspect, provided herein is a method for engraftment of CNS cells in a CNS tissue of a patient, comprising contacting a population of CNS cells with an effective amount of a BRD7 antagonist, Ikaros antagonist, or CRBN activator, and contacting the CNS tissue with the CNS cells, such that engraftment of the CNS cells occurs. In some embodiments, the cells are contacted with a BRD7 antagonist. In another embodiment, the cells are contacted with an Ikaros antagonist. In other embodiments, the cells are contacted with a CRBN activator. In an embodiment, the method further comprises contacting the CNS tissue with a BRD7 antagonist, Ikaros antagonist, or CRBN activator.

In another aspect, provided herein is a method for engraftment of CNS progenitor cells in a CNS tissue of a patient, comprising contacting a population of CNS progenitor cells with an effective amount of a BRD7 antagonist, Ikaros antagonist, or CRBN activator, and contacting the CNS tissue with the CNS progenitor cells, such that engraftment of the CNS progenitor cells occurs. In some embodiments, the cells are contacted with a BRD7 antagonist. In another embodiment, the cells are contacted with an Ikaros antagonist. In other embodiments, the cells are contacted with a CRBN activator. In an embodiment, the method further comprises contacting the CNS tissue with a BRD7 antagonist, Ikaros antagonist, or CRBN activator. In certain embodiment, the CNS progenitor cells are further differentiated into CNS cells. Also provided herein is a method for engraftment of CNS precursor cells in a CNS tissue of a patient, comprising contacting a population of CNS precursor cells with an effective amount of a BRD7 antagonist, Ikaros antagonist, or CRBN activator, and contacting the CNS tissue with the CNS precursor cells, such that engraftment of the CNS precursor cells occurs. In some embodiments, the cells are contacted with a BRD7 antagonist. In another embodiment, the cells are contacted with an Ikaros antagonist. In other embodiments, the cells are contacted with a CRBN activator. In an embodiment, the method further comprises contacting the CNS tissue with a BRD7 antagonist, Ikaros antagonist, or CRBN activator. In certain embodiment, the CNS precursor cells are further differentiated into CNS cells.

In another aspect, provided herein is a method for improving proliferation of CNS cells in a CNS tissue of a patient, comprising contacting a population of CNS cells with an effective amount of a BRD7 antagonist, Ikaros antagonist, or CRBN activator, and contacting the CNS tissue with the CNS cells, such that proliferation of the CNS cells is improved relative to proliferation of CNS cells that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In another aspect, provided herein is a method for improving proliferation of CNS progenitor cells in a CNS tissue of a patient, comprising contacting a population of CNS progenitor cells with an effective amount of a BRD7 antagonist, Ikaros antagonist, or CRBN activator, and contacting the CNS tissue with the CNS progenitor cells, such that proliferation of the CNS progenitor cells is improved relative to proliferation of CNS progenitor cells that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. In one embodiment, the CNS progenitor cells are further differentiated into CNS cells. Also provided herein is a method for improving proliferation of CNS precursor cells in a CNS tissue of a patient, comprising contacting a population of CNS precursor cells with an effective amount of a BRD7 antagonist, Ikaros antagonist, or CRBN activator, and contacting the CNS tissue with the CNS precursor cells, such that proliferation of the CNS precursor cells is improved relative to proliferation of CNS precursor cells that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. In one embodiment, the CNS precursor cells are further differentiated into CNS cells.

In other aspects, provided herein is a method for increasing CNS cell number and/or function in a CNS tissue of a patient, comprising contacting a population of CNS cells with an effective amount of a BRD7 antagonist, Ikaros antagonist, or CRBN activator, and contacting the CNS tissue with the CNS cells, such that CNS cell number and/or function is improved relative to CNS cell number and/or function prior to contact with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In another aspect, provided herein is a method for increasing CNS progenitor cell number and/or function in a CNS tissue of a patient, comprising contacting a population of CNS progenitor cells with an effective amount of a BRD7 antagonist, Ikaros antagonist, or CRBN activator, and contacting the CNS tissue with the CNS progenitor cells, such that CNS progenitor cell number and/or function is improved relative to CNS progenitor cell number and/or function prior to contact with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. In one embodiment, the CNS progenitor cells are further differentiated into CNS cells. In another aspect, provided herein is a method for increasing CNS precursor cell number and/or function in a CNS tissue of a patient, comprising contacting a population of CNS precursor cells with an effective amount of a BRD7 antagonist, Ikaros antagonist, or CRBN activator, and contacting the CNS tissue with the CNS precursor cells, such that CNS precursor cell number and/or function is improved relative to CNS precursor cell number and/or function prior to contact with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. In one embodiment, the CNS precursor cells are further differentiated into CNS cells.

In other aspects, provided herein is a method for increasing CNS cell number and/or function in a CNS tissue of a patient, comprising contacting a population of CNS progenitor cells with an effective amount of a BRD7 antagonist, Ikaros antagonist, or CRBN activator, wherein the CNS progenitor cells are optionally further differentiated into CNS cells, and contacting the CNS tissue with the CNS progenitor cells and/or CNS cells, such that CNS progenitor cell number and/or function is improved relative to CNS cell number and/or function prior to contact with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. Also provided herein is a method for increasing CNS cell number and/or function in a CNS tissue of a patient, comprising contacting a population of CNS precursor cells with an effective amount of a BRD7 antagonist, Ikaros antagonist, or CRBN activator, wherein the CNS precursor cells are optionally further differentiated into CNS cells, and contacting the CNS tissue with the CNS precursor cells and/or CNS cells, such that CNS precursor cell number and/or function is improved relative to CNS cell number and/or function prior to contact with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator.

In certain embodiments of the various methods or compositions provided herein, a population of CNS cells, or CNS progenitor/precursor cells thereof, are contacted with the BRD7 antagonist, Ikaros antagonist, or CRBN activator in vitro. In other embodiments, a population of CNS cells, or CNS progenitor/precursor cells thereof, are contacted with the BRD7 antagonist, Ikaros antagonist, or CRBN activator ex vivo. In some embodiments, the cells are contacted with a BRD7 antagonist. In another embodiment, the cells are contacted with an Ikaros antagonist. In other embodiments, the cells are contacted with a CRBN activator. In some embodiments, the CNS cells, or CNS progenitor/precursor cells thereof, are patient CNS cells, or CNS progenitor/precursor cells thereof. In other embodiments, the CNS cells, or CNS progenitor/precursor cells thereof, are donor CNS cells, or CNS progenitor/precursor cells thereof. In another embodiment, the patient has a CNS cell defective disease, disorder or condition, or a symptom thereof.

In some embodiments, of the various methods or compositions provided herein, the patient is a patient in need thereof.

In certain embodiments of the various methods or compositions provided herein, the CNS cell defective disease, disorder or condition is a disease of cerebral cortex. In other embodiments, the CNS cell defective disease, disorder or condition is a surgical injury of cerebral cortex. Also contemplated, and methods for regenerating cerebral cortex by administering a BRD7 antagonist, Ikaros antagonist, or CRBN activator provided herein. Exemplary diseases of cerebral cortex include Alzheimer's disease, Parkinson's disease, Creutzfeldt-Jakob disease, Huntington's disease, progressive supranuclear palsy, and corticobasal degeneration. In some embodiments, the CNS cell defective disease, disorder or condition is a neurodegenerative disease.

In specific embodiments, provided herein is a method for treating, preventing, or managing a CNS cell defective disease, disorder or condition, or a symptom thereof, wherein the CNS cell defective disease, disorder or condition is selected from the group consisting of Parkinson disease; Alzheimer disease; Creutzfeldt-Jakob disease; corticobasal degeneration; Amyotrophic Lateral Sclerosis; Multiple Sclerosis; progressive motor weakness; neuroimmunological disorders, CNS trauma; Alzheimer disease with parkinsonism; bradykinesia; alkinesia; movement disorders (e.g., those that impair fine motor control and finger dexterity); hypophonia; monotonic speech; rigidity; dystonia; inflammation associated with Parkinson Disease; tremors of the face, jaw, tongue, posture; parkinsonian gait; shuffling; short steps; festinating gait; disorders of mood, cognition, sensation, sleep; dementia; depression; drug induced parkinsonism; vascular parkinsonism; multiple system atrophy; progressive supranuclear palsy; disorders with primary tau pathology; cortical basal ganglia degeneration; parkinsonism with dementia; hyperkinetic disorders; chorea; Huntington's disease; dystonia; Wilson disease; Tourette syndrome; essential tremor; myoclonus; or a tardive movement disorder.

In one embodiment, the methods provided herein are used to prevent or treat disorders related to movement, including, but not limited to, progressive motor deterioration, slow execution or bradykinesia, paucity of movement or akinesia, movement disorders that impair fine motor control and finger dexterity, and other manifestations of bradykinesia, such as, but not limited to, hypophonia and monotonic speech. In another embodiment, the methods provided herein are used to treat or prevent disorders related to muscular rigidity, including, but not limited to, a uniform increase in resistance to passive movement, interruptions to passive movement, and combinations of rigidity and dystonia. In a specific embodiment, methods provided herein are used to treat inflammation associated with Parkinson or related disease. In yet another embodiment, disorders resembling Parkinsonian tremor are treated or prevented by the methods provided herein, including but not limited to, tremors of the face, jaw, tongue, posture, and other tremors that are present at rest and that attenuate during movement. In another embodiment, the methods provided herein are used to treat or prevent disorders in gait, including, but not limited to, those resembling parkinsonian gait, shuffling, short steps, a tendency to turn en bloc, and festinating gait. In another embodiment, nonmotor symptoms are treated or prevented using the methods provided herein, including, but not limited to, disorders of mood, cognition, sensation, sleep, dementia, and depression. In other embodiment, secondary forms of parkinsonism are treated or prevented by the methods provided herein, including, but not limited to, drug induced parkinsonism, vascular parkinsonism, multiple system atrophy, progressive supranuclear palsy, disorders with primary tau pathology, cortical basal ganglia degeneration, parkinsonism with dementia, hyperkinetic disorders, chorea, Huntington's disease, dystonia, Wilson disease, Tourette syndrome, essential tremor, myoclonus, and tardive movement disorders. In other embodiments, other central nervous system disorders are treated or prevented by the methods provided herein, including, but not limited to Alzheimer Disease, Amyotrophic Lateral Sclerosis (ALS) and CNS trauma.

5.2 Methods for Expansion or Other Cells

While several embodiments provided herein relate, for example, to regenerative therapy for CNS, it will be appreciated that the compositions and methods provided herein can also be useful for other tissue and cell types.

Thus, in one aspect, provided herein is a method of expanding a population of cells, the method comprising contacting a population of cells with an effective amount of a BRD7 antagonist, Ikaros antagonist, or CRBN activator, thereby expanding the population of cells. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiments, the cells are neural crest stem cells. Other tissue stem cells and tissue progenitor/precursor cells are also contemplated herein. In some embodiments, the method is an in vitro method. In other embodiments, the method is an in vivo or ex vivo method.

In certain embodiments of the methods provided herein, the population of cells is also contacted with an agent that preserves or enhances the cell proliferation, expansion, differentiation and/or function. In one embodiment, the agent is growth factor or cytokine. In other embodiments, the agent is selected from the group consisting of epidermal growth factor (EGF), erythropoietin, fibroblast growth factor (FGF), galectin-1, G-CSF, Six3, Lhx2, Foxg1, Sox2, Oct3/4, c-Myc, Klf4, Nanog, NeuroD, Ascl1, Pou3f2/3, Myt1l, Wnt3, Frizzled, β-catenin, Tcf, Lef, NeuroD, Shh, Patched, GPCR, BMP, BMPR, Noggin, Chordin, Follistatin, Notch, Nrp2, Elavl3, Zic2/3, P53, P63, Nodal, ADAMTS1, BMI-1, CRABP1, and thyroid releasing hormone. In certain embodiments, the agent is a Yamanaka factor. In other embodiments, the agent is a BAM factor.

In another aspect, provided herein is a method of expanding a population of cells in a patient, comprising contacting the population of cells in the patient with an effective amount of a BRD7 antagonist, Ikaros antagonist, or CRBN activator, thereby expanding the population of cells in the patient. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells and tissue progenitor/precursor cells are also contemplated herein. In some embodiments, the cells are contacted directly with the BRD7 antagonist, Ikaros antagonist, or CRBN activator. In other embodiments, the cells are contacted indirectly with the BRD7 antagonist, Ikaros antagonist, or CRBN activator.

In some embodiments, the cells are expanded by from about 10% to about 100%, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%, or any range of the recited percentages thereof. In certain embodiments, the cell mass or population is increased from about 10% to about 10-fold, e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 2-fold, about 3-fold, about 4-fold, about 5-fold, about 6-fold, about 7-fold, about 8-fold, about 9-fold or about 10-fold, or any range or interval thereof. In some embodiments, the cells are expanded to an amount within about 20%, about 10%, or about 5% of the number of cells present in the general population (e.g., as determined by an average or median).

In some aspects, provided herein are methods for regenerating cells in a subject, comprising administering to the subject an effective amount of a BRD7 antagonist, Ikaros antagonist, or CRBN activator, thereby regenerating the cells in the subject. In some embodiments, a BRD7 antagonist is administered. In another embodiment, an Ikaros antagonist is administered. In other embodiments, a CRBN activator is administered. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells and tissue progenitor/precursor cells are also contemplated herein.

In some embodiments of the methods provided herein, the effective amount is from about 1 mg/kg to about 100 mg/kg.

In certain embodiments, the effective amount is administered in one or more doses, such as 1, 2, 3, 4, 5, 6, 7, 8, 9, 10 or more doses, or any interval thereof. In other embodiments, the effective amount is delivered weekly for four or more weeks, such as about 5 weeks, about 6 weeks, about 8 weeks, about 10 weeks, about 12 weeks, about 4 months, about 5 months, about 6 months, about 1 year, about 2 years or longer, or any interval thereof.

In certain embodiments, antagonists of BRD7 include, but not limited to, inhibitors of BRD7 protein, a nucleic acid comprising at least part of nucleic acid sequence of BRD7 gene, or an antisense compound thereof, and a stem cell or a neural progenitor/precursor cell in which BRD7 is down-regulated.

In certain embodiments, antagonists of Ikaros include, but not limited to, inhibitors of Ikaros protein, a nucleic acid comprising at least part of nucleic acid sequence of Ikaros gene, or an antisense compound thereof, and a stem cell or a neural progenitor/precursor cell in which Ikaros is down-regulated.

In certain embodiments, an activator of CRBN includes, but is not limited to, an active modulator of CRBN protein, a nucleic acid comprising at least part of nucleic acid sequence of CRBN gene, or an antisense compound for its inhibitory protein thereof, and a stem cell or a neural progenitor/precursor cell in which CRBN is up-regulated.

In another aspect provided herein is a method for treating an injured tissue in a patient, comprising contacting a population of cells with a BRD7 antagonist, Ikaros antagonist, or CRBN activator, such that the injured tissue is treated. In certain embodiments, the population of cells is within or derived from the injured tissue. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells and tissue progenitor/precursor cells are also contemplated herein.

In another aspect, provided herein is a method for treating an injured tissue in a patient, comprising contacting a population of cells with an effective amount of a BRD7 antagonist, Ikaros antagonist, or CRBN activator, and contacting the injured tissue of the patient with the cells, or progenitor/precursor cells thereof, such that the injured tissue is treated. In some embodiments, the cells are contacted with a BRD7 antagonist. In another embodiment, the cells are contacted with an Ikaros antagonist. In other embodiments, the cells are contacted with a CRBN activator. In certain embodiments, the population of cells, or progenitor/precursor cells thereof, are within or derived from the injured tissue. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells and tissue progenitor/precursor cells are also contemplated herein.

In other aspects, provided herein is a method for treating an injured tissue in a patient, comprising contacting a population of cells with an effective amount of a BRD7 antagonist, Ikaros antagonist, or CRBN activator, contacting the injured tissue of the patient with the cells, or progenitor/precursor cells thereof, and further contacting the injured tissue with a BRD7 antagonist, Ikaros antagonist, or CRBN activator, such that the injured tissue is treated. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiments, the cells are neural crest stem cells. Other tissue stem cells and tissue progenitor/precursor cells are also contemplated herein.

In some embodiments of the methods provided herein the injured tissue is liver tissue. In some embodiments, the injured tissue is breast tissue. In certain embodiments, the injured tissue is colon tissue. In some embodiments, the injured tissue is intestine tissue. In other embodiments, the injured tissue is cartilage or bone tissue. In another embodiment, the injured tissue is endothelial tissue. In other embodiments, the injured tissue is skin tissue. In some embodiments, the injured tissue is CNS tissue.

In another aspect, provided herein is a method of treating or preventing a cancer or tumor, or a symptom thereof, in a patent, comprising: contacting a population of cells, such as stem cells, progenitor cells or precursor cells, with an effective amount of a BRD7 antagonist, Ikaros antagonist, or CRBN activator, wherein the amount is effective to expand the population of cells and/or increase the cell function in the patient, thereby treating or preventing the cancer or tumor, or a symptom thereof. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells and tissue progenitor/precursor cells are also contemplated herein.

In certain embodiments, the cancer or tumor is a blood cancer, and the cells are hematopoietic stem cells, progenitor cells or precursor cells. In certain embodiments, the cancer or tumor is a liver cancer (or cirrhosis), and the cells are liver stem cells, progenitor cells or precursor cells. In certain embodiments, the cancer or tumor is a breast cancer, and the cells are mammary stem cells, progenitor cells, or progenitor cells. In certain embodiments, the cancer or tumor is a colonic cancer, and the cells are intestinal stem cells, progenitor cells or precursor cells. In certain embodiments, the cancer or tumor is a intestinal cancer, and the cells are intestinal stem cells, progenitor cells or precursor cells. In certain embodiments, the cancer or tumor is a chondrosarcoma, hamartoma, neoplasm or other cancer, and the cells are mesenchymal stem cells, progenitor cells or precursor cells. In certain embodiments, the cancer or tumor is a endothelial carcinoma, and the cells are endothelial stem cells, progenitor cells or precursor cells. In certain embodiments, the cancer or tumor is a melanoma or other cancer, and the cells are neural crest stem cells, progenitor cells or precursor cells. In certain embodiments, the cells are embryonic stem cells, progenitor cells or precursor cells. In other embodiments, the cells are olfactory adult stem cells, progenitor cell or precursor cells. Stem cells or progenitor cells derived from the cancerous or tumor tissue are also contemplated. In certain embodiments, the method of treating or preventing comprises regeneration of the tissue.

In certain embodiments, the method further comprises assessing the efficacy of the BRD7 antagonist, Ikaros antagonist, or CRBN activator in preventing or treating the cancer or tumor, or a symptom thereof, in the patient, comprising comparing cell number and/or function in the patient before and after administration of the BRD7 antagonist, Ikaros antagonist, or CRBN activator, wherein an increase in cell number and/or function after administration of the BRD7 antagonist, Ikaros antagonist, or CRBN activator as compared to before administration of the BRD7 antagonist, Ikaros antagonist, or CRBN activator is indicative of the efficacy of the BRD7 antagonist, Ikaros antagonist, or CRBN activator in preventing or treating the cancer or tumor or condition, or symptom thereof. In some embodiments, efficacy of the BRD7 antagonist is assessed. In another embodiment, efficacy of the Ikaros antagonist is assessed. In other embodiments, efficacy of the CRBN activator is assessed.

In some embodiments, the method further comprises assessing the efficacy of the BRD7 antagonist in preventing or treating the CNS cell defective disease, disorder or condition, or a symptom thereof, in the patient, comprising comparing expression levels of Oct 3/4, Nanog, NeuroD, Sox2, Zic3, Huc, Brn2, Ascl1, Myt1l, a BAM factor, or a Yamanaka factor in the patient before and after administration of the antagonist, wherein an increase in expression levels of Oct 3/4, Nanog, NeuroD, Sox2, Zic3, Huc, Brn2, Ascl1, Myt1l, a BAM factor, or a Yamanaka factor after administration of the BRD7 antagonist as compared to before administration of the BRD7 antagonist is indicative of the efficacy of the BRD7 antagonist in preventing or treating the CNS cell defective disease, disorder or condition, or symptom thereof.

In some embodiments, the method further comprises assessing the efficacy of the Ikaros antagonist in preventing or treating the CNS cell defective disease, disorder or condition, or a symptom thereof, in the patient, comprising comparing expression levels of Oct 3/4, Nanog, NeuroD, Sox2, Zic3, Huc, Sox2, Brn2, Ascl1, Pou3f2b, Myt1l, a BAM factor, or a Yamanaka factor in the patient before and after administration of the antagonist, wherein an increase in expression levels of Oct 3/4, Nanog, NeuroD, Sox2, Zic3, Huc, Sox2, Brn2, Ascl1, Pou3f2b, Myt1l, a BAM factor, or a Yamanaka factor after administration of the Ikaros antagonist as compared to before administration of the Ikaros antagonist is indicative of the efficacy of the Ikaros antagonist in preventing or treating the CNS cell defective disease, disorder or condition, or symptom thereof.

In some embodiments, the method further comprises assessing the efficacy of the CRBN activator in preventing or treating the cancer or tumor, or a symptom thereof, in the patient, comprising comparing expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) in the patient before and after administration of the CRBN activator, wherein an increase in expression levels of a Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) after administration of the CRBN activator as compared to before administration of the CRBN activator is indicative of the efficacy of the CRBN activator in preventing or treating the cancer or tumor, or symptom thereof.

In some embodiments, the method further comprises one or more subsequent administrations of the BRD7 antagonist, Ikaros antagonist, or CRBN activator to the patient following the assessment of efficacy. In some embodiments, a BRD7 antagonist is administered. In another embodiment, an Ikaros antagonist is administered. In other embodiments, a CRBN activator is administered. In some embodiments, the expression levels assessed are those of pluripotency genes.

In other embodiments, the method further comprises selecting a group of patients having a cancer or tumor, or a symptom thereof, based on cell number and/or function for the purposes of predicting clinical response, monitoring clinical response, or monitoring patient compliance to dosing with the BRD7 antagonist, Ikaros antagonist, or CRBN activator. In some embodiments, the method is for the purpose of predicting clinical response, monitoring clinical response, or monitoring patient compliance to dosing with the BRD7 antagonist. In some embodiments, the method is for the purpose of predicting clinical response, monitoring clinical response, or monitoring patient compliance to dosing with the Ikaros antagonist. In some embodiments, the method is for the purpose of predicting clinical response, monitoring clinical response, or monitoring patient compliance to dosing with the CRBN activator.

In certain embodiments, the method further comprises selecting a group of patients having a CNS cell defective disease, disorder or condition, or a symptom thereof, based on expression levels of Oct 3/4, Nanog, NeuroD, Sox2, Zic3, Huc, Brn2, Ascl1, Myt1l, a BAM factor, or a Yamanaka factor for the purposes of predicting clinical response, monitoring clinical response, or monitoring patient compliance to dosing with the BRD7 antagonist.

In certain embodiments, the method further comprises selecting a group of patients having a CNS cell defective disease, disorder or condition, or a symptom thereof, based on expression levels of Oct 3/4, Nanog, NeuroD, Sox2, Zic3, Huc, Sox2, Brn2, Ascl1, Pou3f2b, Myt1l, a BAM factor, or a Yamanaka factor for the purposes of predicting clinical response, monitoring clinical response, or monitoring patient compliance to dosing with the Ikaros antagonist.

In certain embodiments, the method further comprises selecting a group of patients having a cancer or tumor, or a symptom thereof, based on expression levels of Yamanaka factor (e.g., Oct 3/4, Sox2, c-Myc, Klf4), Nanog, NeuroD, Zic3, Elavl3, and/or a BAM factor (e.g., Brn2 (Pou3f2), Ascl1, Myt1l) for the purposes of predicting clinical response, monitoring clinical response, or monitoring patient compliance to dosing with the CRBN activator.

In yet another aspect, provided herein is a method for improving survival of cells in a tissue, comprising contacting a population of the cells with an effective amount of a BRD7 antagonist, Ikaros antagonist, or CRBN activator, such that survival of the cells is improved relative to the survival of cells that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells, tissue progenitor cells, and tissue precursor cells are also contemplated herein.

In other aspects, provided herein is a method for generating cells in a patient, comprising contacting a population of the cells with an effective amount of a BRD7 antagonist, Ikaros antagonist, or CRBN activator, such that additional cells are generated. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiments, the cells are neural crest stem cells. Other tissue stem cells, tissue progenitor cells, and tissue precursor cells are also contemplated herein.

In other aspects, provided herein is a method for engraftment of cells in a tissue of a patient, comprising contacting a population of the cells with an effective amount of a BRD7 antagonist, Ikaros antagonist, or CRBN activator, and contacting the tissue with the cells, such that engraftment of the cells occurs. In some embodiments, the cells are contacted with a BRD7 antagonist. In another embodiment, the cells are contacted with an Ikaros antagonist. In other embodiments, the cells are contacted with a CRBN activator. In an embodiment, the method further comprises contacting the tissue with a BRD7 antagonist, Ikaros antagonist, or CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells, tissue progenitor cells and tissue precursor cells are also contemplated herein.

In other aspects, provided herein is a method for improving proliferation of cells in a tissue of a patient, comprising contacting a population of the cells with an effective amount of a BRD7 antagonist, Ikaros antagonist, or CRBN activator, and contacting the tissue with the cells, such that proliferation of the cells is improved relative to proliferation of cells that have not been contacted with the BRD7 antagonist, Ikaros antagonist, or CRBN activator. In some embodiments, the cells are contacted with a BRD7 antagonist. In another embodiment, the cells are contacted with an Ikaros antagonist. In other embodiments, the cells are contacted with a CRBN activator. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells, tissue progenitor cells and tissue precursor cells are also contemplated herein.

In other aspects, provided herein is a method for increasing cell number and/or function in a tissue of a patient, comprising contacting a population of the cells with an effective amount of a BRD7 antagonist, Ikaros antagonist, or CRBN activator, and contacting the tissue with the cells, such that cell number and/or function is improved relative to cell number and/or function prior to contact with the BRD7 antagonist, Ikaros antagonist, or CRBN activator. In one embodiment, the cells are progenitor cells. In some embodiments, the cells are contacted with a BRD7 antagonist. In another embodiment, the cells are contacted with an Ikaros antagonist. In other embodiments, the cells are contacted with a CRBN activator. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells, tissue progenitor cells and tissue precursor cells are also contemplated herein.

In certain embodiments of the various methods or compositions provided herein, a population of cells is contacted with the BRD7 antagonist, Ikaros antagonist, or CRBN activator in vitro. In other embodiments, a population of cells is contacted with the BRD7 antagonist, Ikaros antagonist, or CRBN activator ex vivo. In some embodiments, the cells are contacted with a BRD7 antagonist. In another embodiment, the cells are contacted with an Ikaros antagonist. In other embodiments, the cells are contacted with a CRBN activator. In some embodiments, the cells are patient cells. In other embodiments, the cells are donor cells. In another embodiment, the patient has a cancer or tumor, or a symptom thereof. In one embodiment, the cells are progenitor cells. In one embodiment, the cells are precursor cells. In another embodiment, the cells are stem cells. In some embodiments, the cells are hematopoietic stem cells. In other embodiments, the cells are liver stem cells. In some embodiments, the cells are mammary stem cells. In some embodiments, the cells are intestinal stem cells. In certain embodiments, the cells are mesenchymal stem cells. In some embodiments, the cells are endothelial stem cells. In other embodiments, the cells are olfactory adult stem cells. In one embodiment, the cells are neural crest stem cells. Other tissue stem cells, tissue progenitor cells, and tissue precursor cells are also contemplated herein.

In some embodiments, of the various methods or compositions provided herein, the patient is a patient in need thereof.

In some aspects, provided herein are pharmaceutical compositions, single unit dosage forms, and kits, which comprise a BRD7 antagonist, Ikaros antagonist, or CRBN activator and a carrier, for use in the prevention or treatment of a cancer or tumor, or a symptom thereof.

5.3 BRD7 Antagonists

In some embodiments of the methods provided herein, the antagonist of BRD7 suppresses BRD7's inhibitory functions in CNS nerve cells proliferation and differentiation.

In some aspects, an antagonist of BRD7 is an inhibitor of BRD7 protein. In some embodiments, the inhibitors of BRD7 protein inhibit the production of BRD7 protein Inhibitors of production can be any molecules negatively affecting the synthesis, processing or maturation of BRD7 protein. The inhibitors of BRD7 protein used herein can be, for example, proteins impairing correct folding, or partially or substantially preventing secretion of BRD7 protein, proteases degrading BRD7, once it has been synthesized, or inhibitors of proteases cleaving BRD7 in order to generate mature BRD7, or any combination thereof.

In some embodiments, the inhibitors of BRD7 protein inhibit BRD7 action Inhibitors of BRD7 action can be, for example, soluble natural biological binding partners of BRD7 in the cell or molecules mimicking the such binding partners, or agents blocking such binding partners, or BRD7 antibodies, such as polyclonal or monoclonal antibodies, or any other agent or molecule preventing the binding of BRD7 to its cellular targets, thus diminishing or preventing triggering of the intra- or extracellular reactions and/or pathways mediated by BRD7, or any combination thereof.

In some embodiments, the inhibitors of BRD7 either bind to or sequester the BRD7 molecule itself with sufficient affinity and specificity to partially or substantially neutralize the BRD7 or BRD7 binding site(s) (e.g., bromodomain) responsible for BRD7 binding to its partners. An inhibitor of BRD7 may also inhibit the signaling/biological pathway, which is activated within the cells upon BRD7 binding to its partner(s).

In some embodiments, the inhibitor of BRD7 protein is a compound that inhibits or decreases the interaction between a protein and another molecule, e.g., a target peptide or enzyme substrate. In some embodiments, the inhibitor of BRD7 is a compound that binds to BRD7 protein and changes BRD7 protein structure. In some embodiments, the inhibitor is a compound that down-regulates expression of Brd7 gene or which reduces the amount of expressed BRD7 present.

In some embodiments, the inhibitor of BRD7 protein is a protein. The proteins may be glycosylated or non-glycosylated, they may be derived from natural sources, such as urine, or they may preferably be produced recombinantly. Recombinant expression may be carried out in prokaryotic expression systems like *E. coli*, or in eukaryotic, and preferably in mammalian, expression systems.

In certain embodiments, the BRD7 antagonist is a nucleic acid molecule comprising the coding sequence of a BRD7 inhibitor, in the preparation of a medicament for the treatment, prevention, or management of a CNS disorder, injury or damage.

In one embodiment, the nucleic acid molecule comprises the coding sequence of BRD7's natural binding protein in the cell, a mutein, functional derivative, or active fraction thereof, In one embodiment, a mutein provided herein is an analog of a BRD7's natural binding protein in the cell. Any such mutein preferably has a sequence of amino acids sufficiently duplicative of that of the BRD7 inhibitor, such as to have substantially similar activity to BRD7's natural binding protein in the cell. One activity of BRD7's natural binding protein in the cell is its capability of binding and/or blocking BRD7 protein. As long as the mutein has substantial binding activity to BRD7, it can be used in the purification of BRD7 protein, such as by means of affinity chromatography, and thus can be considered to have substantially similar activity to BRD7's natural binding protein in the cells.

In an embodiment, the nucleic acid molecule comprises coding sequence of a fused protein.

In an embodiment, the nucleic acid molecule comprises a coding sequence of an antibody against BRD7 protein, or a fragment of the antibody against BRD7 protein.

In an embodiment, the nucleic acid molecule further comprises a sequence of an expression vector, e.g., to use gene therapy for administering the BRD7 inhibitor provided herein. In an embodiment, the nucleic acid molecule is administered intramuscularly.

In an embodiment, in order to treat and/or prevent CNS disorder, injury or damage, the gene therapy vector comprising the sequence of an inhibitor of BRD7 production and/or action may be injected directly into the diseased tissue, for example, thus avoiding problems involved in systemic administration of gene therapy vectors, like dilution of the vectors, reaching and targeting of the target cells or tissues, and of side effects.

The use of a vector for inducing and/or enhancing the endogenous production of an inhibitor of BRD7 in a cell normally silent for expression of an BRD7 inhibitor, or which expresses amounts of the inhibitor which are not sufficient, are also contemplated herein for treatment and/or prevention of CNS injury. The vector may comprise regulatory elements functional in the cells desired to express the inhibitor or BRD7. Such regulatory sequences or elements may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "Endogenous Gene Activation" (EGA) in the art.

In some aspects, an antagonist of BRD7 is a nucleic acid comprising at least part of nucleic acid sequence of BRD7 gene. The nucleic acid provided herein may knockdown BRD7 expression.

In an embodiment, an antagonist of BRD7 is an antisense molecule, which is specifically hybridizable or specifically complementary to either mRNA or DNA derived from BRD7 gene. In one embodiment, the antagonist of BRD7 is an antisense molecule specifically hybridizing to BRD7 mRNA and inhibiting its translation.

In some embodiments, the antagonist of BRD7 is RNA. The RNA provided herein includes, but not limited to, siRNA, shRNA, microRNA, which may be used to modulate gene expression of Brd7 gene. Double stranded oligonucleotides may be formed by the assembly of two distinct oligonucleotide sequences where the oligonucleotide sequence of one strand is complementary to the oligonucleotide sequence of the second strand; the double stranded oligonucleotides may be assembled from two separate oligonucleotides (e.g., siRNA), or from a single molecule that folds on itself to form a double stranded structure (e.g., shRNA or short hairpin RNA). Each strand of these double stranded oligonucleotides may have a distinct nucleotide sequence, wherein only one nucleotide sequence region (guide sequence or the antisense sequence) has complementarity to part of nucleic acid sequence of Brd7 gene, and the other strand (sense sequence) comprises nucleotide sequence that is homologous to the part of nucleic acid sequence of Brd7 gene.

In an embodiment, the antagonist of BRD7 is a microRNA (miRNA). In an embodiment, the miRNA is a single-stranded RNA molecule of about 21-23 nucleotides in length, and is partially complementary to a RNA (mRNA) molecule derived from BRD7 gene.

In an embodiment, the antagonist of BRD7 is an inhibitory RNA (RNAi) molecule. In an embodiment, the present disclosure relates to a RNAi molecule comprising a sense strand and an antisense strand, wherein the antisense strand comprises at least part of nucleic acid sequence of Brd7 gene. Preferably the RNAi molecule provided herein has a length of between 10 nucleotide bases (nb)-1000 nb. In one embodiment, the RNAi molecule comprises a modification that causes the RNAi agent to have increased stability in a biological sample or environment. RNAi is a well-known technique in the art, and those skilled in the art will understand the methods for preparing RNAi for knockdown of Brd7 gene (see, e.g., Fraser, A G (2000), "Functional genomics analysis of *C. elegans* chromosome I by systematic RNA interference," Nature 408 (6810): 325-330; Aagaard, L (2007), "RNAi therapeutics: principles, prospects and challenges," Advanced Drug Delivery Review 59 (2-3): 75-86; Kamath, R S (2003), "Genome-wide RNAi screening in *Caenorhabditis elegans*," Methods 30: 313-321).

In an embodiment, the antagonist of BRD7 is a Morpholino oligonucleotide or other RNase-H independent antisense. In one embodiment, the antagonist of BRD7 is a Morpholino oligonucleotide. Morpholino oligoneculeotides are structurally different from natural nucleic acids, and they possess morpholino rings in lieu of the ribose or deoxyribose sugar moieties of RNA or DNA, and possess non-ionic phosphorodiamidate linkages in lieu of the anionic phosphates of RNA or DNA. Each morpholino ring suitably positions one of the standard bases (A, G, C, T/U), so that a 25-base morpholino oligonucleotide strongly and specifically binds to its complementary 25-base target site in a strand of RNA via Watson-Crick pairing. However, because the backbone of the morpholino oligonucleotide is not recognized by cellular enzymes of signaling proteins, it is stable to nucleases and does not trigger an innate immune response through the toll-like receptors. This avoids loss of the oligonucleotide, as well as attenuates inflammation or interferon induction. Morpholino oligonucleotides have no electrical charge, and do not interact strongly with proteins, and do not require the activity of RNase-H, Argonaute, or other catalytic proteins for their activity. Morpholinos provided herein may be delivered by a number of techniques, including direct injection to tissues or via infusion pump and intravenous bolus (Moulton et al. (2009) Gene Knockdowns in Adult Animals: PPMOs and Vivo-Morpholinos, Molecules 14: 1304-1323).

Morpholino oligonucleotides are well-known in the art, and those skilled in the art will understand the methods of making and using Morpholino oligonucleotides for knockdown of a target gene (see, e.g., Amantana et al. (2005) Pharmacokinetics And Biodistribution Of Phosphorodiamidate Morpholino Antisense Oligomers, Current Opinion in Pharmacology 5:550-555; Bill et al. (2009) A Primer for Morpholino Use in Zebrafish, Zebrafish 6(1):69-77; Heasman (2002) Morpholino Oligos: Making Sense of Antisense? Devel. Biol. 243:209-214; Karkare et al. (2006) Promising Nucleic Acid Analogs And Mimics: Characteristic Features And Applications Of PNA, LNA, And Morpholino, Appl. Microbiol. Biotechnol. 71:575-586; Moulton et al. (2009) Gene Knockdowns in Adult Animals: PPMOs and Vivo-Morpholinos, Molecules 14: 1304-1323; Moulton et al. (2010) Morpholinos And Their Peptide Conjugates: Therapeutic Promise And Challenge For Duchenne Muscular Dystrophy, Biochimica et Biophysica Acta 1798:2296-2303).

In a specific embodiment, the antagonist of BRD7 provided herein is a Morpholino oligonucleotide having a sequence of 5'-TGTGTTTCTTGTGCTTTTTGCCCAT-3' (SEQ ID NO: 1).

In some aspects, an antagonist of BRD7 is a stem cell, a neural progenitor cell, or a neural precursor cell in which BRD7 is down-regulated.

In some embodiments, the progenitor cell provided herein is a cell that has the capacity to create progeny that are more differentiated than itself. In some embodiments, the progenitor cell is an undifferentiated cell or a cell differentiated to an extent short of final differentiation that is capable of proliferation and giving rise to more progenitor cells having the ability to generate a large number of mother cells that can in turn give rise to differentiated or differentiable daughter cells. In certain embodiments, the progenitor cell is a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells. In some embodiments, the precursor cell is a partially differentiated cell. In some embodiments, the precursor cell is derived from a progenitor cell. In some embodiments, the precursor cell is not capable of self-renewal. Exemplary precursor cells include osteoprogenitor cells such as for example, mesenchymal precursor cells, osteoblasts, and chondroblasts.

In some embodiments, the stem cells in which BRD7 is down-regulated are ES cells, adult stem cells, or cord blood stem cells. In a preferred embodiment, the stem cell in which BRD7 is down-regulated is an induced pluripotent stem (iPS) cell. In one embodiment, the stem cell in which BRD7 is down-regulated is an induced pluripotent stem (iPS) cell derived from the patient him/her-self so as to be able to avoid rejection. iPS stem cell derived from an adult human is an known art. Somatic cell-derived cell lines induced pluripotent stem (iPS) cells were established by Kazutoshi Takahashi and Shinya Yamanaka, using mouse embryonic fibroblasts (MEFs) and skin fibroblasts by simply expressing four transcription factor genes encoding Oct4, Sox2, Klf4, and c-Myc (Takahashi and Yamanaka, (2006) Induction of pluripotent stem cells from mouse embryonic and adult fibroblast cultures by defined factors, Cell 126, 663-676). Since then multiple groups used the same strategy to generate human iPS cells, which resemble human ES cells by all measured criteria.

In some embodiments, the iPS cells are derived from the patient's neuronal progenitor (or precursor) cells, keratinocytes, hepatocytes, B cells, fibroblasts tips, kidneys, muscles, or adrenal glands. In an embodiment, the iPS cells are derived from fibroblasts. Fibroblasts for reprogramming may be acquired from a skin biopsy of a patient. In another embodiment, human keratinocytes from skin biopsies are reprogrammed to iPS. It has been shown that keratinocytes from skin biopsies can be reprogrammed to pluripotency at much higher frequency and faster speed than fibroblasts. One theory is that this difference is attributed to the finding that keratinocytes express much higher levels of endogenous c-Myc and Klf4 than fibroblasts, which may accelerate the conversion of keratinocytes to iPS cells (Aasen et al., (2008) Efficient and rapid generation of induced pluripotent stem cells from human keratinocytes, Nat Biotechnol., 26(11): 1276-84). In yet another embodiment, hematopoietic (blood) cells collected from a patient's blood are used for reprogramming to produce iPS cells.

5.4 Ikaros Antagonists

In some embodiments of the methods provided herein, the antagonist of Ikaros suppresses Ikaros' inhibitory functions in CNS nerve cells proliferation and differentiation.

In some aspects, an antagonist of Ikaros is an inhibitor of Ikaros protein. In some embodiments, the inhibitors of Ikaros protein inhibit the production of Ikaros protein Inhibitors of production can be any molecules negatively affecting the synthesis, processing or maturation of Ikaros protein. The inhibitors of Ikaros protein used herein can be, for example, proteins impairing correct folding, or partially or substantially preventing secretion of Ikaros protein, proteases degrading Ikaros, once it has been synthesized, or inhibitors of proteases cleaving Ikaros in order to generate mature Ikaros, or any combination thereof.

In some embodiments, the inhibitors of Ikaros protein inhibit Ikaros action Inhibitors of Ikaros action can be, for example, soluble natural biological binding partners of Ikaros in the cell or molecules mimicking the such binding partners, or agents blocking such binding partners, or Ikaros antibodies, such as polyclonal or monoclonal antibodies, or any other agent or molecule preventing the binding of Ikaros to its cellular targets, thus diminishing or preventing triggering of the intra- or extracellular reactions and/or pathways mediated by Ikaros, or any combination thereof.

In some embodiments, the inhibitors of Ikaros either bind to or sequester the Ikaros molecule itself with sufficient affinity and specificity to partially or substantially neutralize the Ikaros or Ikaros binding site(s) (e.g., bromodomain) responsible for Ikaros binding to its partners. An inhibitor of Ikaros may also inhibit the signaling/biological pathway, which is activated within the cells upon Ikaros binding to its partner(s).

In some embodiments, the inhibitor of Ikaros protein is a compound that inhibits or decreases the interaction between a protein and another molecule, e.g., a target peptide or enzyme substrate. In some embodiments, the inhibitor of Ikaros is a compound that binds to Ikaros protein and changes Ikaros protein structure. In some embodiments, the inhibitor is a compound that down-regulates expression of Ikaros gene or which reduces the amount of expressed Ikaros present.

In some embodiments, the inhibitor of Ikaros protein is a protein. The proteins may be glycosylated or non-glycosylated, they may be derived from natural sources, such as urine, or they may preferably be produced recombinantly. Recombinant expression may be carried out in prokaryotic expression systems like *E. coli*, or in eukaryotic, and preferably in mammalian, expression systems.

In certain embodiments, the Ikaros antagonist is a nucleic acid molecule comprising the coding sequence of an Ikaros inhibitor, in the preparation of a medicament for the treatment, prevention, or management of a CNS disorder, injury or damage.

In one embodiment, the nucleic acid molecule comprises the coding sequence of Ikaros' natural binding protein in the cell, a mutein, functional derivative, or active fraction thereof, In one embodiment, a mutein provided herein is an analog of an Ikaros' natural binding protein in the cell. Any such mutein preferably has a sequence of amino acids sufficiently duplicative of that of the Ikaros inhibitor, such as to have substantially similar activity to Ikaros' natural binding protein in the cell. One activity of Ikaros' natural binding protein in the cell is its capability of binding and/or blocking Ikaros protein. As long as the mutein has substantial binding activity to Ikaros, it can be used in the purification of Ikaros protein, such as by means of affinity chromatography, and thus can be considered to have substantially similar activity to Ikaros' natural binding protein in the cells.

In an embodiment, the nucleic acid molecule comprises coding sequence of a fused protein.

In an embodiment, the nucleic acid molecule comprises a coding sequence of an antibody against Ikaros protein, or a fragment of the antibody against Ikaros protein.

In an embodiment, the nucleic acid molecule further comprises a sequence of an expression vector, e.g., to use gene therapy for administering the Ikaros inhibitor provided herein. In an embodiment, the nucleic acid molecule is administered intramuscularly.

In an embodiment, in order to treat and/or prevent CNS disorder, injury or damage, the gene therapy vector comprising the sequence of an inhibitor of Ikaros production and/or action may be injected directly into the diseased tissue, for example, thus avoiding problems involved in systemic administration of gene therapy vectors, like dilution of the vectors, reaching and targeting of the target cells or tissues, and of side effects.

The use of a vector for inducing and/or enhancing the endogenous production of an inhibitor of Ikaros in a cell normally silent for expression of an Ikaros inhibitor, or which expresses amounts of the inhibitor which are not sufficient, are also contemplated herein for treatment and/or prevention of CNS injury. The vector may comprise regulatory elements functional in the cells desired to express the inhibitor or Ikaros. Such regulatory sequences or elements may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "Endogenous Gene Activation" (EGA) in the art.

In some aspects, an antagonist of Ikaros is a nucleic acid comprising at least part of nucleic acid sequence of Ikaros gene. The nucleic acid provided herein may knockdown Ikaros expression.

In an embodiment, an antagonist of Ikaros is an antisense molecule, which is specifically hybridizable or specifically complementary to either mRNA or DNA derived from Ikaros gene. In one embodiment, the antagonist of Ikaros is an antisense molecule specifically hybridizing to Ikaros mRNA and inhibiting its translation.

In some embodiments, the antagonist of Ikaros is RNA. The RNA provided herein includes, but not limited to, siRNA, shRNA, microRNA, which may be used to modulate gene expression of Ikaros gene. Double stranded oligonucleotides may be formed by the assembly of two distinct oligonucleotide sequences where the oligonucleotide sequence of one strand is complementary to the oligonucleotide sequence of the second strand; the double stranded oligonucleotides may be assembled from two separate oligonucleotides (e.g., siRNA), or from a single molecule that folds on itself to form a double stranded structure (e.g., shRNA or short hairpin RNA). Each strand of these double stranded oligonucleotides may have a distinct nucleotide sequence, wherein only one nucleotide sequence region (guide sequence or the antisense sequence) has complementarity to part of nucleic acid sequence of Ikaros gene, and the other strand (sense sequence) comprises nucleotide sequence that is homologous to the part of nucleic acid sequence of Ikaros gene.

In an embodiment, the antagonist of Ikaros is a microRNA (miRNA). In an embodiment, the miRNA is a single-stranded RNA molecule of about 21-23 nucleotides in length, and is partially complementary to a RNA (mRNA) molecule derived from Ikaros gene.

In an embodiment, the antagonist of Ikaros is an inhibitory RNA (RNAi) molecule. In an embodiment, the present disclosure relates to a RNAi molecule comprising a sense strand and an antisense strand, wherein the antisense strand comprises at least part of nucleic acid sequence of Ikaros gene. Preferably the RNAi molecule provided herein has a length of between 10 nucleotide bases (nb)-1000 nb. In one embodiment, the RNAi molecule comprises a modification that causes the RNAi agent to have increased stability in a biological sample or environment. RNAi is a well-known technique in the art, and those skilled in the art will understand the methods for preparing RNAi for knockdown of Ikaros gene (see, e.g., Fraser, A G (2000), "Functional genomics analysis of C. elegans chromosome I by systematic RNA interference," Nature 408 (6810): 325-330; Aagaard, L (2007), "RNAi therapeutics: principles, prospects and challenges," Advanced Drug Delivery Review 59 (2-3): 75-86; Kamath, R S (2003), "Genome-wide RNAi screening in Caenorhabditis elegans," Methods 30: 313-321).

In an embodiment, the antagonist of Ikaros is a Morpholino oligonucleotide or other RNase-H independent antisense. In one embodiment, the antagonist of Ikaros is a Morpholino oligonucleotide. Morpholino oligoneculeotides are structurally different from natural nucleic acids, and they possess morpholino rings in lieu of the ribose or deoxyribose sugar moieties of RNA or DNA, and possess non-ionic phosphorodiamidate linkages in lieu of the anionic phosphates of RNA or DNA. Each morpholino ring suitably positions one of the standard bases (A, G, C, T/U), so that a 25-base morpholino oligonucleotide strongly and specifically binds to its complementary 25-base target site in a strand of RNA via Watson-Crick pairing. However, because the backbone of the morpholino oligonucleotide is not recognized by cellular enzymes of signaling proteins, it is stable to nucleases and does not trigger an innate immune response through the toll-like receptors. This avoids loss of the oligonucleotide, as well as attenuates inflammation or interferon induction. Morpholino oligonucleotides have no electrical charge, and do not interact strongly with proteins, and do not require the activity of RNase-H, Argonaute, or other catalytic proteins for their activity. Morpholinos provided herein may be delivered by a number of techniques, including direct injection to tissues or via infusion pump and intravenous bolus (Moulton et al. (2009) Gene Knockdowns in Adult Animals: PPMOs and Vivo-Morpholinos, Molecules 14: 1304-1323).

Morpholino oligonucleotides are well-known in the art, and those skilled in the art will understand the methods of making and using Morpholino oligonucleotides for knockdown of a target gene (see, e.g., Amantana et al. (2005) Pharmacokinetics And Biodistribution Of Phosphorodiamidate Morpholino Antisense Oligomers, Current Opinion in Pharmacology 5:550-555; Bill et al. (2009) A Primer for Morpholino Use in Zebrafish, Zebrafish 6(1):69-77; Heasman (2002) Morpholino Oligos: Making Sense of Antisense? Devel. Biol. 243:209-214; Karkare et al. (2006) Promising Nucleic Acid Analogs And Mimics: Characteristic Features And Applications Of PNA, LNA, And Morpholino, Appl. Microbiol. Biotechnol. 71:575-586; Moulton et al. (2009) Gene Knockdowns in Adult Animals: PPMOs and Vivo-Morpholinos, Molecules 14: 1304-1323; Moulton et al. (2010) Morpholinos And Their Peptide Conjugates: Therapeutic Promise And Challenge For Duchenne Muscular Dystrophy, Biochimica et Biophysica Acta 1798:2296-2303).

In a specific embodiment, the antagonist of Ikaros provided herein is a Morpholino oligonucleotide having a sequence of 5'-TTCCTGTGCCTCCTCAGTCTCCATC-3' (SEQ ID NO: 2).

In some aspects, an antagonist of Ikaros is a stem cell, a neural progenitor cell, or a neural precursor cell in which Ikaros is down-regulated.

In some embodiments, the progenitor cell provided herein is a cell that has the capacity to create progeny that are more differentiated than itself. In some embodiments, the progenitor cell is an undifferentiated cell or a cell differentiated to an extent short of final differentiation that is capable of proliferation and giving rise to more progenitor cells having the ability to generate a large number of mother cells that can in turn give rise to differentiated or differentiable daughter cells. In certain embodiments, the progenitor cell is a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells. In some embodiments, the precursor cell is a partially differentiated cell. In some embodiments, the precursor cell is derived from a progenitor cell. In some embodiments, the precursor cell is not capable of self-renewal. Exemplary precursor cells include osteoprogenitor cells such as for example, mesenchymal precursor cells, osteoblasts, and chondroblasts.

In some embodiments, the stem cells in which Ikaros is down-regulated are ES cells, adult stem cells, or cord blood stem cells. In a preferred embodiment, the stem cell in which Ikaros is down-regulated is an induced pluripotent stem (iPS) cell. In one embodiment, the stem cell in which Ikaros is down-regulated is an induced pluripotent stem (iPS) cell derived from the patient him/her-self so as to be able to avoid rejection. iPS stem cell derived from an adult human is an known art. Somatic cell-derived cell lines induced pluripotent stem (iPS) cells were established by Kazutoshi Takahashi and Shinya Yamanaka, using mouse embryonic fibroblasts (MEFs) and skin fibroblasts by simply expressing four transcription factor genes encoding Oct4, Sox2, Klf4, and c-Myc (Takahashi and Yamanaka, (2006) Induction of pluripotent stem cells from mouse embryonic and adult fibroblast cultures by defined factors, Cell 126, 663-676). Since then multiple groups used the same strategy to generate human iPS cells, which resemble human ES cells by all measured criteria.

In some embodiments, the iPS cells are derived from the patient's neuronal progenitor (or precursor) cells, keratinocytes, hepatocytes, B cells, fibroblasts tips, kidneys, muscles, or adrenal glands. In an embodiment, the iPS cells are derived from fibroblasts. Fibroblasts for reprogramming may be acquired from a skin biopsy of a patient. In another embodiment, human keratinocytes from skin biopsies are reprogrammed to iPS. It has been shown that keratinocytes from skin biopsies can be reprogrammed to pluripotency at much higher frequency and faster speed than fibroblasts.

One theory is that this difference is attributed to the finding that keratinocytes express much higher levels of endogenous c-Myc and Klf4 than fibroblasts, which may accelerate the conversion of keratinocytes to iPS cells (Aasen et al., (2008) Efficient and rapid generation of induced pluripotent stem cells from human keratinocytes, Nat Biotechnol., 26(11): 1276-84). In yet another embodiment, hematopoietic (blood) cells collected from a patient's blood are used for reprogramming to produce iPS cells.

5.5 CRBN Activators

In some embodiments of the methods provided herein, an activator of CRBN suppresses its substrate or downstream molecules those inhibitory function in CNS nerve cells proliferation and differentiation.

In some aspects, an activator of CRBN is an inhibitor of a CRBN substrate or downstream protein thereof. In some embodiments, an inhibitor of a CRBN's substrate or downstream protein thereof inhibits the production of the CRBN substrate or downstream protein Inhibitors of production can be any molecules negatively affecting the synthesis, processing or maturation of a CRBN substrate or downstream protein. The inhibitors of a CRBN substrate or downstream protein used herein can be, for example, proteins impairing correct folding, or partially or substantially preventing secretion of a CRBN substrate or downstream protein, proteases degrading a CRBN substrate or downstream protein, once it has been synthesized, or inhibitors of proteases cleaving a CRBN substrate or downstream protein in order to generate mature them, or any combination thereof.

In some embodiments, an inhibitor of a CRBN substrate or downstream protein inhibits the action of the CRBN substrate or downstream protein Inhibitors of a CRBN substrate or downstream protein action can be, for example, soluble natural biological binding partners of the CRBN substrate or downstream protein in the cell or molecules mimicking the such binding partners, or agents blocking such binding partners, or antibodies that bind CRBN, a CRBN substrate or downstream protein thereof, such as polyclonal or monoclonal antibodies, or any other agent or molecule preventing the binding of CRBN to its substrate(s) or cellular target(s), thus diminishing or preventing triggering of the intracellular or extracellular reactions and/or pathways mediated by CRBN, a CRBN substrate or downstream protein thereof, or any combination thereof.

In some embodiments, the inhibitors of a CRBN substrate or downstream protein either bind to or sequester the CRBN substrate or downstream protein molecule itself with sufficient affinity and specificity to partially or substantially neutralize the CRBN substrate or downstream protein, or CRBN substrate or downstream protein binding site(s) responsible for the CRBN substrate or downstream protein binding to its partners. An inhibitor of a CRBN substrate or downstream protein may also inhibit the signaling/biological pathway, which is activated within the cells upon CRBN, a CRBN substrate or downstream protein binding to its partner(s).

In some embodiments, the inhibitor of a CRBN substrate or downstream protein is a compound that inhibits or decreases the interaction between a protein and another molecule, e.g., a target peptide or enzyme substrate. In some embodiments, the inhibitor of a CRBN substrate or downstream protein is a compound that binds to a CRBN substrate or downstream protein and changes a CRBN substrate or downstream protein structure. In some embodiments, the inhibitor is a compound that down-regulates expression of a CRBN substrate or downstream protein gene or which reduces the amount of expressed the CRBN substrate or downstream protein present.

In some embodiments, the inhibitor of a CRBN substrate or downstream protein is a protein. The proteins may be glycosylated or non-glycosylated, they may be derived from natural sources, such as urine, or they may preferably be produced recombinantly. Recombinant expression may be carried out in prokaryotic expression systems like E. coli, or in eukaryotic, and preferably in mammalian, expression systems.

In certain embodiments, the CRBN activator is a nucleic acid molecule comprising the coding sequence of an inhibitor of a CRBN substrate or downstream protein, in the preparation of a medicament for the treatment, prevention, or management of a CNS disorder, injury or damage.

In one embodiment, the nucleic acid molecule comprises the coding sequence of a CRBN substrate or downstream protein's natural binding protein in the cell, a mutein, functional derivative, or active fraction thereof, In one embodiment, a mutein provided herein is an analog of a CRBN substrate or downstream protein's natural binding protein in the cell. Any such mutein preferably has a sequence of amino acids sufficiently duplicative of that of the inhibitor of a CRBN substrate or downstream protein, such as to have substantially similar activity to the CRBN substrate or downstream protein's natural binding protein in the cell. One activity of a CRBN substrate or downstream protein's natural binding protein in the cell is its capability of binding and/or blocking the CRBN substrate or downstream protein. As long as the mutein has substantial binding activity to a CRBN substrate or downstream protein, it can be used in the purification of the CRBN substrate or downstream protein, such as by means of affinity chromatography, and thus can be considered to have substantially similar activity to the CRBN substrate or downstream protein's natural binding protein in the cells.

In an embodiment, the nucleic acid molecule comprises coding sequence of a fused protein.

In an embodiment, the nucleic acid molecule comprises a coding sequence of an antibody against a CRBN substrate or downstream protein, or a fragment of the antibody against a CRBN substrate or downstream protein.

In an embodiment, the nucleic acid molecule further comprises a sequence of an expression vector, e.g., to use gene therapy for administering the inhibitor of a CRBN substrate or downstream protein provided herein. In an embodiment, the nucleic acid molecule is administered intramuscularly.

In an embodiment, in order to treat and/or prevent CNS disorder, injury or damage, the gene therapy vector comprising the sequence of an inhibitor of a CRBN substrate or downstream protein production and/or action may be injected directly into the diseased tissue, for example, thus avoiding problems involved in systemic administration of gene therapy vectors, like dilution of the vectors, reaching and targeting of the target cells or tissues, and of side effects.

The use of a vector for inducing and/or enhancing the endogenous production of an inhibitor of a CRBN substrate or downstream protein in a cell normally silent for expression of an inhibitor a CRBN substrate or downstream protein, or which expresses amounts of the inhibitor which are not sufficient, are also contemplated herein for treatment and/or prevention of CNS injury. The vector may comprise regulatory elements functional in the cells desired to express the inhibitor or a CRBN substrate or downstream protein. Such regulatory sequences or elements may be promoters or enhancers, for example. The regulatory sequence may then be introduced into the right locus of the genome by homologous recombination, thus operably linking the regulatory sequence with the gene, the expression of which is required to be induced or enhanced. The technology is usually referred to as "Endogenous Gene Activation" (EGA) in the art.

In some aspects, an activator of CRBN is a nucleic acid comprising at least part of nucleic acid sequence of a CRBN substrate or downstream protein gene. The nucleic acid provided herein may knockdown a CRBN substrate or downstream protein expression.

In an embodiment, an activator of CRBN is an antisense molecule, which is specifically hybridizable or specifically complementary to either mRNA or DNA derived from a CRBN substrate or downstream protein gene. In one embodiment, the activator of CRBN is an antisense molecule specifically hybridizing to a CRBN substrate or downstream protein mRNA and inhibiting its translation.

In some embodiments, the activator of CRBN is RNA. The RNA provided herein includes, but not limited to, siRNA, shRNA, microRNA, which may be used to modulate gene expression of a CRBN substrate or downstream protein gene. Double stranded oligonucleotides may be formed by the assembly of two distinct oligonucleotide sequences where the oligonucleotide sequence of one strand is complementary to the oligonucleotide sequence of the second strand; the double stranded oligonucleotides may be assembled from two separate oligonucleotides (e.g., siRNA), or from a single molecule that folds on itself to form a double stranded structure (e.g., shRNA or short hairpin RNA). Each strand of these double stranded oligonucleotides may have a distinct nucleotide sequence, wherein only one nucleotide sequence region (guide sequence or the antisense sequence) has complementarity to part of nucleic acid sequence of a CRBN substrate or downstream protein gene, and the other strand (sense sequence) comprises nucleotide sequence that is homologous to the part of nucleic acid sequence of a CRBN substrate or downstream protein gene.

In an embodiment, the activator of CRBN is a microRNA (miRNA). In an embodiment, the miRNA is a single-stranded RNA molecule of about 21-23 nucleotides in length, and is partially complementary to a RNA (mRNA) molecule derived from a CRBN substrate or downstream protein gene.

In an embodiment, the activator of CRBN is an inhibitory RNA (RNAi) molecule. In an embodiment, the present disclosure relates to an RNAi molecule comprising a sense strand and an antisense strand, wherein the antisense strand comprises at least part of nucleic acid sequence of a CRBN substrate or downstream protein gene. Preferably the RNAi molecule provided herein has a length of between 10 nucleotide bases (nb)-1000 nb. In one embodiment, the RNAi molecule comprises a modification that causes the RNAi agent to have increased stability in a biological sample or environment. RNAi is a well-known technique in the art, and those skilled in the art will understand the methods for preparing RNAi for knockdown of a CRBN substrate or downstream protein gene (see, e.g., Fraser, A G (2000), "Functional genomics analysis of *C. elegans* chromosome I by systematic RNA interference," Nature 408 (6810): 325-330; Aagaard, L (2007), "RNAi therapeutics: principles, prospects and challenges," Advanced Drug Delivery Review 59 (2-3): 75-86; Kamath, R S (2003), "Genome-wide RNAi screening in *Caenorhabditis elegans*," Methods 30: 313-321).

In an embodiment, the activator of CRBN is a Morpholino oligonucleotide or other RNase-H independent antisense. In one embodiment, the activator of CRBN is a Morpholino oligonucleotide. Morpholino oligoneculeotides are structurally different from natural nucleic acids, and they possess morpholino rings in lieu of the ribose or deoxyribose sugar moieties of RNA or DNA, and possess non-ionic phosphorodiamidate linkages in lieu of the anionic phosphates of RNA or DNA. Each morpholino ring suitably positions one of the standard bases (A, G, C, T/U), so that a 25-base morpholino oligonucleotide strongly and specifically binds to its complementary 25-base target site in a strand of RNA via Watson-Crick pairing. However, because the backbone of the morpholino oligonucleotide is not recognized by cellular enzymes of signaling proteins, it is stable to nucleases and does not trigger an innate immune response through the toll-like receptors. This avoids loss of the oligonucleotide, as well as attenuates inflammation or interferon induction. Morpholino oligonucleotides have no electrical charge, and do not interact strongly with proteins, and do not require the activity of RNase-H, Argonaute, or other catalytic proteins for their activity. Morpholinos provided herein may be delivered by a number of techniques, including direct injection to tissues or via infusion pump and intravenous bolus (Moulton et al. (2009) Gene Knockdowns in Adult Animals: PPMOs and Vivo-Morpholinos, Molecules 14: 1304-1323).

Morpholino oligonucleotides are well-known in the art, and those skilled in the art will understand the methods of making and using Morpholino oligonucleotides for knockdown of a target gene (see, e.g., Amantana et al. (2005) Pharmacokinetics And Biodistribution Of Phosphorodiamidate Morpholino Antisense Oligomers, Current Opinion in Pharmacology 5:550-555; Bill et al. (2009) A Primer for Morpholino Use in Zebrafish, Zebrafish 6(1):69-77; Heasman (2002) Morpholino Oligos: Making Sense of Antisense? Devel. Biol. 243:209-214; Karkare et al. (2006) Promising Nucleic Acid Analogs And Mimics: Characteristic Features And Applications Of PNA, LNA, And Morpholino, Appl. Microbiol. Biotechnol. 71:575-586; Moulton et al. (2009) Gene Knockdowns in Adult Animals: PPMOs and Vivo-Morpholinos, Molecules 14: 1304-1323; Moulton et al. (2010) Morpholinos And Their Peptide Conjugates: Therapeutic Promise And Challenge For Duchenne Muscular Dystrophy, Biochimica et Biophysica Acta 1798:2296-2303).

In some aspects, an activator of CRBN is a stem cell, a neural progenitor cell or a neural precursor cell in which a CRBN substrate or downstream protein gene is down-regulated.

In some embodiments, the progenitor cell provided herein is a cell that has the capacity to create progeny that are more differentiated than itself. In some embodiments, the progenitor cell is an undifferentiated cell or a cell differentiated to an extent short of final differentiation that is capable of proliferation and giving rise to more progenitor cells having the ability to generate a large number of mother cells that can in turn give rise to differentiated or differentiable daughter cells. In certain embodiments, the progenitor cell is a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells. In some embodiments, the precursor cell is a partially differentiated call. In some embodiments, the precursor cell is derived from a progenitor cell. In some embodiments, the precursor cell is not capable of self-renewal. Exemplary precursor cells include osteoprogenitor cells such as for example, mesenchymal precursor cells, osteoblasts, and chondroblasts.

In some embodiments, the stem cells in which a CRBN substrate or downstream protein is down-regulated are ES cells, adult stem cells, or cord blood stem cells. In a preferred embodiment, the stem cell in which a CRBN substrate or downstream protein is down-regulated is an induced pluripotent stem (iPS) cell. In one embodiment, the stem cell in which a CRBN substrate or downstream protein is down-regulated is an induced pluripotent stem (iPS) cell derived from the patient him/her-self so as to be able to avoid rejection. iPS stem cell derived from an adult human is an known art. Somatic cell-derived cell lines induced pluripotent stem (iPS) cells were established by Kazutoshi Takahashi and Shinya Yamanaka, using mouse embryonic fibroblasts (MEFs) and skin fibroblasts by simply expressing four transcription factor genes encoding Oct4, Sox2, Klf4, and c-Myc (Takahashi and Yamanaka, (2006) Induction of pluripotent stem cells from mouse embryonic and adult fibroblast cultures by defined factors, Cell 126, 663-676). Since then multiple groups used the same strategy to generate human iPS cells, which resemble human ES cells by all measured criteria.

In some embodiments, the iPS cells are derived from the patient's neuronal progenitor (or precursor) cells, keratinocytes, hepatocytes, B cells, fibroblasts tips, kidneys, muscles, or adrenal glands. In an embodiment, the iPS cells are derived from fibroblasts. Fibroblasts for reprogramming may be acquired from a skin biopsy of a patient. In another embodiment, human keratinocytes from skin biopsies are reprogrammed to iPS. It has been shown that keratinocytes from skin biopsies can be reprogrammed to pluripotency at much higher frequency and faster speed than fibroblasts. One theory is that this difference is attributed to the finding that keratinocytes express much higher levels of endogenous c-Myc and Klf4 than fibroblasts, which may accelerate the conversion of keratinocytes to iPS cells (Aasen et al., (2008) Efficient and rapid generation of induced pluripotent stem cells from human keratinocytes, Nat Biotechnol., 26(11): 1276-84). In yet another embodiment, hematopoietic (blood) cells collected from a patient's blood are used for reprogramming to produce iPS cells.

5.6 Pharmaceutical Compositions

Also provided herein are pharmaceutical compositions, particularly useful for treatment, prevention and/or management of a CNS cell defective disease, disorder or condition, or a symptom thereof which comprise a therapeutically effective amount of a BRD7 antagonist, Ikaros antagonist, or CRBN activator. In some embodiments, the pharmaceutical composition comprises a BRD7 antagonist. In another embodiment, the pharmaceutical composition comprises an Ikaros antagonist. In yet another embodiment, the pharmaceutical composition comprises a CRBN activator.

In some embodiments, the pharmaceutical composition comprises an inhibitor of BRD7 protein. In an embodiment, the inhibitor of BRD7 is an inhibitor of BRD7 production. In an embodiment, the inhibitor of BRD7 is an inhibitor of BRD7 action. In an embodiment, an inhibitor of BRD7 is a nucleic acid comprising a coding region of an inhibitor of BRD7. In certain embodiments, as antagonists of BRD7, the composition may comprise antibodies against BRD7, antibodies against BRD7 biological binding partners, inhibitors of BRD7 signaling/biological pathways, molecules which compete with BRD7 and block the BRD7' binding to the partners, and BRD7' binding proteins, isoforms, muteins, fused proteins, functional derivatives, active fractions or circularly permutated derivatives thereof having the same activity.

In some embodiments, the pharmaceutical composition comprises an inhibitor of Ikaros protein. In an embodiment, the inhibitor of Ikaros is an inhibitor of Ikaros production. In an embodiment, the inhibitor of Ikaros is an inhibitor of Ikaros action. In an embodiment, an inhibitor of Ikaros is a nucleic acid comprising a coding region of an inhibitor of Ikaros. In certain embodiments, as antagonists of Ikaros, the composition may comprise antibodies against Ikaros, antibodies against Ikaros biological binding partners, inhibitors of Ikaros signaling/biological pathways, molecules which compete with Ikaros and block the Ikaros' binding to the partners, and Ikaros' binding proteins, isoforms, muteins, fused proteins, functional derivatives, active fractions or circularly permutated derivatives thereof having the same activity.

In some embodiments, the pharmaceutical composition comprises an inhibitor of a CRBN substrate or downstream protein. In an embodiment, the inhibitor of a CRBN substrate or downstream protein is an inhibitor of a CRBN substrate or downstream protein production. In an embodiment, the inhibitor of a CRBN substrate or downstream protein is an inhibitor of a CRBN substrate or downstream protein action. In an embodiment, an inhibitor of a CRBN substrate or downstream protein is a nucleic acid comprising a coding region of an inhibitor of a CRBN substrate or downstream protein. In certain embodiments, as activators of CRBN, the composition may comprise antibodies against a CRBN substrate or downstream protein, antibodies against a CRBN substrate or downstream protein biological binding partners, inhibitors of a CRBN substrate or downstream protein signaling/biological pathways, molecules which compete with a CRBN substrate or downstream protein and block the a CRBN substrate or downstream protein's binding to the partners, and a CRBN substrate or downstream protein's binding proteins, isoforms, muteins, fused proteins, functional derivatives, active fractions or circularly permutated derivatives thereof having the same activity.

In some embodiments, the pharmaceutical composition provided herein comprises a nucleic acid comprising at least part of nucleic acid sequence of BRD7 gene. In an embodiment, the nucleic acid is inserted in a vector. In an embodiment, the nucleic acid is an antisense molecule specific to an BRD7 gene. In an embodiment, the antisense molecule is an RNAi molecule. In an embodiment, the antagonist of BRD7 is a Morpholino oligonucleotide specific to BRD7 gene. In a specific embodiment, a Morpholino oligonucleotide comprises a sequence selected from a group consisting of 5'-TGTGTTTCTTGTGCTTTTTGCCCAT-3' (SEQ ID NO: 1).

In some embodiments, the pharmaceutical composition provided herein comprises a nucleic acid comprising at least part of nucleic acid sequence of Ikaros gene. In an embodiment, the nucleic acid is inserted in a vector. In an embodiment, the nucleic acid is an antisense molecule specific to an Ikaros gene. In an embodiment, the antisense molecule is an RNAi molecule. In an embodiment, the antagonist of Ikaros is a Morpholino oligonucleotide specific to Ikaros gene. In a specific embodiment, a Morpholino oligonucleotide comprises a sequence selected from a group consisting of 5'-TTCCTGTGCCTCCTCAGTCTCCATC-3' (SEQ ID NO:2).

In some embodiments, the pharmaceutical composition provided herein comprises a nucleic acid comprising at least part of nucleic acid sequence of a CRBN substrate or downstream protein gene. In an embodiment, the nucleic acid is inserted in a vector. In an embodiment, the nucleic acid is an antisense molecule specific to a CRBN substrate or downstream protein gene. In an embodiment, the antisense molecule is an RNAi molecule. In an embodiment, the BRD7 antagonist, Ikaros antagonist, or CRBN activator is a Morpholino oligonucleotide specific to a CRBN substrate or downstream protein gene.

In some embodiments, the pharmaceutical composition provided herein comprises a stem cell, a neural progenitor cell, or neural precursor cell in which BRD7 is down-regulated. In an embodiment, the antagonist of BRD7 is an induced pluripotent stem (iPS) cell derived from the subject in need of the pharmaceutical composition.

In some embodiments, the pharmaceutical composition provided herein comprises a stem cell, a neural progenitor cell, or neural precursor cell in which Ikaros is down-regulated. In an embodiment, the antagonist of Ikaros is an iPS cell derived from the subject in need of the pharmaceutical composition.

In some embodiments, the pharmaceutical composition provided herein comprises a stem cell, neural progenitor cell, or neural precursor cell in which a CRBN substrate or downstream protein is down-regulated. In an embodiment, the CRBN activator is an iPS cell derived from the subject in need of the pharmaceutical composition.

Pharmaceutical compositions and dosage forms provided herein comprise a BRD7 antagonist, Ikaros antagonist, or CRBN activator provided herein, or a pharmaceutically acceptable salt, solvate, hydrate, stereoisomer, clathrate, or prodrug thereof.

In one embodiment, the pharmaceutical compositions provided herein are used in the preparation of individual, single unit dosage forms. In some embodiments, the BRD7 antagonist, Ikaros antagonist, or CRBN activator is formulated and administered in multiple-dosage forms. Unit-dose forms as used herein refer to physically discrete units suitable for human and animal subjects and packaged individually as is known in the art. Each unit-dose contains a predetermined quantity of the BRD7 antagonist, Ikaros antagonist, or CRBN activator sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The pharmaceutical compositions provided herein can contain one or more BRD7 antagonists. The pharmaceutical compositions provided herein can contain one or more Ikaros antagonists. The pharmaceutical compositions provided herein can contain one or more activators of CRBN. The pharmaceutical compositions and dosage forms can also comprise one or more additional active ingredients. In certain embodiments, formulations comprise a BRD7 antagonist, Ikaros antagonist, or CRBN activator, and one or more additional active ingredients with complementary activities that do not adversely affect each other. Such molecules are suitably present in combination in amounts that are effective for the purpose intended. Such combined therapy can be administered to the patient serially or simultaneously or in sequence.

Combinations of one or more BRD7 antagonists, one or more Ikaros antagonists, and/or one or more CRBN activators are also contemplated for use in the compositions and methods provided herein.

The combination of therapies (e.g., use of prophylactic or therapeutic agents) as used herein may be more effective than the additive effects of any two or more single therapy. For example, a synergistic effect of a combination of prophylactic and/or therapeutic agents permits the use of lower dosages of one or more of the agents and/or less frequent administration of the agents to a subject with a CNS cell defective disease, disorder or condition. The ability to utilize lower dosages of prophylactic or therapeutic therapies and/or to administer the therapies less frequently reduces the toxicity associated with the administration of the therapies to a subject without reducing the efficacy of the therapies in the prevention, management, treatment or amelioration of a CNS cell defective disease, disorder or condition. In addition, a synergistic effect can result in improved efficacy of therapies in the prevention, or in the management, treatment or amelioration of a CNS cell defective disease, disorder or condition. Finally, synergistic effect of a combination of therapies (e.g., prophylactic or therapeutic agents) can avoid or reduce adverse or unwanted side effects associated with the use of any single therapy.

The pharmaceutical compositions provided herein may further comprise a pharmaceutically acceptable carrier. Pharmaceutical carriers suitable for administration of the active ingredient provided herein include any such carriers known to those skilled in the art to be suitable for the particular mode of administration.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed provided herein will vary from one another will be readily apparent to those skilled in the art. See, e.g., Remington's Pharmaceutical Sciences, 18th ed., Mack Publishing, Easton Pa. (1990).

Therapeutic formulations containing one or more BRD7 antagonists, Ikaros antagonists, or CRBN activators (e.g., an inhibitor of a CRBN substrate or downstream protein) provided herein can be prepared for storage by mixing the BRD7 antagonist(s), Ikaros antagonist(s), or CRBN activator(s) with optional physiologically acceptable carriers, excipients or stabilizers (Remington's Pharmaceutical Sciences (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

The BRD7 antagonists, Ikaros antagonists, or CRBN activators provided herein can also, for example, be formulated in liposomes. Liposomes containing the molecule of interest are prepared by methods known in the art, such as described in Epstein et al. (1985) Proc. Natl. Acad. Sci. USA, 82:3688; Hwang et al. (1980) Proc. Natl. Acad. Sci. USA, 77:4030; and U.S. Pat. Nos. 4,485,045 and 4,544,545. Liposomes with enhanced circulation time are disclosed in U.S. Pat. No. 5,013,556.

In one embodiment, the BRD7 antagonist, Ikaros antagonist, or CRBN activator is an antibody. The antibody provided herein may be formed as immunoliposomes. Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. The BRD7 antagonist, Ikaros antagonist, or CRBN activator provided herein can be conjugated to the liposomes as described in Martin et al. (1982) J. Biol. Chem., 257:286-288 via a disulfide interchange reaction. A chemotherapeutic agent (such as Doxorubicin) is optionally contained within the liposome (Gabizon et al., (1989) J. National Cancer Inst., 81(19):1484).

A BRD7 antagonist, Ikaros antagonist, or CRBN activator can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences (1990) Mack Publishing Co., Easton, Pa.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the BRD7 antagonist, Ikaros antagonist, or CRBN activator, which matrices are in the form of shaped articles, e.g., films, or microcapsule. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. Certain activators of CRBN provided herein when encapsulated remain in the body for a long time, and can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, active ingredients provided herein are administered by controlled release means or by delivery devices that are well known to those of ordinary skill in the art. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In some embodiments, parenteral dosage forms are administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient.

In certain embodiments, the pharmaceutical composition is administered by injection or drip infusion. In certain embodiments, the pharmaceutical composition is administered to or into the cerebral ventricle, skin, intraperitoneal cavity, vein, artery or spinal marrow fluid.

Examples of parenteral dosage forms include, but are not limited to, solutions ready for injection, dry products ready to be dissolved or suspended in a pharmaceutically acceptable vehicle for injection, suspensions ready for injection, and emulsions.

In some embodiments, preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active ingredient is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active ingredient to the treated tissue(s).

The BRD7 antagonist, Ikaros antagonist, or CRBN activator can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and can be empirically determined.

In other embodiments, the pharmaceutical formulations are lyophilized powders, which can be reconstituted for administration as solutions, emulsions and other mixtures. They can also be reconstituted and formulated as solids or gels.

The lyophilized powder is prepared by dissolving a BRD7 antagonist, Ikaros antagonist, or CRBN activator provided herein, or a pharmaceutically acceptable derivative thereof, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical and mucosal dosage forms provided herein include, but are not limited to, sprays, aerosols, solutions, emulsions, suspensions, or other forms known to one of skill in the art. See, e.g., Remington's Pharmaceutical Sciences, 16th and 18th eds., Mack Publishing, Easton, Pa. (1980 & 1990); and Introduction to Pharmaceutical Dosage Forms, 4th ed., Lea & Febiger, Philadelphia (1985).

Suitable excipients (e.g., carriers and diluents) and other materials that can be used to provide topical and mucosal dosage forms are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton, Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

The BRD7 antagonist, Ikaros antagonist, or CRBN activator provided herein; or compositions containing the BRD7 antagonist, Ikaros antagonist, or CRBN activator thereof provided herein, can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the compositions provided herein are targeted (or otherwise administered) to a tissue of CNS, such as in a patient having or at risk of having a CNS cell defective disease, disorder, condition, or a symptom thereof.

In one embodiment, liposomal suspensions, including tissue-targeted liposomes, can also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) can be formed by drying down egg phosphatidyl choline and brain phosphatidyl serine (7:3 molar ratio) on the inside of a flask. A solution of a BRD7 antagonist, Ikaros antagonist, or CRBN activator provided herein in phosphate buffered saline lacking divalent cations (PBS) is added and the flask shaken until the lipid film is dispersed. The resulting vesicles are washed to remove unencapsulated antagonist, pelleted by centrifugation, and then resuspended in PBS.

The therapeutically effective concentration can be determined empirically by testing the compounds in in vitro and in vivo systems using routine methods and then extrapolated therefrom for dosages for humans. The concentration of BRD7 antagonist, Ikaros antagonist, or CRBN activator in the pharmaceutical composition will depend on, e.g., the physicochemical characteristics of the BRD7 antagonist, Ikaros antagonist, or CRBN activator, the dosage schedule, and amount administered as well as other factors known to those of skill in the art.

In one embodiment, a therapeutically effective dosage produces a serum concentration of BRD7 antagonist, Ikaros antagonist, or CRBN activator of from about 0.1 ng/ml to about 50-100 µg/ml. The pharmaceutical compositions, in another embodiment, provide a dosage of from about 0.001 mg to about 2000 mg of BRD7 antagonist, Ikaros antagonist, or CRBN activator per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the BRD7 antagonist, Ikaros antagonist, or CRBN activator and/or a combination of other optional essential ingredients per dosage unit form.

The BRD7 antagonist, Ikaros antagonist, or CRBN activator can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the BRD7 antagonist, Ikaros antagonist, or CRBN activator, the resulting mixture can be a solution, suspension, emulsion or the like. The form of the resulting mixture depends upon a number of factors, including the intended mode of administration and the solubility of the antagonist in the selected carrier or vehicle. The effective concentration is sufficient for ameliorating the symptoms of the disease, disorder or condition treated and can be empirically determined.

5.7 Methods of Administration and Dosing

In certain embodiments, provided herein are methods of preventing, managing, treating and/or ameliorating a CNS cell defective disease, disorder or condition, or a symptom thereof in a subject, by administrating to a subject of an effective amount of a BRD7 antagonist, Ikaros antagonist, or CRBN activator, or pharmaceutical composition comprising a BRD7 antagonist, Ikaros antagonist, or CRBN activator provided herein. In some embodiments, a BRD7 antagonist is administered. In another embodiment, an Ikaros antagonist is administered. In other embodiments, a CRBN activator is administered. In some embodiments, a pharmaceutical composition comprising a BRD7 antagonist is administered. In another embodiment, a pharmaceutical composition comprising an Ikaros antagonist is administered. In other embodiments, a pharmaceutical composition comprising a CRBN activator is administered.

Also provided herein are compositions comprising one or more BRD7 antagonists, Ikaros antagonists, or CRBN activators for use, e.g., in the prevention, management, treatment and/or amelioration of a CNS cell defective disease, disorder or condition provided herein. In some embodiments, the compositions comprises a BRD7 antagonist. In another embodiment, the composition comprises an Ikaros antagonist. In other embodiments, the composition comprises a CRBN activator is administered As discussed in more detail elsewhere herein, a composition provided herein can be used either alone or in combination with other compounds or compositions. Moreover, the BRD7 antagonist, Ikaros antagonist, or CRBN activator can further be recombinantly fused to a heterologous polypeptide at the N- or C-terminus or chemically conjugated (including covalently and non-covalently conjugations) to polypeptides or other compositions. For example, a BRD7 antagonist, Ikaros antagonist, or CRBN activator (e.g., antibody against a CRBN substrate or downstream protein) can be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387. The compositions and methods of administering and dosing can also be useful in the other methods provided herein.

In one embodiment, a BRD7 antagonist, Ikaros antagonist, or CRBN activator is substantially purified (i.e., substantially free from substances that limit its effect or produce undesired side-effects). The subject administered a therapy is, in certain embodiments, a mammal such as non-primate (e.g., cows, pigs, horses, cats, dogs, rats etc.) or a primate (e.g., a monkey, such as a cynomolgous monkey, or a human). In a specific embodiment, the subject is a human. In another embodiment, the subject is a human with a CNS cell defective disease, disorder or condition. In another embodiment, the subject is a human having an injured CNS tissue.

Various delivery systems are known and can be used to administer a prophylactic or therapeutic agent (e.g., a BRD7 antagonist, Ikaros antagonist, or CRBN activator provided herein), including, but not limited to, encapsulation in liposomes, microparticles, microcapsules, recombinant cells capable of expressing the BRD7 antagonist, Ikaros antagonist, or CRBN activator, receptor-mediated endocytosis (see, e.g., Wu and Wu, (1987) J. Biol. Chem., 262:4429-4432), construction of a nucleic acid as part of a retroviral or other vector, etc. Methods of administering a prophylactic or therapeutic agent (e.g., a BRD7 antagonist, Ikaros antagonist, or CRBN activator provided herein), or a pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., a BRD7 antagonist, Ikaros antagonist, or CRBN activator provided herein), or a pharmaceutical composition is administered intranasally, intramuscularly, intravenously, or subcutaneously. The prophylactic or therapeutic agents, or compositions can be administered by any convenient route, for example by infusion or bolus injection, by absorption through epithelial or mucocutaneous linings (e.g., oral mucosa, intranasal mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903.

In therapy or as a prophylactic, the active agent may be administered to an individual as an injectable composition, for example as a sterile aqueous dispersion. The antagonist may be administered directly to a neuron or a region of CNS or may be targeted to the neuron or the region via systemic administration.

In a specific embodiment, it can be desirable to administer a prophylactic or therapeutic agent, or a pharmaceutical composition locally to the area in need of treatment. In certain embodiments, the area is a CNS tissue. In a specific embodiment, the area is brain. This can be achieved by, for example, and not by way of limitation, local infusion, by topical administration (e.g., by intranasal spray), by injection, or by means of an implant, the implant being of a porous, non-porous, or gelatinous material, including membranes, such as sialastic membranes, or fibers. In certain embodiments, when administering a BRD7 antagonist, Ikaros antagonist, or CRBN activator, care must be taken to use materials to which the BRD7 antagonist, Ikaros antagonist, or CRBN activator does not absorb.

In another embodiment, a prophylactic or therapeutic agent, or a composition can be delivered in a vesicle, in particular a liposome (see Langer, (1990) Science 249:1527-1533; Treat et al., (1989) in Liposomes in the Therapy of Infectious Disease and Cancer, Lopez-Berestein and Fidler (eds.), Liss, New York, pp. 353-365; Lopez-Berestein, ibid., pp. 317-327; see generally ibid.).

In another embodiment, a prophylactic or therapeutic agent, or a composition can be delivered in a controlled release or sustained release system. In one embodiment, a pump can be used to achieve controlled or sustained release (see Langer and Sefton, (1987) CRC Crit. Ref. Biomed. Eng., 14:20; Buchwald et al., (1980) Surgery, 88:507; Saudek et al., (1989) N. Engl. J. Med., 321:574). In another embodiment, polymeric materials can be used to achieve controlled or sustained release of a prophylactic or therapeutic agent (e.g., a BRD7 antagonist, Ikaros antagonist, or CRBN activator provided herein) or a composition (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, (1983) J., Macromol. Sci. Rev. Macromol. Chem., 23:61; see also Levy et al., (1985) Science 228:190; During et al., (1989) Ann. Neurol. 25:351; Howard et al., (1989) J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a specific embodiment, the polymer used in a sustained release formulation is inert, free of leachable impurities, stable on storage, sterile, and biodegradable. In yet another embodiment, a controlled or sustained release system can be placed in proximity of the therapeutic target, thus requiring only a fraction of the systemic dose (see, e.g., Goodson, (1984) in Medical Applications of Controlled Release, supra, vol. 2, pp. 115-138). Controlled release systems are discussed in the review by Langer (Langer, (1990) Science 249:1527-1533). Any technique known to one of skill in the art can be used to produce sustained release formulations comprising one or more BRD7 antagonist, Ikaros antagonist, or CRBN activator provided herein. See, e.g., U.S. Pat. No. 4,526,938, PCT publication WO 91/05548, PCT publication WO 96/20698, Ning et al., (1996) Intratumoral Radioimmunotherapy of a Human Colon Cancer Xenograft Using a Sustained-Release Gel, Radiotherapy & Oncology, 39:179-189.

The present disclosure also contemplates the use of nanoparticles for the delivery of the therapeutic agents (e.g., a BRD7 antagonist, Ikaros antagonist, or CRBN activator) described herein. The advantageous characteristics of nanoparticles, generally defined as particles between 1 and 100 nanometers, flow from their high surface area to volume ratio. Nanomedicine—the therapeutic use of nanoparticles—has historically been limited to the clinical evaluation of liposomal nanoparticles as delivery systems for anticancer drugs and vaccines. However, advancements in the field of nanomedicine are expected to result in rapid expansion of the technology's use in the coming years. (See, e.g., Freitas, (2005) Nanomedicine: Nanotech. Biol. Med., 1 (1): 2-9).

Nanomedicine presents the opportunity for delivery of the therapeutic agent to specific cells/sites. Because nanoparticles can deposit the active agent in the morbid region itself, lower doses of the therapeutic agent are often required compared to conventional drug delivery technologies, frequently resulting in the added benefit of a reduction in adverse effects.

In a specific embodiment, where the composition comprises a nucleic acid encoding a prophylactic or therapeutic agent (e.g., a BRD7 antagonist, Ikaros antagonist, or CRBN activator provided herein), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic™, Dupont), or coating with lipids or cell surface receptors or transfecting agents, or by administering it in linkage to a homeobox-like peptide which is known to enter the nucleus (see, e.g., Joliot et al., (1991) Proc. Natl. Acad. Sci. USA, 88:1864-1868), etc. Alternatively, a nucleic acid can be introduced intracellularly and incorporated within host cell DNA for expression by homologous recombination.

In a specific embodiment, a composition comprises one, two or more BRD7 antagonists Ikaros antagonists, or CRBN activators. In another embodiment, a composition comprises one, two or more BRD7 antagonists, Ikaros antagonists, or CRBN activators and a prophylactic or therapeutic agent other than a BRD7 antagonist, Ikaros antagonist, or CRBN activator provided herein. In certain embodiments, the agents are known to be useful for or have been or are currently used for the prevention, management, treatment and/or amelioration of a CNS cell defective disease, disorder or condition. In addition to prophylactic or therapeutic agents, the compositions can also comprise a carrier.

The compositions include bulk drug compositions useful in the manufacture of pharmaceutical compositions (e.g., compositions that are suitable for administration to a subject or patient) that can be used in the preparation of unit dosage forms. In a specific embodiment, a composition is a pharmaceutical composition. Such compositions comprise a prophylactically or therapeutically effective amount of one or more prophylactic or therapeutic agents (e.g., a BRD7 antagonist, Ikaros antagonist, or CRBN activator or other prophylactic or therapeutic agent), and a pharmaceutically acceptable carrier. In certain embodiments, the pharmaceutical compositions are formulated to be suitable for the route of administration to a subject.

In a specific embodiment, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences (1990) Mack Publishing Co., Easton, Pa. Such compositions will contain a prophylactically or therapeutically effective amount of the BRD7 antagonist, Ikaros antagonist, or CRBN activator, preferably in purified form, together with a suitable amount of carrier so as to provide the form for proper administration to the patient. The formulation should suit the mode of administration.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocamne to ease pain at the site of the injection. Such compositions, however, can be administered by a route other than intravenous.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

In certain embodiments, a BRD7 antagonist, Ikaros antagonist, or CRBN activator is packaged in a hermetically sealed container such as an ampoule or sachette indicating the quantity of BRD7 antagonist, Ikaros antagonist, or CRBN activator. In one embodiment, the BRD7 antagonist, Ikaros antagonist, or CRBN activator is supplied as a dry sterilized lyophilized powder or water free concentrate in a hermetically sealed container and can be reconstituted, e.g., with water or saline to the appropriate concentration for administration to a subject. In certain embodiments, the BRD7 antagonist, Ikaros antagonist, or CRBN activator is supplied as a dry sterile lyophilized powder in a hermetically sealed container at a unit dosage of at least 0.1 mg, at least 0.5 mg, at least 1 mg, at least 2 mg, or at least 3 mg, and more preferably at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized BRD7 antagonist, Ikaros antagonist, or CRBN activator can be stored at between 2 and 8° C. in its original container and the BRD7 antagonist, Ikaros antagonist, or CRBN activator can be administered within 12 hours, preferably within 6 hours, within 5 hours, within 3 hours, or within 1 hour after being reconstituted. In an alternative embodiment, a BRD7 antagonist, Ikaros antagonist, or CRBN activator is supplied in liquid form in a hermetically sealed container indicating the quantity and concentration of the BRD7 antagonist, Ikaros antagonist, or CRBN activator. In certain embodiments, the liquid form of the BRD7 antagonist, Ikaros antagonist, or CRBN activator is supplied in a hermetically sealed container at least 0.1 mg/ml, at least 0.5 mg/ml, or at least 1 mg/ml, and more preferably at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The therapeutically effective amounts of the active protein (s) will be a function of many variables, including the type of BRD7 antagonist, Ikaros antagonist, or CRBN activator; the affinity of the BRD7 antagonist, Ikaros antagonist, or CRBN activator; any residual cytotoxic activity exhibited by the BRD7 antagonist, Ikaros antagonist, or CRBN activator; the route of administration, and/or the clinical condition of the patient.

A therapeutically effective amount of a BRD7 antagonist can be such that when administered, the antagonist of BRD7 results in at least partial inhibition of at least one biological activity of BRD7.

A therapeutically effective amount of an Ikaros antagonist can be such that when administered, the antagonist of Ikaros results in at least partial inhibition of at least one biological activity of Ikaros.

A therapeutically effective amount of a CRBN activator can be such that when administered, CRBN activator results in at least partial increase of at least one biological activity of CRBN. A therapeutically effective amount can also be such that when administered, an inhibitor of a CRBN substrate or downstream protein in at least partial inhibition of at least one biological activity of the CRBN substrate or downstream protein.

The dosage administered, as single or multiple doses, to an individual will vary depending upon a variety of factors, including properties of antagonists, the route of administration, patient conditions and characteristics (sex, age, body weight, health, size, and so on), extent of symptoms, concurrent treatments, frequency of treatment and the effect desired.

Adjustment and manipulation of established dosage ranges are well within the ability of those skilled in the art, as well as in vitro and in vivo methods of determining in an individual (i) the inhibition of BRD7, (ii) inhibition of Ikaros, or (iii) the activation of CRBN or inhibition of a CRBN substrate or downstream protein.

In one embodiment, the amount of a prophylactic or therapeutic agent (e.g., a BRD7 antagonist, Ikaros antagonist, or CRBN activator provided herein, such as an inhibitor of a CRBN substrate or downstream protein), or a composition may be effective in the prevention, management, treatment and/or amelioration of a CNS cell defective disease, disorder or condition can be determined by standard clinical techniques.

Accordingly, a dosage of a BRD7 antagonist, Ikaros antagonist, or CRBN activator or a composition that results in a serum concentration of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, and preferably at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for use in a method provided herein, such as the prevention, management, treatment and/or amelioration of a CNS cell defective disease, disorder or condition. In addition, in vitro assays can optionally be employed to help identify optimal dosage ranges. The precise dose to be employed in the formulation will also depend on the route of administration, and the seriousness of a CNS cell defective disease, disorder or condition, and should be decided according to the judgment of the practitioner and each patient's circumstances.

Effective doses can be extrapolated from dose-response curves derived from in vitro or animal model test systems, including those provided in the experimental section and Examples provided herein.

For the BRD7 antagonist, Ikaros antagonist, or CRBN activator provided herein, the dosage administered to a patient is typically 0.1 mg/kg to 100 mg/kg of the patient's body weight. In some embodiments, the dosage administered to the patient is about 1 mg/kg to about 75 mg/kg of the patient's body weight. In certain embodiments, the dosage administered to a patient is between 1 mg/kg and 20 mg/kg of the patient's body weight, more preferably 1 mg/kg to 5 mg/kg of the patient's body weight. Generally, human BRD7 antagonists, Ikaros antagonists, or CRBN activators have a longer half-life within the human body than BRD7 antagonists, Ikaros antagonists, or CRBN activators from other species due to the immune response to the foreign polypeptides. Thus, lower dosages of human BRD7 antagonists, Ikaros antagonists, or CRBN activators and less frequent administration is often possible. Further, the dosage and frequency of administration of the BRD7 antagonists, Ikaros antagonists, or CRBN activators can be reduced by enhancing uptake and tissue penetration of the BRD7 antagonists, Ikaros antagonists, or CRBN activators by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of a BRD7 antagonist, Ikaros antagonist, or CRBN activator is administered 5 times, 4 times, 3 times, 2 times or, in certain embodiments, 1 time to manage a CNS cell defective disease, disorder or condition. In some embodiments, a BRD7 antagonist, Ikaros antagonist, or CRBN activator is administered about 1-12 times, wherein the doses can be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope of the methods provided herein.

In a specific embodiment, about 100 mg/kg, about 75 mg/kg or less, about 50 mg/kg or less, about 25 mg/kg or less, about 10 mg/kg or less, about 5 mg/kg or less, about 1 mg/kg or less, about 0.5 mg/kg or less, about 0.1 mg/kg or less of a BRD7 antagonist, Ikaros antagonist, or CRBN activator provided herein in a sustained release formulation is administered to a subject, preferably a human, to prevent, manage, treat and/or ameliorate a CNS cell defective disease, disorder or condition. In another specific embodiment, an about 100 mg/kg, about 75 mg/kg or less, about 50 mg/kg or less, about 25 mg/kg or less, about 10 mg/kg or less, about 5 mg/kg or less, about 1 mg/kg or less, about 0.5 mg/kg or less, or about 0.1 mg/kg or less bolus of a BRD7 antagonist, Ikaros antagonist, or CRBN activator not in a sustained release formulation is administered to a subject, preferably a human, to prevent, manage, treat and/or ameliorate a CNS cell defective disease, disorder or condition, and after a certain period of time, about 100 mg/kg, about 75 mg/kg or less, about 50 mg/kg or less, about 25 mg/kg or less, about 10 mg/kg or less, about 5 mg/kg or less, about 1 mg/kg or less, about 0.5 mg/kg or less, or about 5 mg/kg or less of a BRD7 antagonist, Ikaros antagonist, or CRBN activator in a sustained release is administered to the subject (e.g., intranasally or intramuscularly) two, three or four times (preferably one time). In accordance with this embodiment, a certain period of time can be 1 to 5 days, a week, two weeks, or a month.

In some embodiments, a single dose of a BRD7 antagonist, Ikaros antagonist, or CRBN activator is administered to a patient for use in the methods provided herein, for example, to prevent, manage, treat and/or ameliorate a CNS cell defective disease, disorder or condition, two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six times at bi-weekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose may or may not be identical).

In another embodiment, a single dose of a BRD7 antagonist, Ikaros antagonist, or CRBN activator is administered to a patient for use in a method provided herein, for example, to prevent, manage, treat and/or ameliorate a CNS cell defective disease, disorder or condition, two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose may or may not be identical).

In one embodiment, a single dose of a BRD7 antagonist, Ikaros antagonist, or CRBN activator is administered to a patient for use in a method provided herein, for example, to prevent, manage, treat and/or ameliorate a CNS cell defective disease, disorder or condition, two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose may or may not be identical).

In some embodiments, a single dose of a BRD7 antagonist, Ikaros antagonist, or CRBN activator is administered to a patient for use in a method provided herein, for example, to prevent, manage, treat and/or ameliorate a CNS cell defective disease, disorder or condition, two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose may or may not be identical).

In another embodiment, the BRD7 antagonist, Ikaros antagonist, or CRBN activator is administered in conjunction with a second active agent. The second active agent is administered orally, intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the disorder being treated or managed, the severity and stage of the central nervous system disorder, and the amount(s) of a BRD7 antagonist, Ikaros antagonist, or CRBN activator and any optional additional active agents concurrently administered to the patient.

In certain embodiments, the prophylactic or therapeutic agents provided herein are cyclically administered to a patient. Cycling therapy involves the administration of a first agent for a period of time, followed by the administration of the agent and/or the second agent for a period of time and repeating this sequential administration. Cycling therapy can reduce the development of resistance to one or more of the therapies, avoid or reduce the side effects of one of the therapies, and/or improves the efficacy of the treatment.

5.8 Recombinant Production of BRD7 Antagonists, Ikaros Antagonists or CRBN Activators In a specific embodiment, nucleic acids comprising sequences encoding a BRD7 antagonist, Ikaros antagonist, or CRBN activator are administered to a subject for use in a method provided herein, for example, to prevent, treat and/or ameliorate a CNS-cell defective disease, disorder or condition, or treat and/or prevent a CNS tissue injury, by way of gene therapy. Such therapy encompasses that performed by the administration to a subject of an expressed or expressible nucleic acid. In an embodiment, the nucleic acids produce their encoded antibody, and the antibody mediates a prophylactic or therapeutic effect.

Any of the methods for recombinant gene expression (or gene therapy) available in the art can be used. Exemplary methods are described below and are provided in the Examples section.

For general review of the methods of gene therapy, see Goldspiel et al., (1993) Clinical Pharmacy 12:488-505; Wu and Wu, (1991) Biotherapy 3:87-95; Tolstoshev, (1993) Ann. Rev. Pharmacol. Toxicol., 32:573-596; Mulligan, (1993) Science 260:926-932; and Morgan and Anderson, (1993) Ann. Rev. Biochem. 62:191-217; May, (1993) TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a specific embodiment, a composition comprises nucleic acids encoding a BRD7 antagonist, Ikaros antagonist, or CRBN activator provided herein, the nucleic acids being part of an expression vector that expresses the BRD7 antagonist, Ikaros antagonist, or CRBN activator in a suitable host. In particular, such nucleic acids have promoters, preferably heterologous promoters, operably linked to the antagonist's coding region, the promoter being inducible or constitutive, and, optionally, tissue-specific. In another particular embodiment, nucleic acid molecules are used in which the BRD7 antagonist, Ikaros antagonist, or CRBN activator coding sequences and any other desired sequences are flanked by regions that promote homologous recombination at a desired site in the genome, thus providing for intrachromosomal expression of the antagonist encoding nucleic acids (Koller and Smithies, (1989) Proc. Natl. Acad. Sci. USA, 86:8932-8935; Zijlstra et al., (1989) Nature, 342:435-438).

Delivery of the nucleic acids into a subject can be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where the sequences are expressed to produce the encoded product. This can be accomplished by any of numerous methods known in the art, e.g., by constructing them as part of an appropriate nucleic acid expression vector and administering the vector so that the sequences become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, (1987) J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO93/14188, WO 93/20221). Alternatively, the nucleic acid can be introduced intracellularly and incorporated within host cell DNA for expression, by homologous recombination (Koller and Smithies, (1989) Proc. Natl. Acad. Sci. USA 86:8932-8935; and Zijlstra et al., (1989) Nature 342: 435-438).

In a specific embodiment, viral vectors that contain nucleic acid sequences encoding a BRD7 antagonist, Ikaros antagonist, or CRBN activator are used. For example, a retroviral vector can be used (see Miller et al., (1993) Meth. Enzymol. 217:581-599). These retroviral vectors contain the components necessary for the correct packaging of the viral genome and integration into the host cell DNA. The nucleic acid sequences encoding the BRD7 antagonist, Ikaros antagonist, or CRBN activator to be used in gene therapy can be cloned into one or more vectors, which facilitate delivery of the gene into a subject. More detail about retroviral vectors can be found in Boesen et al., (1994) Biotherapy, 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., (1994) J. Clin. Invest., 93:644-651; Klein et al., (1994) Blood, 83:1467-1473; Salmons and Gunzberg, (1993) Human Gene Therapy, 4:129-141; and Grossman and Wilson, (1993) Curr. Opin. in Genetics and Devel., 3:110-114.

Adenoviruses are other viral vectors that can be used in the recombinant production of a BRD7 antagonist, Ikaros antagonist, or CRBN activator. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, (1993) Current Opinion in Genetics and Development, 3:499-503 present a review of adenovirus-based gene therapy. Bout et al., (1994) Human Gene Therapy, 5:3-10 demonstrated the use of adenovirus vectors to transfer genes to the respiratory epithelia of rhesus monkeys. Other instances of the use of adenoviruses in gene therapy can be found in Rosenfeld et al., (1991) Science, 252:431-434; Rosenfeld et al., (1992) Cell, 68:143-155; Mastrangeli et al., (1993) J. Clin. Invest., 91:225-234; PCT Publication WO94/12649; and Wang et al., (1995) Gene Therapy 2:775-783. In a specific embodiment, adenovirus vectors are used.

Adeno-associated virus (AAV) can also be utilized (Walsh et al., (1993) Proc. Soc. Exp. Biol. Med., 204:289-300; and U.S. Pat. No. 5,436,146). In a specific embodiment, AAV vectors are used to express a BRD7 antagonist, Ikaros antagonist, or CRBN activator provided herein.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In one embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, (1993) Meth. Enzymol., 217:599-618; Cohen et al., (1993) Meth. Enzymol., 217:618-644; Clin. Pharma. Ther. 29:69-92 (1985)) and can be used in accordance with the methods provided herein, provided that the necessary developmental and physiological functions of the recipient cells are not disrupted. The technique should provide for the stable transfer of the nucleic acid to the cell, so that the nucleic acid is expressible by the cell and in some embodiments heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a specific embodiment, the cell used for gene therapy is autologous to the subject.

In an embodiment in which recombinant cells are used in gene therapy, nucleic acid sequences encoding a BRD7 antagonist, Ikaros antagonist, or CRBN activator are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the methods provided herein (see e.g., PCT Publication WO 94/08598; Stemple and Anderson, (1992) Cell 7 1:973-985; Rheinwald, (1980) Meth. Cell Bio. 21A: 229; and Pittelkow and Scott, (1986) Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

BRD7 antagonists, Ikaros antagonists, or CRBN activators can be produced by any method known in the art for the synthesis of antibodies, in particular, by chemical synthesis or in certain embodiments, by recombinant expression techniques. The practice employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley and Sons (1987 and annual updates); Current Protocols in Immunology, John Wiley and Sons (1987 and annual updates) Gait (ed.) (1984); Oligonucleotide Synthesis: A Practical Approach, IRL Press; Eckstein (ed.) (1991); Oligonucleotides and Analogues: A Practical Approach, IRL Press; Birren et al. (eds.) (1999); Genome Analysis: A Laboratory Manual, Cold Spring Harbor Laboratory Press.

5.9 Kits

Typically, active ingredients provided herein are preferably not administered to a patient at the same time or by the same route of administration. Accordingly, also provided herein are kits which, when used by the medical practitioner, can simplify the administration of appropriate amounts of active ingredients to a patient.

Provided herein is a pharmaceutical pack or kit comprising one or more containers filled with one or more of the ingredients of the pharmaceutical compositions provided herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

A typical kit comprises a dosage form of a BRD7 antagonist, Ikaros antagonist, or CRBN activator provided herein, or a pharmaceutically acceptable salt, solvate, hydrate, stereoisomer, clathrate, or prodrug thereof. Kits may further comprise additional active ingredients.

Kits can further comprise devices that are used to administer the active ingredients. Examples of such devices include, but are not limited to, syringes, drip bags, patches, and inhalers.

Kits can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Also provided herein are kits that can be used in the above methods. In one embodiment, a kit comprises a BRD7 antagonist, Ikaros antagonist, or CRBN activator provided herein in one or more containers.

5.10 Evaluation of the Effect of BRD7 Antagonists on CNS Cell Expansion and Functions In the Examples set forth below the effect of BRD7 antagonists on CNS cell expansion and function is evaluated. As shown below, BRD7 antagonists enlarge brain size and increase neural progenitors cells in developing brain and spinal cord. BRD7 antagonists also induce expression of pluripotency genes.

As shown in Example 19 below, knockdown of BRD7 enlarges the brain in zebrafish embryos. In order to examine the effect of antagonists of BRD7 on brain growth, BRD7 was knocked down or over-expressed in zebrafish embryos. Knockdown of BRD7 was performed by microinjection of antisense morpholino oligonucleotides (AMO). Overexpression of BRD7 was performed by microinjection of synthesized capped mRNA. AMO or capped mRNA was introduced into one-cell stage embryos by using a nitrogen gas-pressure microinjector IM 300 (Narishige). Conditions for microinjection were as follows: gas pressure was about 15 picosiemens; release period was about 30 to about 50 milliseconds per single injection; concentrations of AMOs and capped mRNA were 400 ng/µl and 250 ng/µl in nuclease-free water, respectively. Capped mRNAs were synthesized in vitro using the mMESSAGE mMachine® in vitro transcription kit (Ambion) from cDNAs cloned into pCS2+ plasmids.

Figure 9:
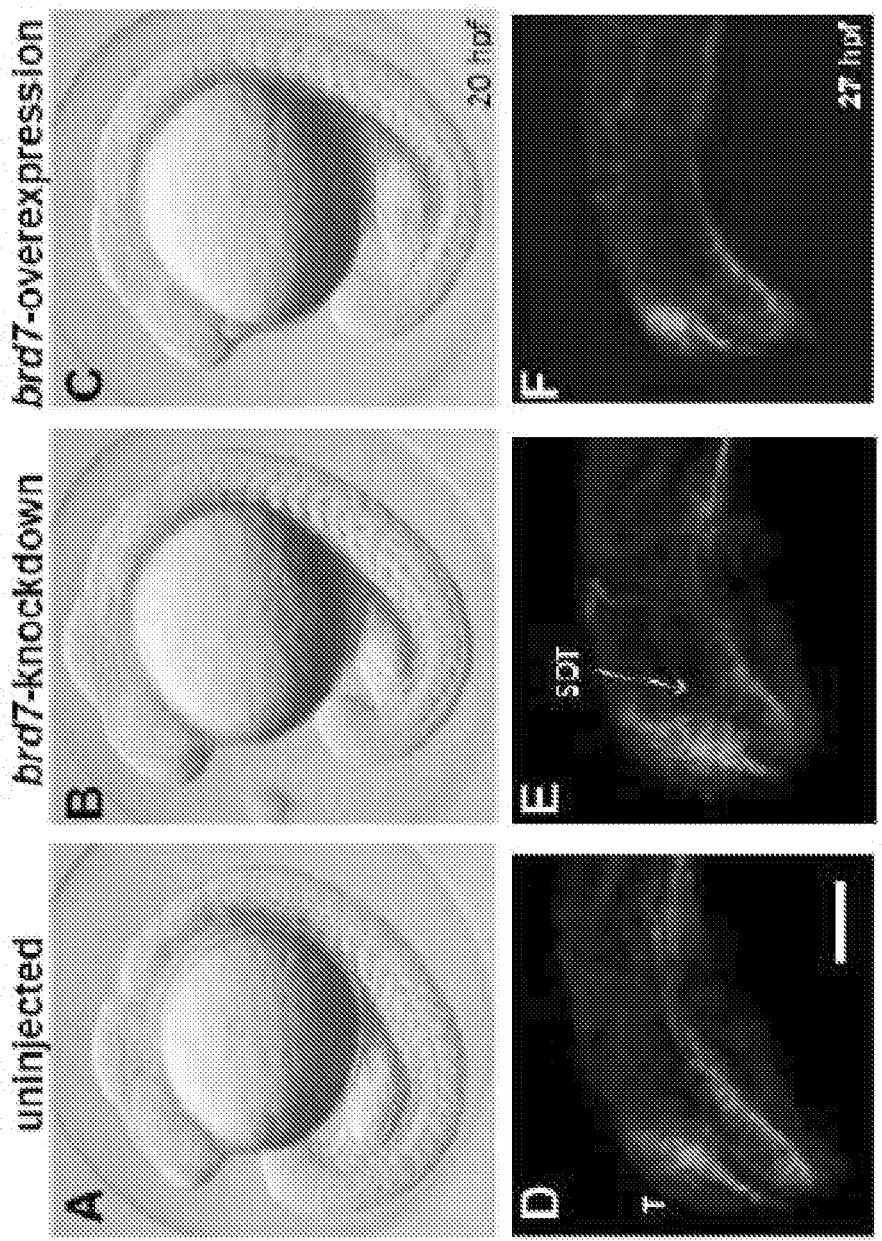

Brains of the embryos were examined for morphology and volume by magnetic resonance imaging (MRI). FIGS. 9A, 9B, and 9C show microscopic pictures of untreated, BRD7 knockdown, and BRD7 overexpression zebrafish embryos, respectively. FIGS. 9D, 9E, and 9F show fluorescence microscopic pictures of brain regions of untreated, BRD7 knockdown, and BRD7 overexpression zebrafish embryos, respectively. As shown in these figures, BRD7 knockdown fish has bigger heads than untreated embryos. In contrast, embryos injected with BRD7 mRNA causing BRD7 overproduction develops smaller heads and eyes than untreated embryos. Measurement of the volume of different regions of the brain by transverse and cross section of captured MRI images of whole brain (telencephalon to spinal cord) revealed that all portions of the brain (telencephalon, diencephalon, midbrain, cerebellum and spinal cord) are affected by BRD7 knockdown or BRD7-overexpression. The volume of whole brain of BRD7 knockdown fish is much bigger than untreated fish, while for BRD7-overexpressing fish, brain volume is smaller.

The effect of BRD7 antagonists on the CNS cell functions was evaluated by in situ hybridization. As shown in Example 20 below, knockdown of BRD7 activates expression of Pou5f1 (Oct3/4), Klf4, c-Myc and HuC (Elavl3) in zebrafish embryos. In particular, expression of Pou5f1 (Oct3/4) in the second and fourth rhombomeres in hindbrain increased in BRD7-knockdown embryo at 10 and 11 hpf. Expression of Klf4 also increased at 18 hpf in the rostral portion of neural tube in BRD7 knockdown zebrafish embryos. In addition, in BRD7 knockdown zebrafish embryos, expression of c-Myc was clearly strengthened at 30 hpf in the tectal proliferation zone in the medial and lateral areas, in which neural stem cells and progenitor cells existed, and in the most peripheral region of the ciliary marginal zone (CMZ) in the retina where retinal stem cells were located. Similarly, expression of Huc, a neural progenitor marker gene, increased in the brain and spinal cord in CRBN-overexpressed embryos and BRD7-knockdown embryos. The number of HuC-positive neural progenitor cells in the brain and spinal cord of BRD7 knockdown embryos increased at 15 hpf and the number of telencephalic neurons and spinal cord neurons increased in BRD7 knockdown embryos at 16 hpf.

As shown in Example 21 below, an increased expression of HuC in BRD7 knockdown embryos at 11 hpf was also demonstrated by quantitative PCR. Also as shown in the quantitative PCR analysis in Example 23 below, expression of Pou5f1 significantly increased in CRBN-overexpressing or BRD7-knockdown embryos at 11 hpf; expression of Pou5f1 target gene Zic3 and another pluripotency gene Nanog also increased in CRBN-overexpressing or BRD7-knockdown embryos. In contrast, in Example 23, expression of Pou5f1, Zic3 and Nanog decreased in CRBN knockdown, BARD-overexpressing, or thalidomide-treated embryos at the same stage.

Figure 10:
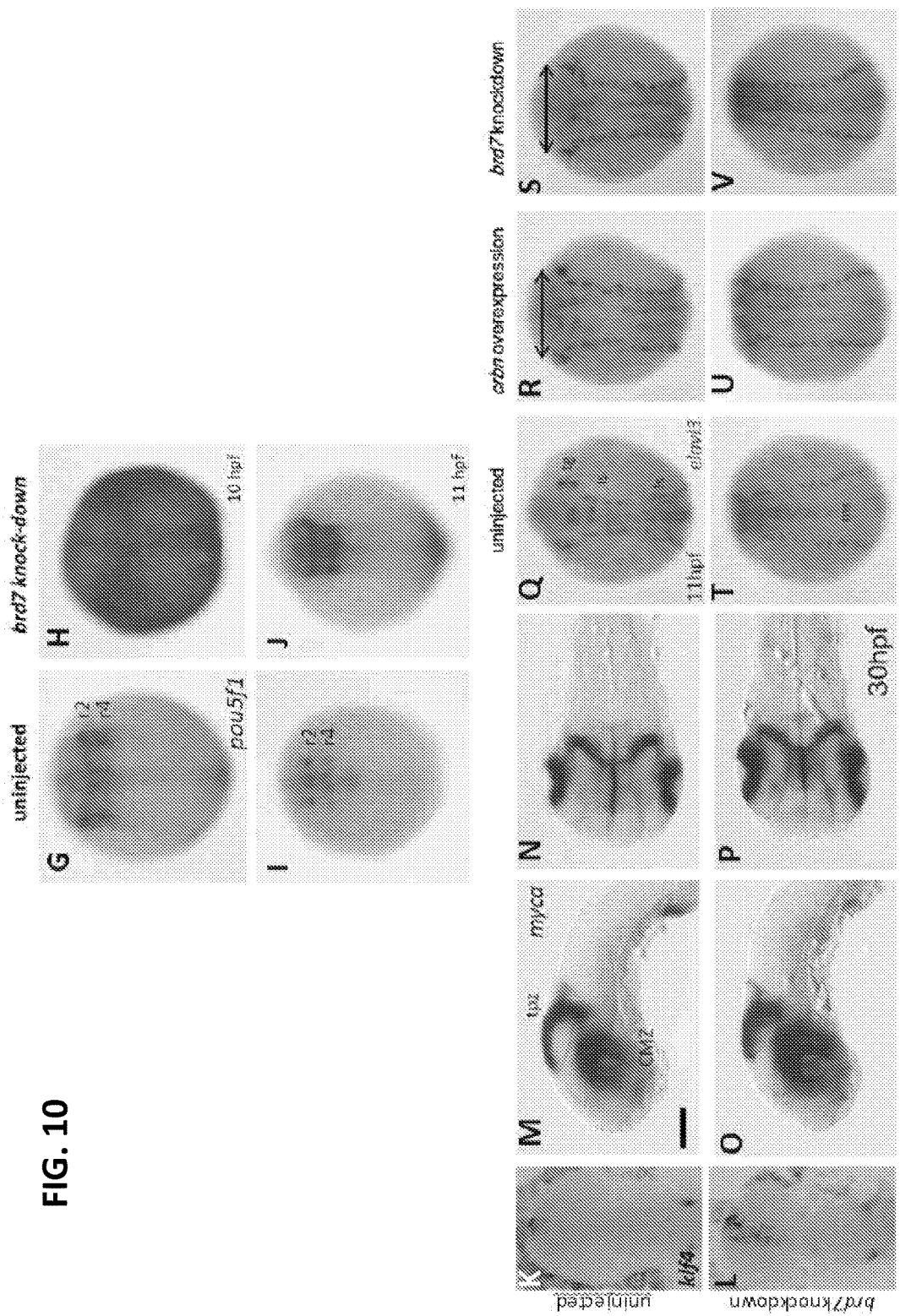

Example 20 shows that knockdown of BRD7 upregulates Pou5f1 (Oct3/4), Klf4, c-Myc and Huc in zebrafish embryos. The expressions of Pou5f1, Klf4, c-Myc and Huc in BRD7 knockdown or BRD7 overexpressing embryos were analyzed by in situ hybridization. These four genes are well known to induce pluripotency in both mouse and human somatic cells. As shown in FIG. 10, knockdown of BRD7 strengthens and expands the expression of these genes in the developing brain.

Expression of a pool of three genes, Ascl1, Brn2 (Pou3f2), and Myt1la, is sufficient to directly reprogram embryonic and postnatal fibroblasts into functional neurons (see, e.g., Vierbuchen and Wernig, (2011) *Nat Biotechnol.* 29:892-907). Therefore, the expression of Ascl1, Pou3f3a, and Myt1la was analyzed by quantitative PCR in untreated and BRD7 knockdown zebrafish embryos at 28 hpf in Example 24 below. As shown, knockdown of BRD7 increased the expression of Ascl1, Pou3f3a, and Myt1la at 28 hpf, and increased the expression of Ascl1, Brn2 (Pou3f2b), and Myt1la at 11 hpf.

5.11 Evaluation of the Effect of Ikaros Antagonists on CNS Cell Expansion and Functions In the Examples set forth below the effect of Ikaros antagonists on CNS cell expansion and function is evaluated. As shown below, Ikaros antagonists enlarge brain size and increase neural progenitors cells in developing brain and spinal cord. Ikaros antagonists also induce expression of pluripotency genes.

As shown in Example 25 below, knockdown of Ikaros enlarges brain in zebrafish embryos. In order to examine the effect of antagonists of Ikaros on brain growth, Ikaros was knocked down or over-expressed in zebrafish embryos. Knockdown of Ikaros was performed by microinjection of antisense morpholino oligonucleotides (AMO). Overexpression of Ikaros was performed by injection of synthesized capped mRNA. AMO or capped mRNA was introduced into one-cell stage embryos by using a nitrogen gas-pressure microinjector IM 300 (Narishige). Conditions for microinjection were as follows: gas pressure was about 15 picosiemens; release period was about 30 to about 50 milliseconds per single injection; concentrations of AMOs and capped mRNA were 400 ng/µl and 250 ng/µl in nuclease-free water, respectively. Capped mRNAs were synthesized in vitro using the mMESSAGE mMachine® in vitro transcription kit (Ambion) from cDNAs cloned into pCS2+ plasmids.

Figure 15:
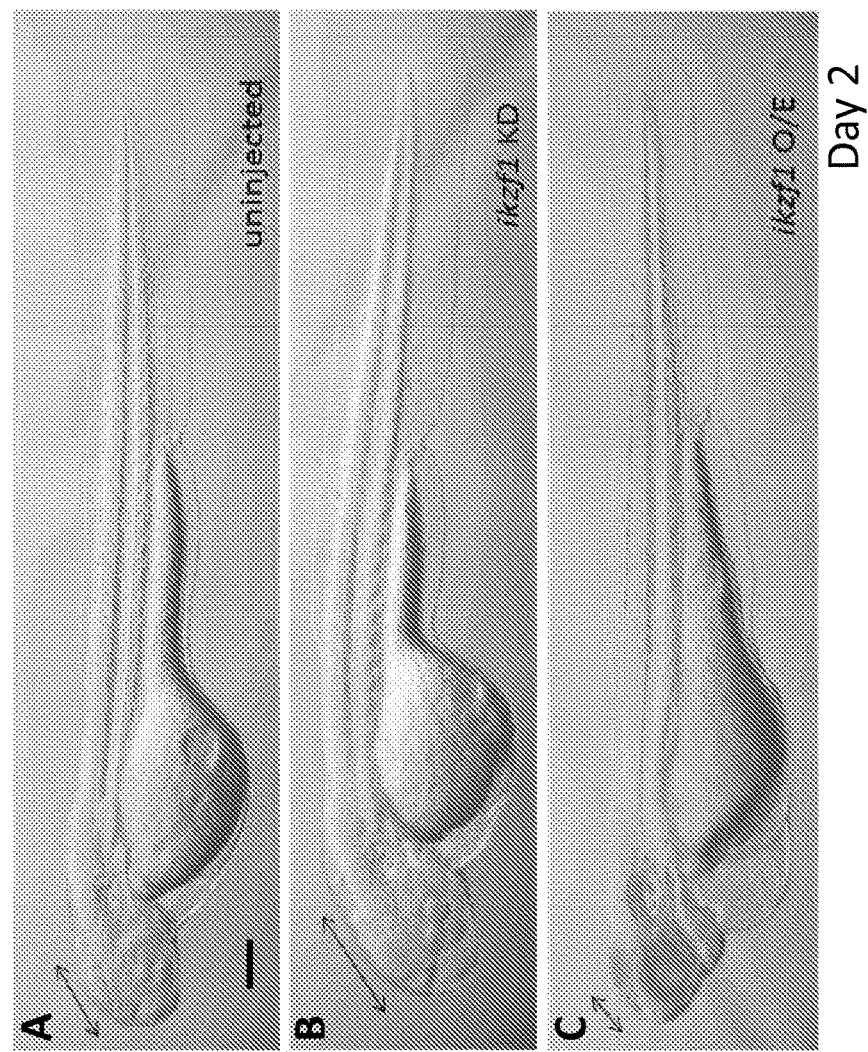

The brains of the embryos were examined for morphology and volume by magnetic resonance imaging (MRI). FIGS. 15A, 15B, and 15C show microscopic pictures of untreated, Ikaros-knockdown, and Ikaros-overexpressing zebrafish embryos at 55 hpf, respectively. As shown in these figures, the Ikaros-knockdown fish had bigger heads than the untreated embryos. In contrast, the embryos injected with Ikaros mRNA causing Ikaros overproduction developed smaller heads and eyes than the untreated embryos. Measurement of the volume of different regions of the brain by transverse and cross section of captured MRI images of the whole brain (the telencephalon to the spinal cord) revealed that all portions of the brain (the telencephalon, the diencephalon, the midbrain, the cerebellum, and the spinal cord) were affected by Ikaros knockdown or Ikaros overexpression. The volume of the whole brain of the Ikaros-knockdown fish was much bigger than that of the untreated fish, while for the Ikaros-overexpressing fish, the brain volume was smaller.

Figure 16:
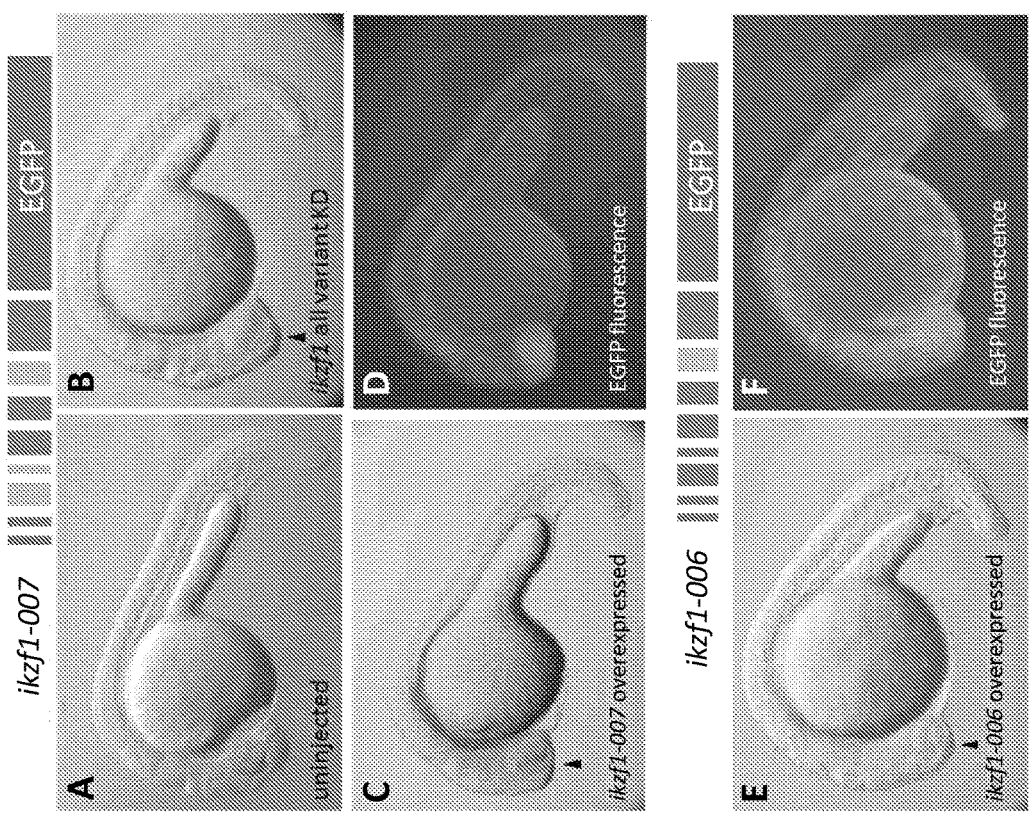

The effects of overexpression of two Ikaros variants on brain development in zebrafish embryos were analyzed in Example 26. Two new Ikaros variants, ikzf1-006 and ikzf1 ikzf1-007 were isolated. Ikzf1-006 lacked exon 7 and ikzf1-007 lacked exon 4 and 7. FIGS. 16A, 16B, 16C, and 16E show microscopic pictures of the brains of untreated, Ikaros-knockdown, ikzf1-007 (an Ikaros variant)-overexpressing, and ikzf1-006 (an Ikaros variant)-overexpressing zebrafish embryos at 22 hpf, respectively. FIGS. 16D and 16F are fluorescent microscopic pictures of the brains of the ikzf1-007-overexpressing and the ikzf1-006-overexpressing zebrafish embryos at 22 hpf, respectively. These pictures were taken at the same magnification. As shown, at 22 hpf, overexpression of fused Ikzf1:EGFP protein caused reduction of brain development in both the ikzf1-006- and the ikzf1-007-overexpressing embryos. Forebrains were truncated by incomplete growth of telencephalon, diencephalon, and midbrain (See FIGS. 16C-16F; 16D and 16F are EGFP fluorescent images). In contrast, knockdown of Ikaros caused macrocephaly, as shown in FIG. 16B.

Figure 17:
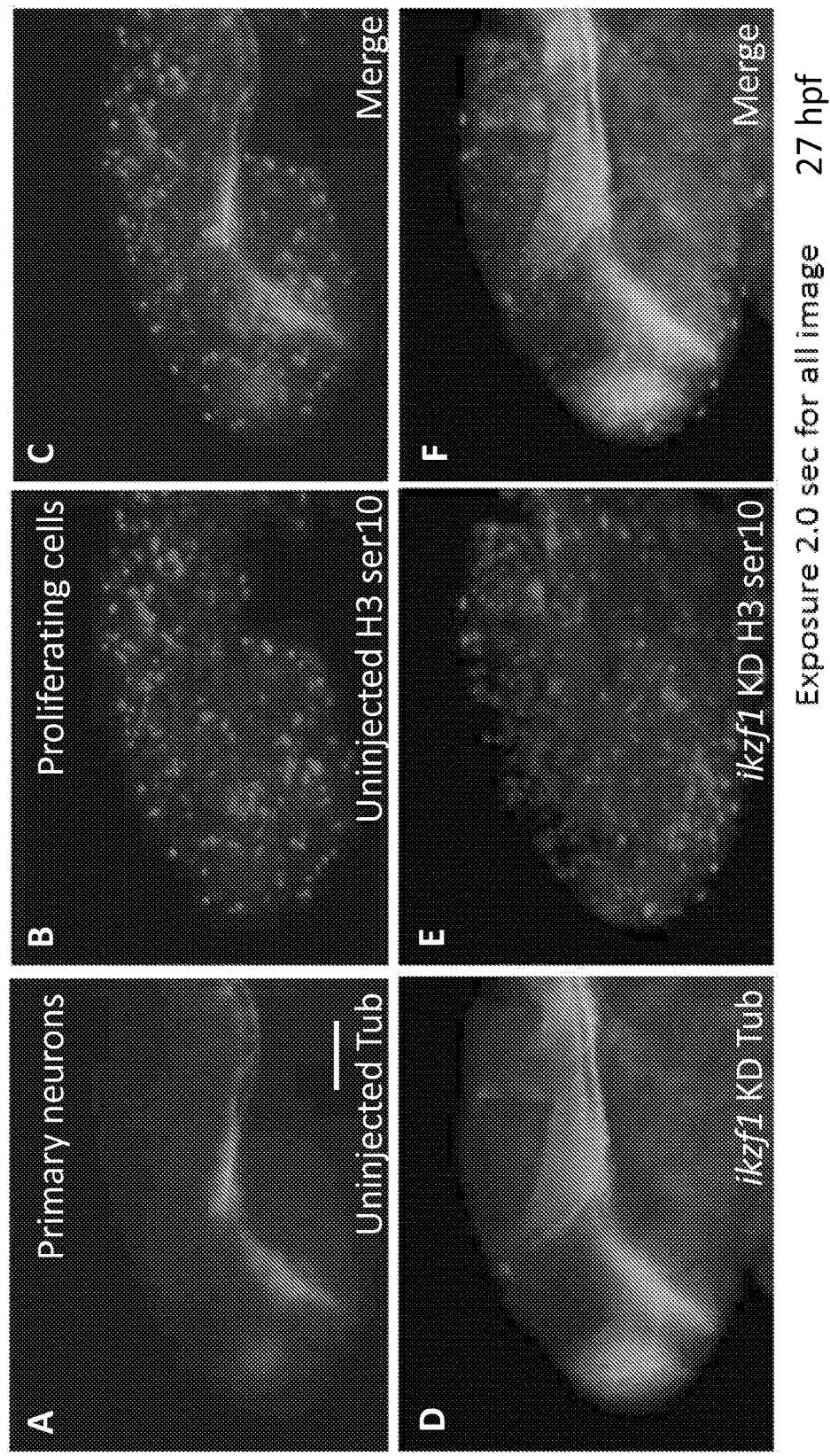
Figure 18:
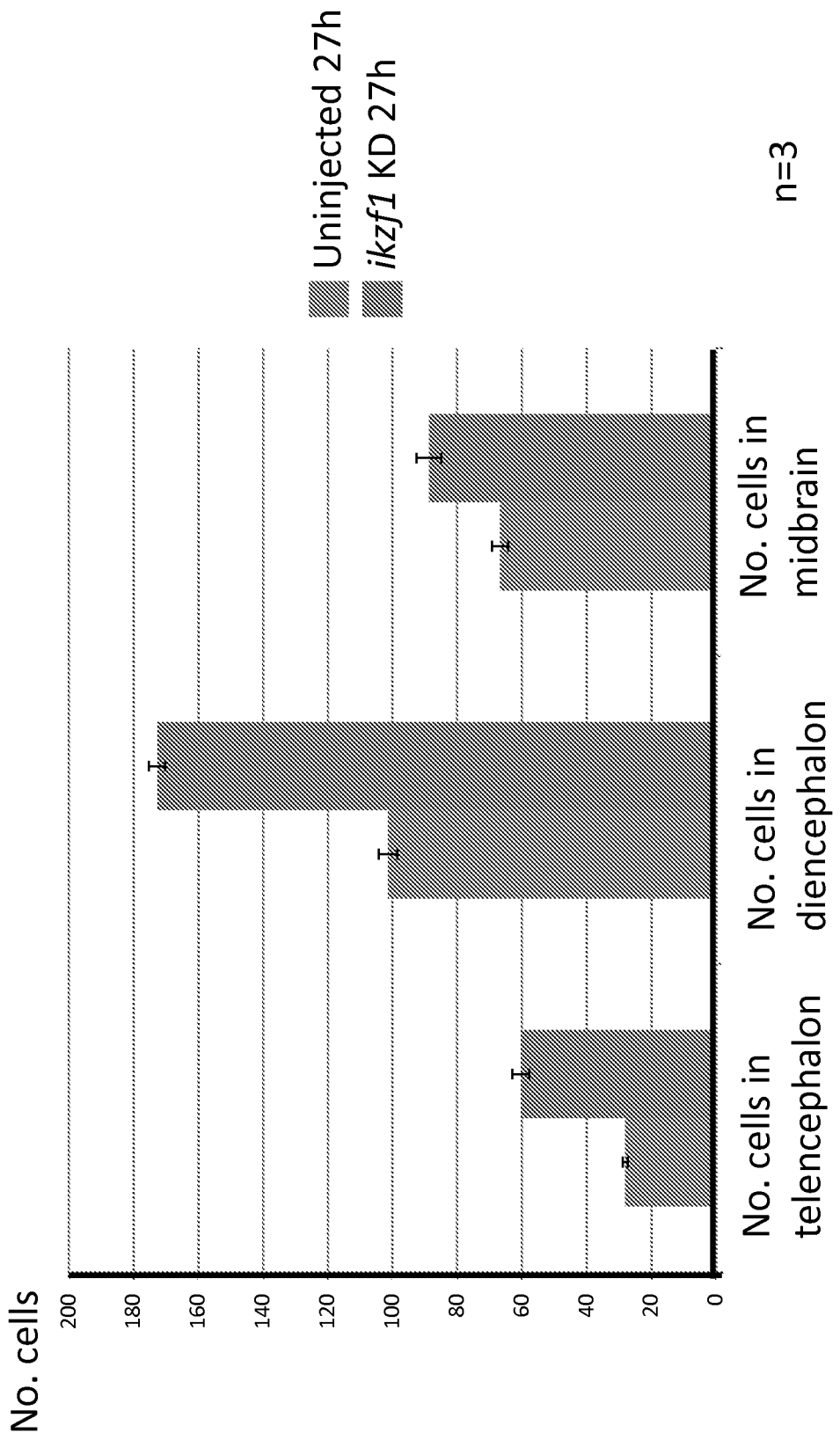
Figure 19:
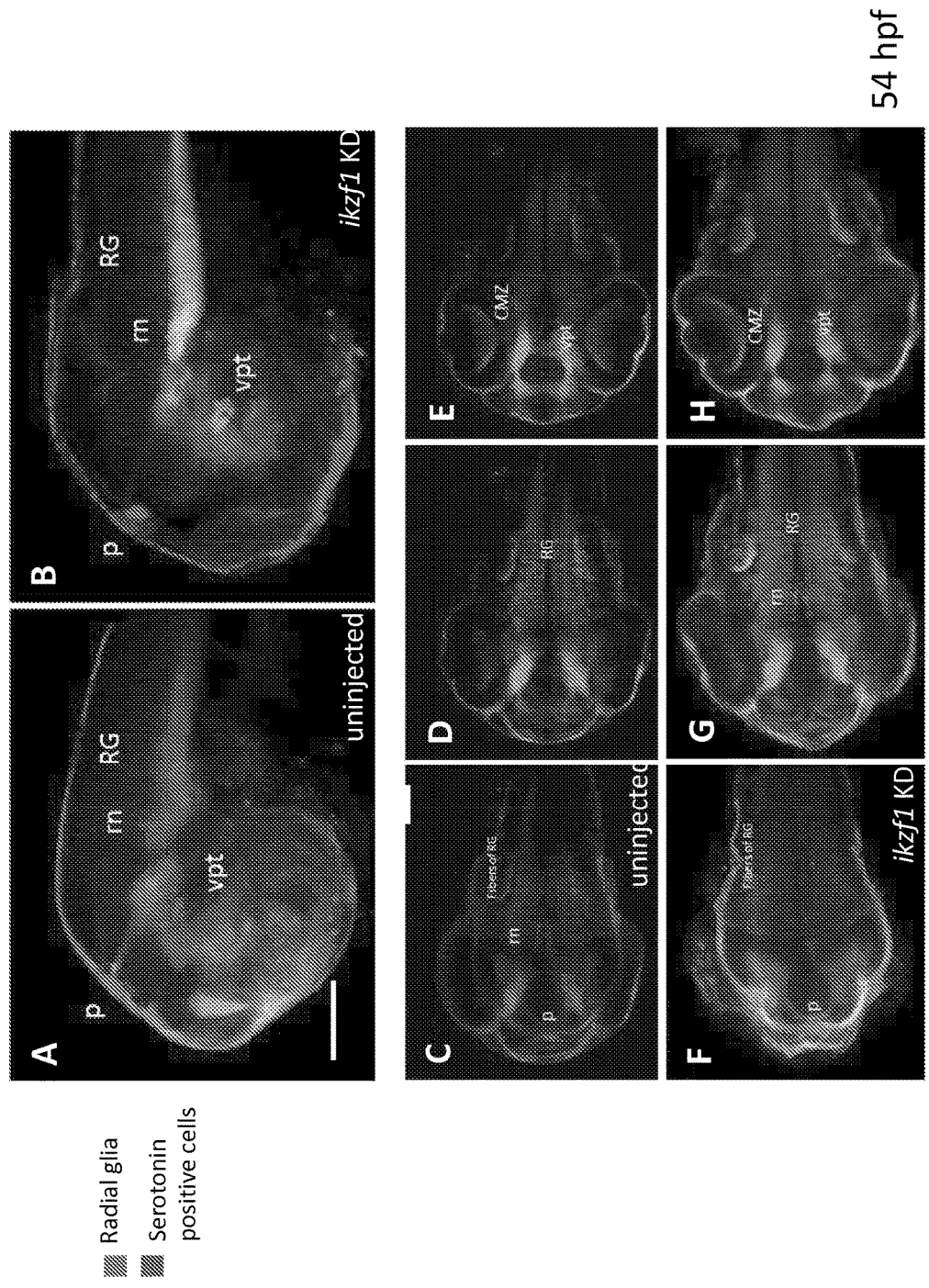

As shown in Example 27, numbers of primary neurons and proliferating cells were analyzed by immunostaining in untreated and Ikaros-knockdown zebrafish embryos at 27 hpf. FIGS. 17A and 17D show the primary neurons in the CNS of the untreated and the Ikaros-knockdown zebrafish embryos, respectively, at 27 hpf by immunostaining with anti-acetylated tubulin antibody. FIGS. 17B and 17E show the proliferating cells in the CNS of the untreated and the Ikaros-knockdown zebrafish embryos, respectively, at 27 hpf by immunostaining with anti-phospho-histone H3 antibodies. FIG. 17C shows merged image of FIGS. 17A and 17B. FIG. 17F shows merged image of FIGS. 17D and 17E. As shown, immunostaining images revealed that the number of the proliferating cells and the number of the primary neurons both increased in the Ikaros-knockdown embryos. Global distribution of the primary neurons was normal as shown (scale bar: 50 μm). The number of phosphorylated histone H3-positive cells was counted in a stacked focal plane of laser confocal microscope at 27 hpf. The average number of the H3-positive cells in the telencephalon, the diencephalon, and the midbrain was statistically compared between the untreated and the Ikaros-knockdown embryos (n=3 in each experiment). As shown in FIG. 18, the number of the H3-positive proliferating cells in the telecephalon, the diencephalon, and the midbrain regions all increased in the Ikaros-knockdown zebrafish embryos at 27 hpf.

As shown in Example 28, the numbers of radial glia cells and serotonin-positive cells in Ikaros-knockdown zebrafish embryos were analyzed by immunostaining FIGS. 19A and 19C-19E show fluorescent microscopic pictures of the brains of untreated zebrafish embryos at 54 hpf. FIGS. 19B and 19F-19H show fluorescent microscopic pictures of the brains of the Ikaros-knockdown zebrafish embryos at 54 hpf. Cells were immunostained with anti-radia glia marker (Zrf-2) antibodies (green) and anti-serotonin antibodies (red). In these figures, rn represents raphe nuclei; RG represents radial glia; vpt represents ventral posterior tuberculum; p represents pineal organ; CMZ represents ciliary marginal zone (scale bar: 50 μm). As shown, the numbers of radial glia cells and serotonin-positive cells increased, while their spatial distribution was normal in the Ikaros-knockdown larvae.

The effects of Ikaros antagonists on expression of pluripotency genes were analyzed. As shown in Example 29 below, Ikaros knockdown activated expression of c-Myc, Sox2 and Nanog in zebrafish embryos by quantitative PCR.

The expression of Ascl1, Pou3f3a, Pou3f2b, and Myt1la was analyzed by quantitative PCR in untreated, Ikaros knockdown, and Ikaros overexpressing zebrafish embryos at 28 hpf in Example 30. As shown, knockdown of Ikaros increased the expression of Ascl1, Pou3f3a, Pou3f2b, and Myt1la in zebrafish embryos at 28 hpf, and overexpression of Ikaros decreased the expression of Ascl1, Pou3f3a, Pou3f2b, and Myt1la in zebrafish embryos at 28 hpf.

The expression of Ascl1a and Pou3f2b in Ikaros knockdown zebrafish embryos was also analyzed by in situ hybridization in Example 31. As shown, the expression of Ascl1a and Pou3f2b increased in Ikaros knockdown zebrafish embryos. In particular, the expression of Ascl1a in epiphysis, prethalamus, thalamus and hypothalamus was remarkably increased in Ikaros-knockdown embryo at 25 hpf. The expression of Pou3f2b also increased at 26 hpf in the diencephalon, midbrain hindbrain boundary and cerebellum primordium. All regions marked with Ascl1a and Pou3f2b were spatially corresponded to the proliferating zone, pool of neural stem and progenitor cells in CNS.

5.12 Evaluation of the Effect of CRBN Activators on CNS Cell Expansion and Functions In the Examples set forth below the effect of CRBN activators on CNS cell expansion and function is evaluated. As shown below, CRBN activators enlarge brain size and increase neural progenitors cells in developing brain and spinal cord. CRBN activators also induce expression of pluripotency genes.

As shown in Example 36 below, overexpression of CRBN activates expression of Sox2, Pou5f1 (Oct 3/4), c-Myc and Klf in zebrafish embryos as determined by in situ hybridization. FIGS. 27A and 27B show Sox2 expression in untreated and CRBN-overexpressing zebrafish embryos at 9 hpf, respectively, by in situ hybridization. As shown, the expression of Sox2 in the anterior brain region (ab) expanded at 9 phf (79.4%, n=68 in the CRBN-overexpressing embryos; see FIG. 27B). FIGS. 27C and 27D show Pou5f1 expression in the untreated and the CRBN-overexpressing zebrafish embryos at 10 hpf, respectively, by in situ hybridization. As shown, at 10 hpf, Pou5f1 was expressed in close to the midbrain-hindbrain boundary, presumptive rhombomere 2 and 4 in the hindbrain (r2 and r4), as well as in the axial mesodermal tissues such as the medial longitudinal strip (mls) (see FIG. 27C). When CRBN was overexpressed, the expression of Pou5f1 increased and expanded especially in the early brain region (81.9%, n=72; see FIG. 27D). FIGS. 27E, 27G, 27I, and 27K show c-Myc expression in the untreated zebrafish embryos at 30 hpf by in situ hybridization. FIGS. 27F, 27H, 27J, and 27L show c-Myc expression in the CRBN-overexpressing zebrafish embryos at 30 hpf by in situ hybridization. As shown, at 30 hpf, c-Myc was abundantly expressed in the tectal proliferation zone (tpz) at the medial and the lateral areas, where neural stem cells exist, and in the most peripheral region of the circumferential marginal zone (CMZ) in the retina, where retinal stem cells are located. The expression of m-Myc was apparently higher and distributed broader in both zones of the CRBN-overexpressing embryos (73.5%, n=68 in the CRBN-overexpressing embryos; see FIGS. 27F, 27H, 27J, and 27L). In the CMZ, the numbers of c-Myc-expressing cells increased in the CRBN-overexpressing embryos (see FIG. 27H), and the thickness of c-Myc-expressing cells in the tectal proliferation zone also increased (see FIG. 27L). FIGS. 27M and 27N show Klf4 expression in the untreated and the CRBN-overexpressing zebrafish embryos at 18 hpf, respectively, by in situ hybridization. As shown, at 18 hpf, Klf4 was expressed in trigeminal placode, hatching gland, and rostral portion of neural tube. In the CRBN-overexpressing embryos, Klf4 expression apparently increased in trigeminal placode (tgp) and anterior neural tube (bars) (see FIG. 27N).

As shown in Example 37 below, overexpression of CRBN increases the number of radial glial cells and matured neurons. Radial glial cells in the CNS function as a precursor of neurons and oligodendrocytes, and as a scaffold to support neuronal migration. FIGS. 28A and 28B show the brain regions of the untreated zebrafish embryos at 56 hpf immunostained with Zrf-1 antibodies, which label glial fibrillary acidic protein (GFAP) in astrocytes. FIGS. 28C and 28D show the brain regions of the CRBN-overexpressing zebrafish embryos at 56 hpf immunostained with Zrf-1 antibodies, which label glial fibrillary acidic protein (GFAP) in astrocytes. As shown, at 56 hpf, in the CRBN-overexpressing larvae, the number of GFAP-positive astrocytes detected by Zrf-1 increased in both cell bodies and fibers (see FIGS. 28C and 28D; bracket indicates the cell bodies of GFAP-positive glia). FIGS. 28E and 28F show the brain regions of the untreated zebrafish embryos at 56 hpf immunostained with Zrf-2 antibodies, which label radial glial cells. FIGS. 28G and 28H show the brain regions of the CRBN-overexpressing zebrafish embryos at 56 hpf immunostained with Zrf-2 antibodies, which label radial glial cells. As shown, the number of radial glial cells in the hindbrain increased in the CRBN-overexpressing larvae (see FIGS. 28G and 28H). FIGS. 28I and 28J show the brain regions of the untreated and the CRBN-overexpressing zebrafish embryos at 48 hpf immunostained with Zrf-2 antibodies, which label Müller glia in the retina. Müller glia had the potential to serve as neural stem cells in the retina and was labeled by Zrf-2. As shown, the number of Müller glia increased in the CRBN-overexpressing larvae at 48 hpf (see FIG. 28J), proportionally to the larger size of the eyes (see FIGS. 28I and 28J). FIGS. 28K and 28L show Sox10 in the otic vesicles and the neural crest cells (NCCs) in the spinal cord in the untreated and the CRBN-overexpressing zebrafish embryos at 33 hpf, respectively. As shown, at 33 hpf, Sox10 was expressed in the otic vesicles and the neural crest cells (NCCs) in the spinal cord (see FIG. 28K). At this stage, Sox10-positive NCCs contained unspecified neurons and glial cells. These cells increased in the CRBN-overexpressing embryos (see FIG. 28L). FIG. 28M is a histogram showing the Gfap mRNA level in the untreated and the CRBN-overexpressing zebrafish embryos at 11 hpf, respectively, by quantitative PCR. As shown, Gfap in the CRBN-overexpressing embryos increased to over 4-fold of the level in the untreated embryos at 11 hpf (see FIG. 28M).

As shown in Example 38 below, overexpression of CRBN increases positive regulatory genes for cell proliferation. Notch3 and Neuropilin2b (Nrp2b) are required for cell proliferation progression. Notch3 plays a role in the regulation of the timing of neural differentiation from undifferentiated or immature cells, and Nrp2b also regulates cell proliferation and remodeling in mesenchymal stem cells by cooperating with PDGF (platelet-derived growth factor). Therefore, expression of Notch3 and Neuropilin 2b (Nrp2b) was analyzed in untreated and CRBN overexpressed zebrafish embryos by quantitative PCR. FIG. 29A is a histogram showing the mRNA level of Notch3 and Nrp2b in untreated, CRBN-overexpressing, and thalidomide-treated zebrafish embryos at 11 hpf by quantitative PCR. As shown, expression of Notch3 in the CRBN-overexpressing embryos increased to 1.8-fold of the level in the untreated embryos at 11 hpf, and expression of Nrp2b in the CRBN-overexpressing embryos increased to 2.7-fold of the level in the untreated embryos at the same stage. In contrast, thalidomide treatment decreased the expression of both genes to 0.3-fold and 0.4-fold of the level in the untreated embryos, respectively. These data strongly suggest that CRBN activates cell proliferation by upregulating the expression of these signal molecules. Elval3 (Huc) is a neural progenitor marker. Expression of Elavl3 (Huc) was also analyzed by quantitative PCR and in situ hybridization. FIG. 29B is a histogram showing the Elavl3 mRNA level in untreated and CRBN-overexpressing zebrafish embryos at 11 hpf by quantitative PCR. As shown, expression of Elavl3 in the CRBN-overexpressing zebrafish embryos increased to 1.7-fold of the level in the untreated embryos at 11 hpf. The increased expression of Elavl3 was confirmed by in situ hybridization. FIGS. 29C and 29D show Elavl3-positive neural progenitor cells in the untreated and the CRBN-overexpressing zebrafish embryos at 14 hpf by in situ hybridization. As shown, the number of the Elavl3-positive neural progenitor cells in the CNS increased in the CRBN-overexpressing embryos at 14 hpf. Differential Interference Contrast (DIC) images of the telencephalon and the spinal cord clearly showed that the Elavl3-positive neural progenitor cells increased in each region (see FIG. 29D).

As shown in Example 39, overexpression of CRBN increases oligodendrocytes. Distribution and growth of oligodendrocytes in forebrain, otic vesicle and spinal cord of untreated and CRBN overexpressing zebrafish embryos were analyzed by in situ hybridization. FIGS. 30A and 30B show oligodendrocytes in the forebrain, the otic vesicle, and the spinal cord of the untreated and the CRBN-overexpressing zebrafish embryos at 36 hpf by in situ hybridization. FIGS. 30C and 30D show oligodendrocytes in the epiphysis of the untreated and the CRBN-overexpressing zebrafish embryos at 36 hpf. As shown, spatial distribution of oligodendrocytes in the forebrain, the otic vesicle, and the spinal cord appeared to be identical in the untreated and the CRBN-overexpressing embryos (see FIGS. 30A and 30B). However, Differential Interference Contrast (DIC) images indicated that the number of olig2-positive cells was apparently higher in the forebrain of the CRBN-overexpressing embryos (see FIGS. 30C and 30D).

As shown in Example 40, overexpression of Six3b, Lhx2b, and CRBN increases expression of pluripotency genes as determined by quantitative PCR. FIG. 31A is a histogram showing expression levels of Lhx2b, Wnt3a, CRBN, Sox2, Pou5f1, and Nanog in untreated and Six3b-overexpressing zebrafish embryos at 11 hpf by quantitative PCR. As shown, overexpression of Six3b increased the expression levels of Lhx2b, Wnt3a, CRBN, and pluripotency genes (Sox2, Pou5f1, and Nanog). Relative expression of mRNAs was indicated by the vertical axis. Compared to the untreated embryos, the expression of Lhx2b increased to about 1.2-fold, the expression of Wnt3a, CRBN, and Sox2 increased to about 1.5-fold, the expression of pou5f1 increased to about 1.7-fold, and the expression of Nanog increased to about 2.4-fold in the Six3b-overexpressing embryos. FIG. 31B is a histogram showing expression levels of CRBN, Sox2, Pou5f1, Nanog, and Zic3 in untreated and Lhx2b-overexpressing zebrafish embryos at 11 hpf by quantitative PCR. As shown, compared to the untreated embryos, the expression of CRBN, Sox2, Pou5f1, and Nanog increased to about 1.2-, 2.3-, 1.6-, and 1.3-fold in the Lhx2b-overexpressing embryos, respectively. FIG. 31C is a histogram showing expression levels of Sox2, Pou5f1, Nanog, and Zic3 in untreated, CRBN-overexpressing, CRBN-knockdown, and 100 µM thalidomide-treated zebrafish embryos at 11 hpf by quantitative PCR. As shown, overexpression and knockdown of CRBN showed opposite effects on the expression of pluripotency genes. Thalidomide treatment reduced the expression of the pluripotency genes to about the level observed in the CRBN-knockdown embryos. In the CRBN-overexpressing embryos, expression of Sox2, Pou5f1, Nanog, and Zic3 increased to 1.2-, 1.9-, 4.6-, 1.3-fold of that in uninjected embryos, respectively. In contrast, expression of each gene decreased to 0.7-, 0.8-, 0.8-, 0.8-fold of that in untreated embryos when CRBN was knocked down. Thalidomide treatment decreased expression of each gene more severely (from about 0.5- to 0.7-fold).

As shown in Example 41, overexpression of CRBN increases expression of neural reprogramming genes. The expression of Ascl1, Pou3f3a, and Myt1la was analyzed by quantitative PCR in untreated and CRBN overexpressing zebrafish embryos at 24 hpf. FIG. 32 is a histogram showing expression levels of Ascl1a, Pou3f2b, and Myt1la in untreated and CRBN-overexpressing zebrafish embryos at 24 hpf by quantitative PCR. As shown, overexpression of CRBN increased the expression of Ascl1, Pou3f3a, and Myt1la at 24 hpf.

It is understood that modifications that do not substantially affect the substance of the various embodiments of this invention are also included within the definition of the invention provided herein. Accordingly, the following examples are intended to illustrate but not limit the present invention.

6. EXAMPLES

6.1 Example 1

Systemic Gene Overexpression in the Zebrafish Embryo

The zebrafish is an important vertebrate model for analysis of vertebrate development and a model system for human disease. See Barbazuk et al., The Syntenic Relationship of the Zebrafish and Human Genomes, *Genome Res.*, 10: 1351-1358 (2000). High syntenic relationship exists between the human genome and the zebrafish genome, and 70 to 80% of the genome synteny is conserved between human and zebrafish. See Lieschke and Currie, Animal Models of Human Disease: Zebrafish Swim into View, *Nature Reviews Genetics.*, 8, 353-367 (2007). Accordingly, the zebrafish model has been used for many years as the model of choice amongst developmental biologists. See Fleisch et al., Investigating Regeneration and Functional Integration of CNS Neurons: Lessons from Zebrafish Genetics and Other Fish Species, *Biochim. Biophys. Acta,* 1812: 364-380 (2011); Kishimoto et al., Neuronal Regeneration in Zebrafish Model of Adult Brain Injury, *Disease Models and Mechanisms,* 5:200-209 (2012); and Becker et al., Adult Zebrafish as a Model for Successful Central Nervous System Regeneration, *Restorative Neurol. Neurosci.,* 26:71-80 (2008).

Adult fish were reared at a constant temperature of 28.5° C. and maintained and bred under a diurnal cycle of 14 hours of light-on and 10 hours of light-off. Fertilized eggs were secured by natural mating between males and females, and an aqueous solution of 600 ng/µl capped mRNA synthesized in vitro was injected into the cytoplasm of the embryos before the first cleavage (1-cell stage) under conditions of a nitrogen gas pressure of 30 psi and a valve opening time of 30 msec (millisecond). Because the expression of all the genes except the lhx2 gene (i.e., the CRBN gene, the six3.2 gene, and a gene encoding a protein composing an E3 ubiquitin ligase complex with CRBN) has little impact on the embryonic development, even when systemically expressed, this method was used to obtain the first data.

6.2 Example 2

Localized Gene Overexpression in the Head of Zebrafish Embryos

For studying the lhx2 gene, which exhibits non-specific dorsalization of the embryo when systemically expressed, and for precise experiments specifically examining the effect exerted on the brain volume, in vivo RNA lipofection into the prospective head region of the embryo was carried out. The method of lipofection was entirely in accordance with the technique developed and published by Ando et al. See Ando and Okamoto, Efficient Transfection Strategy for the Spatiotemporal Control of Gene Expression in Zebrafish, *Biotechnol.*, 8(3): 295-303 (2006).

6.3 Example 3

Gene Knockdown Using Zebrafish Embryos

An aqueous solution of a 25-mer antisense morpholino oligonucleotide (AMO, Gene Tools, LLC) corresponding to the vicinity of the translation initiation codon in the cDNA sequence of the gene to be knocked down (700 ng/µl injection conditions were the same as those used for RNA) was injected into the embryos at the 1-cell stage. The sequence of AMO used for the CRBN gene knockdown is 5'-AGAGCTGTAGCTGGTTCCCCATTTC-3' (SEQ ID NO: 3). The sequence of AMO used for the Lhx2 gene knockdown is 5'-TCTGCAACCCAAGATTTCCGTGAGA-3' (SEQ ID NO:4). The sequence of AMO used for the BRD7 gene knockdown is 5'-TGTGTTTCTTGTGCTTTTT-GCCCAT-3' (SEQ ID NO:1). The sequence of AMO used for the Ikaros gene knockdown is 5'-TTCCTGTGCCTC-CTCAGTCTCCATC-3' (SEQ ID NO:2).

6.4 Example 4

Determination of Functional Hierarchy of Genes Using Zebrafish

This process was carried out entirely in accordance with the technique of Ando et al., See Ando et al., Lhx2 Mediates the Activity of Six3 in Zebrafish Forebrain Growth, *Dev. Biol.*, 287(2): 456-468 (2005), except for the following procedures. Head-specific gene expression was performed by the in vivo lipofection method described in Example 2 above instead of RNA uncaging. See Japanese Patent No. 2002-315576, and Ando et al., Photo-mediated Gene Activation Using Caged RNA/DNA in Zebrafish Embryos, *Nat. Genet.*, 28, 317-325 (2001). The basic principle is as follows: embryos in which one (A) of the two genes suggested to have a functional association is knocked down by the method described in Example 3 above are cultured up to six hours after fertilization (gastrula stage), and in the prospective forebrain region of the embryos, the expression of the other gene (B) is induced by the in vivo lipofection method described in Example 2 above. When the effect of knocking down A is rescued, whereas the effect of knocking down B is not rescued by an inverted combination of A and B, within a 24-hour period after fertilization, it is determined that A lies functionally upstream of B.

6.5 Example 5

Immunohistochemistry

Antibody staining of early neurons of zebrafish was performed by the following technique. The embryos 24 to 28 hours after fertilization were fixed at 4° C. for 12 hours in a 4% paraformaldehyde/phosphate buffer (pH 8.0). After washing four times with phosphate buffer, where each wash was performed for 15 minutes, blocking was carried out at normal temperature for one hour in 5% newborn goat serum dissolved in 0.5% Triton X-100/phosphate buffer. Primary antibody reaction was carried out using a monoclonal anti-acetylated tubulin antibody diluted at 1:1000 in the same solution at 4° C. for 12 hours. Then, after washing the embryos similarly with phosphate buffer, secondary antibody reaction was carried out using an anti-mouse antibody conjugated with Alexa Fluoro 488 (Molecular Probes) under the same conditions as those applied in the primary antibody reaction. The embryos were then washed with phosphate buffer and transparentized in 30%/50%/70% glycerol (dissolved in phosphate buffer), and then observed with a fluorescent microscope under excitation at 488 nm.

6.6 Example 6

Whole-Mount In Situ Hybridization

This process was carried out basically in accordance with the technique of Thisse et al. See High-resolution In Situ Hybridization to Whole-mount Zebrafish Embryos, *Nat. Protcol.*, 3 (1) 59-69, (2008). The differences were that 5 mg/ml Torula yeast RNA was used as a blocker in the probe hybridization solution, and that 0.5% Blocking Reagent (Roche) was used as a blocker in the antibody reaction solution. The cDNA of the genes used as the probe (the six3.2 gene, the emx1 gene, the pax2.1 gene, the foxg1 gene, and the otx2 gene) were presents of the original provider. As the probe for the lhx2 gene, the one initially cloned by Ando was used. For the probes of the CRBN gene and related genes, primers were designed based on the EST database of zebrafish, and the probes were cloned from a cDNA library.

Zebrafish BRD7 cDNA was cloned from pools of reverse transcribed template that was synthesized from total RNAs extracted from 24 h embryos. 1.7 µg of random and oligo-dT primed cDNA synthesized by ReverTra Ace® qPCR RT Kit (Toyobo, Japan) was used as template. Primers for cloning BRD7 gene into pCS2+ vector were as follows: forward 5'-TTT<u>AAGCTT</u>ATGGGCAAAAA GCACAAGAA-3' (SEQ ID NO: 5) (HindIII recognition sequence underlined); and reverse 5'-TTT<u>TCTAGA</u>TCAGCTCCTACGACGCGTGCA-3'(SEQ ID NO: 6) (XbaI recognition sequence underlined). Amplified fragment was cloned into HindIII/XbaI site in pCS2+ vector. Probe was synthesized by T7 RNA polymerase from HindIII-linealised vector using Digoxigenin labeling mix (Roche).

Zebrafish Ikaros cDNA was cloned from pools of reverse transcribed template that was synthesized from total RNAs extracted from 24 h embryos. 1.7 µg of random and oligo-dT primed cDNA synthesized by ReverTra Ace® qPCR RT Kit (Toyobo, Japan) was used as template. Primers for cloning Ikaros gene into pCS2+ vector were as follows: forward 5'-TTT<u>GAATTC</u>ATGGAGACTGAGGAGGCACAGGAAA-3' (SEQ ID NO: 7) (underline; EcoRI recognition sequence); reverse 5'-TTT<u>CTCGAG</u>TCAGATGCGGTGCTCTCCACGTGT-3' (SEQ ID NO: 8) (underline; XhoI recognition sequence). Amplified fragment was cloned into EcoRI/XhoI site in pCS2+ vector. Probe was synthesized by T7 RNA polymerase from EcoRI-linealised vector using Digoxigenin labeling mix (Roche).

6.7 Example 7

Cell Transplantation

An appropriate concentration of rhodamine dextran (molecular weight 10,000) and a final concentration of 600 ng/µl CRBN RNA were dissolved in nuclease-free water, and then were injected into zebrafish embryos at the 1-cell stage under the conditions of the method described in Example 1 above. The resulting embryos served as the donors. At three to four hours after fertilization of the donors, 10 to 50 cells were suctioned by a glass microcapillary under fluorescent microscopic observation. These cells were transplanted into the animal pole of the host embryos at the same stage. After culturing the host embryos for two days without adding any modification, localization of differentiation of the CRBN-expressing donor-derived cells was observed under a fluorescent microscope. Also, as a negative control, cells in which green fluorescence protein (GFP) was expressed, which was assumed to have no effect on the embryonic development, were transplanted under the same conditions, and localization of the differentiation was compared between the experimental and control embryos.

6.8 Example 8

Detection and Measurement of the Ubiquitin Ligase Activity of CRBN Using an In Vitro Reaction System This process was carried out basically in accordance with the method of Groisman et al. See Groisman et al., *Cell*, 113:357-367 (2003); Groisman et al., *Genes Dev.*, 20:1429-1434 (2006). First, CRBN and a binding protein (referred to as a CRBN complex) were purified from a cell lysate solution of mammalian cells expressing CRBN fused with a FLAG epitope tag using M2 FLAG agarose beads (SIGMA). Subsequently, the CRBN complex thus purified was mixed with an aqueous solution containing Uba1 (E1), UbcH5b (E2), and a recombinant GST fusion ubiquitin (Ub) protein, and after addition of ATP, the mixture was left to stand at 30 to 37° C. for two hours. Thereafter, the reaction was terminated by SDS, and self-ubiquitination and ubiquitination of the binding protein were visualized by polyacrylamide gel electrophoresis and immunoblotting, whereby the ubiquitin ligase activity was detected and measured.

6.9 Example 9

Detection and Measurement of the CRBN Ubiquitin Ligase Activity Using Live Cells This process was carried out basically in accordance with the method of Ohtake et al. See Ohtake et al., *Nature*, 446:562-566 (2007). MG132, which was a proteasome inhibitor, was applied to mammalian cells expressing CRBN fused with a FLAG epitope tag, and the cells were left still. Subsequently, the cells were disrupted, and from the resulting cell lysate solution, FLAG was purified, and CRBN was extracted. Then immunoblotting was performed under similar, but stricter, conditions to the above, whereby self-ubiquitination was detected and measured.

6.10 Example 10

Fluorescent Staining of Glia Cells and Serotonin-Producing Cells

Two-days-old zebrafish were used (for glia cell staining and serotonin-producing cell staining, zebrafish 56 hours and 49 hours after fertilization were used, respectively). Zebrafish were fixed with 4% paraformaldehyde (PFA) and then washed with phosphate buffer (PBS), followed by treatment with 10 µg/ml protease K for partial digestion of the epidermis. After the digestion reaction, the zebrafish were washed with PBST (PBS+0.5% Triton X-100) for 20 minutes and then fixed with PFA again. The fixed zebrafish were washed with PBST at room temperature for one hour, followed by blocking using PBST+5% goat serum. The resulting specimens were reacted with a monoclonal anti-glia antibody (zrf-1/zrf-2) or a rabbit anti-serotonin antibody at 4° C. overnight (12 to 18 hours). Subsequently, the specimens were washed with PBST+5% goat serum for one hour at room temperature, and secondary antibody reaction was carried out by substituting the antibody for a goat anti-mouse IgG antibody (Cy-2 conjugate for glia cell staining) or a goat anti-rabbit IgG antibody (Cy-5 conjugate for serotonin-producing cell staining) at 4° C. overnight (12 to 18 hours). Subsequently, the specimens were washed with PBST at room temperature for one hour. After washing, PBST was replaced by 30%, 50%, and 70% glycerol/PBS, and the whole zebrafish were mounted on glass slides to obtain preparations. Fluorescence was observed under excitation wavelength of Cy-2 and Cy-5, and the distribution of the glia cells or the serotonin-producing cells was recorded. Glia cells were observed from the lateral side of zebrafish, while the serotonin-producing cells were photographed from the dorsal side in order to observe the distribution of the cells along the midline.

6.11 Example 11

Transplantation of CRBN-Expressing Cells into the Diencephalic Ventricle

A mixed solution of CRBN-coding RNA (700 ng/µl) and 2% rhodamine dextran was injected into zebrafish embryos at the 1-cell stage immediately after fertilization. The embryos were cultured up to four hours after fertilization, and 10 to 20 cells were collected by a suction capillary, which were injected into the diencephalic ventricle of embryos 30 hours after fertilization, whereby the cells were transplanted. Zebrafish having undergone transplantation were reared up to three days after fertilization in zebrafish physiological saline (E3 Ringer) and then fixed with 4% paraformaldehyde. Following the ordinary method, primary antibody reaction and secondary antibody reaction were carried out using a monoclonal anti-acetylated tubulin antibody and an anti-mouse IgG antibody conjugated with Alexa Fluor® (excited at 488 nm), respectively. Then, while observing the fluorescently-labeled nerve cell axon, distribution of the transplanted cells labeled with rhodamine dextran (excited at 543 nm) was studied.

6.12 Example 12

Determination of Functional Hierarchy of Lhx2 and CRBN

Figure 1:
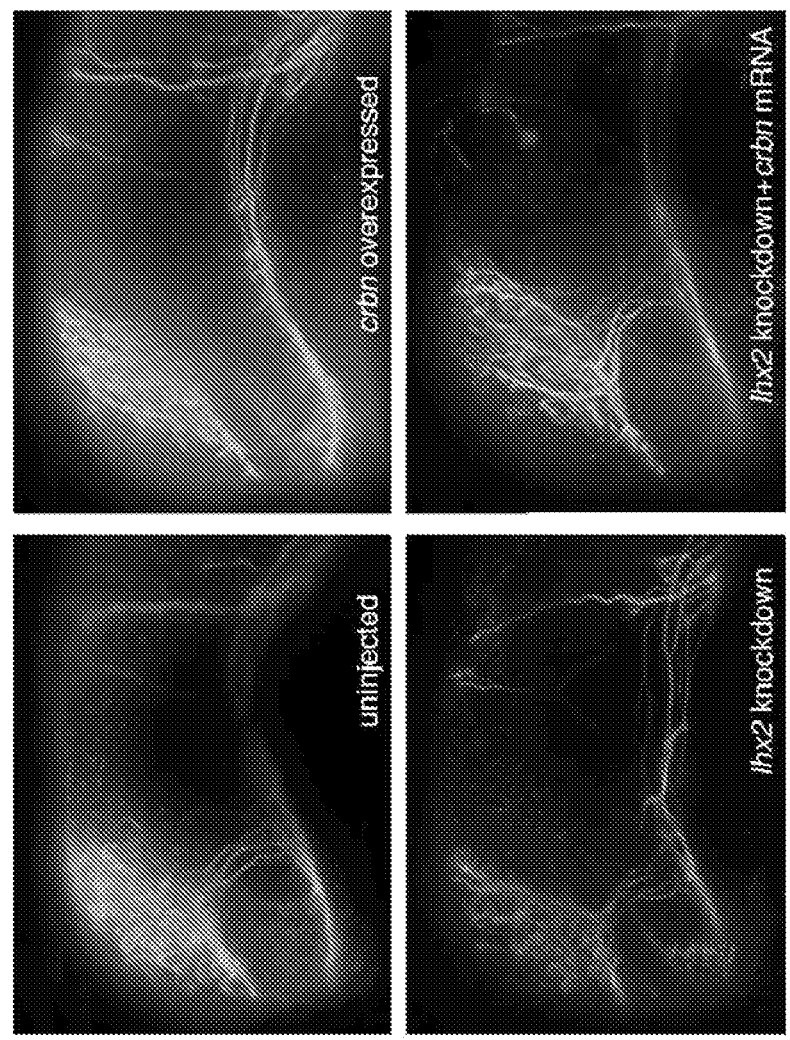

Compared to the normal embryo (FIG. 1, upper left panel), brain shrinkage was observed in the lhx2 gene-knockdown embryo (FIG. 1, lower left panel). Meanwhile, similarly to the CRBN gene-overexpressing embryo (FIG. 1, upper right panel), brain enlargement was observed in the embryo in which lhx2 gene was knocked down, and in which CRBN gene was overexpressed (FIG. 1, lower right panel). From this observation, it is considered that CRBN functions downstream of Lhx2, directly inducing proliferation of central nervous stem cells and differentiation of these cells into nerve cells.

6.13 Example 13

CRBN Overexpression Experiment

Figure 2:
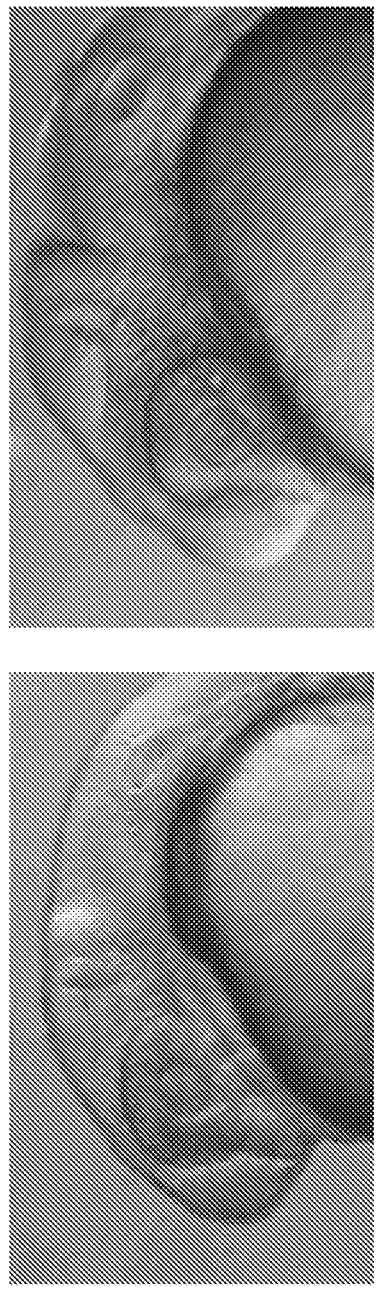

In order to verify induction of differentiation into neural stem cells by CRBN in the cerebrum, a CRBN overexpression experiment was carried out in the forebrain and midbrain of zebrafish embryos. As a result, both brains enlarged approximately 1.5 times in volume, while retaining their shape (FIG. 2, right). Moreover, the neuron network in the brain was morphologically normal (FIG. 2, right).

6.14 Example 14

Transplantation Experiment of CRBN-Overexpressing Cells

Figure 3:
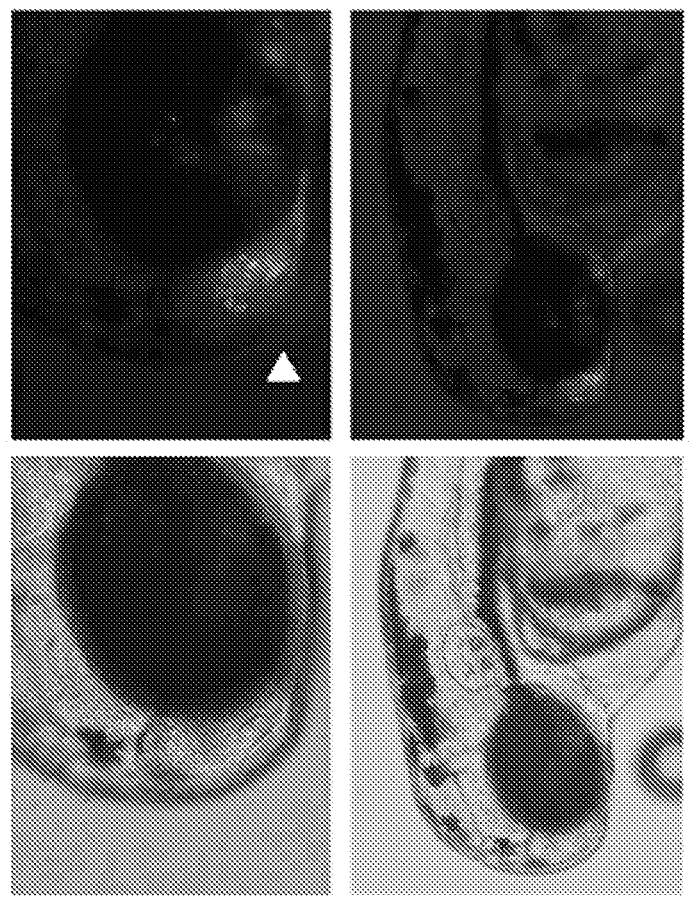

First, mRNA encoding CRBN and a fluorescent substance (rhodamine) were injected together into donor embryos, so that CRBN was overexpressed. The resulting blastula was transplanted into another individual, and differentiation of donor-derived cells distributed in the cerebral ventricle was observed under a fluorescent microscope. As a result, the transplanted donor-derived cells significantly differentiated into the olfactory bulb, which is the telencephalon tissue of zebrafish (FIG. 3, arrowhead). This indicates that when the CRBN-expressing cells were distributed into the cerebral ventricle, they differentiated into neural stem cells, migrated along a cell migration pathway called Rostral Migratory Stream (RMS), and differentiated into the brain tissue in the dorsal telencephalon, where the cerebral cortex develops in mammals.

6.15 Example 15

Figure 4:
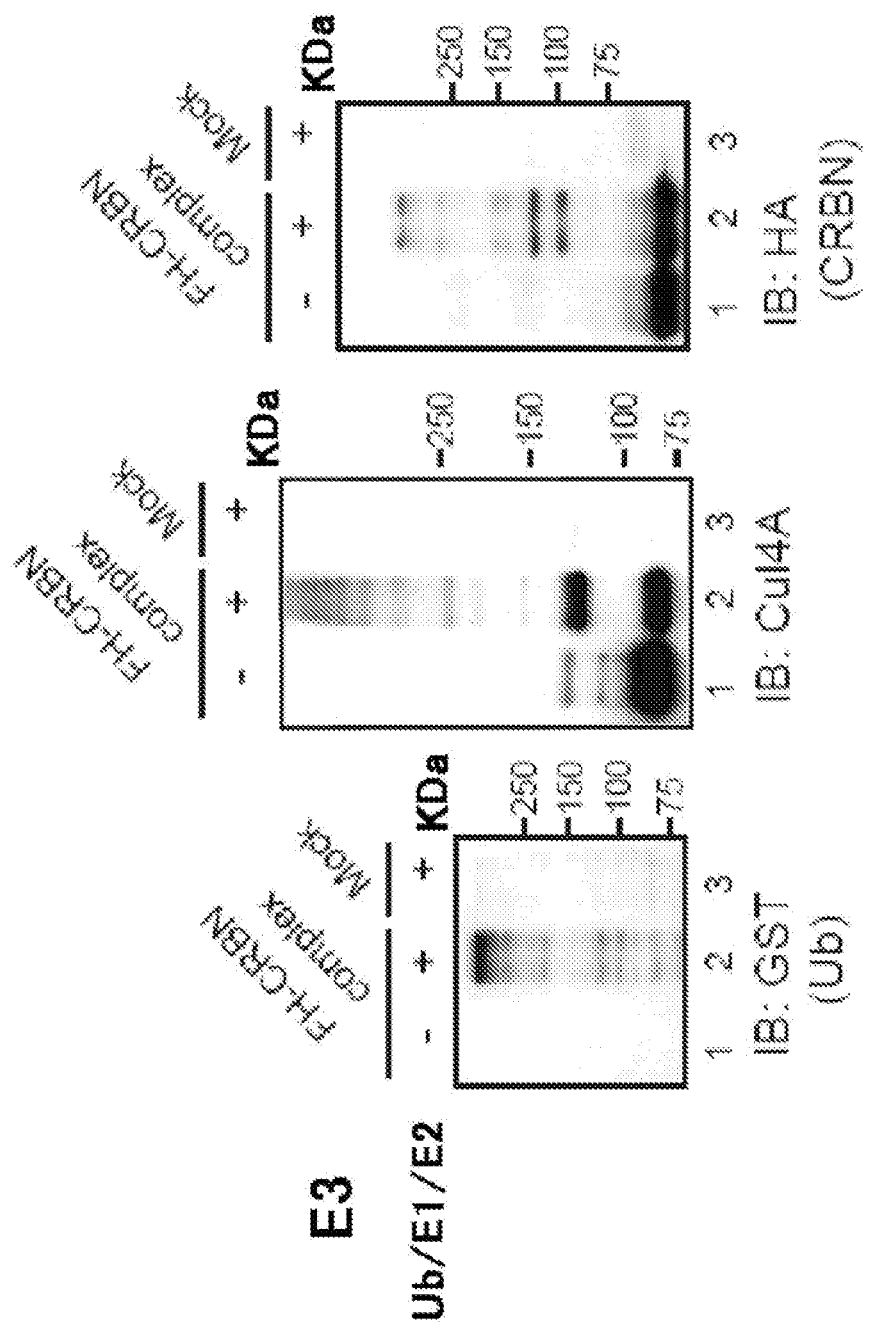

Detection and Measurement of the Ubiquitin Ligase Activity of CRBN Using an In Vitro Reaction System When CRBN (FH-CRBN complex) was added to an aqueous solution containing Uba1 (ubiquitin activating enzyme), UbcH5b (ubiquitin transfer enzyme), and a recombinant GST fusion ubiquitin protein (Ub/E1/E2), proteins that would not be detected in the absence of CRBN were detected (FIG. 4, lane 2 in the left, middle, and right images). For ubiquitination of a protein, in addition to ubiquitin, three kinds of enzymes, namely an ubiquitin activating enzyme, an ubiquitin transfer enzyme, and an ubiquitin ligase are usually needed. Ubiquitinated proteins were not detected in lane 1 of the left, middle, and right images because no ubiquitin ligase was present. Meanwhile, in lane 2 of the left, middle, and right images, ubiquitinated proteins were detected by electrophoresis likely due to the function of CRBN as an ubiquitin ligase to produce ubiquitinated proteins.

6.16 Example 16

Figure 5:
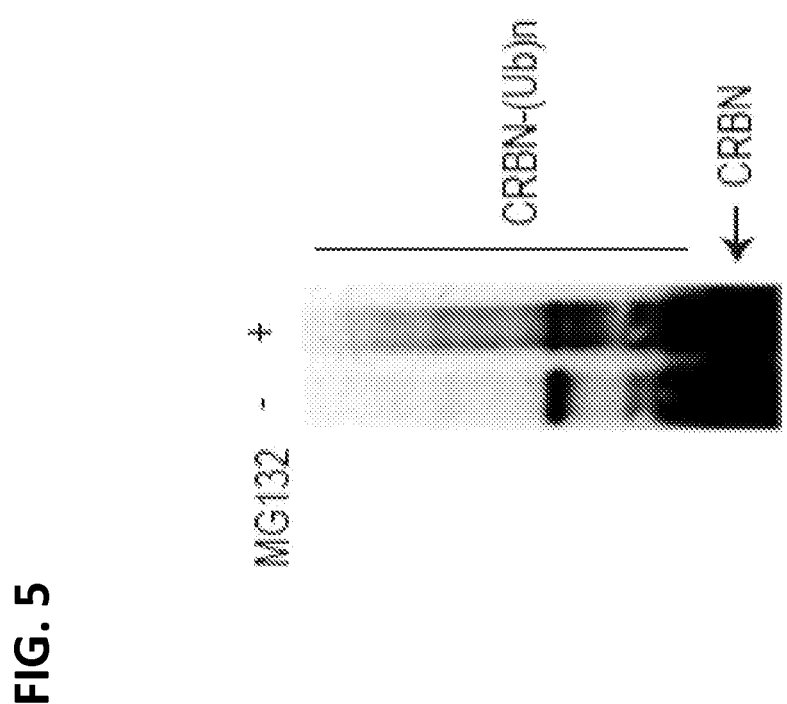

Detection and Measurement of the CRBN Ubiquitin Ligase Activity Using Live Cells When MG132 was added, a number of bands representing CRBN-containing proteins were detected (FIG. 5, right lane). In contrast, when MG132 was not added, very few bands representing the CRBN-containing proteins were detected (FIG. 5, left lane).

These results indicate CRBN in live cells undergoes self-ubiquitination in cooperation with other factors and yields ubiquitinated proteins of various molecular weights. However, most of them are assumed to be degraded by intracellular proteasome. In the left lane of FIG. 5, a number of bands were detected, indicating that proteasome was inhibited by MG132, enabling proteins produced through self-ubiquitination to remain, leading to the detection of a number of bands. In contrast, in the right lane of FIG. 5, very few bands were detected likely because that most of the proteins produced were degraded by proteasome.

6.17 Example 17

Fluorescent Staining of Glia Cells and Serotonin-Producing Cells

Figure 6:
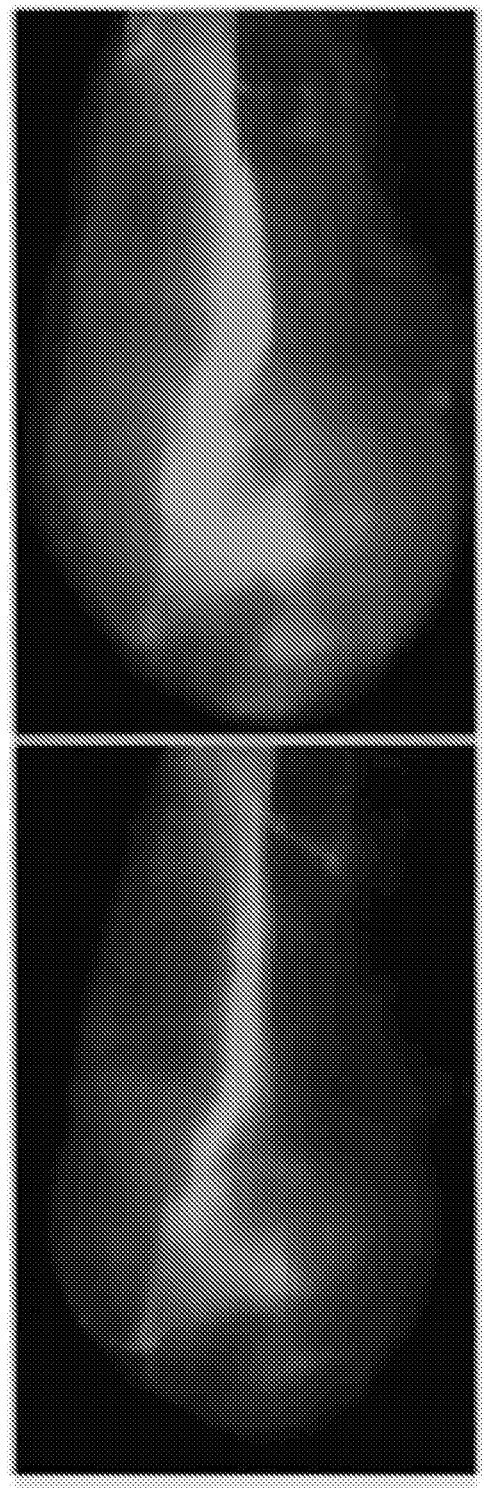
Figure 7:
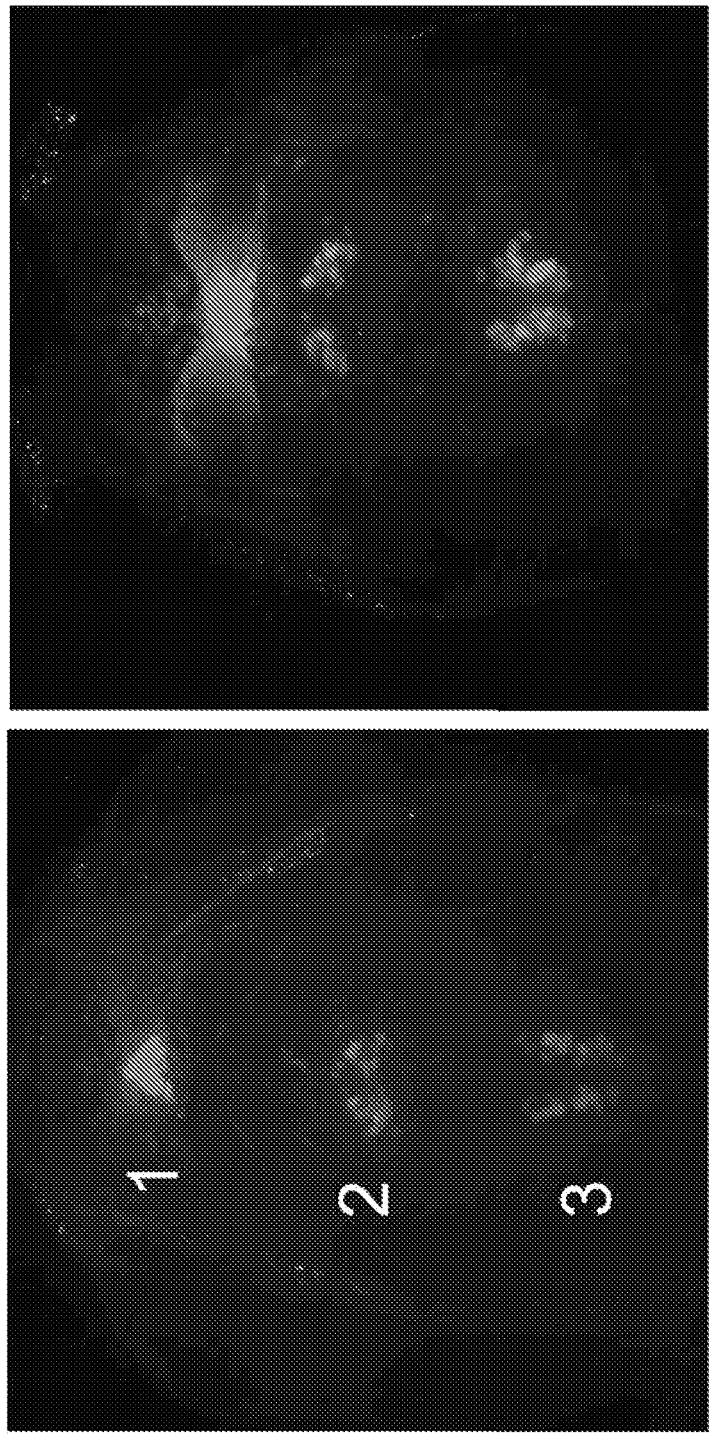
Figure 8:
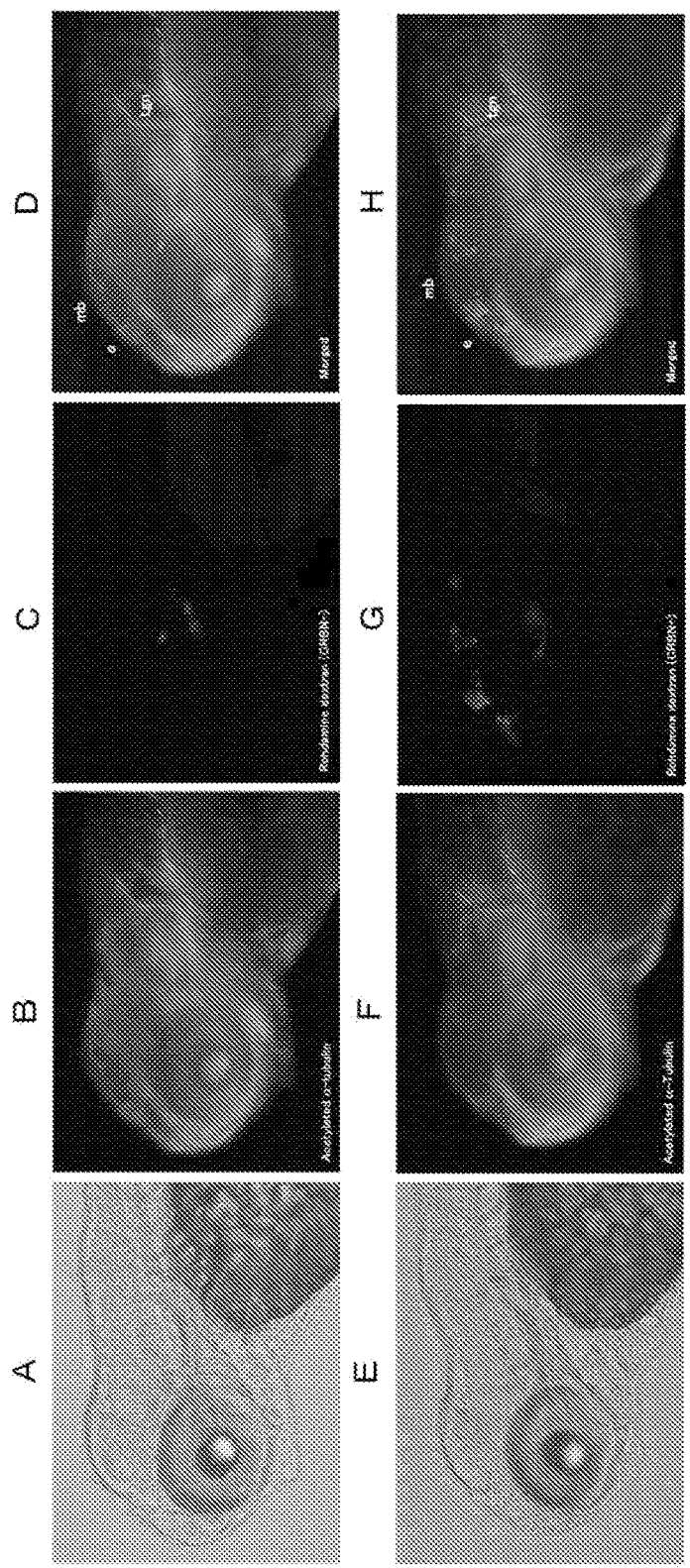

In CRBN-overexpressing individuals (see FIGS. 6 and 7, right pictures), glia cells (see FIG. 6) and serotonin-producing cells (see FIG. 7) increased, while normal spatial distribution was maintained. This means that CRBN acts to proliferate and to differentiate cells, while normally recognizing the spatial pattern of the brain.

6.18 Example 18

Transplantation of CRBN-Expressing Cells into the Diencephalic Ventricle

When cells that do not express CRBN were transplanted, the cells did not differentiate into the brain tissue (FIGS. 8A to 8D), whereas when cells that express CRBN were transplanted, the cells differentiated into the brain tissue (FIGS. 8E to 8H). Nuclease-free water, in which an appropriate concentration of rhodamine dextran (molecular weight 10,000) and a final concentration of 600 ng/µl CRBN RNA were dissolved, was injected into zebrafish embryos at the 1-cell stage under the conditions of the method described above, and the resulting embryos served as the donors. At three to four hours after fertilization of the donors, 10 to 50 cells were suctioned by a glass microcapillary under fluorescent microscopic observation. The cells were further transplanted into the animal pole of host embryos at the same stage. After culturing the host embryos for two days without adding any modification, localization of differentiation of the CRBN-expressing donor-derived cells was observed under a fluorescent microscope. Also, as a negative control, cells in which green fluorescence protein (GFP) was expressed, assumably having no effect on embryonic development, were transplanted under the same conditions, and localization of the differentiation was compared between the experimental and the control embryos.

6.19 Example 19

Knockdown of BRD7 Enlarges the Brain in Zebrafish Embryos

Example 19 showed that knockdown of BRD7 enlarges the brain in zebrafish embryos. In order to examine the effect of antagonists of BRD7 on brain growth, BRD7 was knocked down or over-expressed in zebrafish embryos. Knockdown of BRD7 was performed by microinjection of antisense morpholino oligonucleotides (AMO). Overexpression of BRD7 was performed by microinjection of synthesized capped mRNA. AMO or capped mRNA was introduced into one-cell stage embryos by using a nitrogen gas-pressure microinjector IM 300 (Narishige). Conditions for microinjection were as follows: gas pressure was about 15 picosiemens; release period was about 30 to about 50 milliseconds per single injection; concentrations of AMOs and capped mRNA were 400 ng/µl and 250 ng/µl in nuclease-free water, respectively. Capped mRNAs were synthesized in vitro using the mMESSAGE mMachine® in vitro transcription kit (Ambion) from cDNAs cloned into pCS2+ plasmids.

The brains of the embryos were examined for morphology and volume by magnetic resonance imaging (MRI). FIGS. 9A, 9B, and 9C show microscopic pictures of the untreated, the BRD7-knockdown, and the BRD7-overexpressing zebrafish embryos, respectively. FIGS. 9D, 9E, and 9F show fluorescent microscopic pictures of the brain regions of the untreated, the BRD7-knockdown, and the BRD7-overexpressing zebrafish embryos, respectively. As shown in these figures, the BRD7-knockdown zebrafish embryos had bigger heads than the untreated embryos. In contrast, the embryos injected with BRD7 mRNA causing BRD7 overproduction developed smaller heads and eyes than the untreated embryos. Measurement of the volume of different regions of the brain by transverse and cross section of captured MRI images of the whole brain (the telencephalon to the spinal cord) revealed that all portions of the brain (the telencephalon, the diencephalon, the midbrain, the cerebellum, and the spinal cord) were affected by BRD7 knockdown or BRD7 overexpression. The volume of the whole brain of the BRD7-knockdown fish was much bigger than that of the untreated fish, while for the BRD7-overexpressing fish, the brain volume was smaller. Interestingly, the volume of the telencephalon (the area of cross section at the mid region of the midbrain and diencephalon) proportionally changed in the BRD7-knockdown fish.

6.20 Example 20

Knockdown of BRD7 Upregulates Pou5f1 (Oct3/4), Klf4, c-Myc, and HuC (Elavl3) in Zebrafish Embryos Expression of Pou5f1 (Oct3/4), Klf4, c-Myc, and HuC (Elavl3) in zebrafish embryos was analyzed by in situ hybridization. The embryos were fixed with 4% paraformaldehyde for 1 hour at room temperature and rinsed with phosphate buffered saline (PBS). The fixed embryos were refixed with 100% methanol and placed at −80° C. for over 12 hours. The embryos were defixed by rinsing with PBS, and the skin was digested with pronase (2 mg/ml), followed by refixation and defixation, and prehybridized in HYB* buffer (50% formamide, 5×SSC, 10 mM Citric acid, 0.1% Tween 20) for 15 minutes and in HYB+(added as 5 mg/ml torula (yeast) RNA, 50 μg/ml heparin to HYB*) for 1 hour at 65° C. After addition of 1 ng/μl of DIG (digoxigenin)-labeled probe, hybridization was performed for overnight at 65° C. After hybridization, the embryos were washed by 50% formamide in 2×SSC for 30 minutes (twice), 2×SSC for 15 minutes, 0.2×SSC for 30 minutes (twice) at 65° C. Then blocking treatment was done by 0.5% purified casein in PBSTw (PBS plus 0.1% Tween 20) at room temperature for 1 hour. After that, immunostaining was performed in 1/4000 dilution of anti-DIG Fab-AP fragment in 0.5% purified casein in PBSTw for 4 hours at room temperature.

After washing with PBSTw for 90 minutes, staining was carried out in the presence of substrate of alkaline phosphatase (Nitro blue tetrazolium and 5-bromo 4-chloro 3-indolyl phosphate) in 100 mM Tris pH 9.5, 50 mM $MgCl_2$, 100 mM NaCl, and 0.1% Tween-20. Reaction was stopped by rapid exchange of reaction buffer to PBSTw and cleaned with glycerol serials (30%, 50%, and 70% in PBS).

As shown in FIG. 10, knockdown of BRD7 activates expression of Pou5f1 (Oct3/4), Klf4, c-Myc, and HuC (Elavl3) in zebrafish embryos. FIGS. 10G and 10I show Pou5f1 (Oct3/4) expression in untreated zebrafish embryos by in situ hybridization at 10 hpf and 11 hpf, respectively. FIGS. 10H and 10J show Pou5f1 (Oct3/4) expression in BRD7-knockdown zebrafish embryos by in situ hybridization at 10 hpf and 11 hpf, respectively. As shown, expression of Pou5f1 (Oct3/4) in the second and fourth rhombomeres in the hindbrain increased in the BRD7-knockdown embryos at 10 hpf and 11 hpf.

FIGS. 10K and 10L show Klf4 expression in untreated and BRD7-knockdown zebrafish embryos by in situ hybridization at 18 hpf. As shown, expression of Klf4 also increased at 18 hpf in the rostral portion of the neural tube in the BRD7-knockdown zebrafish embryos.

FIGS. 10M and 10N show expression of c-Myc in the tectal proliferation zone in the medial and lateral areas, and in the most peripheral region of the ciliary marginal zone (CMZ) in the retina of untreated zebrafish embryos by in situ hybridization at 30 hpf. FIGS. 10O and 10P show expression of c-Myc in the tectal proliferation zone in the medial and lateral areas, and in the most peripheral region of the ciliary marginal zone (CMZ) in the retina of BRD7-knockdown zebrafish embryos by in situ hybridization at 30 hpf. As shown, expression of c-Myc clearly increased at 30 hpf in the tectal proliferation zone in the medial and lateral areas, where neural stem cells and progenitor cells exist, and in the most peripheral region of the ciliary marginal zone (CMZ) in the retina, where retinal stem cells are located.

Figure 11:
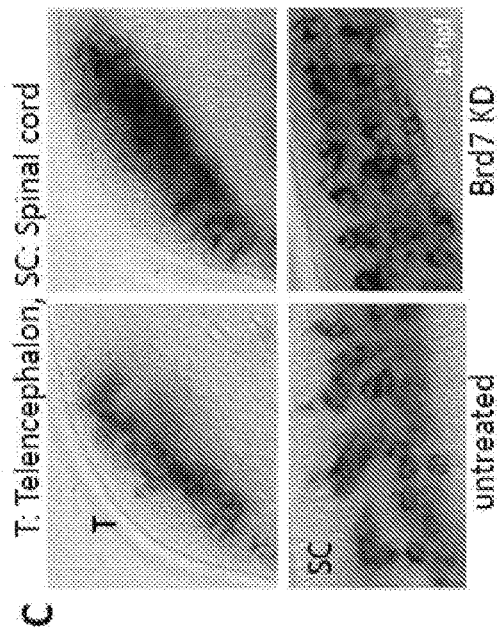
Figure 11:
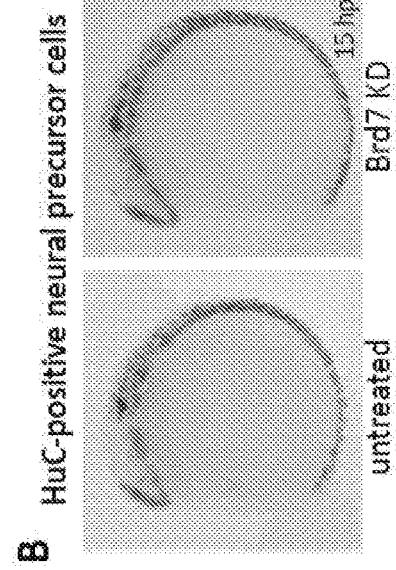
Figure 11:
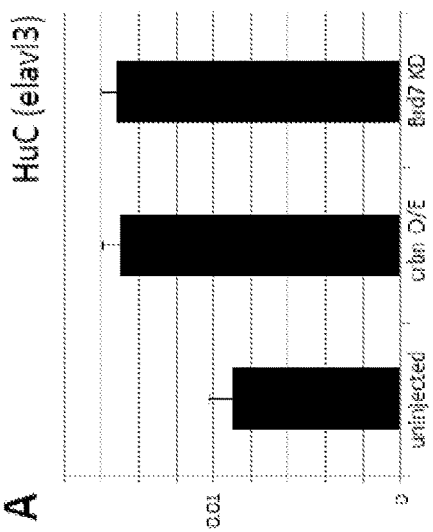

FIGS. 10Q and 10T show HuC (Elavl3) expression in the brain and spinal cord in untreated zebrafish embryos by in situ hybridization at 11 hpf. FIGS. 10R and 10U show HuC expression in the brain and spinal cord in CRBN-overexpressing zebrafish embryos by in situ hybridization at 11 hpf. FIGS. 10S and 10V show HuC expression in the brain and spinal cord in BRD7-knockdown zebrafish embryos by in situ hybridization at 11 hpf. As shown, expression of Huc, a neural progenitor marker gene, increased in the brain and spinal cord in the CRBN-overexpressing embryos and the BRD7-knockdown embryos. HuC-positive neural progenitor cells in the brain and spinal cord of the untreated and the BRD7-knockdown zebrafish embryos were also analyzed by in situ hybridization at 15 hpf and at 16 hpf. As shown in FIG. 11B, the number of HuC-positive neural progenitor cells in the brain and spinal cord of the BRD7-knockdown embryos increased at 15 hpf. As shown in FIG. 11C, the number of the telencephalic neurons and the spinal cord neurons increased in the BRD7-knockdown embryos at 16 hpf.

6.21 Example 21

Comparison of BRD7-Knockdown Zebrafish Embryos with CRBN-Overexpressing Zebrafish Embryos BRD7-knockdown zebrafish embryos show similar phenotypes as CRBN-overexpressing zebrafish embryos. For example, expression of HuC in untreated, CRBN-overexpressing, and BRD7-knockdown zebrafish embryos was compared by quantitative PCR. Quantitative PCR was performed as follows: 1.7 μg of random hexane and oligo-dT primed cDNA synthesized by ReverTra Ace qPCR RT Kit (TOYOBO, Japan) (as template) were used for reverse transcription by THUNDERBIRD™ SYBR® qPCR Mix (Toyobo, Japan). 0.25 mM of each forward and reverse primers were used in the reaction, wherein the sequence of the forward primer was 5'-AAGGCTATCAACACGCT-CAAC-3' (SEQ ID NO: 9); and the sequence of the reverse primer was 5'-TCACATACAGGTTGGCATCG-3' (SEQ ID NO: 10). As shown in FIG. 11A, expression levels of HuC in the CRBN-overexpressing embryos and the BRD7-knockdown embryos were similar, and both increased to 1.7-fold of the level of HuC in the untreated embryo at 11 hpf.

Figure 13:
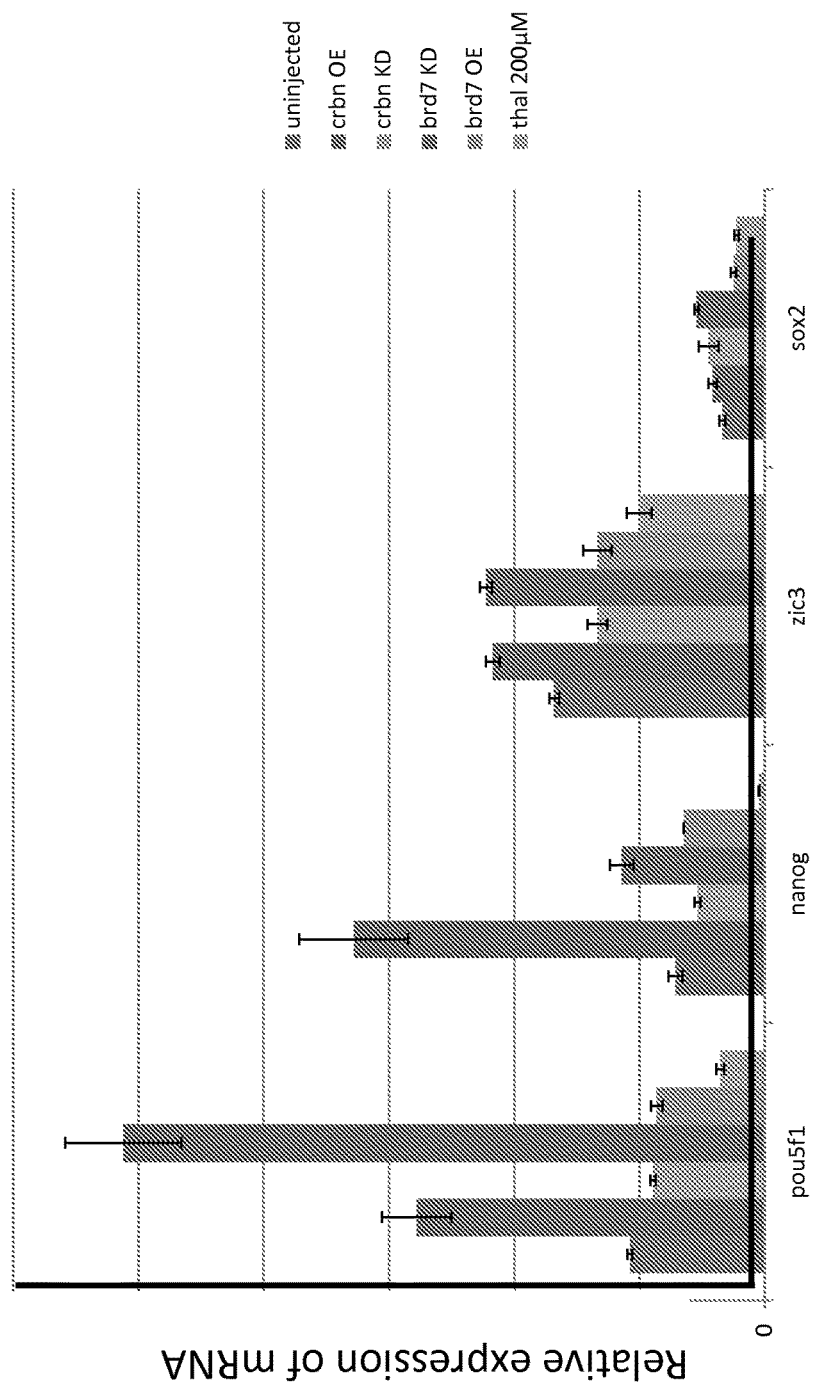

Similarly, as shown in Example 23 below and FIG. 13, expression levels of Pou5f1, Zic3 and Nanog increased in the CRBN-overexpressing or the BRD7-knockdown embryos at 11 hpf. In contrast, the expression of Pou5f1, Zic3 and Nanog decreased in the CRBN-knockdown, the BRD7-overexpressing, or the thalidomide-treated embryos at the same stage.

6.22 Example 22

Figure 12:
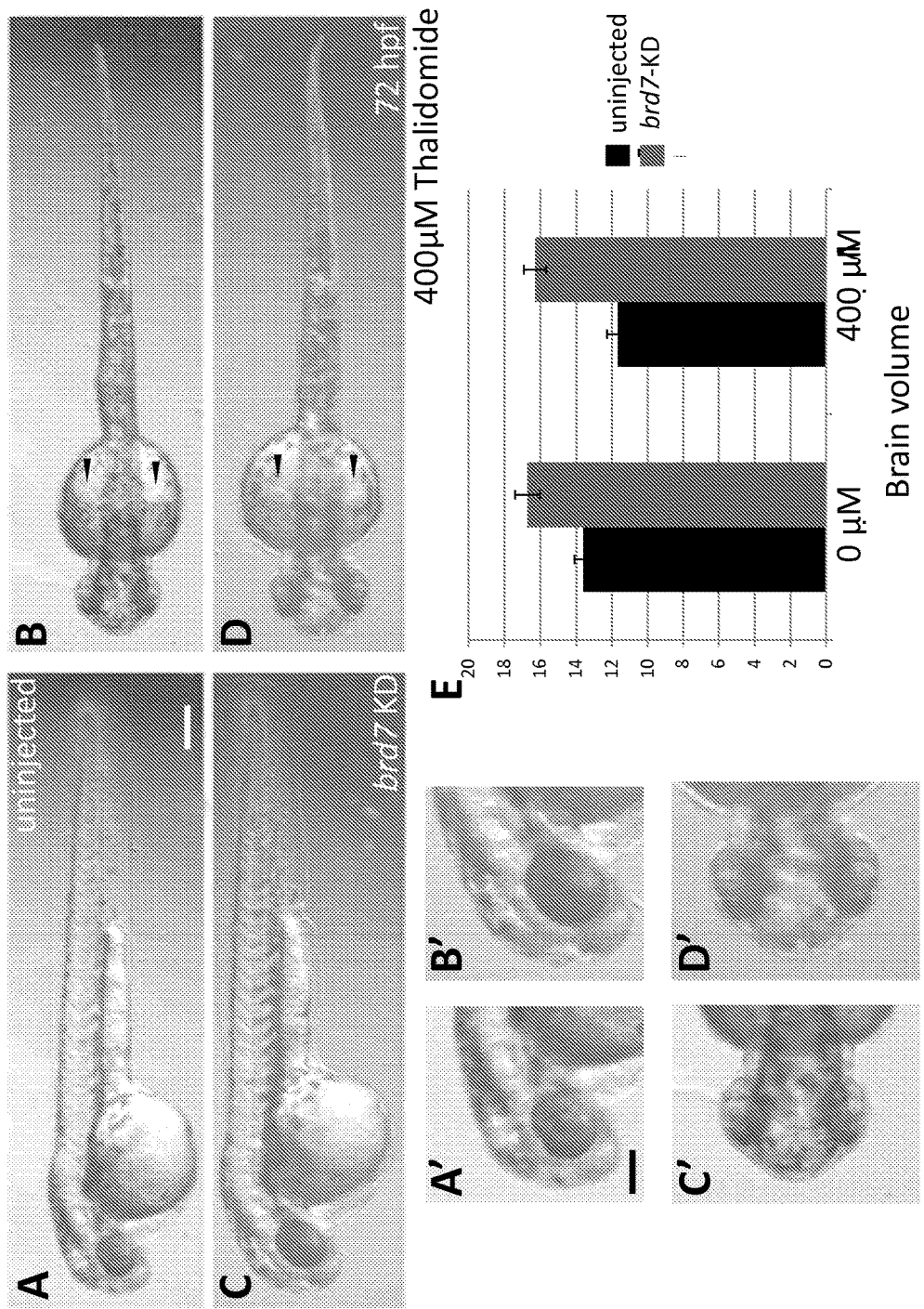

Determination of Resistance to Thalidomide in Brain Development in BRD7-Knockdown Zebrafish To analyze the functional relationship between thalidomide and BRD7, brain development of BRD7-knockdown zebrafish treated with thalidomide was examined and compared with that of normal zebrafish treated with thalidomide. As shown in FIG. 12, the BRD7-knockdown zebrafish is resistant to thalidomide treatment in brain development.

FIGS. 12A and 12B show the normal zebrafish treated with 400 µM thalidomide. FIGS. 12C and 12D show the BRD7-knockdown zebrafish treated with 400 µM thalidomide. FIGS. 12A' and 12C' show the brain regions of the normal zebrafish treated with 400 µM thalidomide. FIGS. 12B' and 12D' show the brain regions of the BRD7-knockdown zebrafish treated with 400 µM thalidomide. As shown, the normal fish showed retardation in brain development in the presence of 400 µM of thalidomide (FIGS. 12A, 12B, 12A', and 12C'). In contrast, the brain of the BRD7-knockdown larvae developed almost normally in thalidomide solution (FIGS. 12C, 12D, 12B', and 12D'). The percentages of brain thickness to body length in the normal and the BRD7-knockdown zebrafish, with or without thalidomide treatments were also measured. As shown in FIG. 12E, without thalidomide treatment, the brain size of the BRD7-knockdown larvae is 120.7% of that of the normal larvae in normal E3 medium, and the brain size of the BRD7-knockdown larvae is 140.0% of that of the normal larvae in 400 µM of thalidomide (n=12). The brain size of the BRD7-knockdown larvae incubated in thalidomide is 98.8% of that of the BRD7-knockdown larvae incubated in the absence of thalidomide.

6.23 Example 23

Determination of Expression Levels of Pou5f1, Nanog, Zic3, and Sox2 in Untreated, CRBN-Overexpressing, and BRD7-Knockdown Zebrafish Expression of Pou5f1, Nanog, Zic3, and Sox2 in untreated, CRBN-overexpressing, CRBN-knockdown, BRD7-overexpressing, BRD7-knockdown, and thalidomide-treated zebrafish embryos at 11 hpf was analyzed by quantitative PCR. As shown in FIG. 13, the expression of Pou5f1 significantly increased in the CRBN-overexpressing and the BRD7-knockdown embryos at 11 hpf. The expression of Zic3 (Pou5f1 target gene) and another pluripotency gene Nanog also increased in the CRBN-overexpressing and the BRD7-knockdown embryos. In contrast, the expression of Pou5f1, Zic3, and Nanog decreased in the CRBN-knockdown, the BRD7-overexpressing, and the thalidomide-treated embryos at the same stage.

6.24 Example 24

Figure 14:
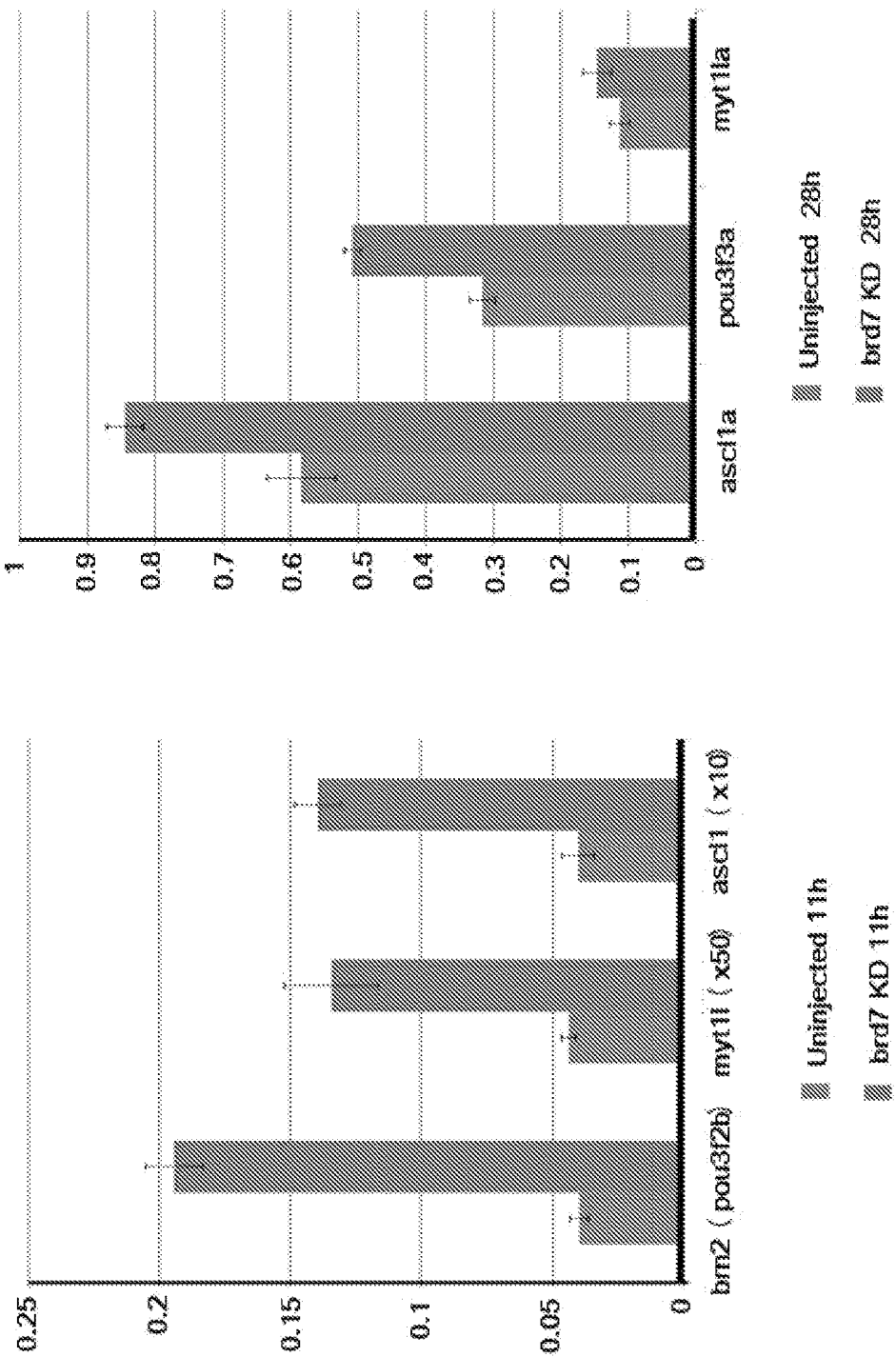

Determination of Expression Levels of Ascl1, Pou3f3a, and Myt1la in Untreated and BRD7-Knockdown Zebrafish Expression of a pool of three genes, Ascl1, Brn2 (Pou3f2), and Myt1l, is sufficient to directly reprogram embryonic and postnatal fibroblasts into functional neurons. See, e.g., Vierbuchen and Wernig, Nat Biotechnol. 29:892-907 (2011). Therefore, the expression of Ascl1, Pou3f3a, Pou3f2b, and Myt1la was analyzed by quantitative PCR in untreated and BRD7-knockdown zebrafish embryos. As shown in FIG. 14, knockdown of BRD7 increased the expression of Ascl1, Pou3f3a, and Myt1la at 28 hpf, and knockdown of BRD7 increased the expression of Ascl1, Myt1l, and Brn2 (Pou3f2b).

6.25 Example 25

Knockdown of Ikaros Enlarges the Brain in Zebrafish Embryos

Example 25 showed that knockdown of Ikaros enlarged the brain in zebrafish embryos. In order to examine the effect of antagonists of Ikaros on brain growth, Ikaros was knocked down or over-expressed in zebrafish embryos. Knockdown of Ikaros was performed by microinjection of antisense morpholino oligonucleotides (AMO). Overexpression of Ikaros was performed by injection of synthesized capped mRNA. AMO or capped mRNA was introduced into one-cell stage embryos by using a nitrogen gas-pressure microinjector IM 300 (Narishige). Conditions for microinjection were as follows: gas pressure was about 15 picosiemens; release period was about 30 to about 50 milliseconds per single injection; concentrations of AMOs and capped mRNA were 400 ng/µl and 250 ng/µl in nuclease-free water, respectively. Capped mRNAs were synthesized in vitro using the mMESSAGE mMachine® in vitro transcription kit (Ambion) from cDNAs cloned into pCS2+ plasmids.

The brains of the embryos were examined for morphology and volume by magnetic resonance imaging (MRI). FIGS. 15A, 15B, and 15C show microscopic pictures of untreated, Ikaros-knockdown, and Ikaros-overexpressing zebrafish embryos at 55 hpf, respectively. As shown in these figures, the Ikaros-knockdown fish had bigger heads than the untreated embryos. In contrast, the embryos injected with Ikaros mRNA causing Ikaros overproduction developed smaller heads and eyes than the untreated embryos. Measurement of the volume of different regions of the brain by transverse and cross section of captured MRI images of the whole brain (the telencephalon to the spinal cord) revealed that all portions of the brain (the telencephalon, the diencephalon, the midbrain, the cerebellum, and the spinal cord) were affected by Ikaros knockdown or Ikaros overexpression. The volume of the whole brain of the Ikaros-knockdown fish was much bigger than that of the untreated fish, while for the Ikaros-overexpressing fish, the brain volume was smaller. Interestingly, the volume of the telencephalon (the area of cross section at the mid region of the midbrain and diencephalon) proportionally changed in the Ikaros-knockdown fish.

6.26 Example 26

Determination of Brain Development in Zebrafish Embryos Overexpressing Ikaros Variants Effects of overexpression of two Ikaros variants on brain development in zebrafish embryos were analyzed. Two new Ikaros variants, ikzf1-006 and ikzf1-007, were isolated.

Ikzf1-006 lacks exon 7, and ikzf1-007 lacks exons 4 and 7. The nucleotide sequence of the ikzf1-006 Ikaros variant is as follows (CDS:cDNA sequence) with alternating exons noted:

```
                                      (SEQ ID NO: 11)
ATGGAGACTGAGGAGGCACAGGAAATGTCCCAGATAACAGGAAGAGA

CAGCCCGATGAATGCTAATGAAGGCGGAGAGGATCAAGATGAGGCCA

TGCCTGTTCCTGAAGACTTGTCAGCAAGCACTGGCCTCCAACACAAC

AATCGCACAGATAAACCACTGGCCTGTAATATAAAAGTTGAGGCTCG

GAGTGACGAGGAAACGGTCTGTCCTGTGAGATGAATGGAGAGGCAG

AGGAATGTGCAGCTGAGGACTTGCGCATACTCGATGGCTCTGGGGCC

AAAGTGAACGGCTCCCACGCAGGCCCCGACAGCAAGCCGGCCGCCTA

CCCCACAGCCGGGGGCATCCGCCTCCCCAACGGGAAGCTGAAGTGCG
```

```
ATATCTGTGGGATAGTTTGCATTGGGCCCAATGTGTTGATGGTTCAC

AAGCGAAGTCACACTGAAGAAAGAAAGTCAGTTTTGGAACAACAAAA

AGGTGAAAGGCCATTCCAGTGCAATCAATGTGGTGCTTCATTCACTC

AGAAGGGTAACCTGCTCCGACACATCAAACTTCACTCTGGCGAGAAA

CCTTTCAAATGTCACCTGTGCAACTATGCTTGCCGCCGCAGAGACGC

TCTCACTGGACATCTGCGCACTCATTCGGTTGGAAAGCCCCATAAGT

GTGCATATTGCGGACGCAGTTACAAGCAGCGGAGCTCACTGGAGGAA

CATAAGGAGAGATGTCACAACTACTTGCAGTGCATGGGCCTTCAGAA

CAGCATTTATACAGGAGAGAATCGTCTGTCAGAGCTATCTTTCGAGA

GTGGCTCANGTGAGCTGATGCAGCCCCATGTGATTGATCAGGCCATC

AACAGTGCAATTAGCTATCTGGGTGCAGAGTCCTTGCGGCCTCTGGT

TCAGACCTCTCCTGGGTCCGCCGACATGGTGGTCAGCCCTCTATACA

ACCTGCACAAGTCACAAACAGCTGAAGGCAATGGTGTTTCTGCTAAA

GACAGCGCCGCAGAGCACCTTCTCCTACTCTCTAAGTCCAAATCCGC

CTCTGTTGACAAAGACGGTTCCCCCAGTCCCAGCGGGCAGGATTCCA

CTGACACTGAGAGCAACAACGAGGAGCGTTCGGCCGGGGTAAGCGGA

ACAGCAGCCACAGGTGGTCTCATCTACCTGACCAACCACATGGCTCC

AGGTATGAGAAATGGAGGCCTGCCAGGGGTAAAGGAAGAACAACACC

GGCAGTTTGAGGCTTTGCGAGCAGCAGGAATGGATTTGAGTATAGCG

TCATCAGAAGGATTTAAGGTGCTAAGTGGAGATGGAGAAGAATTGAG

GGCGTACCGCTGTATCCACTGCAGAGTTTTGTTCCTGGATCATGTCA

TGTACACCATCCACATGGGCTGTCATGGCTTCCGAGACCCCTTTGAG

TGCAACCTATGCGGGTACCGCAGTCAGGACCGTTATGAGTTCTCATC

GCACATCACACGTGGAGAGCACCGCATCTGA.
```

The amino acid sequence of the ikzf1-006 Ikaros variant translation product is as follows (495 amino acids; 54.45 kDa; exon 7 missing):

```
(SEQ ID NO: 12)
METEEAQEMSQITGRDSPMNANEGGEDQDEAMPVPEDLSASTGLQHN

NRTDKPLACNIKVEARSDEENGLSCEMNGEAEECAAEDLRILDGSGA

KVNGSHAGPDSKPAAYPTAGGIRLPNGKLKCDICGIVCIGPNVLMVH

KRSHTEERKSVLEQQKGERPFQCNQCGASFTQKGNLLRHIKLHSGEK

PFKCHLCNYACRRRDALTGHLRTHSVGKPHKCAYCGRSYKQRSSLEE

HKERCHNYLQCMGLQNSIYTGENRLSELSFESGSXELMQPHVIDQAI

NSAISYLGAESLRPLVQTSPGSADMVVSPLYNLHKSQTAEGNGVSAK

DSAAEHLLLLSKSKSASVDKDGSPSPSGQDSTDTESNNEERSAGVSG

TAATGGLIYLTNHMAPGMRNGGLPGVKEEQHRQFEALRAAGMDLSIA

SSEGFKVLSGDGEELRAYRCIHCRVLFLDHVMYTIHMGCHGFRDPFE

CNLCGYRSQDRYEFSSHITRGEHRI.
```

The nucleotide sequence of the ikzf1-007 Ikaros variant is as follows (CDS:cDNA sequence) with alternating exons noted:

```
(SEQ ID NO: 13)
ATGGAGACTGAGGAGGCACAGGAAATGTCCCAGATAACAGGAAGAGA

CAGCCCGATGAATGCTAATGAAGGCGGAGAGGATCAAGATGAGGCCA

TGCCTGTTCCTGAAGACTTGTCAGCAAGCACTGGCCTCCAACACAAC

AATCGCACAGATAAACCACTGGCCTGTAATATAAAAGTTGAGGCTCG

GAGTGACGAGGAAAACGGTCTGTCCTGTGAGATGAATGGAGAGGCAG

AGGAATGTGCAGCTGAGGACTTGCGCATACTCGATGGCTCTGGGGCC

AAAGTGAACGGCTCCCACGCAGGCCCCGACAGCAAGCCGGCCGCCTA

CCCCACAGCCGGGGGCATCCGCCTCCCCAACGGGAAGCTGAAGTGCG

ATATCTGTGGGATAGTTTGCATTGGGCCCAATGTGTTGATGGTTCAC

AAGCGAAGTCACACTGGTGAAAGGCCATTCCAGTGCAATCAATGTGG

TGCTTCATTCACTCAGAAGGGTAACCTGCTCCGACACATCAAACTTC

ACTCTGGCGAGAAACCTTTCAAATGTCACCTGTGCAACTATGCTTGC

CGCCGCAGAGACGCTCTCACTGGACATCTGCGCACTCATTCGGTTGG

AAAGCCCCATAAGTGTGCATATTGCGGACGCAGTTACAAGCAGCGGA

GCTCACTGGAGGAACATAAGGAGAGATGTCACAACTACTTGCAGTGC

ATGGGCCTTCAGAACAGCATTTATACAGGAGAGAATCGTCTGTCAGA

GCTATCTTTCGAGAGTGGCTCANGTGAGCTGATGCAGCCCCATGTGA

TTGATCAGGCCATCAACAGTGCAATTAGCTATCTGGGTGCAGAGTCC

TTGCGGCCTCTGGTTCAGACCTCTCCTGGGTCCGCCGACATGGTGGT

CAGCCCTCTATACAACCTGCACAAGTCACAAACAGCTGAAGGCAATG

GTGTTTCTGCTAAAGACAGCGCCGCAGAGCACCTTCTCCTACTCTCT

AAGTCCAAATCCGCCTCTGTTGACAAAGACGGTTCCCCCAGTCCCAG

CGGGCAGGATTCCACTGACACTGAGAGCAACAACGAGGAGCGTTCGG

CCGGGGTAAGCGGAACAGCAGCCACAGGTGGTCTCATCTACCTGACC

AACCACATGGCTCCAGGTATGAGAAATGGAGGCCTGCCAGGGGTAAA

GGAAGAACAACACCGGCAGTTTGAGGCTTTGCGAGCAGCAGGAATGG

ATTTGAGTATAGCGTCATCAGAAGGATTTAAGGTGCTAAGTGGAGAT

GGAGAAGAATTGAGGGCGTACCGCTGTATCCACTGCAGAGTTTTGTT

CCTGGATCATGTCATGTACACCATCCACATGGGCTGTCATGGCTTCC

GAGACCCCTTTGAGTGCAACCTATGCGGGTACCGCAGTCAGGACCGT

TATGAGTTCTCATCGCACATCACACGTGGAGAGCACCGCATCTGA.
```

The amino acid sequence of the ikzf1-007 Ikaros variant translation product is as follows (484 amino acids; 54.24 kDa; exons 4 and 7 missing):

```
(SEQ ID NO: 14)
METEEAQEMSQITGRDSPMNANEGGEDQDEAMPVPEDLSASTGLQHN

NRTDKPLACNIKVEARSDEENGLSCEMNGEAEECAAEDLRILDGSGA

KVNGSHAGPDSKPAAYPTAGGIRLPNGKLKCDICGIVCIGPNVLMVH

KRSHTGERPFQCNQCGASFTQKGNLLRHIKLHSGEKPFKCHLCNYAC

RRRDALTGHLRTHSVGKPHKCAYCGRSYKQRSSLEEHKERCHNYLQC

MGLQNSIYTGENRLSELSFESGSXELMQPHVIDQAINSAISYLGAES
```

-continued

LRPLVQTSPGSADMVVSPLYNLHKSQTAEGNGVSAKDSAAEHLLLLS

KSKSASVDKDGSPSPSGQDSTDTESNNEERSAGVSGTAATGGLIYLT

NHMAPGMRNGGLPGVKEEQHRQFEALRAAGMDLSIASSEGFKVLSGD

GEELRAYRCIHCRVLFLDHVMYTIHMGCHGFRDPFECNLCGYRSQDR

YEFSSHITRGEHRI.

FIGS. 16A, 16B, 16C, and 16E show microscopic pictures of the brains of untreated, Ikaros-knockdown, ikzf1-007 (an Ikaros variant)-overexpressing, and ikzf1-006 (an Ikaros variant)-overexpressing zebrafish embryos at 22 hpf, respectively. FIGS. 16D and 16F are fluorescent microscopic pictures of the brains of the ikzf1-007-overexpressing and the ikzf1-006-overexpressing zebrafish embryos at 22 hpf, respectively. These pictures were taken at the same magnification. As shown, at 22 hpf, overexpression of fused Ikzf1:EGFP protein caused reduction of brain development in both the ikzf1-006- and the ikzf1-007-overexpressing embryos. Forebrains were truncated by incomplete growth of telencephalon, diencephalon, and midbrain (See FIGS. 16C-16F; 16D and 16F are EGFP fluorescent images). In contrast, knockdown of Ikaros caused macrocephaly, as shown in FIG. 16B.

6.27 Example 27

Analysis of Cell Proliferation and Neural Differentiation in Ikaros-Knockdown Zebrafish Numbers of primary neurons and proliferating cells were analyzed by immunostaining in untreated and Ikaros-knockdown zebrafish embryos at 27 hpf. FIGS. 17A and 17D show the primary neurons in the CNS of the untreated and the Ikaros-knockdown zebrafish embryos, respectively, at 27 hpf by immunostaining with anti-acetylated tubulin antibody. FIGS. 17B and 17E show the proliferating cells in the CNS of the untreated and the Ikaros-knockdown zebrafish embryos, respectively, at 27 hpf by immunostaining with anti-phospho-histone H3 antibodies. FIG. 17C shows merged image of FIGS. 17A and 17B. FIG. 17F shows merged image of FIGS. 17D and 17E. As shown, immunostaining images revealed that the number of the proliferating cells and the number of the primary neurons both increased in the Ikaros-knockdown embryos. Global distribution of the primary neurons was normal as shown (scale bar: 50 µm).

The number of phosphorylated histone H3-positive cells was counted in a stacked focal plane of laser confocal microscope at 27 hpf. The average number of the H3-positive cells in the telencephalon, the diencephalon, and the midbrain was statistically compared between the untreated and the Ikaros-knockdown embryos (n=3 in each experiment). As shown in FIG. 18, the number of the H3-positive proliferating cells in the telecephalon, the diencephalon, and the midbrain regions all increased in the Ikaros-knockdown zebrafish embryos at 27 hpf.

6.28 Example 28

Determination of the Numbers of Radial Glia Cells and Serotonin-Positive Cells in Ikaros-Knockdown Zebrafish The numbers of radial glia cells and serotonin-positive cells in Ikaros-knockdown zebrafish embryos were analyzed by immunostaining FIGS. 19A and 19C-19E show fluorescent microscopic pictures of the brains of untreated zebrafish embryos at 54 hpf. FIGS. 19B and 19F-19H show fluorescent microscopic pictures of the brains of the Ikaros-knockdown zebrafish embryos at 54 hpf. Cells were immunostained with anti-radia glia marker (Zrf-2) antibodies (green) and anti-serotonin antibodies (red). In these figures, rn represents raphe nuclei; RG represents radial glia; vpt represents ventral posterior tuberculum; p represents pineal organ; CMZ represents ciliary marginal zone (scale bar: 50 µm). As shown, the numbers of radial glia cells and serotonin-positive cells increased, while their spatial distribution was normal in the Ikaros-knockdown larvae.

6.29 Example 29

Determination of Expression Levels of Pluripotency Genes in Ikaros-Knockdown Zebrafish Expression of Pou5f1 (Oct3/4), c-Myc, Sox2, and Nanog in zebrafish embryos was analyzed by quantitative PCR. Quantitative RT (qRT)-PCR was performed as follows: 1.7 µg of random hexamer and oligo-dT primed cDNA synthesized by ReverTra Ace qPCR RT Kit (TOYOBO, Japan) (as template) were used for reverse transcription by THUNDERBIRD™ SYBR® qPCR Mix (Toyobo, Japan). 0.25 mM of each forward and reverse primers was used in the reaction. The sequences of primers for c-Myc are as follows: forward primer is 5'-AACAGCTATGACCATGATTAC-3' (SEQ ID NO: 15), and reverse primer is 5'-GTAAAAC-GACGGCCAGT-3' (SEQ ID NO: 16). The sequences of primers for sox2 are as follows: forward primer is 5'-AC-CCCGGAGGAAAACCAA-3' (SEQ ID NO: 17), and reverse primer is 5'-CCCGGCAGGGTGTACTTG-3' (SEQ ID NO: 18). The sequences of primers for nanog are as follows: forward primer is 5'-TACCCAACACACCA-GCTTC-3' (SEQ ID NO: 19), and reverse primer is 5'-GAAGGGTGTTTTTGGAGGA-3' (SEQ ID NO: 20).

Figure 20:
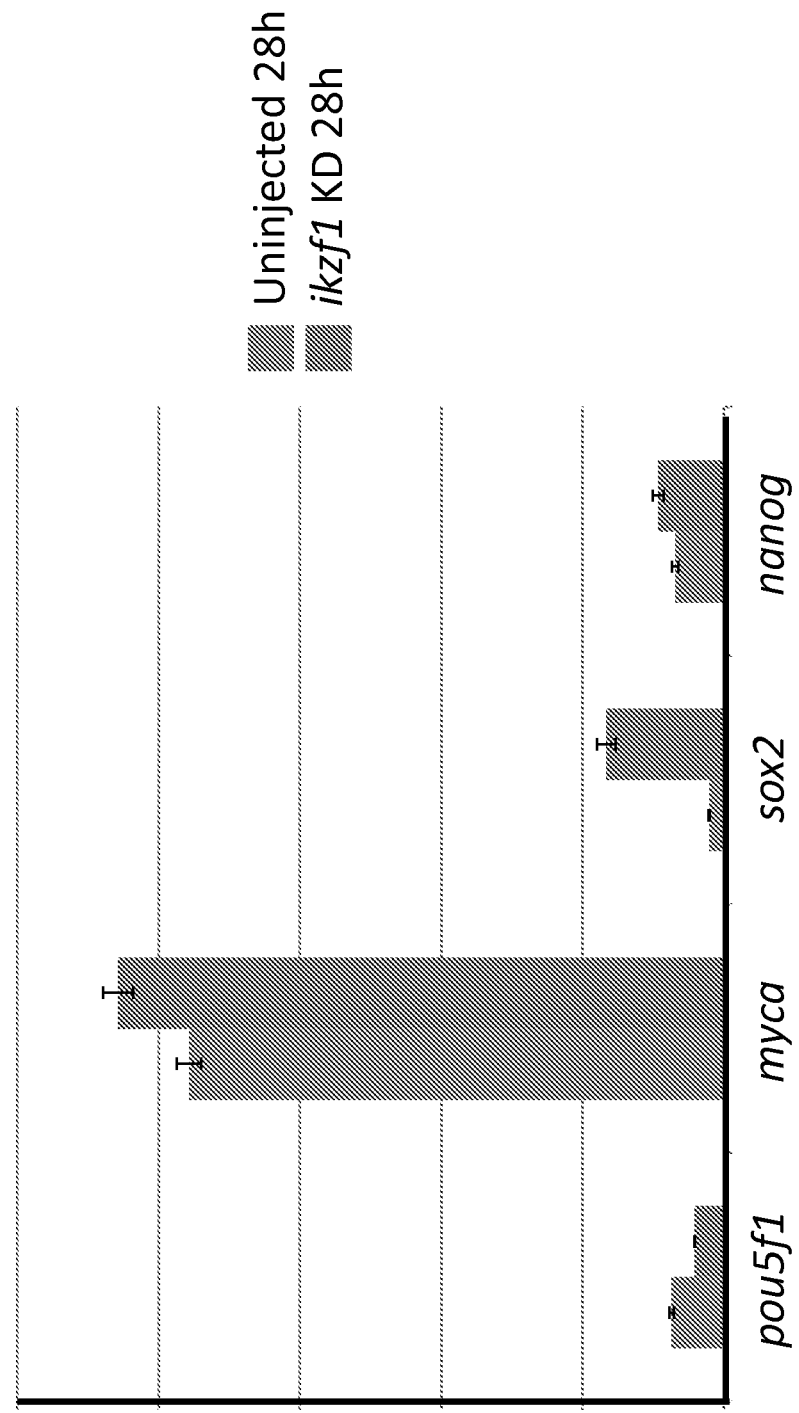
FIG. 20 shows knockdown of Ikaros activates expression of c-Myc, Sox2 and Nanog in zebrafish embryos.

FIG. 20 is a histogram showing Pou5f1, c-Myc, Sox2, and Nanog expression levels by quantitative PCR in the untreated and the Ikaros-knockdown zebrafish embryos at 28 hpf. As shown, Ikaros knockdown activated expression of c-Myc, Sox2, and Nanog in zebrafish embryos.

6.30 Example 30

Figure 21:
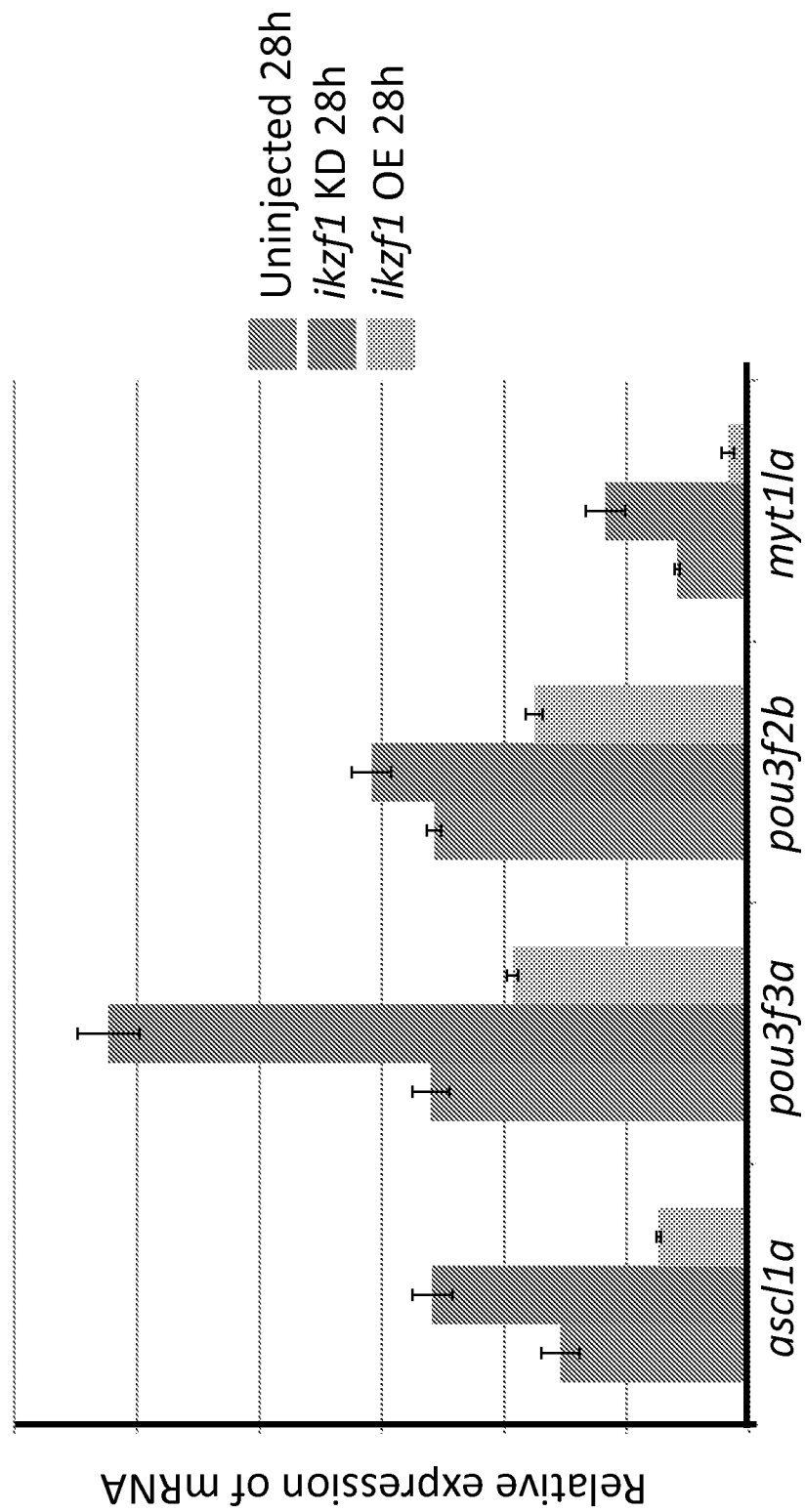

Determination of Expression Levels of Ascl1, Pou3f3a, Pou3f2b, and Myt1la in Ikaros-Knockdown and Ikaros-Overexpressing Zebrafish Expression of a pool of three genes, Ascl1, Brn2 (Pou3f2), and Myt1la, is sufficient to directly reprogram embryonic and postnatal fibroblasts into functional neurons. See, e.g., Vierbuchen and Wernig, Nat Biotechnol. 29:892-907 (2001). Therefore, the expression of Ascl1, Pou3f3a, Pou3f2b, and Myt1la was analyzed by quantitative PCR in untreated, Ikaros-knockdown, and Ikaros-overexpressing zebrafish embryos at 28 hpf. Primer sequences for amplification for Ascl1a are as follows: forward primer is 5'-AC-GAGCATGACGCCGTA-3' (SEQ ID NO: 21), and reverse primer is 5'-TTTTAAGTTTCCTTTTACGAACGCT-3' (SEQ ID NO: 22). Primer sequences for amplification for Pou3f2b are as follows: forward primer is 5'-CCGAGAGT-CATGGCGACTAC-3' (SEQ ID NO: 23), and reverse primer is 5'-CTTCTCCGTGTGACAAGGCT-3'(SEQ ID NO: 24). Primer sequences for amplification for Myt1la are as follows: forward primer is 5'-ACTCAACAGCCACTGC-TACC-3' (SEQ ID NO: 25), and reverse primer is 5'-AGCT-TGATAGCGTGAGGAGC-3' (SEQ ID NO: 26). FIG. 21 is a histogram showing the expression levels of Ascl1, Pou3f3a, Pou3f2b, and Myt11a by quantitative PCR in the untreated and the Ikaros-knockdown zebrafish embryos at 28 hpf. As shown, knockdown of Ikaros increased the expression of Ascl1, Pou3f3a, Pou3f2b, and Myt11a in zebrafish embryos at 28 hpf, and overexpression of Ikaros decreased the expression of Ascl1, Pou3f3a, Pou3f2b, and Myt11a in zebrafish embryos at 28 hpf.

6.31 Example 31

Determination of Expression Levels of Ascl1 and Pou3f2b in Ikaros-Knockdown and CRBN-Overexpressing Zebrafish Expression of Ascl1a and Pou3f2b in CRBN-overexpressing and Ikaros-knockdown zebrafish embryos was analyzed by in situ hybridization. The embryos were fixed with 4% paraformaldehyde for 1 hour at room temperature and rinsed with phosphate buffered saline (PBS). The fixed embryos were refixed with 100% methanol and placed at −80° C. for over 12 hours. The embryos were defixed by rinsing with PBS, and the skin was digested with pronase (2 mg/ml), followed by refixation and defixation, and prehybridized in HYB* buffer (50% formamide, 5×SSC, 10 mM Citric acid, 0.1% Tween 20) for 15 minutes and in HYB+(added as 5 mg/ml torula (yeast) RNA, 50 µg/ml heparin to HYB*) for 1 hour at 65° C. After addition of 1 ng/µl of DIG (digoxigenin)-labeled probe, hybridization was performed for overnight at 65° C. After hybridization, the embryos were washed by 50% formamide in 2×SSC for 30 minutes twice, 2×SSC for 15 minutes, 0.2×SSC for 30 minutes twice at 65° C. Then blocking treatment was done by 0.5% purified casein in PBSTw (PBS plus 0.1% Tween 20) at room temperature for 1 hour. After that, immunostaining was performed in 1/4000 dilution of anti-DIG Fab-AP fragment in 0.5% purified casein in PBSTw for 4 hours at room temperature.

After washing with PBSTw for 90 minutes, staining was carried out in the presence of substrate of alkaline phosphatase (Nitro blue tetrazolium and 5-bromo 4-chloro 3-indolyl phosphate) in 100 mM Tris pH 9.5, 50 mM $MgCl_2$, 100 mM NaCl, and 0.1% Tween-20. Reaction was stopped by rapid exchange of reaction buffer to PBSTw and cleaned with glycerol serials (30%, 50%, and 70% in PBS).

The upper panel of FIG. 22 shows Ascl1a expression in untreated, CRBN-overexpressing, and Ikaros-knockdown zebrafish embryos by in situ hybridization at 25 hpf. The lower panel of FIG. 22 shows Pou3f2b expression in untreated, CRBN-overexpressing, and Ikaros-knockdown zebrafish embryos by in situ hybridization at 26 hpf. As shown, the expression of Ascl1a and Pou3f2b increased in the CRBN-overexpressing and the Ikaros-knockdown zebrafish embryos. In particular, the expression of Ascl1a in the epiphysis, the prethalamus, the thalamus, and the hypothalamus remarkably increased in the Ikaros-knockdown embryo at 25 hpf. The expression of Pou3f2b also increased at 26 hpf in the diencephalon, the midbrain hindbrain boundary, and the cerebellum primordium. All regions marked with Ascl1a and Pou3f2b spatially correspond to the proliferating zone, the pool of neural stem, and the progenitor cells in the CNS.

6.32 Example 32

Determination of Expression Level of Ikaros in CRBN-Overexpressing Zebrafish

To investigate genetic relationship between CRBN and Ikaros, Ikaros expression was analyzed in CRBN-overexpressing embryos at 24 hpf by in situ hybridization. FIGS. 23A and 23B show Ikaros expression by in situ hybridization in untreated and the CRBN-overexpressing zebrafish embryos at 24 hpf. FIG. 23C shows Ikaros, Tp53, and Tp63 expression by quantitative PCR in the untreated and the CRBN-overexpressing zebrafish embryos at 24 hpf. As shown, expression of Ikaros was mainly observed in the central nervous system and the intermediate cell mass ICM in the untreated embryos (purple signal in FIG. 23A). In contrast, expression of Ikaros significantly decreased in the CRBN-overexpressing embryos (see FIG. 23B). Quantitative PCR confirmed severe decrease of Ikaros expression in the CRBN-overexpressing zebrafish embryos at the same stage (see FIG. 23C).

6.33 Example 33

Determination of Brain Development in Ikaros-Knockdown, Ikaros-Overexpressing, Ikaros- and CRBN-Double Knockdown, and CRBN-Knockdown Zebrafish Brain development in untreated, Ikaros-knockdown, Ikaros-overexpressing, Ikaros- and CRBN-double knockdown, and CRBN-knockdown zebrafish was analyzed. FIG. 24 shows microscopic pictures of the untreated, the Ikaros-knockdown, the Ikaros-overexpressing, the Ikaros- and CRBN-double knockdown, and the CRBN-knockdown zebrafish embryos at day 2 (from left to right). These pictures were taken at the same magnification. As shown, the Ikaros-knockdown larvae had enlarged brains at day 2; the CRBN-knockdown and the Ikaros-overexpressing larvae had smaller brains at day 2; and the CRBN- and Ikaros-double knockdown larvae had enlarged brain at day 2.

6.34 Example 34

Determination of Expression Levels of Ascl1a and Pou3f2b in CRBN-Knockdown, Ikaros-Knockdown, and Ikaros- and CRBN-Double Knockdown Zebrafish Expression levels of Ascl1 and Pou3f2b in untreated, CRBN-knockdown, Ikaros-knockdown, and Ikaros- and CRBN-double knockdown zebrafish embryos were analyzed by quantitative PCR at 23 hpf. FIG. 25 is a histogram showing the expression levels of Ascl1 and Pou3f2b by quantitative PCR in the untreated, the CRBN-knockdown, the Ikaros-knockdown, and the Ikaros- and CRBN-double knockdown zebrafish embryos at 23 hpf. As shown, the expression of Ascl1a and Pou3f2b increased in the Ikaros-knockdown and the Ikaros- and CRBN-double knockdown zebrafish embryos, while the expression of Ascl1a and Pou3f2b decreased in the CRBN-knockdown zebrafish embryos.

6.35 Example 35

Determination of the Numbers of Radial Glia and Serotonin-Positive Cells in Ikaros-Knockdown, Ikaros- and CRBN-Double Knockdown, and CRBN-Knockdown Zebrafish Embryos The numbers of radial glia and serotonin-positive cells in Ikaros-knockdown, Ikaros- and CRBN-double knockdown, and CRBN-knockdown zebrafish embryos were analyzed by immunostaining FIGS. 26A, 26B, 26C, and 26D show fluorescent microscopic pictures of the brains of untreated, the Ikaros-knockdown, the Ikaros- and CRBN-double knockdown, and the CRBN-knockdown zebrafish embryos, respectively, at 55 hfp. The embryos were immunostained with anti-radial glia marker antibodies (Zrf-2) (green) and anti-serotonin antibodies (red). In these figures, rn represents raphe nuclei; RG represents radial glia; vpt represents ventral posterior tuberculum; p represents pineal organ; CMZ represents ciliary marginal zone (scale bar: 50 μm). As shown, the numbers of radial glia cells and serotonin-positive cells increased in the Ikaros-knockdown and the Ikaros- and CRBN-double knockdown fish, while the numbers of radial glia cells and serotonin-positive cells decreased in the CRBN-knockdown fish.

6.36 Example 36

Overexpression of CRBN Activates Expression of Sox 2, Pou5f1 (Oct3/4), c-Myc, and Klf4

Expression of Sox2, Pou5f1 (Oct3/4), c-Myc, and Klf4 in zebrafish embryos was analyzed in untreated and CRBN-overexpressing zebrafish embryos by in situ hybridization. Overexpression was performed as follows: single-cell stage embryos were microinjected with 250 ng/μl of capped mRNA synthesized in vitro. Capped mRNA was injected to cytoplasm according to the following conditions: the gas pressure was 15 picosiemens; the release period was 30 to 50 milliseconds per single injection.

Activated expression of Sox2, Pou5f1, c-Myc, and Klf4 by overexpression of CRBN was observed by in situ hybridization. Embryos were fixed with 4% paraformaldehyde for 1 hour at room temperature and rinsed with phosphate buffered saline (PBS). The fixed embryos were refixed with 100% methanol and placed at −80° C. for over 12 hours. The embryos were defixed by rinsing with PBS, and the skin was digested with pronase (2 mg/ml), followed by refixation and defixation, and prehybridized in HYB* buffer (50% formamide, 5×SSC, 10 mM Citric acid, 0.1% Tween 20) for 15 minutes and in HYB+(added as 5 mg/ml torula (yeast) RNA, 50 μg/ml heparin to HYB*) for 1 hour at 65° C. After addition of 1 ng/μl of DIG (digoxigenin)-labeled probe, hybridization was performed for overnight at 65° C. After hybridization, the embryos were washed by 50% formamide in 2×SSC for 30 minutes (twice), 2×SSC for 15 minutes, 0.2×SSC for 30 minutes (twice) at 65° C. Then blocking treatment was done by 0.5% purified casein in PBSTw (PBS plus 0.1% Tween 20) at room temperature for 1 hour. After that, immunostaining was performed in 1/4000 dilution of anti-DIG Fab-AP fragment in 0.5% purified casein in PBSTw for 4 hours at room temperature.

After washing with PBSTw for 90 minutes, staining was carried out in the presence of substrate of alkaline phosphatase (Nitro blue tetrazolium and 5-bromo 4-chloro 3-indolyl phosphate) in 100 mM Tris pH 9.5, 50 mM $MgCl_2$, 100 mM NaCl and 0.1% Tween-20. Reaction was stopped by rapid exchange of reaction buffer to PBSTw and cleaned with glycerol serials (30%, 50%, and 70% in PBS).

Morphology of the embryos was photographed by Differential Interference Contrast (DIC) imaging by objective microscope. FIGS. 27A and 27B show Sox2 expression in untreated and CRBN-overexpressing zebrafish embryos at 9 hpf, respectively, by in situ hybridization. As shown, the expression of Sox2 in the anterior brain region (ab) expanded at 9 phf (79.4%, n=68 in the CRBN-overexpressing embryos; see FIG. 27B).

FIGS. 27C and 27D show Pou5f1 expression in the untreated and the CRBN-overexpressing zebrafish embryos at 10 hpf, respectively, by in situ hybridization. As shown, at 10 hpf, Pou5f1 was expressed in close to the midbrain-hindbrain boundary, presumptive rhombomere 2 and 4 in the hindbrain (r2 and r4), as well as in the axial mesodermal tissues such as the medial longitudinal strip (mls) (see FIG. 27C). When CRBN was overexpressed, the expression of Pou5f1 increased and expanded especially in the early brain region (81.9%, n=72; see FIG. 27D).

FIGS. 27E, 27G, 27I, and 27K show c-Myc expression in the untreated zebrafish embryos at 30 hpf by in situ hybridization. FIGS. 27F, 27H, 27J, and 27L show c-Myc expression in the CRBN-overexpressing zebrafish embryos at 30 hpf by in situ hybridization. As shown, at 30 hpf, c-Myc was abundantly expressed in the tectal proliferation zone (tpz) at the medial and the lateral areas, where neural stem cells exist, and in the most peripheral region of the circumferential marginal zone (CMZ) in the retina, where retinal stem cells are located. The expression of m-Myc was apparently higher and distributed broader in both zones of the CRBN-overexpressing embryos (73.5%, n=68 in the CRBN-overexpressing embryos; see FIGS. 27F, 27H, 27J, and 27L). In the CMZ, the numbers of c-Myc-expressing cells increased in the CRBN-overexpressing embryos (see FIG. 27H), and the thickness of c-Myc-expressing cells in the tectal proliferation zone also increased (see FIG. 27L).

FIGS. 27M and 27N show Klf4 expression in the untreated and the CRBN-overexpressing zebrafish embryos at 18 hpf, respectively, by in situ hybridization. As shown, at 18 hpf, Klf4 was expressed in trigeminal placode, hatching gland, and rostral portion of neural tube. In the CRBN-overexpressing embryos, Klf4 expression apparently increased in trigeminal placode (tgp) and anterior neural tube (bars) (see FIG. 27N).

6.37 Example 37

Overexpression of CRBN Increases the Numbers of Radial Glial Cells and Matured Neurons The numbers of radial glial cells and matured neurons were analyzed in untreated and CRBN-overexpressing zebrafish embryos. The embryos were incubated in 0.003% N-Phenylthiourea (PTU)/E3 medium to block pigmentation. The embryos were fixed in 4% paraformaldehyde (PFA) in phosphate buffered saline (PBS) for 1 hour at room temperature and transferred into PBS. Immunofluorescent labeling was carried out on larvae by incubation with primary antibodies. Zrf-1 and Zrf-2 antibodies were used to label glial fibrillary acidic protein (GFAP) in astrocytes and radial glial cells, respectively. Radial glial cells in the CNS function as a precursor of neurons and oligodendrocytes, and as a scaffold to support neuronal migration. Then, fluorescein-conjugated secondary monoclonal antibodies against rabbit or mouse IgG (Alexa Fluor, Molecular Probes) were used for labeling acetylated tubulin, GFAP, and radial glial marker. Samples were washed with PBS and clearized in glycerol series (30%, 50%, and 70% in PBS), then mounted on a glass slide, and images were obtained using a fluorescent microscope.

FIGS. 28A and 28B show the brain regions of the untreated zebrafish embryos at 56 hpf immunostained with Zrf-1 antibodies, which label glial fibrillary acidic protein (GFAP) in astrocytes. FIGS. 28C and 28D show the brain regions of the CRBN-overexpressing zebrafish embryos at 56 hpf immunostained with Zrf-1 antibodies, which label glial fibrillary acidic protein (GFAP) in astrocytes. As shown, at 56 hpf, in the CRBN-overexpressing larvae, the number of GFAP-positive astrocytes detected by Zrf-1 increased in both cell bodies and fibers (see FIGS. 28C and 28D; bracket indicates the cell bodies of GFAP-positive glia).

FIGS. 28E and 28F show the brain regions of the untreated zebrafish embryos at 56 hpf immunostained with Zrf-2 antibodies, which label radial glial cells. FIGS. 28G and 28H show the brain regions of the CRBN-overexpressing zebrafish embryos at 56 hpf immunostained with Zrf-2 antibodies, which label radial glial cells. As shown, the number of radial glial cells in the hindbrain increased in the CRBN-overexpressing larvae (see FIGS. 28G and 28H).

FIGS. 28I and 28J show the brain regions of the untreated and the CRBN-overexpressing zebrafish embryos at 48 hpf immunostained with Zrf-2 antibodies, which label Müller glia in the retina. Müller glia had the potential to serve as neural stem cells in the retina and was labeled by Zrf-2. As shown, the number of Müller glia increased in the CRBN-overexpressing larvae at 48 hpf (see FIG. 28J), proportionally to the larger size of the eyes (see FIGS. 28I and 28J).

FIGS. 28K and 28L show Sox10 in the otic vesicles and the neural crest cells (NCCs) in the spinal cord in the untreated and the CRBN-overexpressing zebrafish embryos at 33 hpf, respectively. As shown, at 33 hpf, Sox10 was expressed in the otic vesicles and the neural crest cells (NCCs) in the spinal cord (see FIG. 28K). At this stage, Sox10-positive NCCs contained unspecified neurons and glial cells. These cells increased in the CRBN-overexpressing embryos (see FIG. 28L).

FIG. 28M is a histogram showing the Gfap mRNA level in the untreated and the CRBN-overexpressing zebrafish embryos at 11 hpf, respectively, by quantitative PCR. As shown, Gfap in the CRBN-overexpressing embryos increased to over 4-fold of the level in the untreated embryos at 11 hpf (see FIG. 28M).

6.38 Example 38

Overexpression of CRBN Increases Expression of Positive Regulatory Genes for Cell Proliferation Notch3 and Neuropilin2b (Nrp2b) are required for cell proliferation progression. Notch3 regulates the timing of neural differentiation from undifferentiated or immature cells, and Nrp2b regulates cell proliferation and remodeling in mesenchymal stem cells by cooperating with PDGF (platelet-derived growth factor). Therefore, expression of Notch3 and Neuropilin 2b (Nrp2b) was analyzed in untreated and CRBN-overexpressing zebrafish embryos by quantitative PCR. The primers used for Notch3 are as follows: the sequence for forward primer is 5'-ACAACA-GCGAAGGATTGCTC-3' (SEQ ID NO: 27), and the sequence for reverse primer is 5'-TCTAAAGCCTCGCT-GACACA-3' (SEQ ID NO: 28). The primers used for Nrp2b are as follows: the sequence of forward primer is 5'-CCA-GCGGATCGTCTTAAACT-3' (SEQ ID NO: 29), and the sequence of reverse primer is 5'-CAAAACTGGGCCT-GAGGATA-3' (SEQ ID NO: 30). FIG. 29A is a histogram showing the mRNA level of Notch3 and Nrp2b in untreated, CRBN-overexpressing, and thalidomide-treated zebrafish embryos at 11 hpf by quantitative PCR. As shown, expression of Notch3 in the CRBN-overexpressing embryos increased to 1.8-fold of the level in the untreated embryos at 11 hpf, and expression of Nrp2b in the CRBN-overexpressing embryos increased to 2.7-fold of the level in the untreated embryos at the same stage. In contrast, thalidomide treatment decreased the expression of both genes to 0.3-fold and 0.4-fold of the level in the untreated embryos, respectively. These data strongly suggest that CRBN activates cell proliferation by upregulating the expression of these signal molecules.

Elval3 (Huc) is a neural progenitor marker. Expression of Elavl3 (Huc) was also analyzed by quantitative PCR and in situ hybridization. The primers used for Elavl3 are as follows: the sequence of forward primer is 5'-AAGGCTAT-CAACACGCTCAAC-3' (SEQ ID NO: 9), and the sequence of reverse primer is 5'-TCACATACAGGTTGGCATCG-3' (SEQ ID NO: 10). FIG. 29B is a histogram showing the Elavl3 mRNA level in untreated and CRBN-overexpressing zebrafish embryos at 11 hpf by quantitative PCR. As shown, expression of Elavl3 in the CRBN-overexpressing zebrafish embryos increased to 1.7-fold of the level in the untreated embryos at 11 hpf. The increased expression of Elavl3 was confirmed by in situ hybridization. FIGS. 29C and 29D show Elavl3-positive neural progenitor cells in the untreated and the CRBN-overexpressing zebrafish embryos at 14 hpf by in situ hybridization. As shown, the number of the Elav13-positive neural progenitor cells in the CNS increased in the CRBN-overexpressing embryos at 14 hpf. Differential Interference Contrast (DIC) images of the telencephalon and the spinal cord clearly showed that the Elavl3-positive neural progenitor cells increased in each region (see FIG. 29D).

6.39 Example 39

Overexpression of CRBN Increases Oligodendrocytes

Distribution and growth of oligodendrocytes in the forebrain, the otic vesicle, and the spinal cord of untreated and CRBN-overexpressing zebrafish embryos were analyzed by in situ hybridization with olig2 probe, to selectively stain oligodendrocytes at 36 phf.

FIGS. 30A and 30B show oligodendrocytes in the forebrain, the otic vesicle, and the spinal cord of the untreated and the CRBN-overexpressing zebrafish embryos at 36 hpf by in situ hybridization. FIGS. 30C and 30D show oligodendrocytes in the epiphysis of the untreated and the CRBN-overexpressing zebrafish embryos at 36 hpf. As shown, spatial distribution of oligodendrocytes in the forebrain, the otic vesicle, and the spinal cord appeared to be identical in the untreated and the CRBN-overexpressing embryos (see FIGS. 30A and 30B). However, Differential Interference Contrast (DIC) images indicated that the number of olig2-positive cells was apparently higher in the forebrain of the CRBN-overexpressing embryos (see FIGS. 30C and 30D).

6.40 Example 40

Overexpression of Six3b, Lhx2b, and CRBN Increases Expression of Pluripotency Genes Effects of overexpression of Six3b, Lhx2b, and CRBN on expression of pluripotency genes were analyzed by quantitative PCR. Primers used in quantitative PCR for Sox2 are as follows: the sequence of forward primer is 5'-ACCCCG-GAGGAAAACCAA-3' (SEQ ID NO: 17), and the sequence of reverse primer is 5'-CCCGGCAGGGTGTACTTG-3'

(SEQ ID NO: 18). Primers used in quantitative PCR for Pou5f1 are as follows: the sequence of forward primer is 5'-AACTGAAGCCGTTGTTGCAG-3' (SEQ ID NO: 31), and the sequence of reverse primer is 5'-CAAGCTGGTC-CTTCGTTTTC-3' (SEQ ID NO: 32). Primers used in quantitative PCR for Nanog are as follows: the sequence of forward primer is 5'-TACCCAACACACCAGCTTC-3' (SEQ ID NO: 19), and the sequence of reverse primer is 5'-GAAGGGTGTTTTTGGAGGA-3' (SEQ ID NO: 20). Primers used in quantitative PCR for Zic3 are as follows: the sequence of forward primer is 5'-CCCTGGGCTGGGACTCA-3' (SEQ ID NO: 33), and the sequence of reverse primer is 5'-CTTGAAGGCAGC-CGAGTGA-3' (SEQ ID NO: 34). Primers used in quantitative PCR for CRBN are as follows: the sequence of forward primer is 5'-AGAGGTCAGCATGTTTCGCA-3' (SEQ ID NO: 35), and the sequence of reverse primer is 5'-CTGACGAATCCCGTCTGCTT-3' (SEQ ID NO: 36). Primers used in quantitative PCR for Wnt3a are as follows: the sequence of forward primer is 5'-GCTTCTGCCG-CAACTATGTG-3' (SEQ ID NO: 37), and the sequence of reverse primer is 5'-CCGATTCTCTGGTGGCCTTT-3' (SEQ ID NO: 38). Primers used in quantitative PCR for Lhx2b are as follows: the sequence of forward primer is 5'-GGGGGAAACAGAGACGAACA-3' (SEQ ID NO: 39), and the sequence of reverse primer is 5'-TCTCTGCAC-CGAAAACCTTCT-3' (SEQ ID NO: 40). Primers used in quantitative PCR for Pou3f2b are as follows: the sequence of forward primer is 5'-CCGAGAGTCATGGCGACTAC-3' (SEQ ID NO: 23), and the sequence of reverse primer is 5'-CTTCTCCGTGTGACAAGGCT-3' (SEQ ID NO: 24).

FIG. 31A is a histogram showing expression levels of Lhx2b, Wnt3a, CRBN, Sox2, Pou5f1, and Nanog in untreated and Six3b-overexpressing zebrafish embryos at 11 hpf by quantitative PCR. As shown, overexpression of Six3b increased the expression levels of Lhx2b, Wnt3a, CRBN, and pluripotency genes (Sox2, Pou5f1, and Nanog). Relative expression of mRNAs was indicated by the vertical axis. Compared to the untreated embryos, the expression of Lhx2b increased to about 1.2-fold, the expression of Wnt3a, CRBN, and Sox2 increased to about 1.5-fold, the expression of pou5f1 increased to about 1.7-fold, and the expression of Nanog increased to about 2.4-fold in the Six3b-overexpressing embryos.

FIG. 31B is a histogram showing expression levels of CRBN, Sox2, Pou5f1, Nanog, and Zic3 in untreated and Lhx2b-overexpressing zebrafish embryos at 11 hpf by quantitative PCR. As shown, compared to the untreated embryos, the expression of CRBN, Sox2, Pou5f1, and Nanog increased to about 1.2-, 2.3-, 1.6-, and 1.3-fold in the Lhx2b-overexpressing embryos, respectively.

FIG. 31C is a histogram showing expression levels of Sox2, Pou5f1, Nanog, and Zic3 in untreated, CRBN-overexpressing, CRBN-knockdown, and 100 μM thalidomide-treated zebrafish embryos at 11 hpf by quantitative PCR. As shown, overexpression and knockdown of CRBN showed opposite effects on the expression of pluripotency genes. Thalidomide treatment reduced the expression of the pluripotency genes to about the level observed in the CRBN-knockdown embryos. In the CRBN-overexpressing embryos, expression of Sox2, Pou5f1, Nanog, and Zic3 increased to 1.2-, 1.9-, 4.6-, 1.3-fold of that in uninjected embryos, respectively. In contrast, expression of each gene decreased to 0.7-, 0.8-, 0.8-, 0.8-fold of that in untreated embryos when CRBN was knocked down. Thalidomide treatment decreased expression of each gene more severely (from about 0.5- to 0.7-fold).

6.41 Example 41

Overexpression of CRBN Increases Expression of Neural Reprogramming Genes

Expression of a pool of three genes, Ascl1, Brn2 (Pou3f2), and Myt1la, has been shown to be sufficient to directly reprogram embryonic and postnatal fibroblasts into functional neurons. See, e.g., Vierbuchen and Wernig, Nat Biotechnol. 29:892-907 (2011). Therefore, the expression of Ascl1, Pou3f3a, and Myt1la was analyzed by quantitative PCR in untreated and CRBN-overexpressing zebrafish embryos at 24 hpf. Primers used in quantitative PCR for Ascl1 are as follows: the sequence of forward primer is 5'-ACGAGCATGACGCCGTA-3' (SEQ ID NO: 21), and the sequence of reverse primer is 5'-TTTTAAGTTTCCTTT-TACGAACGCT-3' (SEQ ID NO: 22). Primers used in quantitative PCR for Pou3f2 are as follows: the sequence of forward primer is 5'-CCGAGAGTCATGGCGACTAC-3' (SEQ ID NO: 23), and the sequence of reverse primer is 5'-CTTCTCCGTGTGACAAGGCT-3' (SEQ ID NO: 24). Primers used in quantitative PCR for Myt1la are as follows: the sequence of forward primer is 5'-ACTCAACAGC-CACTGCTACC-3' (SEQ ID NO: 25), and the sequence of reverse primer is 5'-AGCTTGATAGCGTGAGGAGC-3' (SEQ ID NO: 26).

FIG. 32 is a histogram showing expression levels of Ascl1a, Pou3f2b, and Myt1la in untreated and CRBN-overexpressing zebrafish embryos at 24 hpf by quantitative PCR. As shown, overexpression of CRBN increased the expression of Ascl1, Pou3f3a, and Myt1la at 24 hpf.

Throughout this application various publications have been referenced. The disclosures of these publications in their entireties are hereby incorporated by reference in this application in order to more fully describe the state of the art to which this invention pertains. Although the invention has been described with reference to the examples and embodiments provided above, it should be understood that various modifications can be made without departing from the spirit of the invention.

7. SEQUENCE LISTING

The present specification is being filed with a computer readable form (CRF) copy of the Sequence Listing. The CRF entitled 12827-711-999-SequenceListing.txt was created on Aug. 23, 2016, and is 20,469 bytes in size, and is incorporated herein by reference in its entirety.

What is claimed is:

1. A method for assessing efficacy of a Bromodomain Containing 7 (BRD7) antagonist or an Ikaros antagonist in treating a central nervous system (CNS) cell defective disease, disorder or condition, or a symptom thereof, in a patient, comprising:
   (i) administering the BRD7 antagonist or Ikaros antagonist to the patient; and
   (ii)(A) comparing a CNS cell mass in the patient before and after administration of the BRD7 antagonist or Ikaros antagonist,
   wherein an increase in CNS cell mass after administration of the BRD7 antagonist or Ikaros antagonist as compared to before administration of the BRD7 antagonist or Ikaros antagonist is indicative of the efficacy of the BRD7 antagonist or Ikaros antagonist in treating the CNS-cell defective disease, disorder or condition, or symptom thereof; or
   (ii)(B) comparing expression level of a Yamanaka factor, Nanog, NeuroD, Zic3, Elavl3, and/or a BAM factor in the patient before and after administration of the BRD7 antagonist or Ikaros antagonist, wherein an increase in the expression levels of the Yamanaka factor, Nanog, NeuroD, Zic3, Elavl3, and/or BAM factor after administration of the BRD7 antagonist or Ikaros antagonist as compared to before administration of the BRD7 antagonist or Ikaros antagonist is indicative of the efficacy of the BRD7 antagonist or Ikaros antagonist in treating the CNS-cell defective disease, disorder or condition, or symptom thereof.

2. The method of claim 1, wherein the Yamanaka factor is Oct 3/4, Sox2, c-Myc, or Klf4.

3. The method of claim 1, wherein the BAM factor is Brn2 (Pou3f2), Ascl1 or Mytl1.

4. The method of claim 1, further comprising one or more subsequent administrations of the BRD7 antagonist or Ikaros antagonist to the patient following the assessment of efficacy.

5. The method of claim 1, further comprising
   (I) selecting a group of patients having a CNS cell defective disease, disorder or condition, or a symptom thereof, based on CNS cell mass for the purposes of predicting clinical response, monitoring clinical response, or monitoring patient compliance to dosing with the BRD7 antagonist or Ikaros antagonist; or
   (II) selecting a group of patients having a CNS cell defective disease, disorder or condition, or a symptom thereof, based on expression level of a Yamanaka factor, Nanog, NeuroD, Zic3, Elavl3, and/or BAM factor in the patient, for the purposes of predicting clinical response, monitoring clinical response, or monitoring patient compliance to dosing with a BRD7 antagonist or Ikaros antagonist.

6. The method of claim 5, wherein the Yamanaka factor is Oct 3/4, Sox2, c-Myc, or Klf4.

7. The method of claim 5, wherein and the BAM factor is Brn2 (Pou3f2), Ascl1 or Mytl1.

8. The method of claim 1, wherein the CNS cell defective disease, disorder or condition is a disease of cerebral cortex, a surgical injury of cerebral cortex, or a neurodegenerative disease.

9. The method of claim 1, wherein the CNS cell disease, disorder or condition is selected from a group consisting of Parkinson's disease; Alzheimer's disease; Creutzfeldt-Jakob disease; corticobasal degeneration; Amyotrophic Lateral Sclerosis; Multiple Sclerosis; progressive motor weakness; neuroimmunological disorders, CNS trauma; Alzheimer disease with parkinsonism; bradykinesia; alkinesia; movement disorders that impair fine motor control and finger dexterity; hypophonia; monotonic speech; rigidity; dystonia; inflammation associated with Parkinson Disease; tremors of the face, jaw, tongue, posture; parkinsonian gait; shuffling; short steps; festinating gait; disorders of mood, cognition, sensation, sleep; dementia; depression; drug induced parkinsonism; vascular parkinsonism; multiple system atrophy; progressive supranuclear palsy; disorders with primary tau pathology; cortical basal ganglia degeneration; parkinsonism with dementia; hyperkinetic disorders; chorea; Huntington's disease; dystonia; Wilson's disease; Tourette syndrome; essential tremor; myoclonus; and a tardive dyskinesia movement disorder.

10. The method of claim 9, wherein the CNS cell disease, disorder or condition is Alzheimer's disease.

11. The method of claim 9, wherein the CNS cell disease, disorder or condition is Parkinson's disease.

12. The method of claim 1, wherein the BRD7 antagonist is selected from a group consisting of an inhibitor of BRD7 protein, a nucleic acid comprising at least part of nucleic acid sequence of BRD7 gene, and a stem cell, neural progenitor cell, or neural precursor cell in which BRD7 is down-regulated.

13. The method of claim 12, wherein the BRD7 antagonist is an inhibitor of BRD7 protein, wherein the inhibitor of BRD7 protein is selected from a group consisting of an inhibitor of BRD7 production, an inhibitor of BRD7 action, and a nucleic acid comprising a coding region of an inhibitor of BRD7.

14. The method of claim 12, wherein the BRD7 antagonist is a nucleic acid comprising at least part of nucleic acid sequence of BRD7 gene, wherein the nucleic acid is inserted in a vector or the nucleic acid is an antisense molecule specific to a BRD7 gene, the antisense molecule being optionally an RNAi molecule.

15. The method of claim 12, wherein the BRD7 antagonist is a Morpholino oligonucleotide specific to BRD7 gene.

16. The method of claim 15, wherein the Morpholino oligonucleotide comprises a sequence of SEQ ID NO: 1.

17. The method of claim 12, wherein the BRD7 antagonist is a stem cell, neural progenitor cell or neural precursor cell in which BRD7 is down-regulated; an induced pluripotent stem (iPS) cell; an antagonist inducing proliferation of cells selected from a group consisting of nerve cells, progenitors of nerve cells, and precursors of nerve cells;
or an antagonist inducing differentiation into nerve cells.

18. The method of claim 1, wherein the Ikaros antagonist is selected from a group consisting of an inhibitor of Ikaros protein, a nucleic acid comprising at least part of nucleic acid sequence of Ikaros gene, and a stem cell, neural progenitor cell, or neural precursor cell in which Ikaros is down-regulated.

19. The method of claim 18, wherein the Ikaros antagonist is an inhibitor of Ikaros protein, wherein the inhibitor of Ikaros protein is selected from a group consisting of an inhibitor of Ikaros production, an inhibitor of Ikaros action, and a nucleic acid comprising a coding region of an inhibitor of Ikaros.

20. The method of claim 18, wherein the Ikaros antagonist is a nucleic acid comprising at least part of nucleic acid sequence of Ikaros gene, wherein the nucleic acid is inserted in a vector or the nucleic acid is an antisense molecule specific to an Ikaros gene, the antisense molecule being optionally an RNAi molecule.

21. The method of claim 18, wherein the Ikaros antagonist is a Morpholino oligonucleotide specific to Ikaros gene.

22. The method of claim 21, wherein the Morpholino oligonucleotide comprises a sequence of SEQ ID NO: 2.

23. The method of claim 18, wherein the Ikaros antagonist is a stem cell, neural progenitor cell or neural precursor cell in which Ikaros is down-regulated; an induced pluripotent stem (iPS) cell; an antagonist inducing proliferation of cells selected from a group consisting of nerve cells, progenitors of nerve cells, and precursors of nerve cells; or an antagonist inducing differentiation into nerve cells.

* * * * *

SEQUENCE LISTING

<160> NUMBER OF SEQ ID NOS: 40

<210> SEQ ID NO 1
<211> LENGTH: 25
<212> TYPE: DNA

```
<213> ORGANISM: Artificial Sequence
<220> FEATURE:
<223> OTHER INFORMATION: antagonist of BRD7 - a Morpholino
      oligonucleotide

<400> SEQUENCE: 1
tgtgtttctt gtgcttttg cccat                                          25

<210> SEQ ID NO 2
<211> LENGTH: 25
<212> TYPE: DNA
<213> ORGANISM: Artificial Sequence
<220> FEATURE:
<223> OTHER INFORMATION: AMO sequence used for the Ikaros gene knockdown

<400> SEQUENCE: 2
ttcctgtgcc tcctcagtct ccatc                                         25

<210> SEQ ID NO 3
<211> LENGTH: 25
<212> TYPE: DNA
<213> ORGANISM: Artificial Sequence
<220> FEATURE:
<223> OTHER INFORMATION: AMO sequence used for the CRBN gene knockdown

<400> SEQUENCE: 3
agagctgtag ctggttcccc atttc                                         25

<210> SEQ ID NO 4
<211> LENGTH: 25
<212> TYPE: DNA
<213> ORGANISM: Artificial Sequence
<220> FEATURE:
<223> OTHER INFORMATION: AMO sequence used for the Lhx2 gene knockdown

<400> SEQUENCE: 4
tctgcaaccc aagatttccg tgaga                                         25

<210> SEQ ID NO 5
<211> LENGTH: 29
<212> TYPE: DNA
<213> ORGANISM: Artificial Sequence
<220> FEATURE:
<223> OTHER INFORMATION: forward primer for cloning BRD7 gene into pCS2+
      vector

<400> SEQUENCE: 5
tttaagctta tgggcaaaaa gcacaagaa                                     29

<210> SEQ ID NO 6
<211> LENGTH: 30
<212> TYPE: DNA
<213> ORGANISM: Artificial Sequence
<220> FEATURE:
<223> OTHER INFORMATION: reverse primer for cloning BRD7 gene into pCS2+
      vector

<400> SEQUENCE: 6
ttttctagat cagctcctac gacgcgtgca                                    30

<210> SEQ ID NO 7
<211> LENGTH: 34
<212> TYPE: DNA
<213> ORGANISM: Artificial Sequence
<220> FEATURE:
<223> OTHER INFORMATION: forward primer for cloning Ikaros gene into
      pCS2+ vector
```

<400> SEQUENCE: 7
tttgaattca tggagactga ggaggcacag gaaa        34

<210> SEQ ID NO 8
<211> LENGTH: 33
<212> TYPE: DNA
<213> ORGANISM: Artificial Sequence
<220> FEATURE:
<223> OTHER INFORMATION: reverse primer for cloning Ikaros gene into
      pCS2+ vector

<400> SEQUENCE: 8
tttctcgagt cagatgcggt gctctccacg tgt        33

<210> SEQ ID NO 9
<211> LENGTH: 21
<212> TYPE: DNA
<213> ORGANISM: Artificial Sequence
<220> FEATURE:
<223> OTHER INFORMATION: forward primer used in reverse transcription of
      Quantitative PCR

<400> SEQUENCE: 9
aaggctatca acacgctcaa c        21

<210> SEQ ID NO 10
<211> LENGTH: 20
<212> TYPE: DNA
<213> ORGANISM: Artificial Sequence
<220> FEATURE:
<223> OTHER INFORMATION: reverse primer used in reverse transcription of
      Quantitative PCR

<400> SEQUENCE: 10
tcacatacag gttggcatcg        20

<210> SEQ ID NO 11
<211> LENGTH: 1488
<212> TYPE: DNA
<213> ORGANISM: Artificial Sequence
<220> FEATURE:
<223> OTHER INFORMATION: nucleotide sequence of ikzf1-006 Ikaros variant
<220> FEATURE:
<221> NAME/KEY: misc_feature
<222> LOCATION: 808
<223> OTHER INFORMATION: n = A,T,C or G

<400> SEQUENCE: 11
atggagactg aggaggcaca ggaaatgtcc cagataacag aagagacag cccgatgaat        60 gctaatgaag gcggagagga tcaagatgag gccatgcctg ttcctgaaga cttgtcagca      120
agcactggcc tccaacacaa caatcgcaca gataaaccac tggcctgtaa tataaaagtt      180
gaggctcgga gtgacgagga aaacggtctg tcctgtgaga tgaatggaga ggcagaggaa      240
tgtgcagctg aggacttgcg catactcgat ggctctgggg ccaaagtgaa cggctcccac      300
gcaggccccg acagcaagcc ggccgcctac cccacagccg ggggcatccg cctccccaac      360
gggaagctga agtgcgatat ctgtgggata gtttgcattg gcccaatgt gttgatggtt      420 cacaagcgaa gtcacactga gaaagaaag tcagttttgg aacaacaaaa aggtgaaagg      480
ccattccagt gcaatcaatg tggtgcttca ttcactcaga gggtaacct gctccgacac      540 atcaaacttc actctggcga gaaacctttc aaatgtcacc tgtgcaacta tgcttgccgc      600
cgcagagacg ctctcactgg acatctgcgc actcattcgg ttggaaagcc cataagtgt      660

```
gcatattgcg gacgcagtta caagcagcgg agctcactgg aggaacataa ggagagatgt    720
cacaactact tgcagtgcat gggccttcag aacagcattt atacaggaga gaatcgtctg    780
tcagagctat ctttcgagag tggctcangt gagctgatgc agccccatgt gattgatcag    840
gccatcaaca gtgcaattag ctatctgggt gcagagtcct tgcggcctct ggttcagacc    900
tctcctgggt ccgccgacat ggtggtcagc cctctataca acctgcacaa gtcacaaaca    960
gctgaaggca atggtgtttc tgctaaagac agcgccgcag agcaccttct cctactctct   1020
aagtccaaat ccgcctctgt tgacaaagac ggttccccca gtcccagcgg gcaggattcc   1080
actgacactg agagcaacaa cgaggagcgt tcggccgggg taagcggaac agcagccaca   1140
ggtggtctca tctacctgac caaccacatg gctccaggta tgagaaatgg aggcctgcca   1200
ggggtaaagg aagaacaaca ccggcagttt gaggctttgc gagcagcagg aatggatttg   1260
agtatagcgt catcagaagg atttaaggtg ctaagtggag atggagaaga attgagggcg   1320
taccgctgta tccactgcag agttttgttc ctggatcatg tcatgtacac catccacatg   1380
ggctgtcatg gcttccgaga ccccttgag tgcaacctat gcgggtaccg cagtcaggac   1440
cgttatgagt tctcatcgca catcacacgt ggagagcacc gcatctga              1488
```

```
<210> SEQ ID NO 12
<211> LENGTH: 495
<212> TYPE: PRT
<213> ORGANISM: Artificial Sequence
<220> FEATURE:
<223> OTHER INFORMATION: amino acid sequence of ikzf1-006 Ikaros variant
<220> FEATURE:
<221> NAME/KEY: VARIANT
<222> LOCATION: 270
<223> OTHER INFORMATION: Xaa = Any Amino Acid

<400> SEQUENCE: 12

Met Glu Thr Glu Glu Ala Gln Glu Met Ser Gln Ile Thr Gly Arg Asp
  1               5                  10                  15

Ser Pro Met Asn Ala Asn Glu Gly Gly Glu Asp Gln Asp Glu Ala Met
                 20                  25                  30

Pro Val Pro Glu Asp Leu Ser Ala Ser Thr Gly Leu Gln His Asn Asn
             35                  40                  45

Arg Thr Asp Lys Pro Leu Ala Cys Asn Ile Lys Val Glu Ala Arg Ser
         50                  55                  60

Asp Glu Glu Asn Gly Leu Ser Cys Glu Met Asn Gly Glu Ala Glu Glu
     65                  70                  75                  80

Cys Ala Ala Glu Asp Leu Arg Ile Leu Asp Gly Ser Gly Ala Lys Val
                 85                  90                  95

Asn Gly Ser His Ala Gly Pro Asp Ser Lys Pro Ala Ala Tyr Pro Thr
            100                 105                 110

Ala Gly Gly Ile Arg Leu Pro Asn Gly Lys Leu Lys Cys Asp Ile Cys
        115                 120                 125

Gly Ile Val Cys Ile Gly Pro Asn Val Leu Met Val His Lys Arg Ser
    130                 135                 140

His Thr Glu Glu Arg Lys Ser Val Leu Glu Gln Gln Lys Gly Glu Arg
145                 150                 155                 160

Pro Phe Gln Cys Asn Gln Cys Gly Ala Ser Phe Thr Gln Lys Gly Asn
                165                 170                 175

Leu Leu Arg His Ile Lys Leu His Ser Gly Glu Lys Pro Phe Lys Cys
            180                 185                 190
```

```
His Leu Cys Asn Tyr Ala Cys Arg Arg Arg Asp Ala Leu Thr Gly His
            195                 200                 205

Leu Arg Thr His Ser Val Gly Lys Pro His Lys Cys Ala Tyr Cys Gly
    210                 215                 220

Arg Ser Tyr Lys Gln Arg Ser Ser Leu Glu Glu His Lys Glu Arg Cys
225                 230                 235                 240

His Asn Tyr Leu Gln Cys Met Gly Leu Gln Asn Ser Ile Tyr Thr Gly
                245                 250                 255

Glu Asn Arg Leu Ser Glu Leu Ser Phe Glu Ser Gly Ser Xaa Glu Leu
            260                 265                 270

Met Gln Pro His Val Ile Asp Gln Ala Ile Asn Ser Ala Ile Ser Tyr
        275                 280                 285

Leu Gly Ala Glu Ser Leu Arg Pro Leu Val Gln Thr Ser Pro Gly Ser
    290                 295                 300

Ala Asp Met Val Val Ser Pro Leu Tyr Asn Leu His Lys Ser Gln Thr
305                 310                 315                 320

Ala Glu Gly Asn Gly Val Ser Ala Lys Asp Ser Ala Ala Glu His Leu
                325                 330                 335

Leu Leu Leu Ser Lys Ser Lys Ser Ala Ser Val Asp Lys Asp Gly Ser
            340                 345                 350

Pro Ser Pro Ser Gly Gln Asp Ser Thr Asp Thr Glu Ser Asn Asn Glu
        355                 360                 365

Glu Arg Ser Ala Gly Val Ser Gly Thr Ala Ala Thr Gly Gly Leu Ile
    370                 375                 380

Tyr Leu Thr Asn His Met Ala Pro Gly Met Arg Asn Gly Gly Leu Pro
385                 390                 395                 400

Gly Val Lys Glu Glu His Arg Gln Phe Glu Ala Leu Arg Ala Ala
                405                 410                 415

Gly Met Asp Leu Ser Ile Ala Ser Ser Glu Gly Phe Lys Val Leu Ser
            420                 425                 430

Gly Asp Gly Glu Glu Leu Arg Ala Tyr Arg Cys Ile His Cys Arg Val
        435                 440                 445

Leu Phe Leu Asp His Val Met Tyr Thr Ile His Met Gly Cys His Gly
    450                 455                 460

Phe Arg Asp Pro Phe Glu Cys Asn Leu Cys Gly Tyr Arg Ser Gln Asp
465                 470                 475                 480

Arg Tyr Glu Phe Ser Ser His Ile Thr Arg Gly Glu His Arg Ile
                485                 490                 495

<210> SEQ ID NO 13
<211> LENGTH: 1455
<212> TYPE: DNA
<213> ORGANISM: Artificial Sequence
<220> FEATURE:
<223> OTHER INFORMATION: nucleotide sequence of ikzf1-007 Ikaros variant
<220> FEATURE:
<221> NAME/KEY: misc_feature
<222> LOCATION: 775
<223> OTHER INFORMATION: n = A,T,C or G

<400> SEQUENCE: 13
atggagactg aggaggcaca ggaaatgtcc cagataacag aagagacag cccgatgaat      60 gctaatgaag gcggagagga tcaagatgag gccatgcctg ttcctgaaga cttgtcagca    120
agcactggcc tccaacacaa caatcgcaca gataaaccac tggcctgtaa tataaaagtt    180
gaggctcgga gtgacgagga aaacggtctg tcctgtgaga tgaatggaga ggcagaggaa    240
```

```
tgtgcagctg aggacttgcg catactcgat ggctctgggg ccaaagtgaa cggctcccac    300
gcaggccccg acagcaagcc ggccgcctac cccacagccg ggggcatccg cctccccaac    360
gggaagctga agtgcgatat ctgtgggata gtttgcattg ggcccaatgt gttgatggtt    420
cacaagcgaa gtcacactgg tgaaaggcca ttccagtgca atcaatgtgg tgcttcattc    480
actcagaagg gtaacctgct ccgacacatc aaacttcact ctggcgagaa acctttcaaa    540
tgtcacctgt gcaactatgc ttgccgccgc agagacgctc tcactggaca tctgcgcact    600
cattcggttg gaaagcccca taagtgtgca tattgcggac gcagttacaa gcagcggagc    660
tcactggagg aacataagga gagatgtcac aactacttgc agtgcatggg ccttcagaac    720
agcatttata caggagagaa tcgtctgtca gagctatctt tcgagagtgg ctcangtgag    780
ctgatgcagc cccatgtgat tgatcaggcc atcaacagtg caattagcta tctgggtgca    840
gagtccttgc ggcctctggt tcagacctct cctgggtccg ccgacatggt ggtcagccct    900
ctatacaacc tgcacaagtc acaaacagct gaaggcaatg gtgtttctgc taaagacagc    960
gccgcagagc accttctcct actctctaag tccaaatccg cctctgttga caaagacggt   1020
tcccccagtc ccagcgggca ggattccact gacactgaga gcaacaacga ggagcgttcg   1080
gccggggtaa gcggaacagc agccacaggt ggtctcatct acctgaccaa ccacatggct   1140
ccaggtatga aaatggagg cctgccaggg gtaaaggaag aacaacaccg gcagtttgag    1200
gctttgcgag cagcaggaat ggatttgagt atagcgtcat cagaaggatt taaggtgcta   1260
agtggagatg agaagaatt gagggcgtac cgctgtatcc actgcagagt tttgttcctg   1320
gatcatgtca tgtacaccat ccacatgggc tgtcatggct ccgagaccc ctttgagtgc    1380 aacctatgcg ggtaccgcag tcaggaccgt tatgagttct catcgcacat cacacgtgga   1440
gagcaccgca tctga                                                    1455
```

<210> SEQ ID NO 14
<211> LENGTH: 484
<212> TYPE: PRT
<213> ORGANISM: Artificial Sequence
<220> FEATURE:
<223> OTHER INFORMATION: amino acid sequence of ikzf1-007 Ikaros variant
<220> FEATURE:
<221> NAME/KEY: VARIANT
<222> LOCATION: 259
<223> OTHER INFORMATION: Xaa = Any Amino Acid

<400> SEQUENCE: 14

```
Met Glu Thr Glu Glu Ala Gln Glu Met Ser Gln Ile Thr Gly Arg Asp
 1               5                  10                  15

Ser Pro Met Asn Ala Asn Glu Gly Gly Glu Asp Gln Asp Glu Ala Met
            20                  25                  30

Pro Val Pro Glu Asp Leu Ser Ala Ser Thr Gly Leu Gln His Asn Asn
        35                  40                  45

Arg Thr Asp Lys Pro Leu Ala Cys Asn Ile Lys Val Glu Ala Arg Ser
    50                  55                  60

Asp Glu Glu Asn Gly Leu Ser Cys Glu Met Asn Gly Glu Ala Glu Glu
65                  70                  75                  80

Cys Ala Ala Glu Asp Leu Arg Ile Leu Asp Gly Ser Gly Ala Lys Val
                85                  90                  95

Asn Gly Ser His Ala Gly Pro Asp Ser Lys Pro Ala Ala Tyr Pro Thr
            100                 105                 110

Ala Gly Gly Ile Arg Leu Pro Asn Gly Lys Leu Lys Cys Asp Ile Cys
        115                 120                 125
```

-continued

Gly Ile Val Cys Ile Gly Pro Asn Val Leu Met Val His Lys Arg Ser
130                 135                 140

His Thr Gly Glu Arg Pro Phe Gln Cys Asn Gln Cys Gly Ala Ser Phe
145                 150                 155                 160

Thr Gln Lys Gly Asn Leu Leu Arg His Ile Lys Leu His Ser Gly Glu
                165                 170                 175

Lys Pro Phe Lys Cys His Leu Cys Asn Tyr Ala Cys Arg Arg Arg Asp
            180                 185                 190

Ala Leu Thr Gly His Leu Arg Thr His Ser Val Gly Lys Pro His Lys
        195                 200                 205

Cys Ala Tyr Cys Gly Arg Ser Tyr Lys Gln Arg Ser Ser Leu Glu Glu
    210                 215                 220

His Lys Glu Arg Cys His Asn Tyr Leu Gln Cys Met Gly Leu Gln Asn
225                 230                 235                 240

Ser Ile Tyr Thr Gly Glu Asn Arg Leu Ser Glu Leu Ser Phe Glu Ser
                245                 250                 255

Gly Ser Xaa Glu Leu Met Gln Pro His Val Ile Asp Gln Ala Ile Asn
            260                 265                 270

Ser Ala Ile Ser Tyr Leu Gly Ala Glu Ser Leu Arg Pro Leu Val Gln
        275                 280                 285

Thr Ser Pro Gly Ser Ala Asp Met Val Val Ser Pro Leu Tyr Asn Leu
    290                 295                 300

His Lys Ser Gln Thr Ala Glu Gly Asn Gly Val Ser Ala Lys Asp Ser
305                 310                 315                 320

Ala Ala Glu His Leu Leu Leu Ser Lys Ser Lys Ser Ala Ser Val
                325                 330                 335

Asp Lys Asp Gly Ser Pro Ser Pro Ser Gly Gln Asp Ser Thr Asp Thr
            340                 345                 350

Glu Ser Asn Asn Glu Glu Arg Ser Ala Gly Val Ser Gly Thr Ala Ala
        355                 360                 365

Thr Gly Gly Leu Ile Tyr Leu Thr Asn His Met Ala Pro Gly Met Arg
    370                 375                 380

Asn Gly Gly Leu Pro Gly Val Lys Glu Glu Gln His Arg Gln Phe Glu
385                 390                 395                 400

Ala Leu Arg Ala Ala Gly Met Asp Leu Ser Ile Ala Ser Ser Glu Gly
                405                 410                 415

Phe Lys Val Leu Ser Gly Asp Gly Glu Leu Arg Ala Tyr Arg Cys
            420                 425                 430

Ile His Cys Arg Val Leu Phe Leu Asp His Val Met Tyr Thr Ile His
        435                 440                 445

Met Gly Cys His Gly Phe Arg Asp Pro Phe Glu Cys Asn Leu Cys Gly
    450                 455                 460

Tyr Arg Ser Gln Asp Arg Tyr Glu Phe Ser Ser His Ile Thr Arg Gly
465                 470                 475                 480

Glu His Arg Ile

<210> SEQ ID NO 15
<211> LENGTH: 21
<212> TYPE: DNA
<213> ORGANISM: Artificial Sequence
<220> FEATURE:
<223> OTHER INFORMATION: forward primer of quantitative PCR of c-Myc

<400> SEQUENCE: 15

```
aacagctatg accatgatta c                                     21

<210> SEQ ID NO 16
<211> LENGTH: 17
<212> TYPE: DNA
<213> ORGANISM: Artificial Sequence
<220> FEATURE:
<223> OTHER INFORMATION: reverse primer of quantitative PCR of c-Myc

<400> SEQUENCE: 16
gtaaaacgac ggccagt                                          17

<210> SEQ ID NO 17
<211> LENGTH: 18
<212> TYPE: DNA
<213> ORGANISM: Artificial Sequence
<220> FEATURE:
<223> OTHER INFORMATION: forward primer of quantitative PCR of sox2

<400> SEQUENCE: 17
accccggagg aaaaccaa                                         18

<210> SEQ ID NO 18
<211> LENGTH: 18
<212> TYPE: DNA
<213> ORGANISM: Artificial Sequence
<220> FEATURE:
<223> OTHER INFORMATION: reverse primer of quantitative PCR of sox2

<400> SEQUENCE: 18
cccggcaggg tgtacttg                                         18

<210> SEQ ID NO 19
<211> LENGTH: 19
<212> TYPE: DNA
<213> ORGANISM: Artificial Sequence
<220> FEATURE:
<223> OTHER INFORMATION: forward primer of quantitative PCR of nanog

<400> SEQUENCE: 19
tacccaacac accagcttc                                        19

<210> SEQ ID NO 20
<211> LENGTH: 19
<212> TYPE: DNA
<213> ORGANISM: Artificial Sequence
<220> FEATURE:
<223> OTHER INFORMATION: reverse primer of quantitative PCR of nanog

<400> SEQUENCE: 20
gaagggtgtt tttggagga                                        19

<210> SEQ ID NO 21
<211> LENGTH: 17
<212> TYPE: DNA
<213> ORGANISM: Artificial Sequence
<220> FEATURE:
<223> OTHER INFORMATION: forward primer for amplification of Ascl1a

<400> SEQUENCE: 21
acgagcatga cgccgta                                          17

<210> SEQ ID NO 22
<211> LENGTH: 25
<212> TYPE: DNA
<213> ORGANISM: Artificial Sequence
```

```
<220> FEATURE:
<223> OTHER INFORMATION: reverse primer for amplification of Ascl1a

<400> SEQUENCE: 22
ttttaagttt ccttttacga acgct                                         25

<210> SEQ ID NO 23
<211> LENGTH: 20
<212> TYPE: DNA
<213> ORGANISM: Artificial Sequence
<220> FEATURE:
<223> OTHER INFORMATION: forward primer for amplification of Pou3f2b

<400> SEQUENCE: 23
ccgagagtca tggcgactac                                               20

<210> SEQ ID NO 24
<211> LENGTH: 20
<212> TYPE: DNA
<213> ORGANISM: Artificial Sequence
<220> FEATURE:
<223> OTHER INFORMATION: reverse primer for amplification of Pou3f2b

<400> SEQUENCE: 24
cttctccgtg tgacaaggct                                               20

<210> SEQ ID NO 25
<211> LENGTH: 20
<212> TYPE: DNA
<213> ORGANISM: Artificial Sequence
<220> FEATURE:
<223> OTHER INFORMATION: forward primer for amplification of Myt1la

<400> SEQUENCE: 25
actcaacagc cactgctacc                                               20

<210> SEQ ID NO 26
<211> LENGTH: 20
<212> TYPE: DNA
<213> ORGANISM: Artificial Sequence
<220> FEATURE:
<223> OTHER INFORMATION: reverse primer for amplification of Myt1la

<400> SEQUENCE: 26
agcttgatag cgtgaggagc                                               20

<210> SEQ ID NO 27
<211> LENGTH: 20
<212> TYPE: DNA
<213> ORGANISM: Artificial Sequence
<220> FEATURE:
<223> OTHER INFORMATION: forward primer for amplification of Notch3

<400> SEQUENCE: 27
acaacagcga aggattgctc                                               20

<210> SEQ ID NO 28
<211> LENGTH: 20
<212> TYPE: DNA
<213> ORGANISM: Artificial Sequence
<220> FEATURE:
<223> OTHER INFORMATION: reverse primer for amplification of Notch3

<400> SEQUENCE: 28
tctaaagcct cgctgacaca                                               20
```

<210> SEQ ID NO 29
<211> LENGTH: 20
<212> TYPE: DNA
<213> ORGANISM: Artificial Sequence
<220> FEATURE:
<223> OTHER INFORMATION: forward primer for amplification of Nrp2b

<400> SEQUENCE: 29
ccagcggatc gtcttaaact                                                 20

<210> SEQ ID NO 30
<211> LENGTH: 20
<212> TYPE: DNA
<213> ORGANISM: Artificial Sequence
<220> FEATURE:
<223> OTHER INFORMATION: reverse primer for amplification of Nrp2b

<400> SEQUENCE: 30
caaaactggg cctgaggata                                                 20

<210> SEQ ID NO 31
<211> LENGTH: 20
<212> TYPE: DNA
<213> ORGANISM: Artificial Sequence
<220> FEATURE:
<223> OTHER INFORMATION: forward primer used in quantitative PCR for
      Pou5f1

<400> SEQUENCE: 31
aactgaagcc gttgttgcag                                                 20

<210> SEQ ID NO 32
<211> LENGTH: 20
<212> TYPE: DNA
<213> ORGANISM: Artificial Sequence
<220> FEATURE:
<223> OTHER INFORMATION: reverse primer used in quantitative PCR for
      Pou5f1

<400> SEQUENCE: 32
caagctggtc cttcgttttc                                                 20

<210> SEQ ID NO 33
<211> LENGTH: 17
<212> TYPE: DNA
<213> ORGANISM: Artificial Sequence
<220> FEATURE:
<223> OTHER INFORMATION: forward primer used in quantitative PCR for
      Zic3

<400> SEQUENCE: 33
ccctgggctg ggactca                                                    17

<210> SEQ ID NO 34
<211> LENGTH: 19
<212> TYPE: DNA
<213> ORGANISM: Artificial Sequence
<220> FEATURE:
<223> OTHER INFORMATION: reverse primer used in quantitative PCR for
      Zic3

<400> SEQUENCE: 34
cttgaaggca gccgagtga                                                  19

<210> SEQ ID NO 35
<211> LENGTH: 20

```
<212> TYPE: DNA
<213> ORGANISM: Artificial Sequence
<220> FEATURE:
<223> OTHER INFORMATION: forward primer used in quantitative PCR for
      CRBN

<400> SEQUENCE: 35
agaggtcagc atgtttcgca                                              20

<210> SEQ ID NO 36
<211> LENGTH: 20
<212> TYPE: DNA
<213> ORGANISM: Artificial Sequence
<220> FEATURE:
<223> OTHER INFORMATION: reverse primer used in quantitative PCR for
      CRBN

<400> SEQUENCE: 36
ctgacgaatc ccgtctgctt                                              20

<210> SEQ ID NO 37
<211> LENGTH: 20
<212> TYPE: DNA
<213> ORGANISM: Artificial Sequence
<220> FEATURE:
<223> OTHER INFORMATION: forward primer used in quantitative PCR for
      Wnt3a

<400> SEQUENCE: 37
gcttctgccg caactatgtg                                              20

<210> SEQ ID NO 38
<211> LENGTH: 20
<212> TYPE: DNA
<213> ORGANISM: Artificial Sequence
<220> FEATURE:
<223> OTHER INFORMATION: reverse primer used in quantitative PCR for
      Wnt3a

<400> SEQUENCE: 38
ccgattctct ggtggccttt                                              20

<210> SEQ ID NO 39
<211> LENGTH: 20
<212> TYPE: DNA
<213> ORGANISM: Artificial Sequence
<220> FEATURE:
<223> OTHER INFORMATION: forward primer used in quantitative PCR for
      Lhx2b

<400> SEQUENCE: 39
gggggaaaca gagacgaaca                                              20

<210> SEQ ID NO 40
<211> LENGTH: 21
<212> TYPE: DNA
<213> ORGANISM: Artificial Sequence
<220> FEATURE:
<223> OTHER INFORMATION: reverse primer used in quantitative PCR for
      Lhx2b

<400> SEQUENCE: 40
tctctgcacc gaaaaccttc t                                            21
```